(12) United States Patent
Furlong et al.

(10) Patent No.: US 10,265,087 B2
(45) Date of Patent: Apr. 23, 2019

(54) METHODS AND APPARATUS FOR REMOVING MATERIAL FROM WITHIN A MAMMALIAN CAVITY USING AN INSERTABLE ENDOSCOPIC INSTRUMENT

(71) Applicant: Interscope, Inc., Whitinsville, MA (US)

(72) Inventors: Cosme Furlong, Whitinsville, MA (US); Michael W. Marcoux, Whitinsville, MA (US); Richard Stephen Wisdom, Hydepark, MA (US); William R. Rebh, Jr., Shrewsbury, MA (US); Evan Costa, Newton, MA (US); Stephen C. Evans, Westford, MA (US)

(73) Assignee: INTERSCOPE, INC., Whitinsville, MA (US)

( * ) Notice: Subject to any disclaimer, the term of this patent is extended or adjusted under 35 U.S.C. 154(b) by 503 days.

(21) Appl. No.: 14/961,425

(22) Filed: Dec. 7, 2015

(65) Prior Publication Data
US 2016/0081705 A1 Mar. 24, 2016

Related U.S. Application Data

(63) Continuation of application No. 14/501,957, filed on Sep. 30, 2014, now Pat. No. 9,204,868, which is a (Continued)

(51) Int. Cl.
*A61B 17/32* (2006.01)
*A61B 1/00* (2006.01)
(Continued)

(52) U.S. Cl.
CPC ............ *A61B 17/221* (2013.01); *A61B 1/005* (2013.01); *A61B 1/00094* (2013.01);
(Continued)

(58) Field of Classification Search
CPC . A61B 1/00094; A61B 1/00133; A61B 1/015; A61B 1/018; A61B 1/31;
(Continued)

(56) References Cited

U.S. PATENT DOCUMENTS 3,760,810 A 9/1973 Van Hoorn
3,834,392 A 9/1974 Lampman et al.
(Continued)

FOREIGN PATENT DOCUMENTS

CN 202051784 11/2011
DE 33 39 322 A1 5/1984
(Continued)

OTHER PUBLICATIONS

First Office Action dated Feb. 3, 2016 in Chinese Patent Application No. 201280068003.8.
(Continued)

*Primary Examiner* — Devin B Henson
(74) *Attorney, Agent, or Firm* — Shabbi S. Khan; Foley & Lardner LLP

(57) ABSTRACT

An endoscope for removing tissue at a surgical site includes an elongated tubular body insertable within a mammalian cavity of a patient. An instrument channel extends between a first opening at a distal end and a second opening at a proximal end of the tubular body and is sized and configured to receive a surgical cutting assembly that includes an aspiration channel configured to remove material entering the endoscope via a distal end of the surgical cutting assembly. A torque generation component configured to generate torque is positioned within the distal end and configured to provide the generated torque to a coupling component. The coupling component is positioned at the distal end of the elongated tubular member and configured to actuate a cutting component of the surgical cutting
(Continued)

assembly responsive to actuation of the torque generation component.

20 Claims, 109 Drawing Sheets

Related U.S. Application Data continuation-in-part of application No. 14/280,202, filed on May 16, 2014, now Pat. No. 8,882,680, which is a continuation-in-part of application No. 13/336,491, filed on Dec. 23, 2011, now Pat. No. 9,808,146.

(60) Provisional application No. 61/824,760, filed on May 17, 2013, provisional application No. 61/566,472, filed on Dec. 2, 2011.

(51) Int. Cl.
| | |
|---|---|
| A61B 10/04 | (2006.01) |
| A61B 1/015 | (2006.01) |
| A61B 1/018 | (2006.01) |
| A61B 10/02 | (2006.01) |
| A61B 1/005 | (2006.01) |
| A61B 17/3207 | (2006.01) |
| A61B 17/00 | (2006.01) |
| A61B 17/221 | (2006.01) |
| A61B 1/31 | (2006.01) |
| A61B 90/00 | (2016.01) |

(52) U.S. Cl.
CPC ...... *A61B 1/00119* (2013.01); *A61B 1/00128* (2013.01); *A61B 1/00133* (2013.01); *A61B 1/015* (2013.01); *A61B 1/018* (2013.01); *A61B 1/31* (2013.01); *A61B 10/0275* (2013.01); *A61B 10/04* (2013.01); *A61B 17/32002* (2013.01); *A61B 10/0283* (2013.01); *A61B 17/32* (2013.01); *A61B 17/320016* (2013.01); *A61B 17/320758* (2013.01); *A61B 17/320783* (2013.01); *A61B 90/361* (2016.02); *A61B 2010/0208* (2013.01); *A61B 2010/0225* (2013.01); *A61B 2010/045* (2013.01); *A61B 2017/0034* (2013.01); *A61B 2017/00553* (2013.01); *A61B 2017/00818* (2013.01); *A61B 2017/00862* (2013.01); *A61B 2017/320032* (2013.01); *A61B 2017/320064* (2013.01); *A61B 2217/005* (2013.01); *A61B 2217/007* (2013.01)

(58) Field of Classification Search
CPC . A61B 10/04; A61B 10/0266; A61B 10/0275; A61B 17/320016; A61B 17/32002; A61B 2017/320032; A61B 2017/320064; A61B 2017/00973; A61B 2217/005; A61B 2217/007

See application file for complete search history.

(56) References Cited

U.S. PATENT DOCUMENTS

| | | | |
|---|---|---|---|
| 3,911,923 A | 10/1975 | Yoon | |
| 4,222,380 A | 9/1980 | Terayama | |
| 4,226,239 A | 10/1980 | Polk et al. | |
| 4,257,419 A | 3/1981 | Goltner et al. | |
| 4,548,201 A | 10/1985 | Yoon | |
| 4,646,738 A | 3/1987 | Trott | |
| 4,756,309 A | 7/1988 | Sachse et al. | |
| 4,763,667 A | 8/1988 | Manzo | |
| 4,834,729 A | 5/1989 | Sjostrom | |
| 4,950,278 A | 8/1990 | Sachse et al. | |
| 4,966,162 A | 10/1990 | Wang | |
| 5,269,789 A | 12/1993 | Chin et al. | |
| 5,287,845 A * | 2/1994 | Faul | A61B 1/00135 600/135 |
| 5,320,630 A | 6/1994 | Ahmed | |
| 5,320,635 A | 6/1994 | Smith | |
| 5,349,940 A | 9/1994 | Takahashi et al. | |
| 5,417,697 A | 5/1995 | Wilk et al. | |
| 5,423,834 A | 6/1995 | Ahmed | |
| 5,462,559 A | 10/1995 | Ahmed | |
| 5,507,797 A | 4/1996 | Suzuki et al. | |
| 5,529,580 A | 6/1996 | Kusunoki et al. | |
| 5,662,671 A | 9/1997 | Barbut et al. | |
| 5,871,453 A | 2/1999 | Banik et al. | |
| 5,906,615 A | 5/1999 | Thompson | |
| 5,961,534 A | 10/1999 | Banik et al. | |
| 6,059,719 A | 5/2000 | Yamamoto et al. | |
| 6,068,603 A | 5/2000 | Suzuki | |
| 6,193,672 B1 | 2/2001 | Clement | |
| 6,245,011 B1 | 6/2001 | Dudda et al. | |
| 6,517,560 B1 | 2/2003 | Toth et al. | |
| 6,572,578 B1 | 6/2003 | Blanchard | |
| 6,585,694 B1 | 7/2003 | Smith et al. | |
| 6,645,218 B1 | 11/2003 | Cassidy et al. | |
| 6,666,854 B1 | 12/2003 | Lange | |
| 6,689,146 B1 | 2/2004 | Himes | |
| 7,247,161 B2 | 7/2007 | Johnston et al. | |
| 7,276,074 B2 | 10/2007 | Adams et al. | |
| 7,625,347 B2 | 12/2009 | Burbank et al. | |
| 7,691,110 B2 | 4/2010 | Secrest et al. | |
| 7,857,784 B2 | 12/2010 | Schmidberger et al. | |
| 8,070,756 B2 | 12/2011 | Secrest et al. | |
| 8,070,762 B2 | 12/2011 | Escudero et al. | |
| 8,123,750 B2 | 2/2012 | Norton et al. | |
| 8,277,474 B2 | 10/2012 | Norman et al. | |
| 8,435,259 B2 | 5/2013 | Dierck | |
| 8,475,484 B2 | 7/2013 | Wulfman et al. | |
| 8,528,563 B2 | 9/2013 | Gruber | |
| 8,574,254 B2 | 11/2013 | Hedstrom et al. | |
| 8,696,621 B2 | 4/2014 | Gunday et al. | |
| 9,095,367 B2 | 8/2015 | Olson et al. | |
| 2002/0013570 A1 | 1/2002 | Ruegg et al. | |
| 2003/0055315 A1 | 3/2003 | Gatto et al. | |
| 2004/0147934 A1 | 7/2004 | Kiester | |
| 2004/0162572 A1 | 8/2004 | Sauer | |
| 2005/0090848 A1 | 4/2005 | Adams | |
| 2005/0159767 A1 | 7/2005 | Adams et al. | |
| 2005/0272976 A1 | 12/2005 | Tanaka et al. | |
| 2006/0229646 A1 | 10/2006 | Sparks | |
| 2007/0197871 A1 | 8/2007 | Geitz et al. | |
| 2008/0082021 A1 | 4/2008 | Ichikawa et al. | |
| 2008/0183201 A1 | 7/2008 | Berberich | |
| 2008/0194910 A1 | 8/2008 | Miyamoto et al. | |
| 2008/0234602 A1 | 9/2008 | Oostman et al. | |
| 2008/0249553 A1 | 10/2008 | Gruber et al. | |
| 2009/0069806 A1 | 3/2009 | De La Mora Levy et al. | |
| 2009/0234378 A1 | 9/2009 | Escudero et al. | |
| 2009/0240261 A1 | 9/2009 | Drews et al. | |
| 2010/0010525 A1 | 1/2010 | Lockard et al. | |
| 2010/0016757 A1 | 1/2010 | Greenburg et al. | |
| 2010/0036375 A1 | 2/2010 | Regadas | |
| 2010/0048992 A1 | 2/2010 | Okada et al. | |
| 2010/0081874 A1 | 4/2010 | Miyamoto et al. | |
| 2010/0121141 A1 | 5/2010 | Rontal | |
| 2010/0168512 A1 | 7/2010 | Rahmani | |
| 2010/0217245 A1 | 8/2010 | Prescott | |
| 2010/0298855 A1 | 11/2010 | Dierck | |
| 2011/0270126 A1 | 11/2011 | Gunday et al. | |
| 2012/0109130 A1 | 5/2012 | Casey et al. | |
| 2012/0226101 A1 | 9/2012 | Tinkham et al. | |
| 2012/0226103 A1 | 9/2012 | Gunday et al. | |
| 2013/0016316 A1 | 1/2013 | Cheng et al. | |
| 2013/0046313 A1 | 2/2013 | Sullivan et al. | |
| 2013/0046316 A1 | 2/2013 | Sullivan et al. | |
| 2013/0103067 A1 | 4/2013 | Fabro et al. | |
| 2013/0190561 A1 | 7/2013 | Oskin et al. | |
| 2014/0100567 A1 | 4/2014 | Edwards et al. | |

(56) References Cited

U.S. PATENT DOCUMENTS

| | | | |
|---|---|---|---|
| 2014/0155923 | A1 | 6/2014 | Edwards et al. |
| 2014/0236165 | A1 | 8/2014 | Ries et al. |
| 2014/0249448 | A1 | 9/2014 | Furlong et al. |

FOREIGN PATENT DOCUMENTS

| | | |
|---|---|---|
| DE | 33 20 076 A1 | 12/1984 |
| DE | 19522403 A1 | 9/1997 |
| EP | 0 609 084 A2 | 8/1994 |
| EP | 1 586 275 | 10/2005 |
| EP | 1 875 871 A2 | 9/2008 |
| JP | 2002-503132 | 1/2002 |
| JP | 2003-524479 | 8/2003 |
| WO | WO-95/30377 | 11/1995 |
| WO | WO-01/22889 | 4/2001 |
| WO | WO-2006/122279 | 11/2006 |
| WO | WO-2012/075409 A1 | 6/2012 |
| WO | WO-2013/022525 | 2/2013 |

OTHER PUBLICATIONS

U.S. Office Action for U.S. Appl. No. 13/336,491 dated Mar. 2, 2016.
U.S. Office Action for U.S. Appl. No. 14/316,203 dated Mar. 15, 2016.
U.S. Office Action on U.S. Appl. No. 13/336,491 dated May 11, 2016.
Office Action for CN2014800030452 dated Aug. 22, 2016.
Office Action on U.S. Appl. No. 13/336,491 dated Oct. 26, 2016.
Search Report for CN2012800680038 dated Oct. 18, 2016.
Search Report for CN2014800030452 dated Aug. 22, 2016.
Second Office Action for CN2012800680038 dated Oct. 18, 2016.
Canadian Examination Report on CA Application No. 2911545 dated Nov. 20, 2015.
International Preliminary Report on Patentability dated Nov. 26, 2015 in PCT Application No. PCT/US2014/038443.
International Preliminary Report on Patentability dated Jun. 12, 2014 in PCT Application No. PCT/US2012/067614.
International Search Report and Written Opinion dated May 28, 2013 in PCT App. No. PCT/US2012/067614.
International Search Report and Written Opinion for International Patent Application No. PCT/US2014/038443 dated Sep. 1, 2014.
International Search Report and Written Opinion of the International Searching Authority for International Application No. PCT/US2015/052977 dated Dec. 18, 2015.
International Search Report and Written Opinion of the International Searching Authority for International Application No. PCT/US2015/052979 dated Dec. 17, 2015.
International Search Report and Written Opinion of the International Searching Authority on International Application No. PCT/US2015/052978 dated Dec. 17, 2015.
Office Action in European Patent Application No. 14731875.2 dated Feb. 12, 2016.
U.S. Notice of Allowance in U.S. Appl. No. 14/501,942 dated Mar. 18, 2015.
U.S. Notice of Allowance in U.S. Appl. No. 14/501,957 dated Oct. 21, 2015.
U.S. Notice of Allowance in U.S. Appl. No. 14/280,202 dated Oct. 7, 2014.
U.S. Notice of Allowance in U.S. Appl. No. 14/501,865 dated Feb. 20, 2015.
U.S. Notice of Allowance in U.S. Appl. No. 14/537,362 dated May 26, 2015.
U.S. Office Action for U.S. Appl. No. 14/501,957 dated Nov. 14, 2014.
U.S. Office Action in U.S. Appl. No. 14/501,957 dated Mar. 19, 2015.
U.S. Office Action in U.S. Appl. No. 14/280,202 dated Aug. 20, 2014.
U.S. Office Action in U.S. Appl. No. 14/501,865 dated Dec. 4, 2014.
U.S. Office Action in U.S. Appl. No. 14/501,932 dated Nov. 26, 2014.
U.S. Office Action in U.S. Appl. No. 14/501,942 dated Dec. 15, 2014.
U.S. Office Action in U.S. Appl. No. 14/537,362 dated Feb. 11, 2015.
U.S. Office Action on U.S. Appl. No. 13/336,491 dated Sep. 18, 2015.
Examination Report for EP 12809398.6 dated Jul. 19, 2016.
Examination Report for EP 14731875.2 dated Aug. 17, 2016.
Patent Examination Report for AU 2012345690 dated Jul. 22, 2016.
U.S. Notice of Allowance on U.S. Appl. No. 14/316,203 dated Jun. 23, 2016.
Office Action and Search Report for CN 2014800030452 dated Aug. 22, 2016.
Office Action for JP2008/0249553 dated Nov. 8, 2016.
European Search Report for application 17183220.7-1659 dated Nov. 3, 2017.
Examination Report No. 2 for Standard Patent Application for Application No. 2012345609 dated Jun. 4, 2017.
Examination Search Report for CA Application No. 2,964,001 dated Jun. 19, 2017.
Extended Search Report for EP Application No. 17195661.8 dated Feb. 27, 2018.
Fourth Office Action for CN Application No. 201250068003.8 dated Nov. 3, 2017.
Japanese Office Action for Application No. 2017-517005 dated Apr. 10, 2018.
Office Action for JP Application No. 2016-114249 dated Jun. 6, 2017.
Office Action for JP Application No. 2017-517005 dated Apr. 10, 2018.
Third Office Action for Application No. 201280068003.8 dated Apr. 17, 2017, 6 pages.
Notice of Allowance on U.S. Appl. No. 29/545,289 dated Mar. 20, 2018.

\* cited by examiner

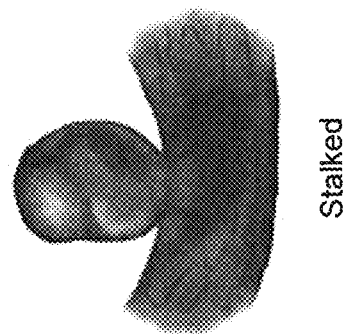
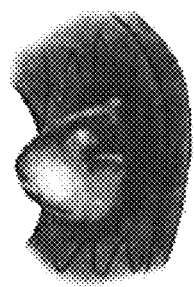
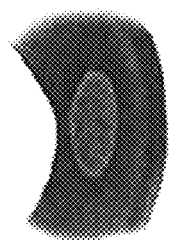
FIG. 1A

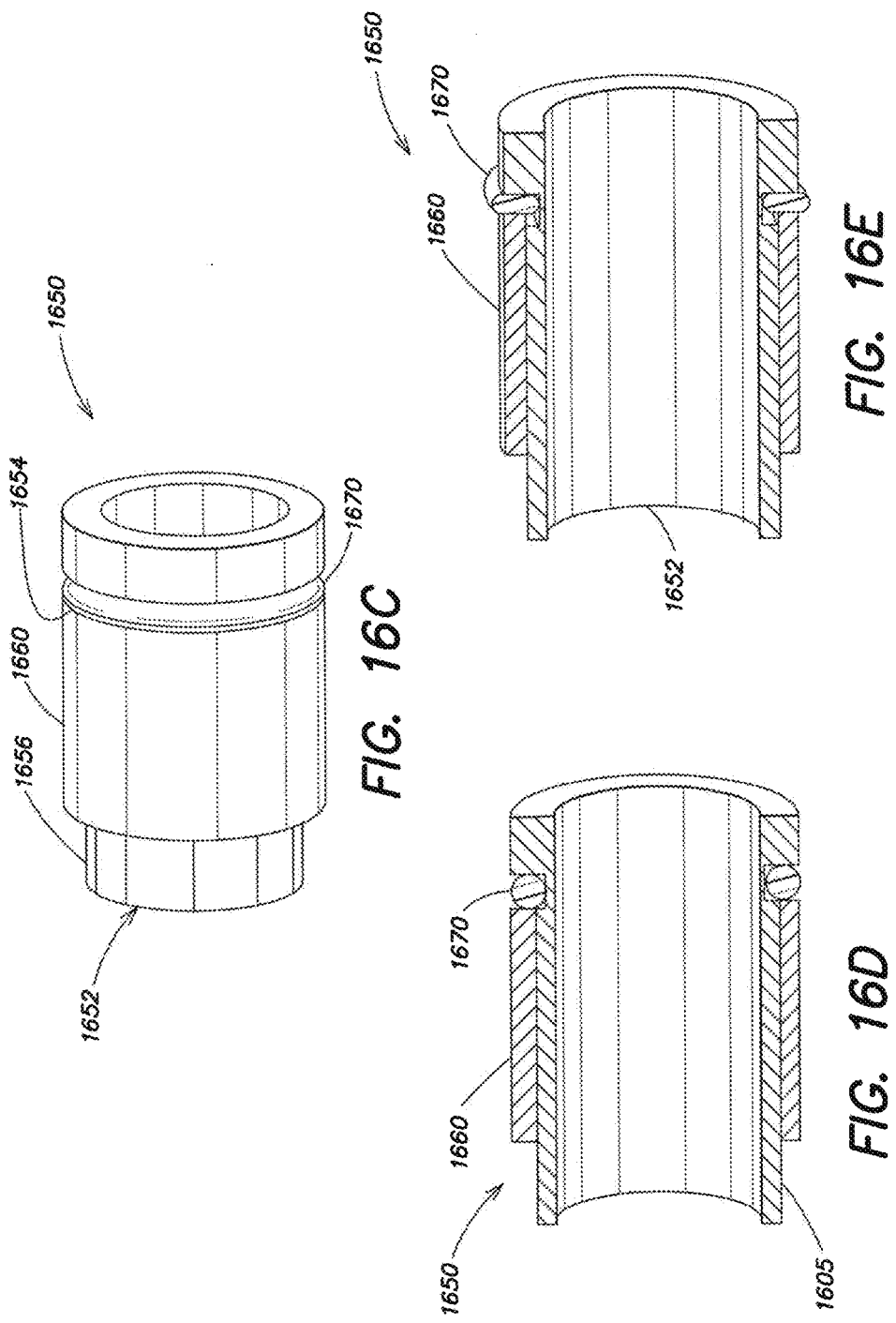

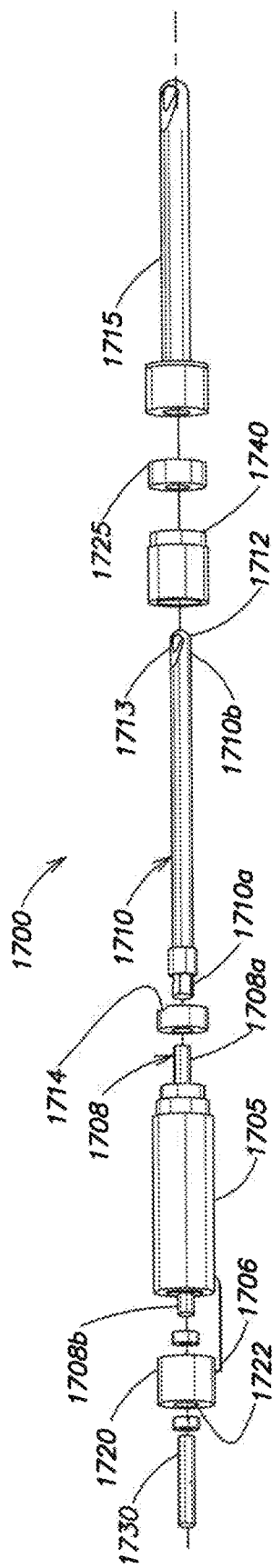
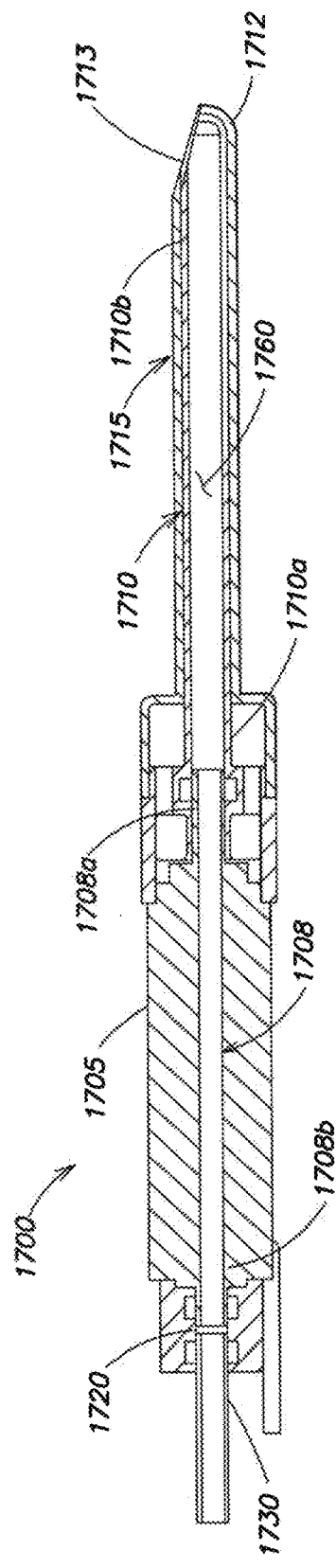
FIG. 17A
FIG. 17B

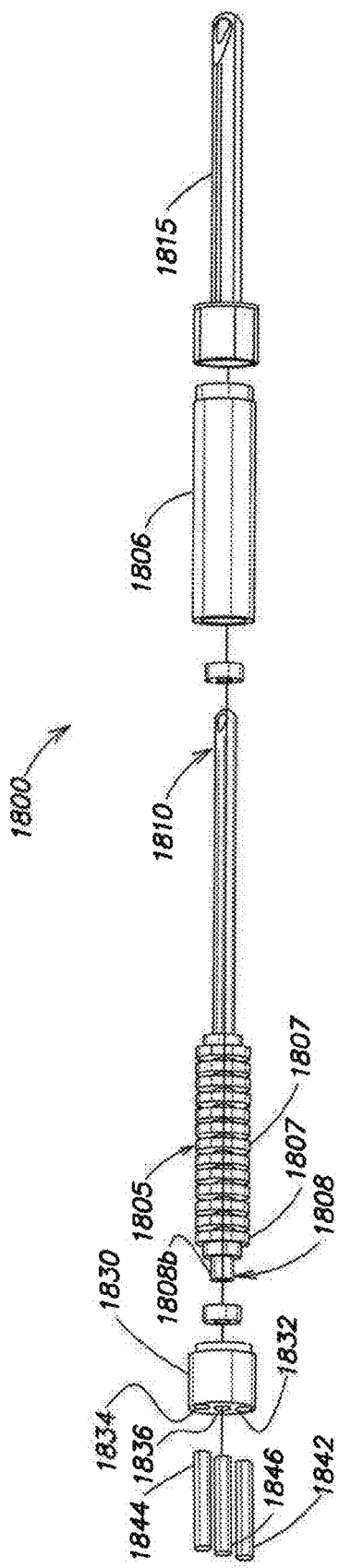
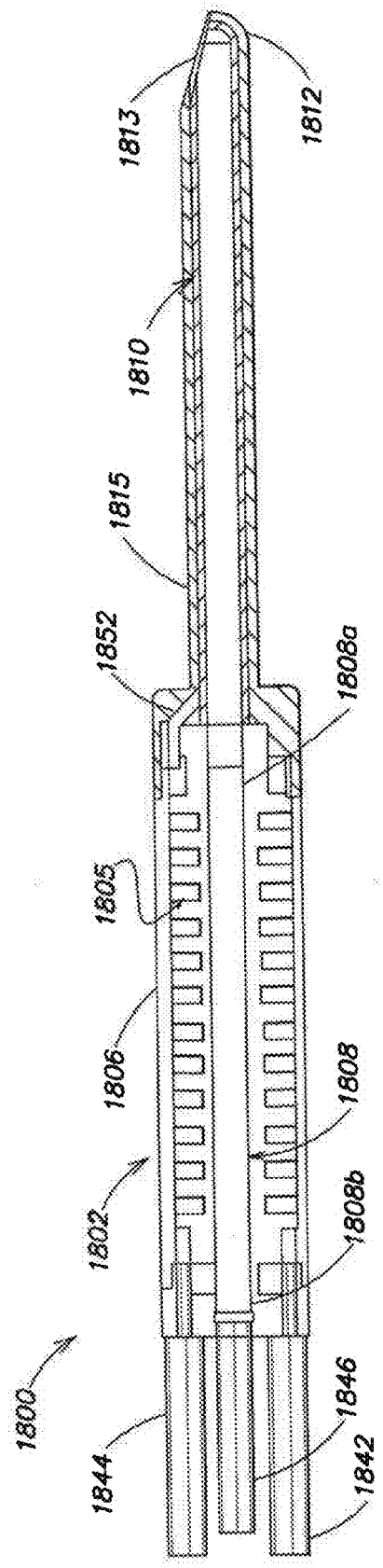
FIG. 18A
FIG. 18B

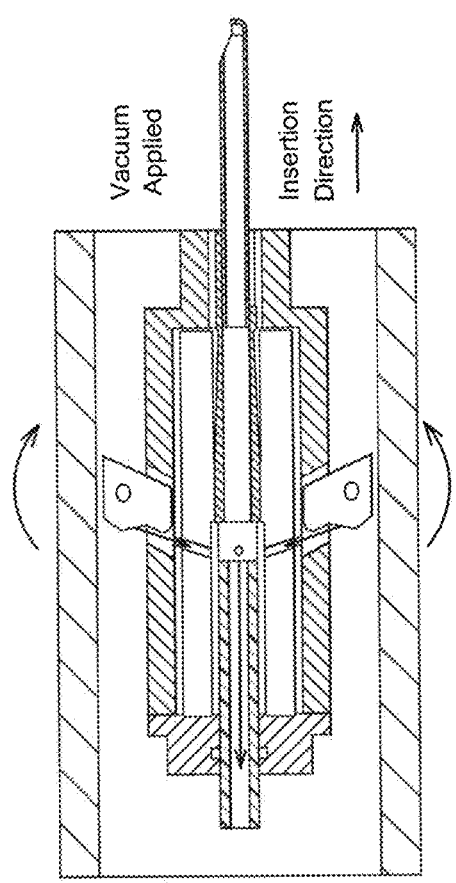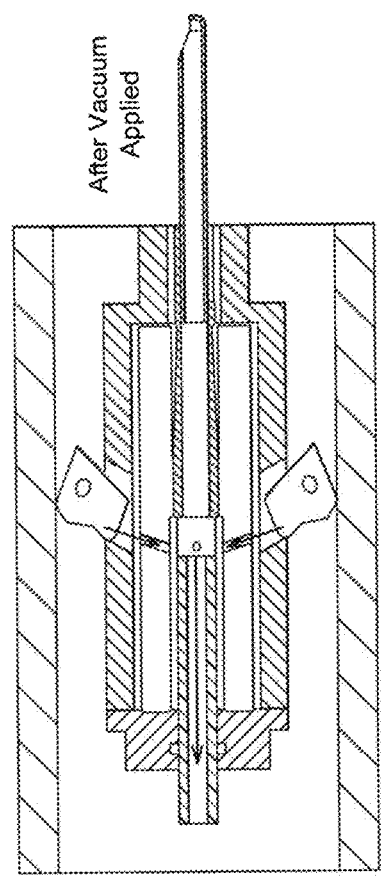

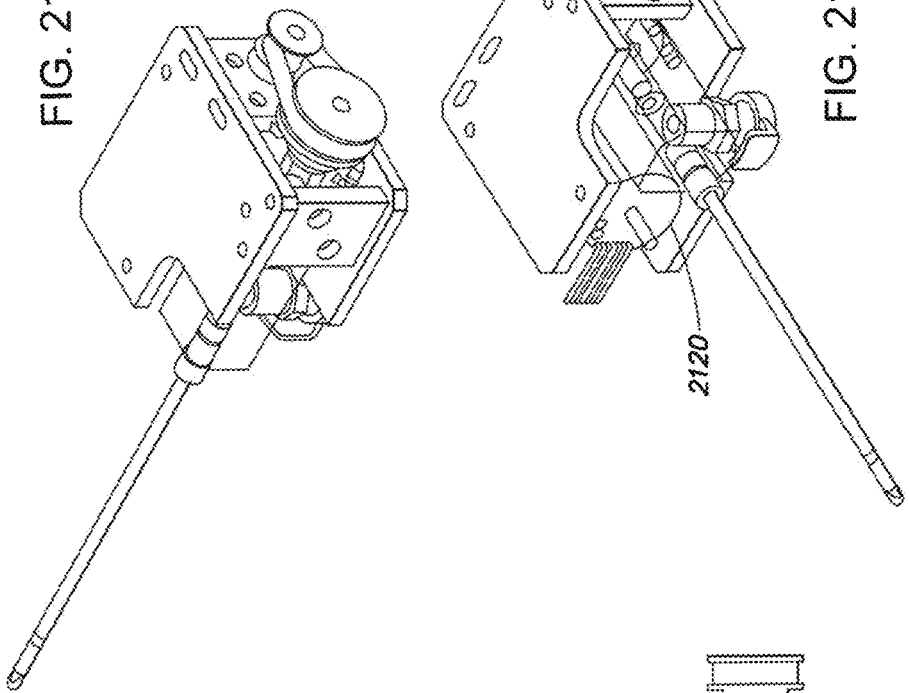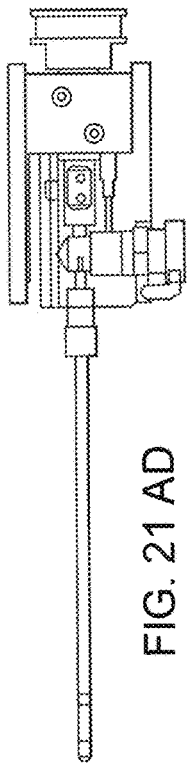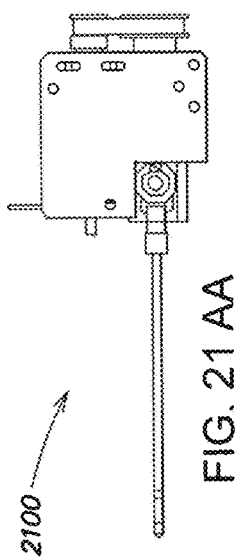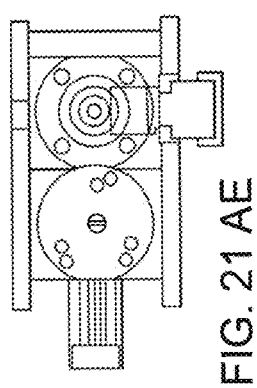
FIG. 21 AB
FIG. 21 AC
FIG. 21 AA
FIG. 21 AE
FIG. 21 AD

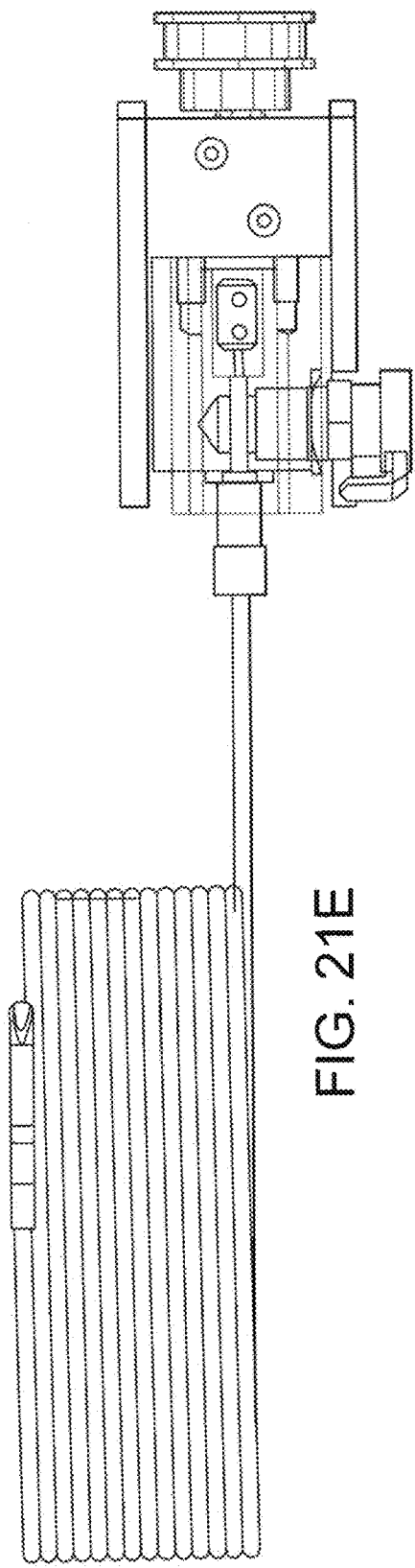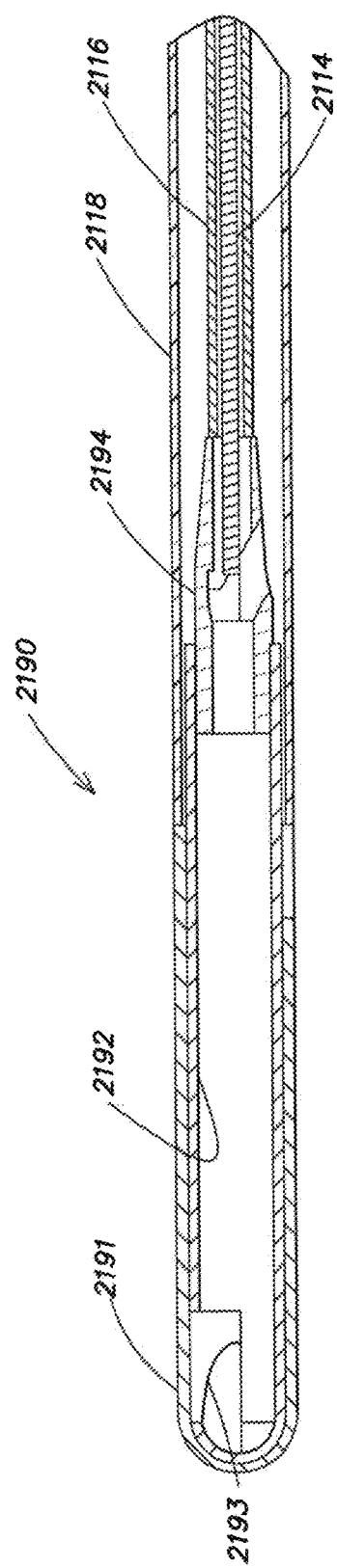
FIG. 21E
FIG. 21F

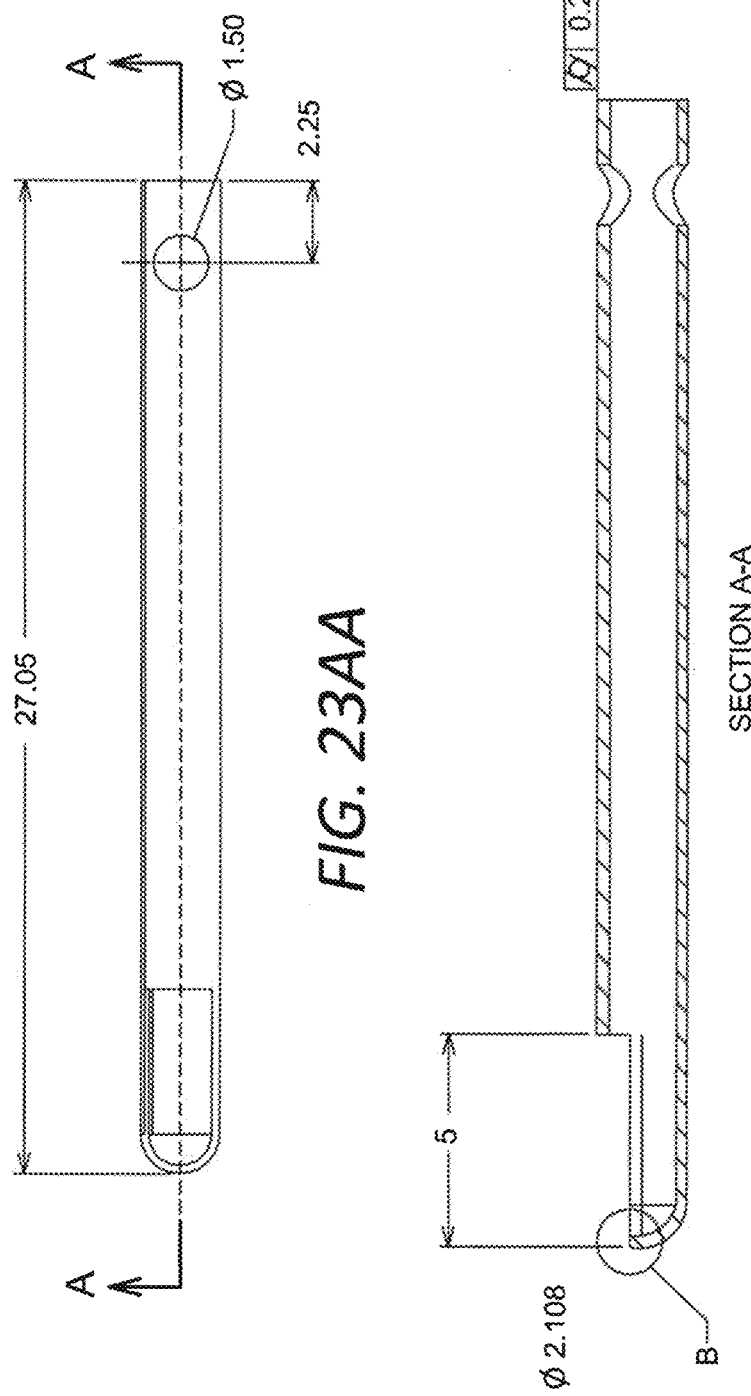

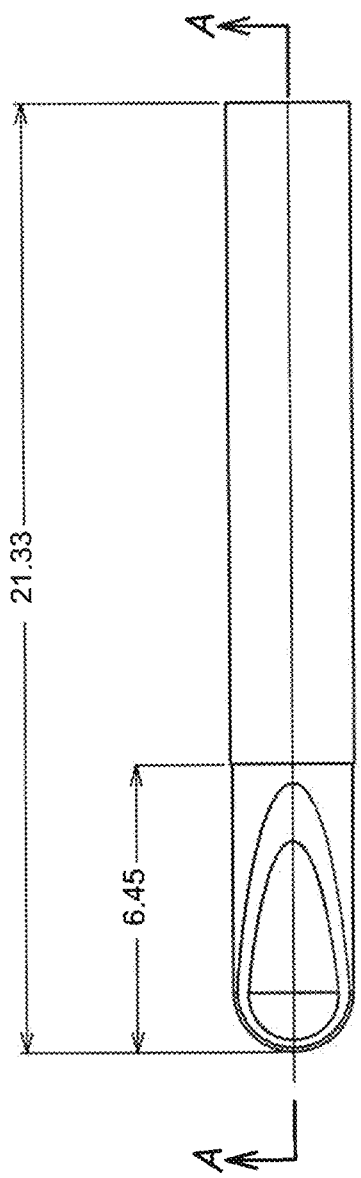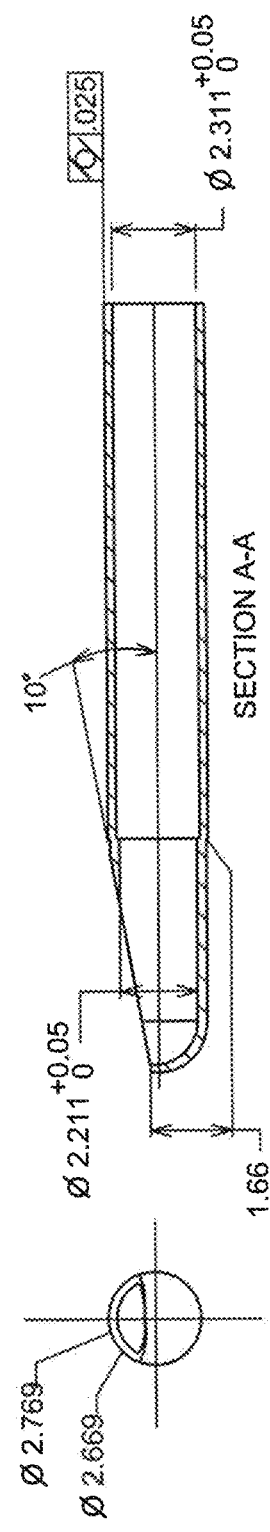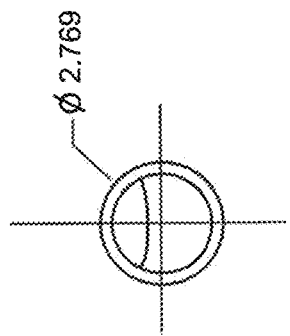
FIG. 23BA
FIG. 23BB

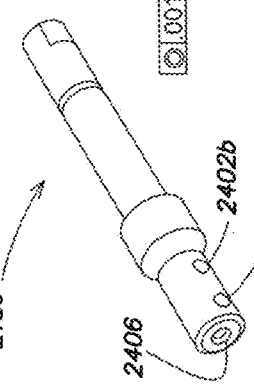
FIG. 24A
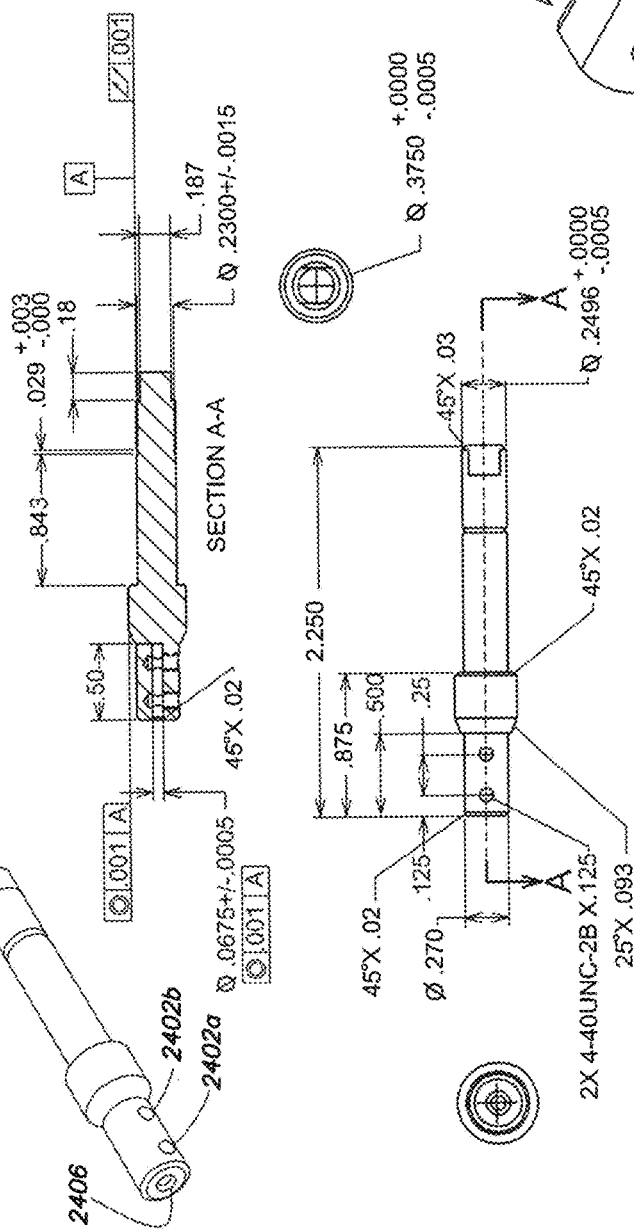
FIG. 24B
FIG. 24C
FIG. 25

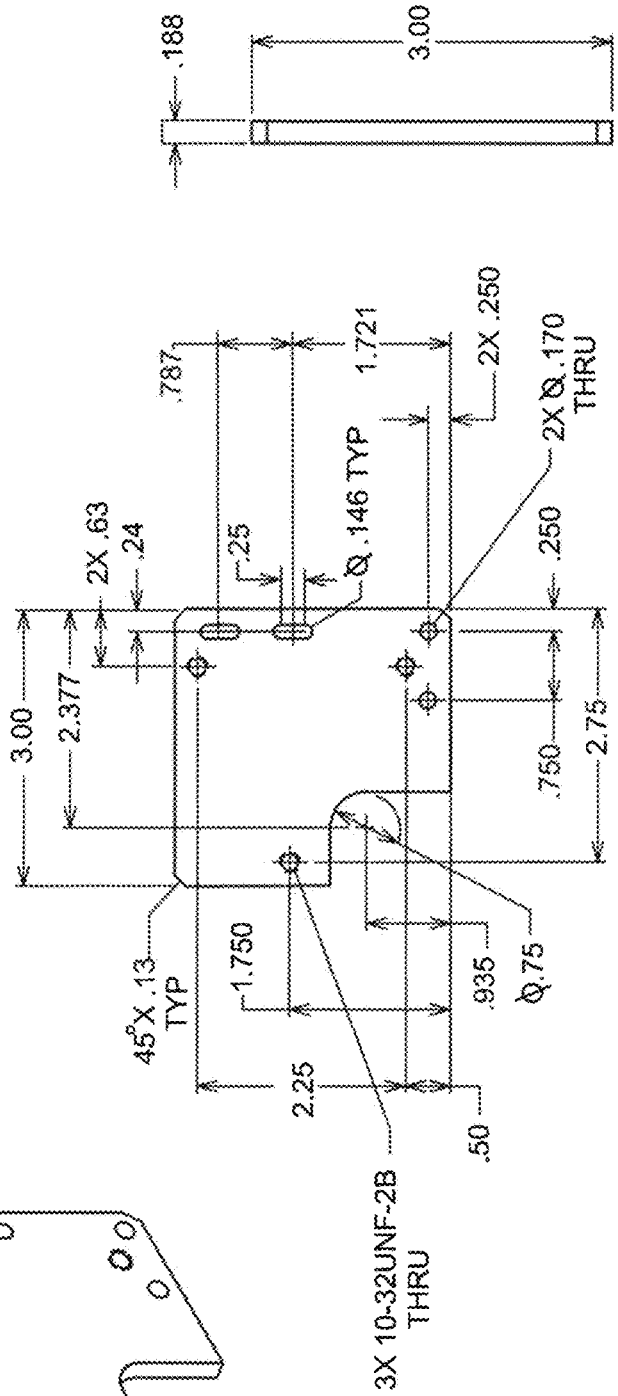
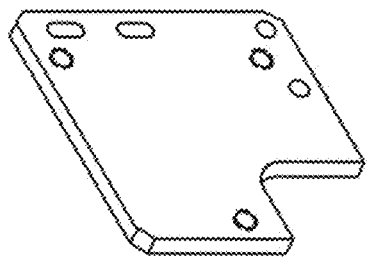
FIG. 27A  FIG. 27B  FIG. 27C

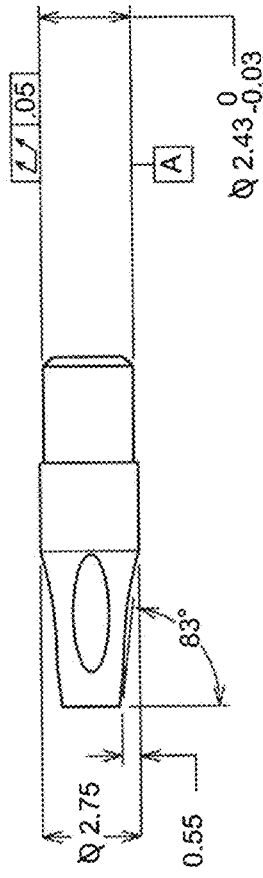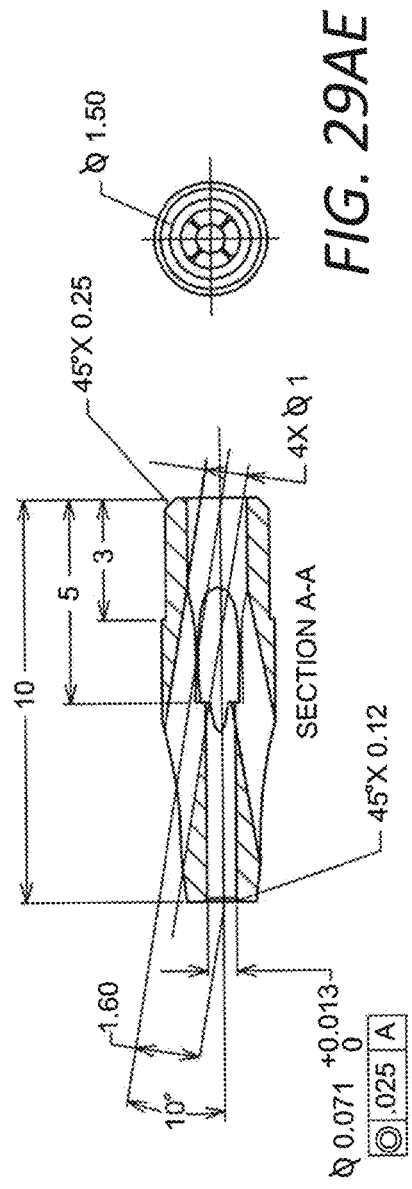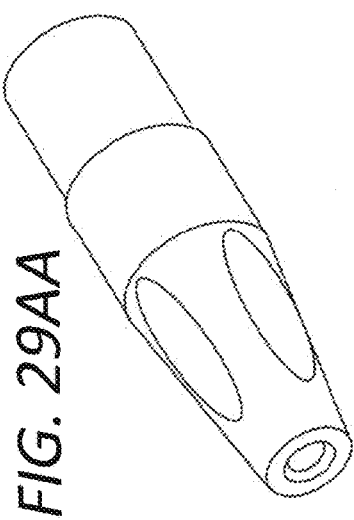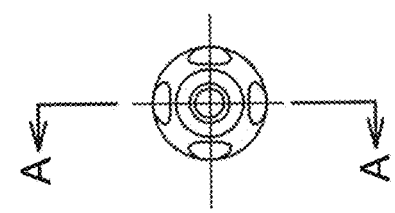

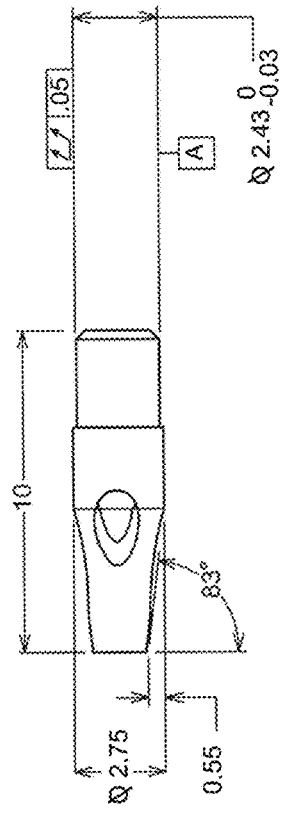
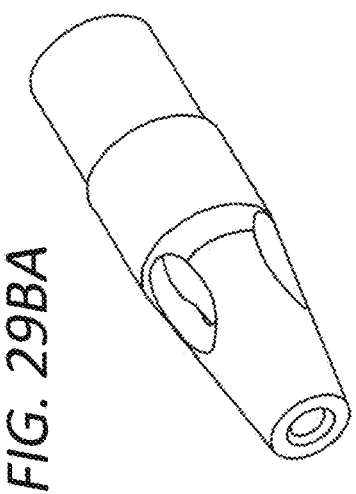
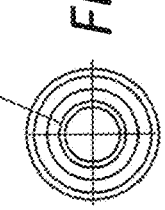
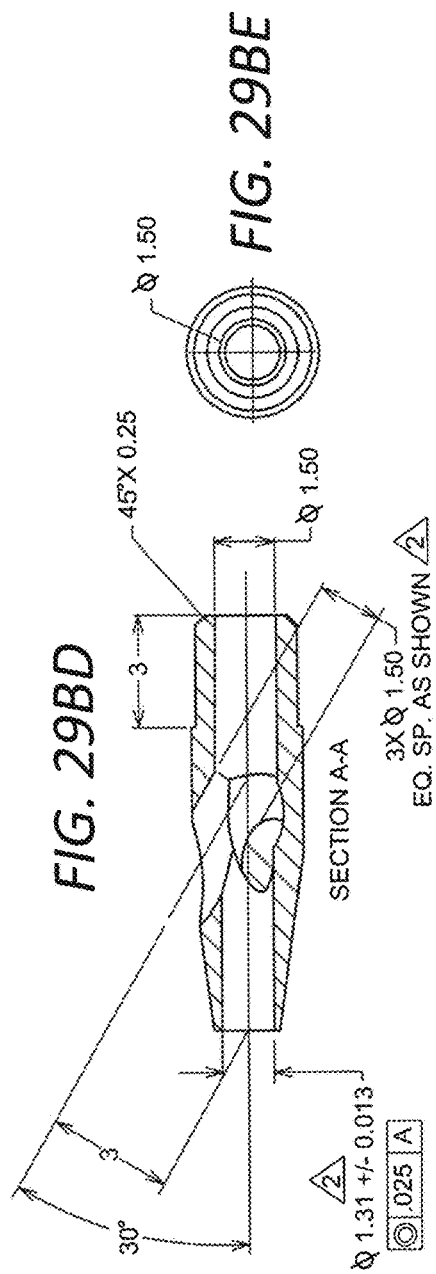
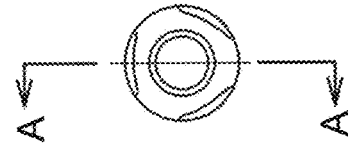

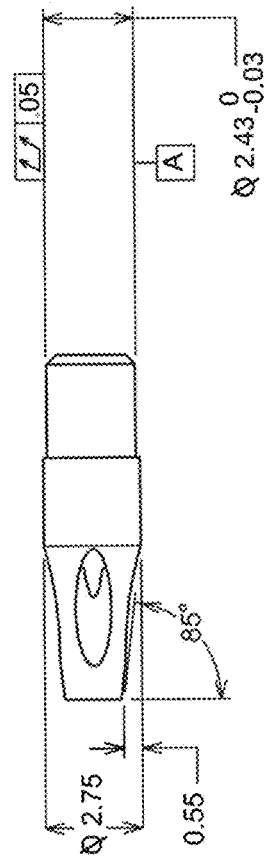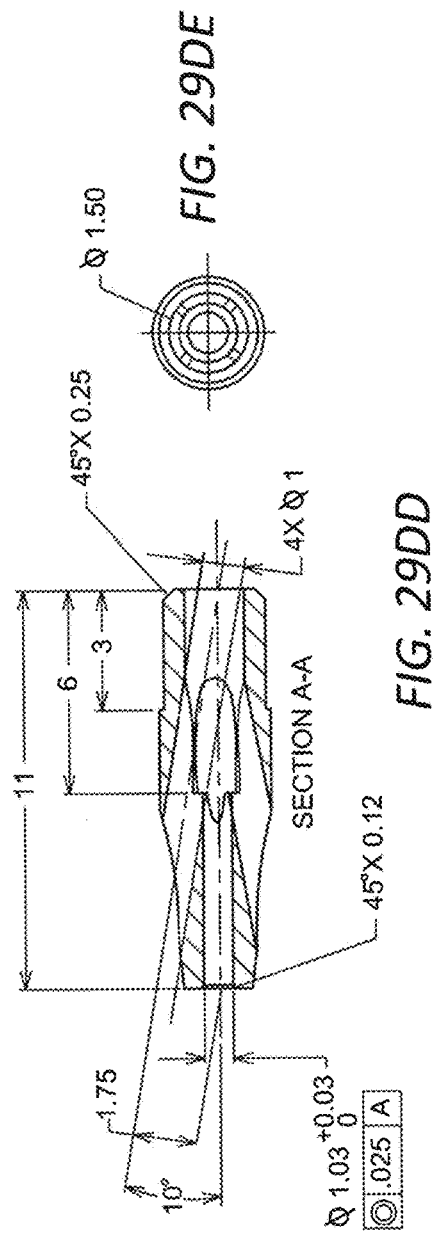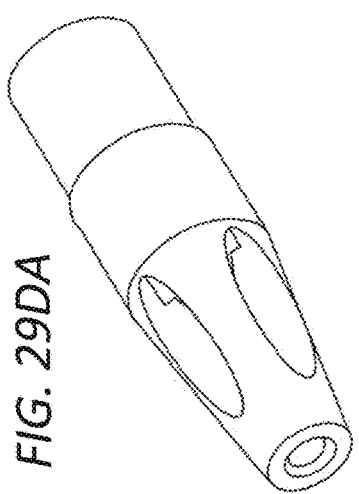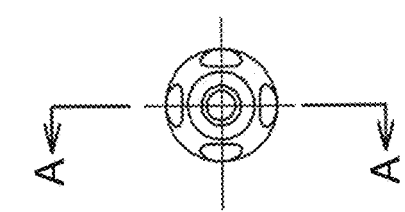

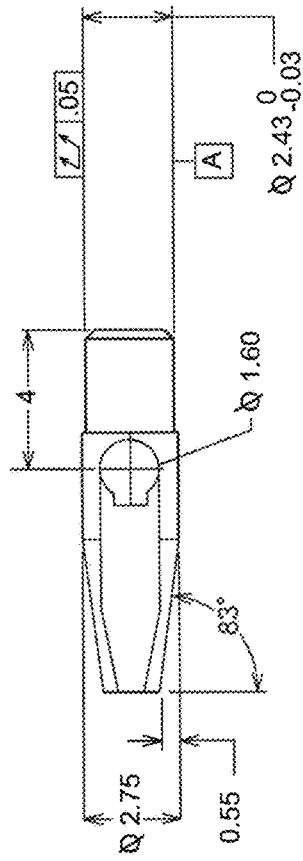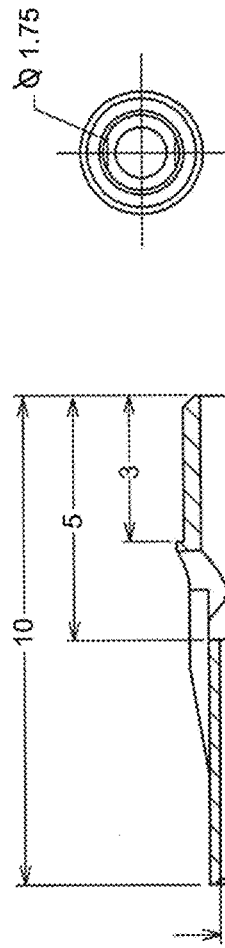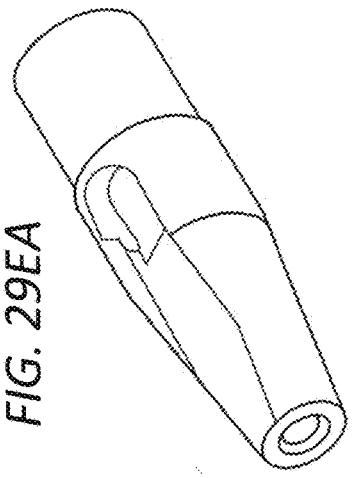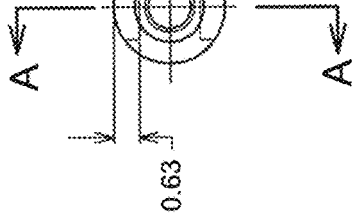
FIG. 29EB
FIG. 29EE
FIG. 29ED
FIG. 29EA
FIG. 29EC

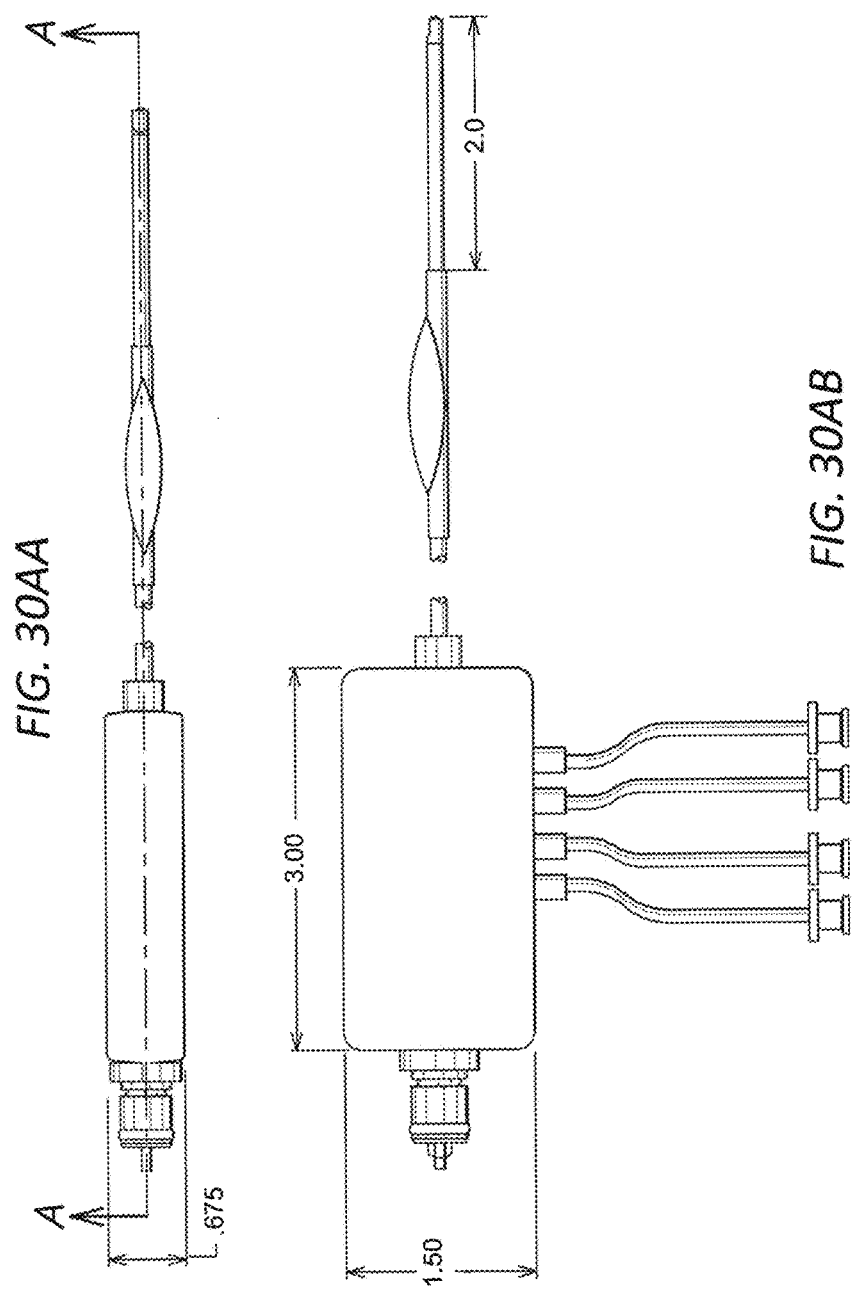

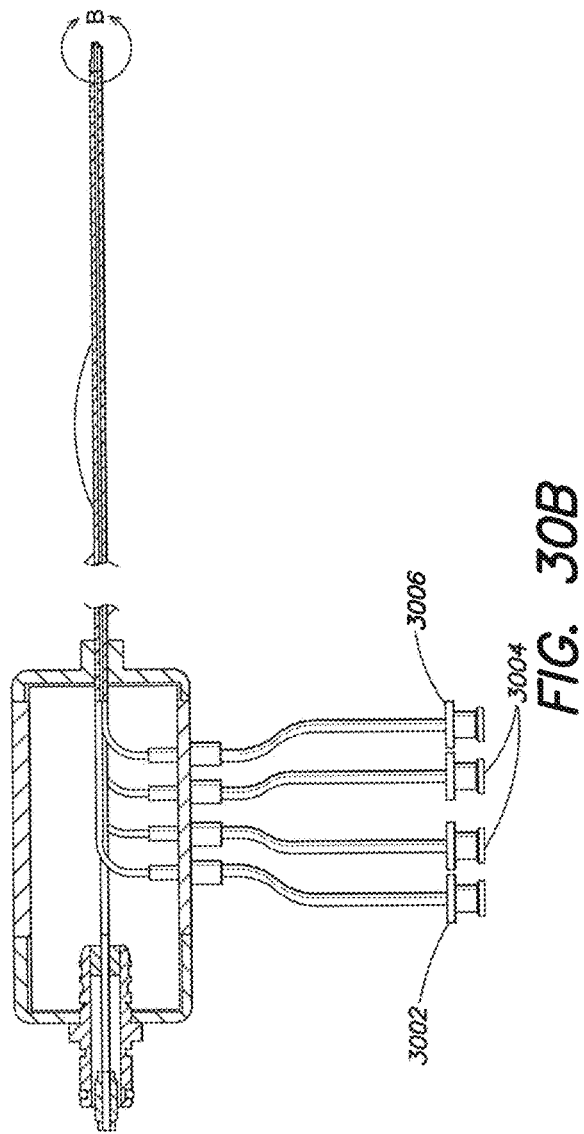
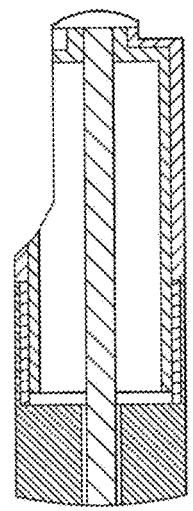
FIG. 30B
FIG. 30C

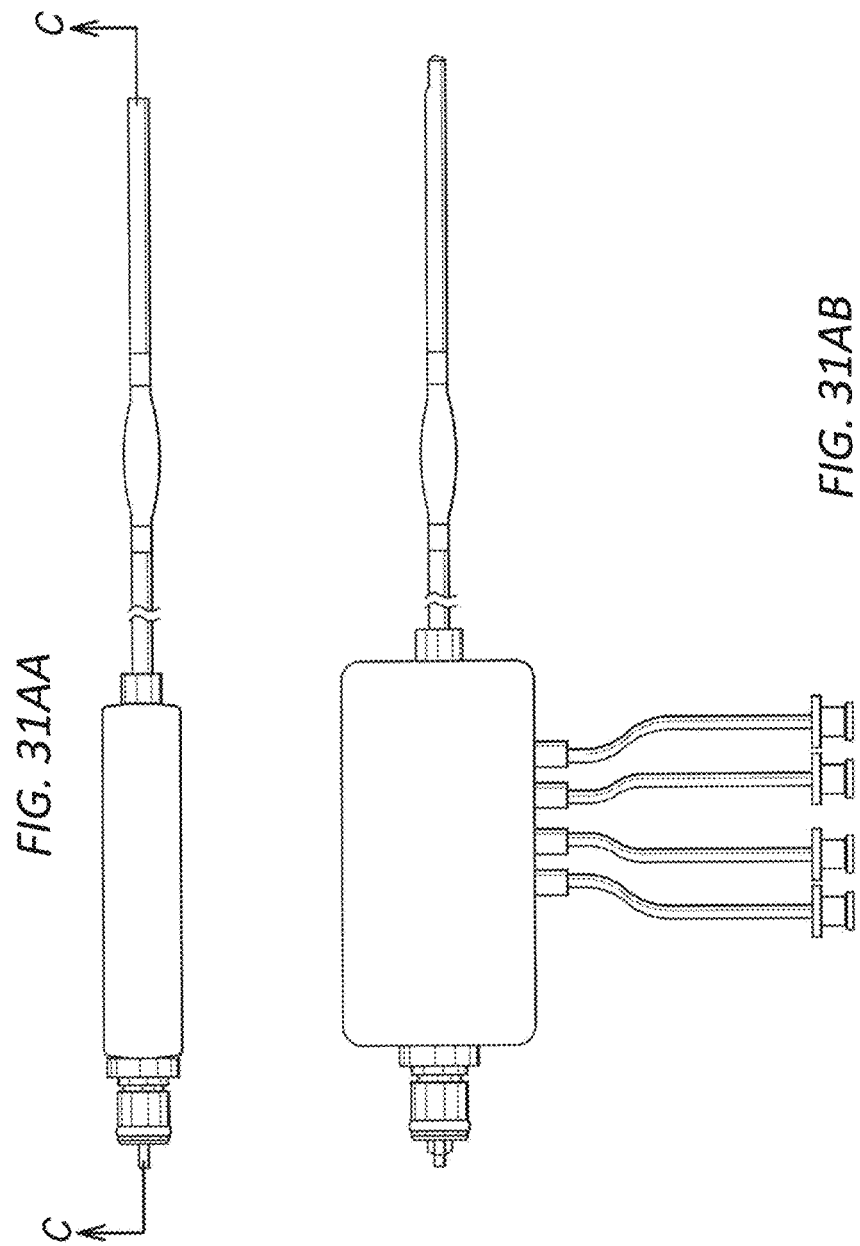

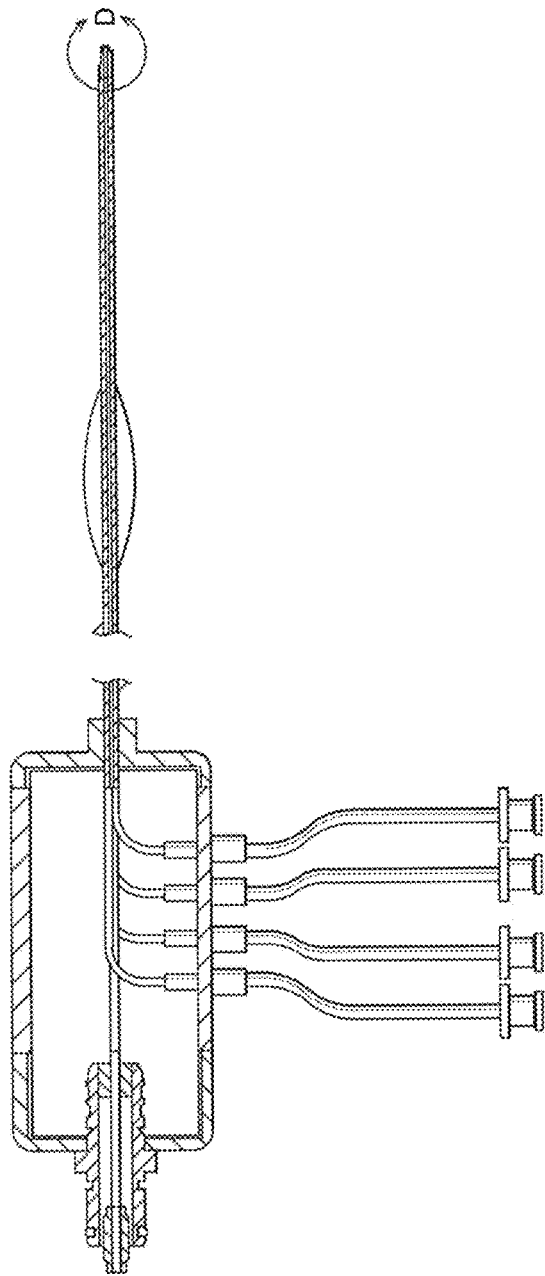
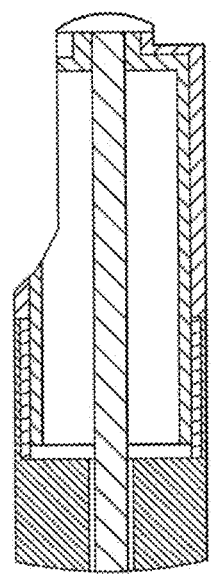
FIG. 31B
FIG. 31C

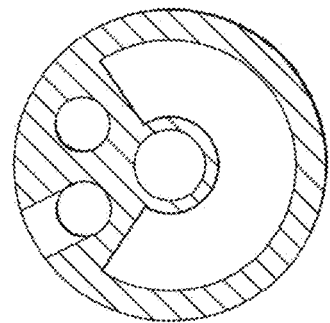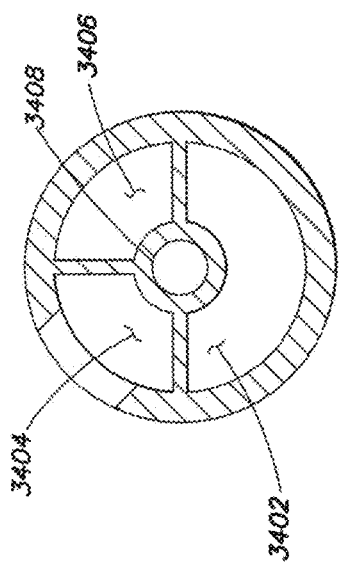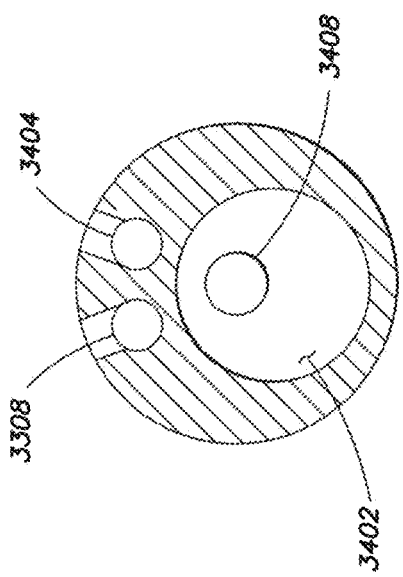

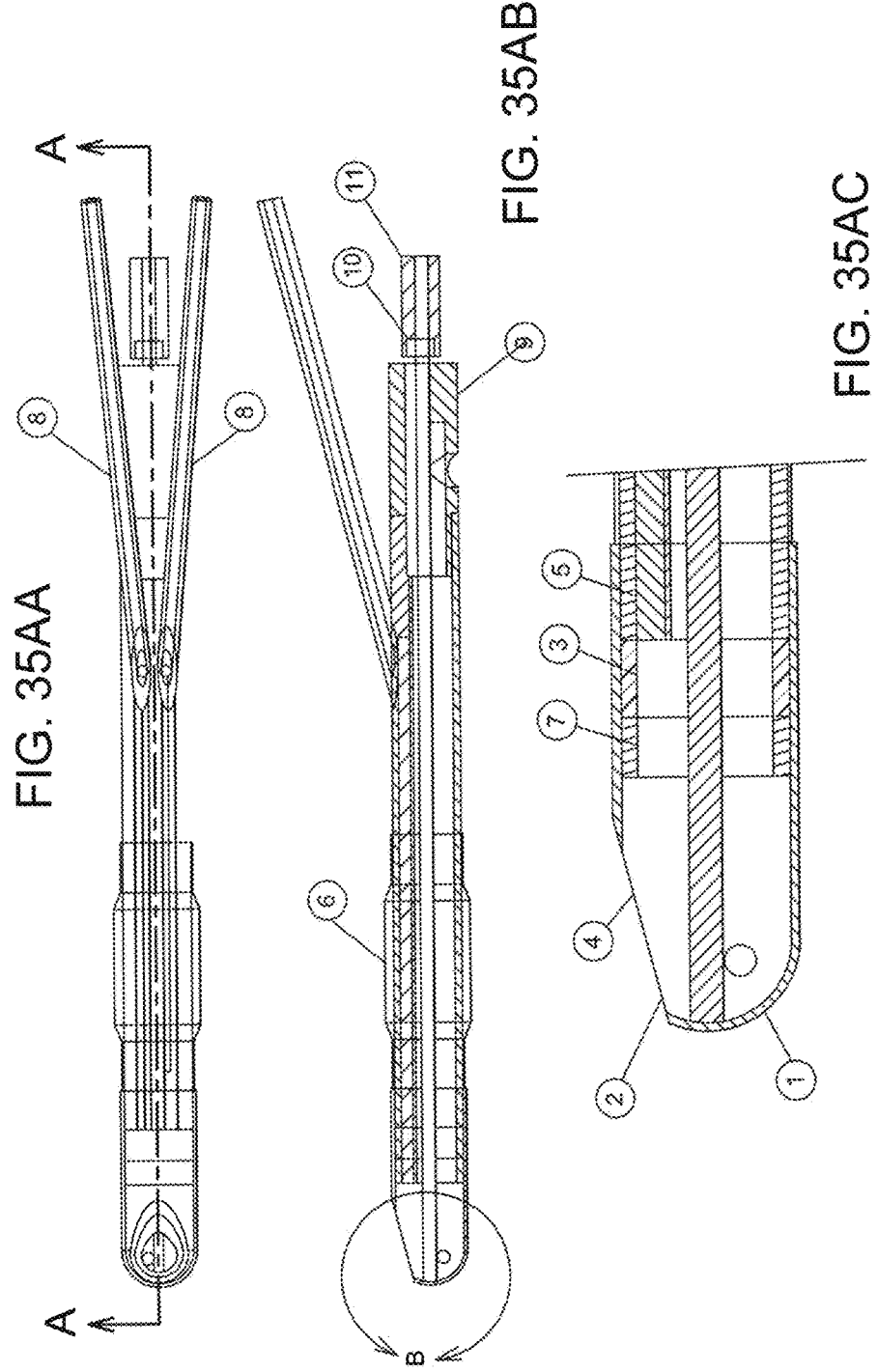

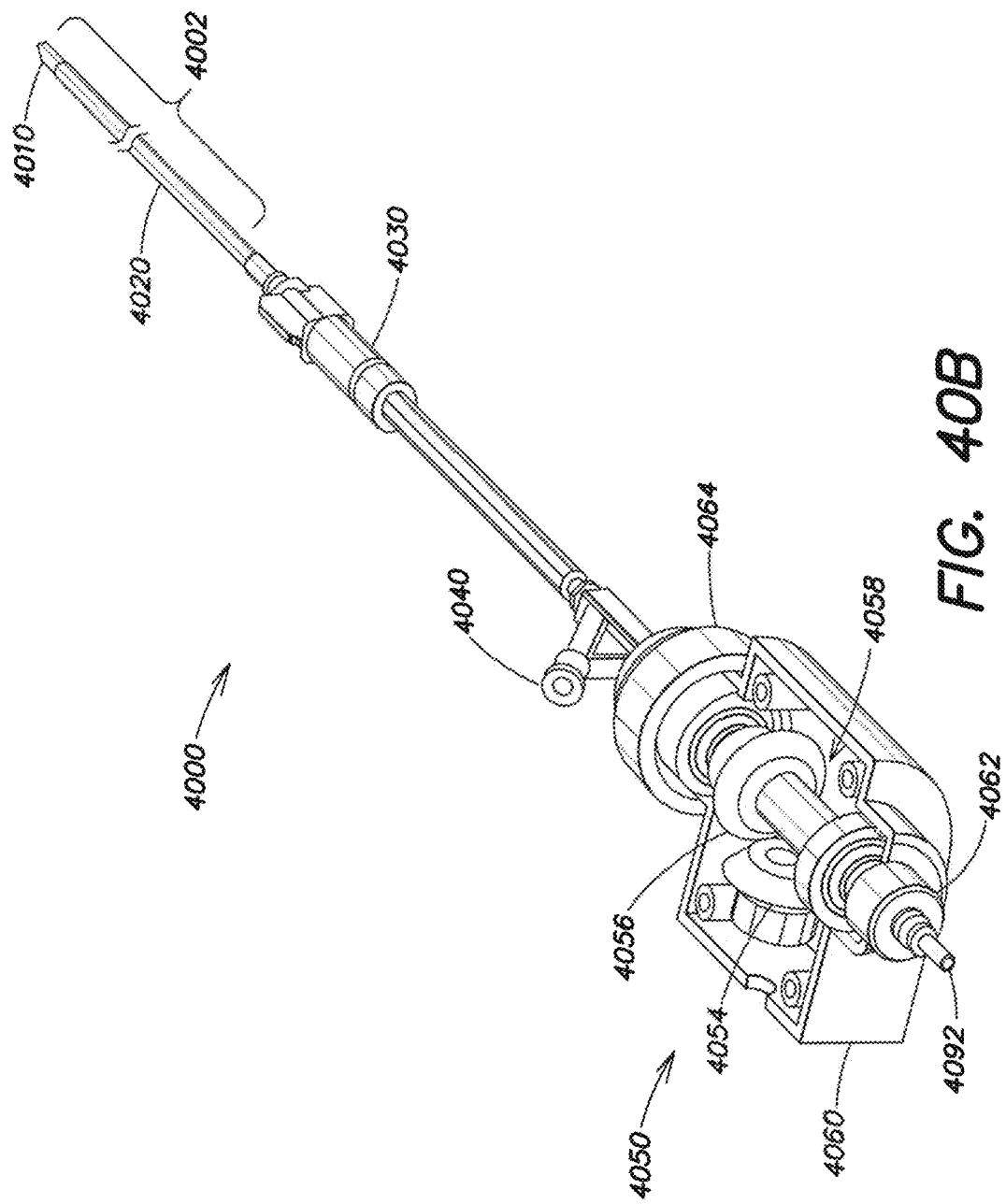

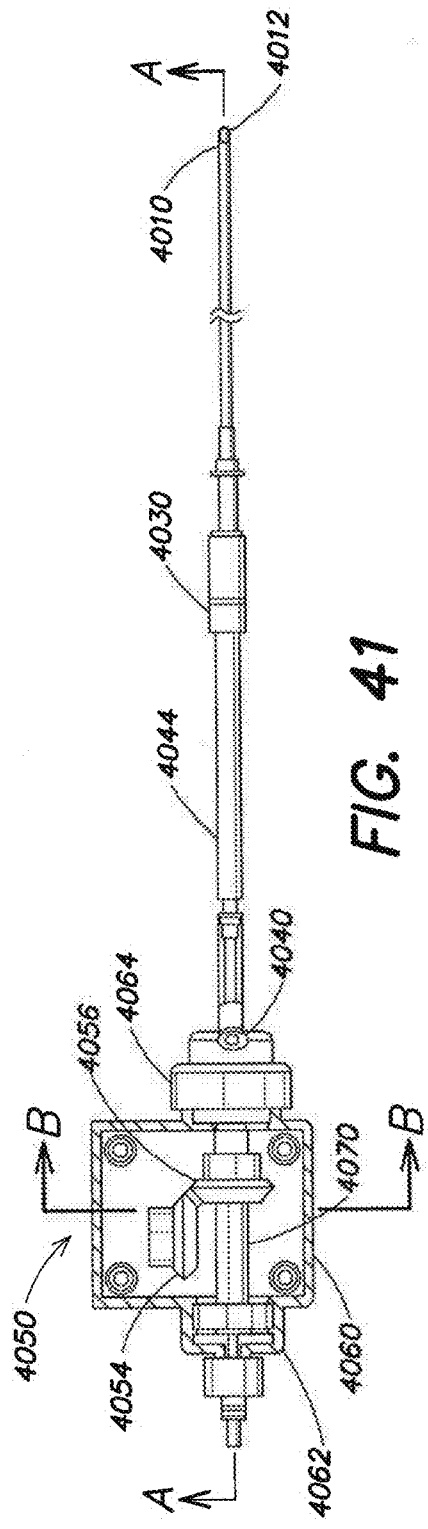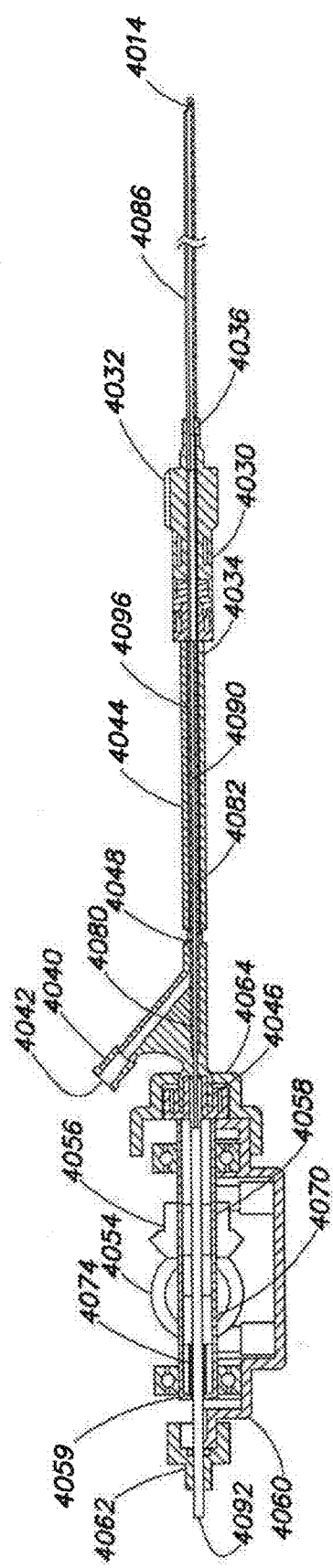
FIG. 41
FIG. 42

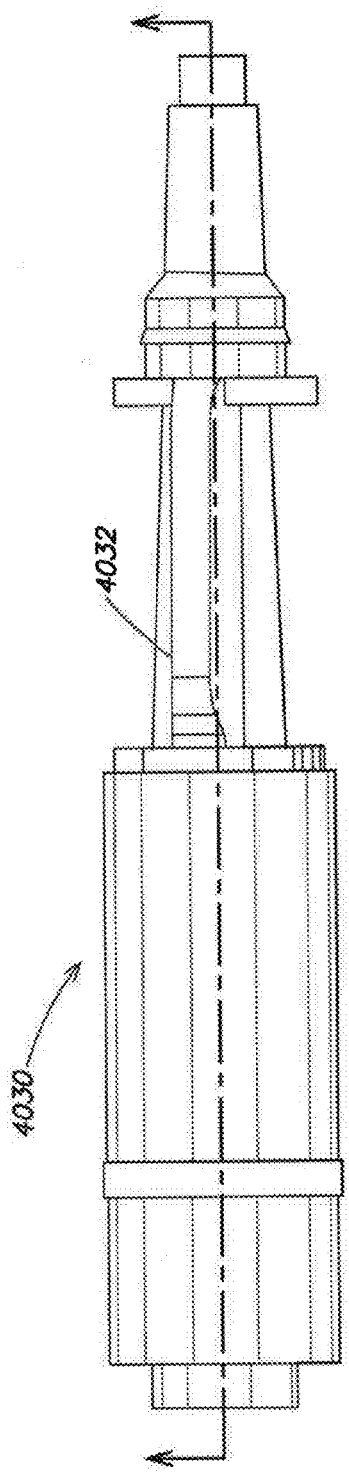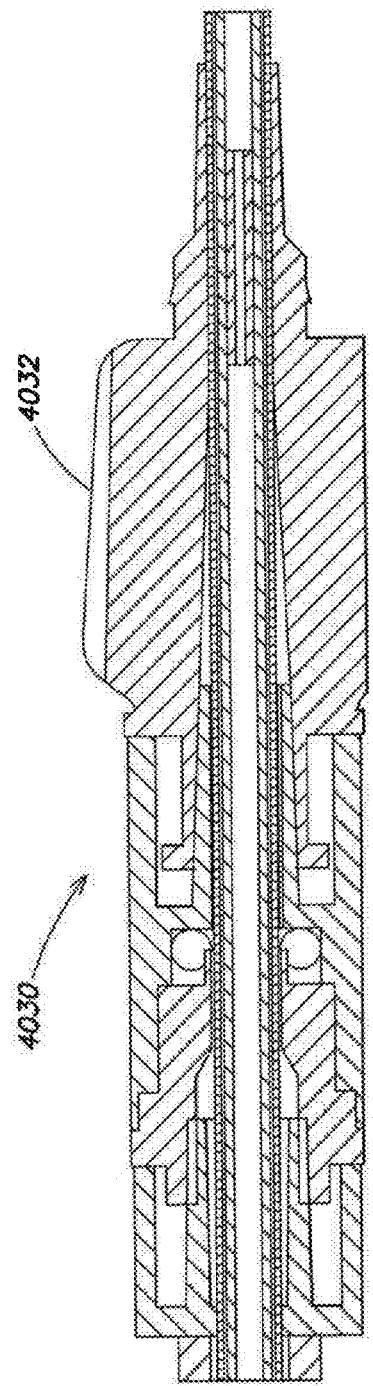

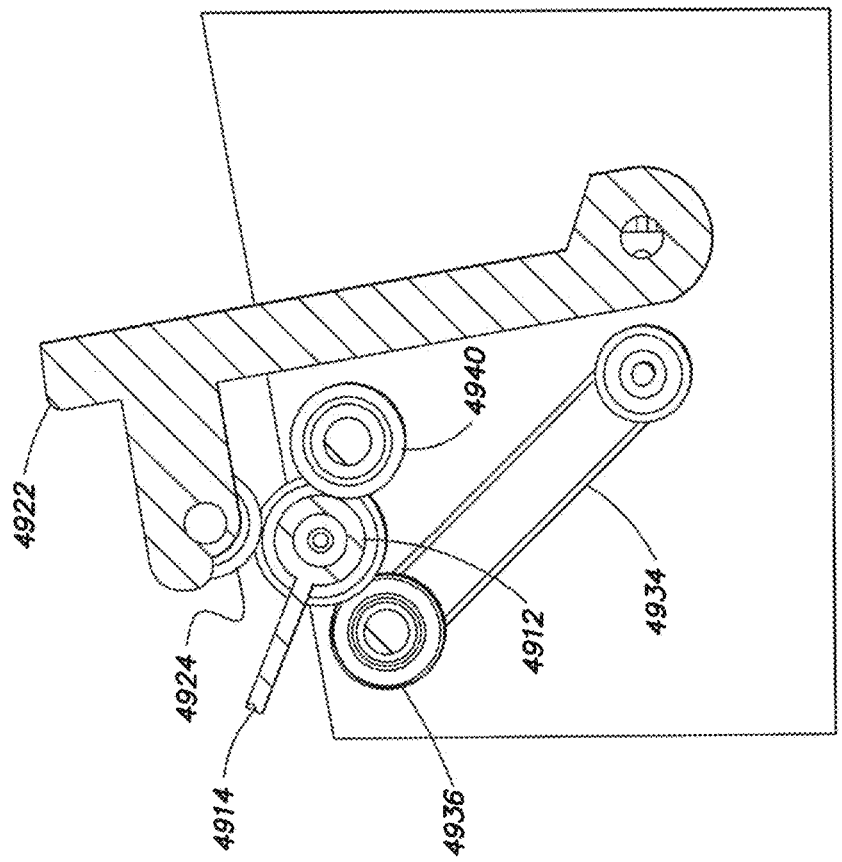
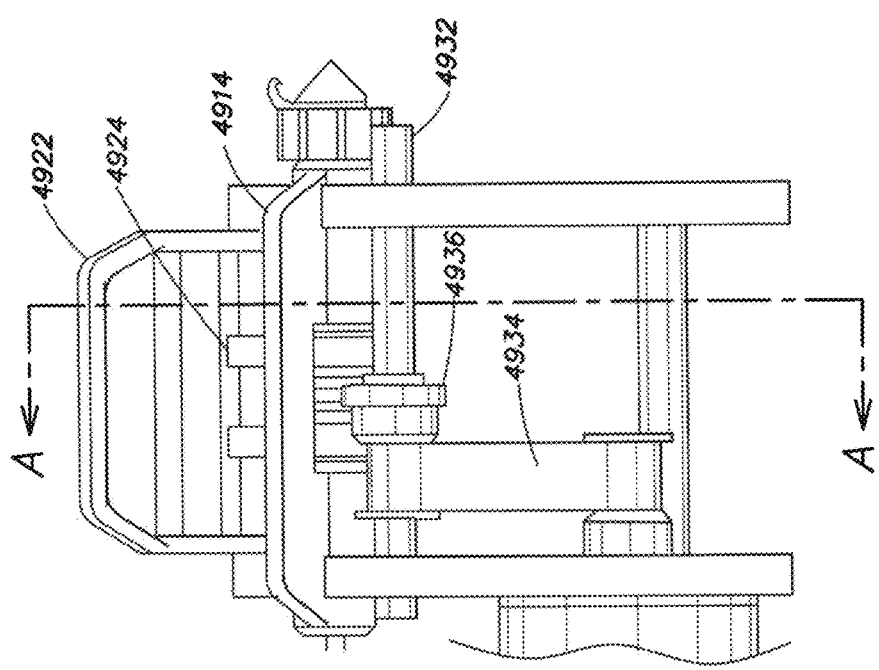
FIG. 50B
FIG. 50A

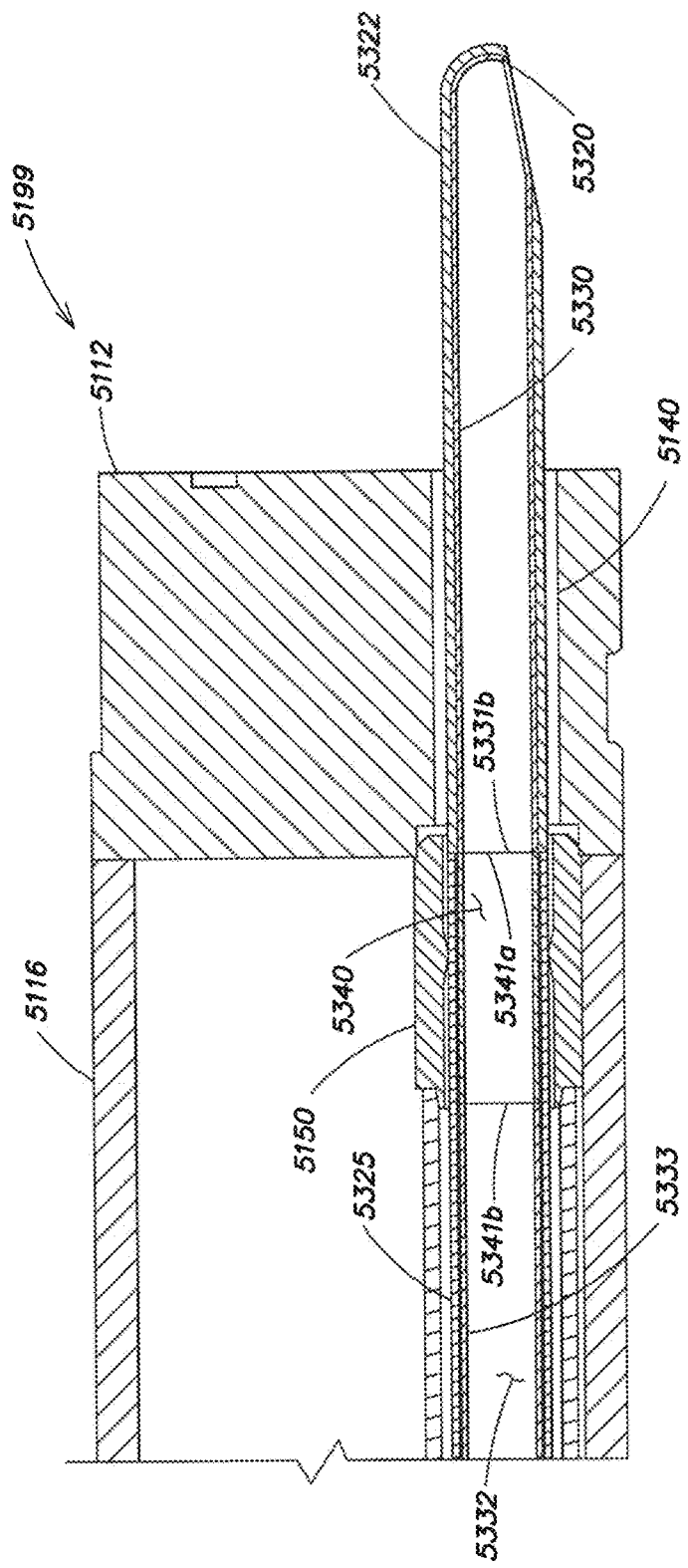

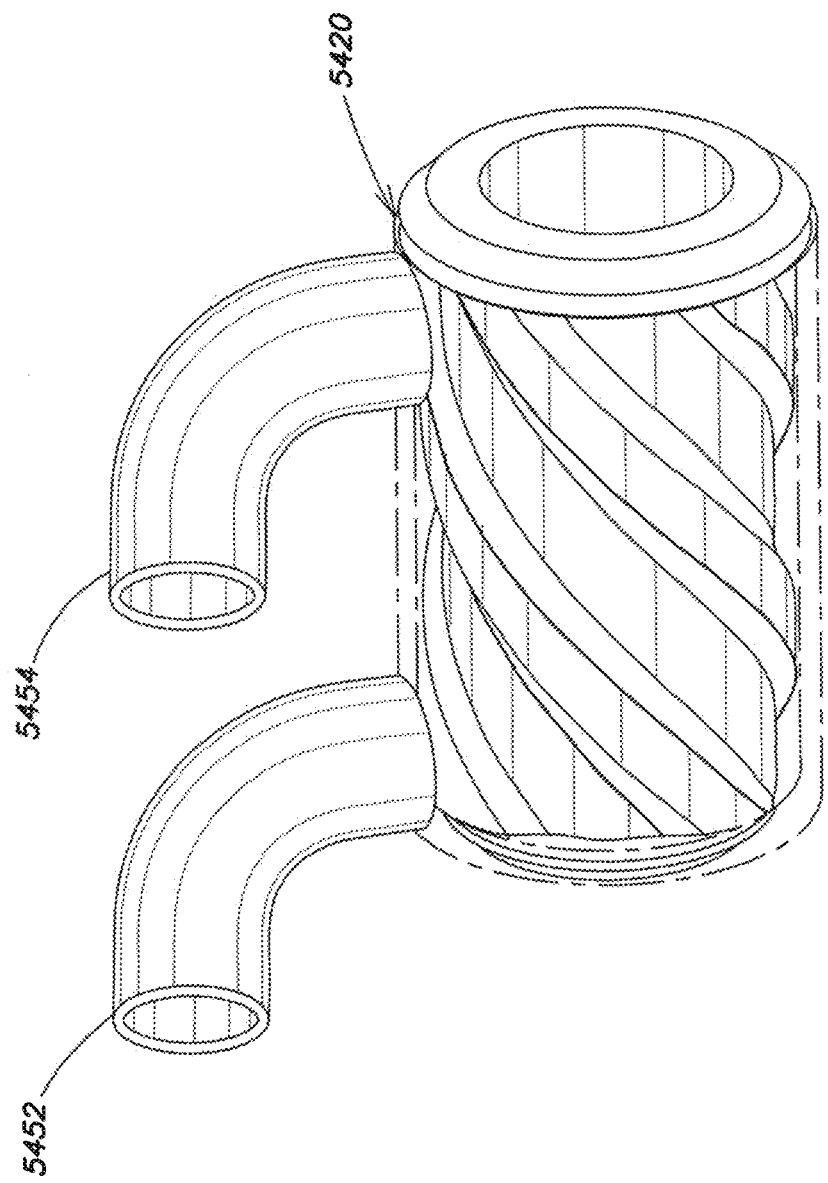

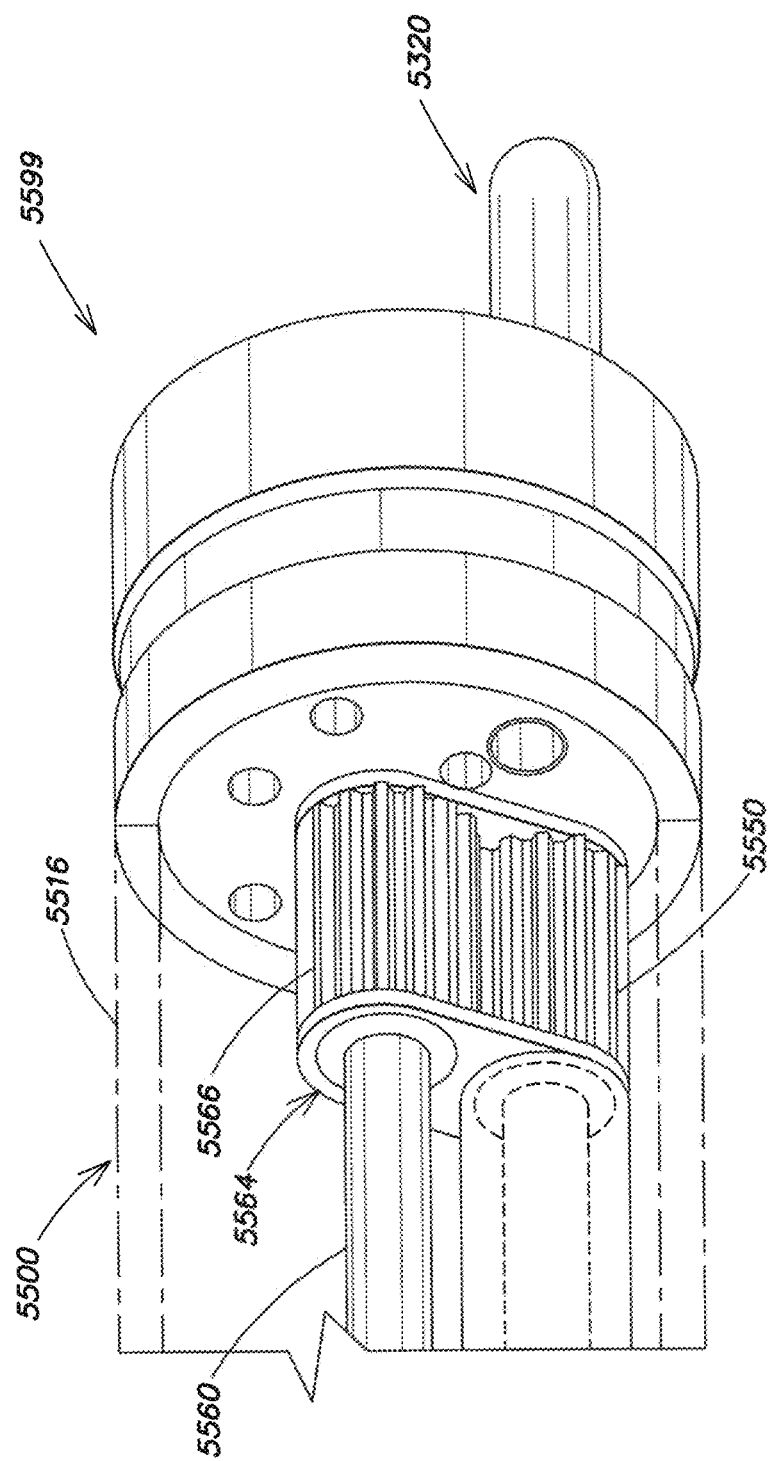

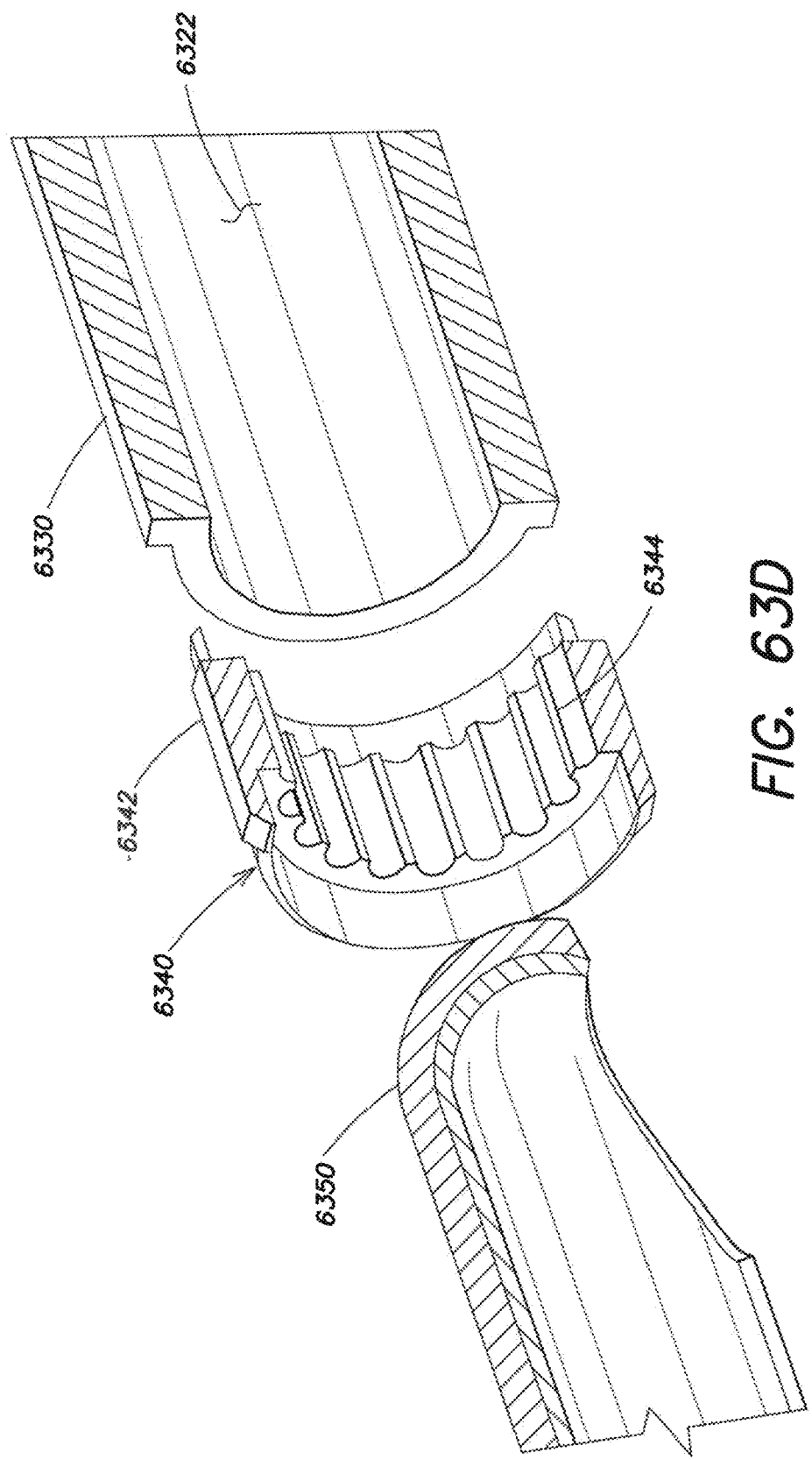

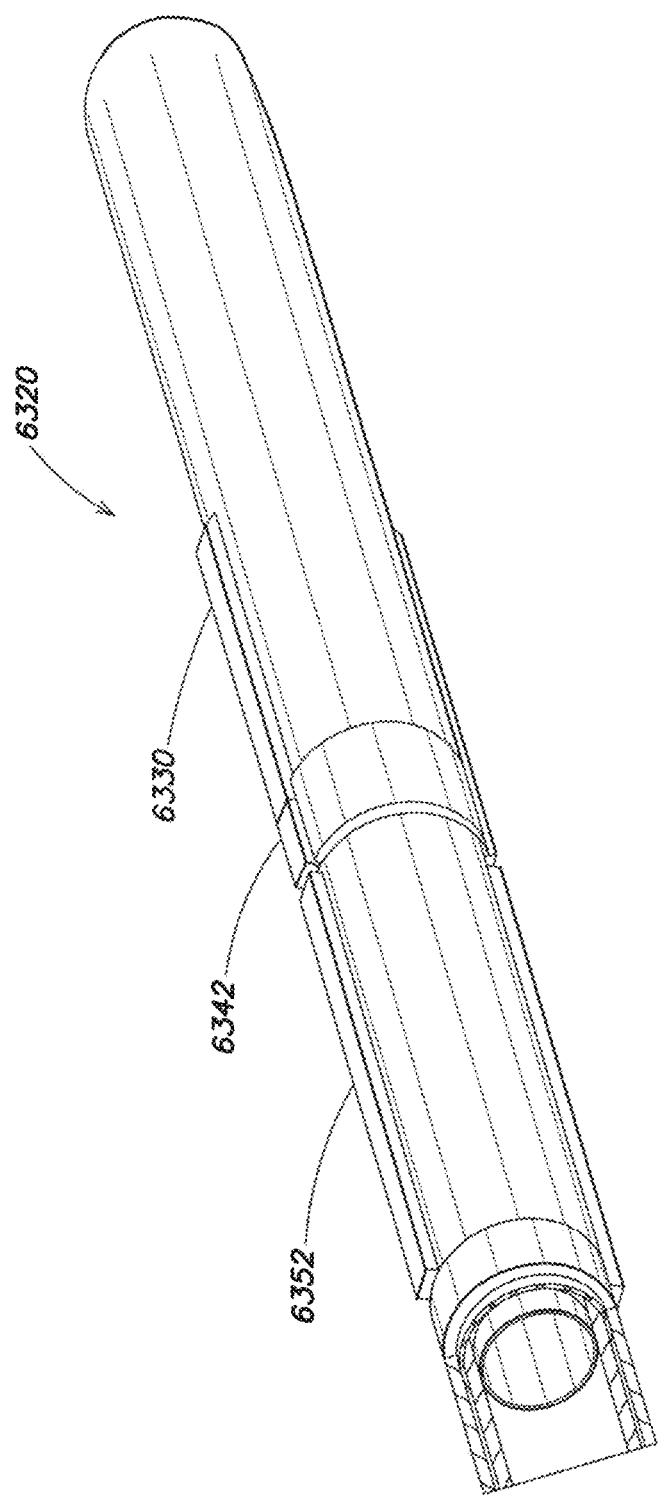

METHODS AND APPARATUS FOR REMOVING MATERIAL FROM WITHIN A MAMMALIAN CAVITY USING AN INSERTABLE ENDOSCOPIC INSTRUMENT

RELATED APPLICATIONS

This application is a continuation of and claims priority to U.S. application Ser. No. 14/501,957, entitled "Methods and Apparatus for Removing Material From Within a Mammalian Cavity Using an Insertable Endoscopic Instrument," filed on Sep. 30, 2014, which is a continuation in part and claims priority to U.S. application Ser. No. 14/280,202, entitled "Insertable Endoscopic Instrument for Tissue Removal," filed on May 16, 2014, which claims the benefit of and priority to U.S. Provisional Patent Application 61/824,760, entitled "Insertable Endoscopic Instrument for Tissue Removal," filed on May 17, 2013. U.S. application Ser. No. 14/280,202 is a continuation in part and claims priority to U.S. patent application Ser. No. 13/336,491, entitled "Endoscopic Tool for Debriding and Removing Polyps," filed on Dec. 23, 2011, which claims the benefit of and priority to U.S. Provisional Patent Application 61/566,472, entitled "Endoscopic Tool for Debriding and Removing Polyps," filed on Dec. 2, 2011. Each of these applications are incorporated herein by reference in their entirety for all purposes.

BACKGROUND

Colon cancer is the third leading cause of cancer in the United States but is the second leading cause of cancer-related deaths. Colon cancer arises from pre-existing colon polyps (adenomas) that occur in as many as 35% of the US population. Colon polyps can either be benign, precancerous or cancerous. Colonoscopy is widely regarded as an excellent screening tool for colon cancer that is increasing in incidence worldwide. According to the literature, a 1% increase in colonoscopy screening results in a 3% decrease in the incidence of colon cancer. The current demand for colonoscopy exceeds the ability of the medical system to provide adequate screening. Despite the increase in colon cancer screening the past few decades, only 55% of the eligible population is screened, falling far short of the recommended 80%, leaving millions of patients at risk.

Due to the lack of adequate resources, operators performing a colonoscopy typically only sample the largest polyps, exposing the patient to sample bias by typically leaving behind smaller less detectable polyps that could advance to colon cancer prior to future colonoscopy. Because of the sample bias, a negative result from the sampled polyps does not ensure the patient is truly cancer-free. Existing polyps removal techniques lack precision and are cumbersome and time consuming.

At present, colon polyps are removed using a snare that is introduced into the patient's body via a working channel defined within an endoscope. The tip of the snare is passed around the stalk of the polyp to cut the polyp from the colon wall. Once the cut has been made, the cut polyp lies on the intestinal wall of the patient until it is retrieved by the operator as a sample. To retrieve the sample, the snare is first removed from the endoscope and a biopsy forceps or suction is fed through the same channel of the endoscope to retrieve the sample.

Accordingly, there is a need for an improved endoscopic instrument that increases the precision and speed of polyp removal for biopsy.

SUMMARY

An improved endoscopic instrument is provided that can precisely remove sessile polyps and efficiently obtain samples of multiple polyps from a patient. In particular, the improved endoscopic instrument is capable of debriding one or more polyps and retrieving the debrided polyps without having to alternate between using a separate cutting tool and a separate sample retrieving tool. The sampling can be integrated with colonoscopy inspection. In some implementations, the endoscopic instrument can cut and remove tissue from within a patient. In some such implementations, the endoscopic instrument can cut and remove tissue substantially simultaneously from within a patient accessed through a flexible endoscope.

In one aspect, an endoscopic instrument insertable within a single instrument channel of an endoscope includes a power-driven instrument head configured to resect material at a site within a subject having been reached by a flexible endoscope with working channel. The power-driven instrument head has a first distal end and a first proximal end. The first distal end of the power-driven instrument head defines a material entry port through which the resected material can enter the flexible endoscopic instrument. A body is coupled to the first proximal end of the power-driven instrument head and configured to drive the power-driven instrument head. The body includes a flexible portion that has a second distal end and a second proximal end. The second proximal end of the flexible portion defines a material exit port. An aspiration channel extends from the material entry port of the power-driven instrument head to the material exit port of the flexible portion. The second proximal end of the flexible portion is configured to couple to a vacuum source such that the resected material entering the aspiration channel via the material entry port is removed from the aspiration channel at the material exit port while the endoscopic instrument is disposed within an instrument channel of a flexible endoscope.

In some implementations, the body further includes a powered actuator. The powered actuator is coupled to the first proximal end of the power-driven instrument head and configured to drive the power-driven instrument head. In some implementations, the powered actuator is one of a hydraulically powered actuator, a pneumatically powered actuator or an electrically powered actuator. In some implementations, the powered actuator includes at least one of an electric motor, a tesla rotor, and a vane rotor. In some implementations, the endoscopic instrument includes an energy storage component configured to power the powered actuator. In some implementations, the aspiration channel is defined by the power-driven instrument head, the powered actuator and the flexible portion.

In some implementations, the powered actuator is one of a hydraulically powered actuator or a pneumatically powered actuator. In some such implementations, the flexible portion includes a fluid inlet tubular member configured to supply irrigation to actuate the power actuator and a fluid outlet tubular member configured to remove the fluid being supplied to actuate the actuator. In some implementations, the flexible portion includes an aspiration tubular member that defines a proximal portion of the aspiration channel.

In some implementations, the powered actuator includes a hollow portion, the hollow portion fluidly coupling the material entry port of the power-driven instrument head and the material exit port of the flexible portion.

In some implementations, the instrument includes an engagement assembly configured to contact the walls of the instrument channel of the endoscope when actuated. In some implementations, the engagement assembly includes a compliant ring structure configured to be deformed.

In some implementations, the power-driven instrument head includes an outer structure and a cutting shaft disposed within the outer structure, the cutting shaft coupled to the powered actuator and configured to rotate relative to the outer structure when the powered actuator is actuated. In some implementations, the cutting shaft includes a hollow portion and the material entry port.

In some implementations, the flexible portion includes a hollow flexible torque cable. The flexible torque cable has a distal region configured to couple to the first proximal end of the power-driven instrument head and has a proximal region configured to couple to a powered actuator. In some implementations, the flexible torque cable defines a portion of the aspiration channel. The distal region of the flexible torque cable is fluidly coupled to the material entry port of the power-driven instrument head and the proximal region of the flexible torque cable includes the material exit port.

In some implementations, the instrument has an outer diameter that is less than about 5 mm. In some implementations, the flexible portion is at least 40 times as long as the power-driven instrument head. In some implementations, the outer diameter of the powered actuator is less than about 4 mm.

According to another aspect, an endoscopic instrument includes a power-driven instrument head configured to resect material at a site within a subject. The power-driven instrument head includes a cutting tip and a material entry port configured to allow material to enter a distal end of the endoscopic instrument. A body is coupled to the power-driven instrument head. The body includes an elongated hollow flexible tubular member that includes a material exit port configured to allow material to exit a proximal end of the endoscopic instrument. An aspiration channel extends from the material entry port of the power-driven instrument head to a material exit port of the elongated hollow flexible tubular member. The second proximal end of the flexible portion is configured to fluidly couple to a vacuum source such that the resected material that enters the aspiration channel via the material entry port of the power-driven instrument head is removed from the endoscopic instrument via the material exit port. The endoscopic instrument is configured to travel through a tortuous instrument channel of an endoscope. In some implementations, the instrument has an outer diameter that is less than about 5 mm and wherein the flexible tubular member is at least 72 inches long.

In some implementations, the body further comprises a powered actuator, the powered actuator coupled to the first proximal end of the power-driven instrument head and configured to drive the power-driven instrument head. In some implementations, the powered actuator is an electrically powered actuator and further comprising an electrically conducting wire configured to couple to a power source. In some implementations, the aspiration channel is defined by the power-driven instrument head, the powered actuator and the flexible portion. In some implementations, the flexible tubular member defines a proximal portion of the aspiration channel.

In some implementations, the powered actuator is one of a hydraulically powered actuator or a pneumatically powered actuator, and further includes a fluid inlet tubular member configured to supply fluid to actuate the power actuator and a fluid outlet tubular member configured to remove the fluid being supplied to actuate the actuator.

In some implementations, the instrument includes an engagement assembly configured to contact the walls of the instrument channel of the endoscope when actuated. In some implementations, the engagement assembly includes a vacuum actuated structure configured to move into an engaged position in which the vacuum actuated structure is not in contact with the instrument channel when the vacuum is actuated and configured to move into a retracted position in which the vacuum actuated structure is not in contact with the instrument channel when the vacuum is not actuated.

In some implementations, the power-driven instrument head includes an outer structure and a cutting shaft disposed within the outer structure, the cutting shaft coupled to the powered actuator and configured to rotate relative to the outer structure when the powered actuator is actuated.

In some implementations, the flexible tubular member includes a hollow flexible torque cable. The flexible torque cable has a distal region configured to couple to the first proximal end of the power-driven instrument head and has a proximal region configured to couple to a powered actuator located external to the endoscopic instrument. In some implementations, the flexible torque cable further defines a portion of the aspiration channel, wherein the distal region of the flexible torque cable is fluidly coupled to the material entry port of the power-driven instrument head and the proximal region of the flexible torque cable includes the material exit port. In some implementations, the instrument includes a sheath surrounding the flexible torque cable.

According to another aspect, a flexible endoscopic biopsy retrieval tool adapted for use with an endoscope includes a housing, a debriding component coupled to the housing, and a sample retrieval conduit disposed within the housing for retrieving debrided material that is debrided by the debriding component. In various embodiments, an improved flexible endoscope may be configured with an integrated endoscopic biopsy retrieval tool that includes a debriding component and a sample retrieval conduit for retrieving debrided material that is debrided by the debriding component.

According to another aspect, a method of retrieving polyps from a patient's body includes disposing an endoscopic instrument within an instrument channel of an endoscope, inserting the endoscope in a patient's body, actuating a debriding component of the endoscopic instrument to cut a polyp within the patient's body, and actuating a sample retrieval component of the endoscopic instrument to remove the cut polyp from within the patient's body.

According to yet another aspect, an endoscope includes a first end and a second end separated by a flexible housing. An instrument channel extends from the first end to the second end and an endoscopic instrument is coupled to the instrument channel at the first end of the endoscope. The endoscopic instrument includes a debriding component and a sample retrieval conduit partially disposed within the instrument channel.

According to yet another aspect, an endoscopic instrument is insertable within a single instrument channel of an endoscope includes a cutting assembly that is configured to resect material at a site within a subject. The cutting assembly includes an outer cannula and an inner cannula disposed within the outer cannula. The outer cannula defines an opening through which material to be resected enters the cutting assembly. The endoscopic instrument also includes a flexible outer tubing coupled to the outer cannula. The flexible outer tubing is configured to cause the outer cannula to rotate relative to the inner cannula. The flexible outer tubing can have an outer diameter that is smaller than the instrument channel in which the endoscopic instrument is insertable. The endoscopic instrument also includes a flexible torque coil having a portion disposed within the flexible outer tubing. The flexible torque coil having a distal end coupled to the inner cannula. The flexible torque coil is configured to cause the inner cannula to rotate relative to the outer cannula. The endoscopic instrument also includes a proximal connector coupled to a proximal end of the flexible torque coil and configured to engage with a drive assembly that is configured to cause the proximal connector, the flexible torque coil and the inner cannula to rotate upon actuation. The endoscopic instrument also includes an aspiration channel having an aspiration port configured to engage with a vacuum source. The aspiration channel is partially defined by an inner wall of the flexible torque coil and an inner wall of the inner cannula and extends from an opening defined in the inner cannula to the aspiration port. The endoscopic instrument also includes an irrigation channel having a first portion defined between an outer wall of the flexible torque coil and an inner wall of the flexible outer tubing and configured to carry irrigation fluid to the aspiration channel.

In some implementations, the proximal connector is hollow and an inner wall of the proximal connector defines a portion of the aspiration channel. In some implementations, the proximal connector is a rigid cylindrical structure and is configured to be positioned within a drive receptacle of the drive assembly. The proximal connector can include a coupler configured to engage with the drive assembly and a tensioning spring configured to bias the inner cannula towards a distal end of the outer cannula. In some implementations, the tensioning spring is sized and biased such that the tensioning spring causes a cutting portion of the inner cannula to be positioned adjacent to the opening of the outer cannula. In some implementations, the proximal connector is rotationally and fluidly coupled to the flexible torque coil.

In some implementations, the endoscopic instrument also includes a lavage connector including an irrigation entry port and a tubular member coupled to the lavage connector and the flexible outer tubing. An inner wall of the tubular member and the outer wall of the flexible torque coil can define a second portion of the irrigation channel that is fluidly coupled to the first portion of the irrigation channel. In some implementations, the endoscopic instrument also includes a rotational coupler coupling the flexible outer tubing to the tubular member and configured to cause the flexible outer tubing to rotate relative to the tubular member and cause the opening defined in the outer cannula to rotate relative to the inner cannula. In some implementations, the lavage connector defines an inner bore within which the flexible torque coil is disposed.

In some implementations, the endoscopic instrument also includes a lining within which the flexible torque coil is disposed, the outer wall of the lining configured to define a portion of the irrigation channel. In some implementations, the inner cannula is configured to rotate axially relative to the outer cannula and the aspiration channel is configured to provide a suction force at the opening of the inner cannula.

In some implementations, the flexible torque coil includes a plurality of threads. Each of the plurality of threads can be wound in a direction opposite to a direction in which one or more adjacent threads of the plurality of threads is wound. In some implementations, the flexible torque coil includes a plurality of layers. Each of the plurality of layers can be wound in a direction opposite to a direction in which one or more adjacent layers of the plurality of layers is wound. In some implementations, each layer can include one or more threads.

In some implementations, the flexible outer tubing has a length that exceeds the length of the endoscope in which the endoscopic instrument is insertable. In some implementations, the flexible outer tubing has a length that is at least 100 times larger than an outer diameter of the flexible outer tubing. In some implementations, the flexible portion is at least 40 times as long as the cutting assembly.

According to another aspect, an endoscopic assembly includes a flexible endoscopic instrument including a cutting assembly configured to resect material at a site within a subject, the cutting assembly including an outer cannula and an inner cannula disposed within the outer cannula, the outer cannula defining an opening through which material to be resected enters the cutting assembly. A flexible outer tubing is coupled to the outer cannula and is configured to cause the outer cannula to rotate relative to the inner cannula, the flexible outer tubing having an outer diameter that is smaller than the instrument channel in which the flexible endoscopic instrument is insertable. An aspiration tube has a portion disposed within the flexible outer tubing. The aspiration tube has a distal end coupled to the inner cannula, the aspiration tube defining a portion of an aspiration channel through which the material resected by the cutting assembly is removed. The aspiration channel is partially defined by an inner wall of the aspiration channel and an inner wall of the inner cannula and extending from an opening defined in the inner cannula to a proximal end of the aspiration tube. An irrigation channel having a first portion defined between an outer wall of the aspiration tube and an inner wall of the flexible outer tubing and configured to carry irrigation fluid to the aspiration channel. The endoscopic assembly also includes an endoscope within which the flexible endoscopic instrument is insertable. The endoscope includes an elongated tubular body having a distal end and a proximal end, the distal end sized to be inserted within a mammalian cavity of a patient and including a camera configured to capture images of the mammalian cavity. The distal end extends a predetermined length from a distal tip that is at least less than half of a length of the elongated tubular body. An instrument channel extending between a first opening at the distal end and a second opening at the proximal end. The instrument channel sized and configured to receive a removable surgical cutting assembly that includes an aspiration channel configured to fluidly couple, at a proximal end of the surgical cutting assembly, to a suction source to remove material entering the endoscope via a distal end of the surgical cutting assembly. A torque generation component configured to generate torque and positioned within the distal end, the torque generation component configured to provide the generated torque to a coupling component responsive to actuation of the torque generation component. The coupling component is positioned at the distal end of the elongated tubular member, the coupling component configured to actuate a cutting component of the surgical cutting assembly responsive to actuation of the torque generation component.

According to another aspect, an endoscope for removing tissue at a surgical site, includes an elongated tubular body having a distal end and a proximal end. The distal end is insertable within a mammalian cavity of a patient. The proximal end configured to remain outside the mammalian cavity of the patient. An instrument channel extends between a first opening at the distal end and a second opening at the proximal end, the instrument channel sized and configured to receive a removable surgical cutting assembly that includes an aspiration channel configured to fluidly couple, at a proximal end of the surgical cutting assembly, to a suction source to remove material entering the endoscope via a distal end of the surgical cutting assembly. A torque generation component configured to generate torque and positioned within the distal end, the torque generation component configured to provide the generated torque to a coupling component responsive to actuation of the torque generation component. The coupling component is positioned at the distal end of the elongated tubular member. The coupling component configured to actuate a cutting component of the surgical cutting assembly responsive to actuation of the torque generation component.

In some implementations, a length of the coupling component is sized to allow the endoscope to be inserted within a mammalian cavity of the patient.

In some implementations, the coupling component includes a magnetic coupler, the magnetic coupler having a magnetic force sufficient to magnetically couple with a magnetic coupling component of the surgical cutting assembly to cause the magnetic coupler of the surgical cutting assembly to rotate relative the first portion of the surgical cutting assembly. In some implementations, the inner diameter of the magnetic coupler is sized to exceed a diameter of the instrument channel. In some implementations, the outer wall of the magnetic coupler includes frictional elements configured to rotatably engage with the torque generation component. In some implementations, the torque generation component includes an electrical rotary actuator, the endoscope further comprising an electrical wire configured to deliver current to the electrical rotary actuator. In some implementations, the magnetic coupler forms a rotatable portion of the torque generation component. In some implementations, the torque generation component is one of a hydraulic driven rotary actuator or a pneumatic driven rotary actuator; and the endoscope further includes a fluid delivery channel configured to deliver fluid to the torque generation component and a fluid removal channel configured to remove the fluid from the torque generation component.

In some implementations, the torque generation component is configured to rotate an inner cannula of the surgical cutting assembly relative to an outer cannula of the surgical cutting assembly.

In some implementations, the torque generation component is configured to couple to a linear motion assembly that converts the torque generated by the torque generation component to linear motion. In some implementations, the torque generation component is configured to rotate in a first direction to cause the coupling component to move from a first position to a second position in a direction from the proximal end to the distal end and to rotate in a second direction to cause the coupling component to move from the second position to the first position, wherein the torque generation component is configured to alternate between rotating in the first direction and the second direction to cause an inner cannula of the surgical cutting assembly to reciprocate between a first open position in which a distal tip of the inner cannula is a first predetermined distance away from a distal tip of an outer cannula of the surgical cutting assembly and a second closed position in which the distal tip of the inner cannula is less than a second predetermined distance away from the distal tip of the outer cannula, wherein the second predetermined distance is less than the first predetermined distance.

In some implementations, the instrument channel is defined to receive the surgical cutting assembly via the second opening at the proximal end of the instrument channel. In some implementations, the instrument channel is configured to include at least one groove configured to engage with a corresponding key of the surgical cutting assembly to ensure that an orientation of an opening of an outer cannula of the surgical cutting assembly is aligned with respect to a camera of the endoscope.

In some implementations, the coupling component is a magnetic coupler that magnetically couples to a coupling member attached to an inner cannula of the surgical cutting assembly such that the coupling component transfers the torque generated by the torque generation component to the inner cannula of the surgical cutting assembly via the coupling member attached to the inner cannula.

In some implementations, the endoscope includes an articulation assembly configured to engage an outer cannula of the surgical cutting assembly, the articulation assembly configured to cause the outer cannula to rotate relative to the inner cannula. In some implementations, the articulation assembly is configured to rotate the outer cannula between a plurality of predetermined positions.

In some implementations, the endoscope includes a deployment component configured to be actuated by an actuator, the deployment component configured to maintain the surgical cutting assembly disposed within the tubular body in a first undeployed position and configured to deploy the surgical cutting assembly from the first undeployed position to a second deployed position upon actuation of the deployment component. In some implementations, the deployment component is configured to move between a closed state in which the surgical cutting assembly is maintained in the first undeployed position and an opened state in which the surgical cutting assembly is deployed to the second deployed position. In some implementations, when the surgical cutting assembly is in the second deployed position, an outer cannula of the surgical cutting assembly extending outwardly along a longitudinal axis of the endoscope from the distal end of the endoscope and having a cutting window that is positioned at a distance away from a camera of the endoscope that allows the cutting window to be viewed in an image captured by the camera.

In some implementations, the endoscope includes an actuation console that includes at least one actuator to actuate the torque generation component. In some implementations, the coupling component has an inner wall through which a longitudinal axis of the instrument channel extends and within which a portion of the instrument channel is disposed.

In some implementations, the torque generation component and the coupling component are disposed within a region of the distal end of the endoscope that extends between the distal tip of the elongated tubular body and a portion of the elongated tubular body within which the steerable assembly is disposed.

In some implementations, the endoscope can include an irrigation channel extending from the proximal end to an opening defined within a wall of the tubular body that defines the instrument channel. The irrigation channel is configured to fluidly connect to an irrigation pathway defined within the surgical cutter assembly. The surgical cutting assembly can be configured to allow irrigation fluid entering the proximal end of the endoscope to flow into the irrigation pathway defined between an outer cannula and an inner cannula of the surgical cutter assembly when the surgical cutter assembly is inserted within the instrument channel of the endoscope.

According to another aspect, an endoscope for removing tissue at a surgical site includes an elongated tubular body having a distal end and a proximal end. The distal end sized to be inserted within a mammalian cavity of a patient. The distal end extends from a distal tip of the elongated tubular body to a portion of the elongated tubular body within which the steerable assembly is disposed. The endoscope includes an instrument channel extends between a first opening at the distal end and a second opening at the proximal end, the instrument channel sized and configured to receive a removable surgical cutting assembly that includes an aspiration channel configured to fluidly couple, at a proximal end of the surgical cutting assembly, to a suction source to remove material entering the endoscope via a distal end of the surgical cutting assembly. The endoscope includes a torque generation component configured to generate torque and positioned within the distal end. The torque generation component configured to provide the generated torque to a coupling component responsive to actuation of the torque generation component. The coupling component is positioned at the distal end of the elongated tubular member, the coupling component configured to actuate a cutting component of the surgical cutting assembly responsive to actuation of the torque generation component.

According to another aspect, an endoscope for removing tissue at a surgical site, includes an elongated tubular body having a distal end and a proximal end. The distal end is insertable within a mammalian cavity of a patient. The proximal end is configured to remain outside the mammalian cavity of the patient. The endoscope includes an instrument channel defined within the elongated tubular body and extending between a first opening at the proximal end and a second opening at the distal end. The instrument channel is sized and configured to receive a removable surgical cutting assembly that defines an aspiration channel configured to fluidly couple, at a proximal end of the surgical cutting assembly, to a suction source to remove material entering the endoscope via a distal end of the surgical cutting assembly. The endoscope includes a flexible torque delivery component configured to deliver torque generated by a torque generation component to an inner cannula of the surgical cutting assembly to cause the inner cannula to move relative to an outer cannula of the surgical cutting assembly to resect material entering the surgical cutting assembly. The flexible torque delivery component extends from the proximal end towards the distal end of the elongated tubular body. The endoscope includes a coupling component is rotatably coupled to the flexible torque delivery component to provide the torque delivered by the flexible torque delivery component to a coupling member of the surgical cutting assembly and configured to cause the coupling member of the surgical cutting assembly to move the inner cannula relative to the outer cannula upon actuation of the flexible torque delivery component.

In some implementations, the flexible torque delivery component is one of a flexible torque coil or a flexible torque rope. In some implementations, the flexible torque delivery component includes a plurality of layers of one or more threads, each of the plurality of layers is wound in a direction opposite to a direction in which one or more adjacent layers of the plurality of layers is wound.

In some implementations, a length of the coupling component is sized to allow the endoscope to be inserted within a mammalian cavity of the patient.

In some implementations, the coupling component is a magnetic coupler surrounding a distal portion of the instrument channel. The magnetic coupler has a magnetic force sufficient to magnetically couple to a coupling member of the surgical cutting assembly to cause the magnetic coupler of the surgical cutting assembly to move t relative the first portion of the surgical cutting assembly. In some implementations, an inner wall of the coupling component has an inner diameter greater than a diameter of the instrument channel and wherein a portion of the instrument channel is disposed within the coupling component. In some implementations, an outer wall of the coupling component includes frictional elements configured to rotatably engage with the flexible torque delivery component. In some implementations, the flexible torque delivery component has an inner wall having an inner diameter that is greater than an outer diameter of the instrument channel and wherein a portion of the instrument channel is disposed within the inner wall of the flexible torque delivery component, and wherein the coupling component is rotatably coupled to the flexible torque delivery component. The coupling component positioned towards the distal end of the elongated tubular member and configured to magnetically couple to a magnetic coupler of the surgical cutting assembly.

In some implementations, the endoscope further including a torque delivery component channel defined within the elongated tubular body and extending from a third opening at the proximal end towards the distal end of the elongated tubular body, and wherein the flexible torque delivery component is sized to be disposed within the torque delivery component channel. In some implementations, the flexible torque delivery component is configured to cause an inner cannula of the surgical cutting assembly to rotate relative to an outer cannula of the surgical cutting assembly.

In some implementations, the flexible torque delivery component is configured to couple to a linear motion assembly that converts the torque delivered from the torque generation component to linear motion. In some implementations, the flexible torque delivery component is configured to rotate in a first direction to cause the coupling component to move from a first position to a second position in a direction from the proximal end to the distal end and to rotate in a second direction to cause the coupling component to move from the second position to the first position, wherein the flexible torque delivery component is configured to alternate between rotating in the first direction and the second direction to cause an inner cannula of the surgical cutting assembly to reciprocate between a first open position in which a distal tip of the inner cannula is a first predetermined distance away from a distal tip of an outer cannula of the surgical cutting assembly and a second closed position in which the distal tip of the inner cannula is less than a second predetermined distance away from the distal tip of the outer cannula, wherein the second predetermined distance is less than the first predetermined distance.

In some implementations, the instrument channel is defined to receive the surgical cutting assembly for removing tissue, the surgical cutting assembly including the inner cannula coupled to a flexible aspiration tube via the coupling member. In some implementations, the instrument channel is configured to include at least one groove configured to engage with a corresponding key of the surgical cutting assembly to cause a cutting window of the outer cannula of the surgical cutting assembly to be aligned with respect to a camera lens of the endoscope.

In some implementations, the endoscope can include an articulation assembly configured to engage an outer cannula of the surgical cutting assembly, the articulation assembly configured to cause the outer cannula to rotate relative to the inner cannula. In some implementations, the articulation assembly is configured to rotate the outer cannula between a plurality of predetermined positions.

In some implementations, the endoscope includes a deployment component configured to be actuated by an actuator. The deployment component configured to maintain the surgical cutting assembly disposed within the tubular body in a first undeployed position and configured to deploy the surgical cutting assembly from the first undeployed position to a second deployed position upon actuation of the deployment component. In some implementations, the deployment component is configured to move between a closed state in which the surgical cutting assembly is maintained in the first undeployed position and an opened state in which the surgical cutting assembly is deployed to the second deployed position. In some implementations, when the surgical cutting assembly is in the second deployed position, an outer cannula of the surgical cutting assembly extending outwardly along a longitudinal axis of the endoscope from the distal end of the endoscope and having a cutting window that is positioned at a distance away from a camera of the endoscope that allows the cutting window to be viewed in an image captured by the camera.

In some implementations, the endoscope can include an irrigation channel extending from the proximal end to an opening defined within a wall of the tubular body that defines the instrument channel. The irrigation channel is configured to fluidly connect to an irrigation pathway defined within the surgical cutter assembly. The surgical cutting assembly can be configured to allow irrigation fluid entering the proximal end of the endoscope to flow into the irrigation pathway defined between an outer cannula and an inner cannula of the surgical cutter assembly when the surgical cutter assembly is inserted within the instrument channel of the endoscope.

In some implementations, the coupling component is disposed within a region of the distal end of the endoscope that extends between the distal tip of the elongated tubular body and a portion of the elongated tubular body within which the steerable assembly is disposed.

According to another aspect, a medical device includes a surgical cutting assembly insertable within an instrument channel of an endoscope having a torque generation component or a torque delivery component disposed within an portion of the endoscope insertable within a mammalian cavity of a patient. The surgical cutting assembly configured to resect material at a surgical site within the mammalian cavity of the patient. The surgical cutting assembly includes an outer cannula including a cutting window and an inner cannula disposed within the outer cannula. The surgical cutting assembly includes a flexible outer tubing coupled to a proximal end of the outer cannula. The inner cannula and the outer tubing having a first length that exceeds a length of the instrument channel of the endoscope within which the surgical cutting assembly is insertable. The surgical cutting assembly includes a coupling member having a distal end coupled to the proximal end of the inner cannula. The surgical cutting assembly includes an aspiration tubing disposed within an inner wall of the flexible outer tubing and fluidly coupled to the inner cannula via the coupling member, wherein the inner cannula, the coupling member and the aspiration tubing having a second length that exceeds the length of the instrument channel of the endoscope within which the surgical cutting assembly is insertable. The inner cannula, the coupling member and the aspiration tubing define an aspiration channel through which the material resected by the surgical cutting assembly is removed from the surgical site within the mammalian cavity of the patient to outside the mammalian cavity. The surgical cutting assembly includes a seal including a stationary portion and a movable portion, the movable portion coupled to the coupling member and the stationary portion coupled to the outer tubing, the seal configured to allow the coupling member to move relative to the outer tubing.

In some implementations, the coupling member includes one or more magnetic surfaces and is configured to magnetically couple to a magnetic coupling component of the endoscope within which the surgical cutting assembly is insertable. In some implementations, the coupling member is configured to rotate about a longitudinal axis of the inner cannula and wherein the inner cannula is configured to rotate about the longitudinal axis relative to the outer cannula. In some implementations, the coupling member is configured to rotate responsive to the coupling component of the endoscope rotating.

In some implementations, a length of the inner cannula and the coupling member is greater than a length of the outer cannula. In some implementations, the coupling member is sized to be disposed within the flexible outer tubing.

In some implementations, the seal includes another portion configured to connect the coupling member to the aspiration tube but rotationally decouple the coupling member and the aspiration tube. In some implementations, the aspiration tubing is configured to be fluidly coupled to a suction source.

In some implementations, the stationary portion of the seal is an outer wall of the seal. The outer wall of the seal includes frictional elements configured to frictionally engage with the inner wall of the outer tubing. In some implementations, the outer tubing is a braided tubing configured to cause the outer cannula to rotate when a proximal end of the braided tubing extending outside the endoscope within which the surgical cutting assembly is insertable is rotated. In some implementations, the surgical cutting assembly includes at least one of a groove or a key defined on an outer wall of the outer tubing, the groove or key configured to engage with a corresponding key or groove defined within the instrument channel of the endoscope within which the surgical cutting assembly is insertable.

In some implementations, the surgical cutting assembly includes an irrigation channel. The irrigation channel includes a first irrigation channel portion defined between an inner wall of the outer cannula and an outer wall of the inner cannula and a second irrigation channel portion defined between an inner wall of the outer tubing and an outer wall of the coupling member and an outer wall of the aspiration tubing.

In some implementations, the surgical cutting assembly includes a lavage connector including an irrigation entry port and a tubular member coupled to the lavage connector and the flexible outer tubing. The aspiration tubing disposed within the tubular member and the outer wall of the aspiration tubing defining a third irrigation channel portion that is fluidly coupled to the first portion of the irrigation channel and the second portion of the irrigation channel. In some implementations, the irrigation channel extends from the irrigation entry port to the cutting window of the outer cannula.

In some implementations, the irrigation channel of the surgical cutting assembly configured to receive a fluid from an irrigation source, wherein the fluid is one of a topical drug or a therapeutic.

In some implementations, the irrigation channel is configured to receive the fluid at a first flow rate to provide irrigation fluid to facilitate aspiration and at a second flow rate to spray the irrigation fluid at a site within the mammalian cavity, the irrigation fluid entering the site from the cutting window of the outer cannula. In some implementations, the medical device can include a flow rate management component configured to manage a flow rate at which to deliver the irrigation fluid to the irrigation channel and an aspiration flow rate at which to aspirate material via the aspiration channel. The flow rate management component is configured to reduce the aspiration flow rate responsive to detecting an increase in the irrigation flow rate beyond a threshold irrigation flow rate.

In some implementations, the outer cannula includes at least one engagement member configured to engage with an articulation assembly defined within the insertable portion of the endoscope. The articulation assembly configured to cause the outer cannula to rotate relative to the endoscope.

In some implementations, the surgical cutting assembly further includes a rotary seal that connects the outer cannula to the outer tubing and rotationally decouples the outer cannula and the outer tubing.

In some implementations, the surgical cutting assembly further includes an outer coupling component including at least one magnet configured to magnetically couple to the coupling member. The outer coupling component positioned adjacent to the coupling member and having an inner wall through which the outer tubing and the coupling member are disposed. In some implementations, the outer coupling component is configured to engage with the coupling component of the endoscope, the coupling component of the endoscope configured to cause the outer coupling component to move. In some implementations, the coupling component of the endoscope is configured to physically engage with the outer coupling component of the surgical cutting assembly to cause the outer coupling component to move relative to the outer tubing of the surgical cutting assembly.

In some implementations, the coupling member of the surgical cutting assembly has a first length extending from a first end coupled to the inner cannula and a second end coupled to the aspiration tube. The first length is greater than a corresponding length of the coupling component of the endoscope within which the surgical cutting assembly is insertable. In some implementations, the coupling member is configured to be rotatably coupled to the coupling component over a distance that extends from a first position where the first end of the inner cannula is adjacent to a proximal end of the coupling component to a second position where the second end of the coupling member is adjacent to a distal end of the coupling component.

In some implementations, the coupling member of the surgical cutting assembly can have a first length extending from a first end coupled to the inner cannula and a second end coupled to the aspiration tube that is less than a corresponding length of the coupling component of the endoscope within which the surgical cutting assembly is insertable. In some such implementations, the coupling member is configured to be rotatably coupled to the coupling component over a distance that extends from a first position where the distal end of the inner cannula is adjacent to a proximal end of the coupling component to a second position where the second end of the coupling member is adjacent to a distal end of the coupling component.

In some implementations, the coupler is a first coupler and the surgical cutting assembly further including a second coupler configured to couple the outer cannula to the coupling member, the first coupler and the second coupler configured to allow the coupling member to rotate relative to the outer tubing and the outer cannula. In some implementations, the coupling member is configured to contact a coupling component of the endoscope within which the surgical cutting assembly is insertable and configured to rotate when the coupling component rotates.

According to yet another aspect, a method of retrieving lesions from a mammalian cavity of a patient, includes inserting a flexible endoscope within an opening to a mammalian cavity of a patient. An endoscopic instrument is disposed or inserted within an instrument channel of the flexible endoscope to resect at least a portion of a lesion from within the mammalian cavity. The endoscopic instrument including a cutting assembly having an outer cannula, an inner cannula disposed within an outer cannula, and a cutting window defined along a portion of a radial wall of the outer cannula, the inner cannula rotatably coupled to a flexible torque component having a length that extends along a length of the flexible endoscope, the flexible torque component, upon actuation, providing torque to the inner cannula to rotate relative to the outer cannula to resect the portion of the lesion. Irrigation fluid is then provided from a lavage port of the endoscopic instrument that remains outside the flexible endoscope while the endoscopic instrument is disposed within the instrument channel. The lavage port is fluidly coupled to the outer cannula through a rotational coupler coupling the lavage port to an outer tubing connected to the outer cannula. The rotational coupler can allow the outer tubing and the outer cannula to rotate relative to the lavage port upon rotating a portion of the rotational coupler. The outer cannula is then rotated, via rotation of the portion of the rotational coupler, to a position in which the opening of the outer cannula is viewable via a camera of the flexible endoscope. The cutting window of the outer cannula is then positioned at the lesion of the mammalian cavity. The flexible torque component is then actuated to rotate the inner cannula relative to the outer cannula, the inner cannula cutting the portion of the lesion as the inner cannula rotates adjacent to the cutting window. A sample retrieval component of the surgical cutting assembly is actuated to remove the cut portions of the lesion from within the mammalian cavity via an aspiration channel defined by an inner wall of the inner cannula and the flexible torque component.

In some implementations, disposing the endoscopic instrument within the instrument channel of the flexible endoscope includes inserting a distal end of the endoscopic instrument in the instrument channel of the flexible endoscope.

In some implementations, a proximal connector that is coupled to the flexible torque component and positioned at a proximal end of the endoscopic instrument is engaged with a drive assembly configured to provide torque to the flexible torque component.

In some implementations, a vacuum source is fluidly coupled to a distal end of the endoscopic instrument to remove, from the endoscopic instrument, portions of the lesion entering the endoscopic instrument via the opening of the outer cannula.

In some implementations, the flexible torque component includes a flexible torque coil having a plurality of layers of one or more threads, each of the plurality of layers is wound in a direction opposite to a direction in which one or more adjacent layers of the plurality of layers is wound and the aspiration channel is partially defined by an inner wall of the flexible torque coil.

In some implementations, actuating the flexible torque component and actuating the sample retrieval component of the endoscopic instrument includes actuating the flexible torque component and actuating the sample retrieval component of the endoscopic instrument simultaneously.

In some implementations, actuating the flexible torque component includes providing torque to the inner cannula that is sufficient to cut at least a portion of the lesion. In some implementations, actuating the flexible torque component includes actuating the flexible torque component to cause an inner cannula of the cutting assembly to rotate relative to the outer cannula via a foot pedal.

In some implementations, the lesion is a first lesion and the mammalian cavity is a colon. Upon cutting at least a portion of the first lesion and without removing the endoscopic instrument from the flexible endoscope, the opening of the outer cannula is positioned at a second lesion within the colon. The flexible torque component is actuated to rotate the inner cannula relative to the outer cannula, the inner cannula cutting at least a portion of the second lesion. The sample retrieval component of the endoscopic instrument is actuated to remove the cut portion of the second lesion from within the colon.

According to another aspect, a method of removing lesions from within a patient, includes inserting a flexible endoscope within an opening of a patient, disposing an endoscopic instrument within an instrument channel of the flexible endoscope to remove a lesion from the surgical site, the endoscopic instrument including a cutting assembly having an outer cannula, an inner cannula disposed within an outer cannula, and an opening defined along a portion of a radial wall of the outer cannula, the inner cannula rotatably coupled to a flexible torque component having a length that extends along a length of the flexible endoscope, the flexible torque component, upon actuation, providing torque to the inner cannula, positioning the opening of the outer cannula at the lesion, actuating the flexible torque component to rotate the inner cannula relative to the outer cannula, the inner cannula cutting a portion of the lesion as the inner cannula rotates adjacent to the opening, and actuating a sample retrieval component of the endoscopic instrument to remove the cut portions of the lesion from within the patient via an aspiration channel defined by an inner wall of the inner cannula and the flexible torque component.

In some implementations, the method includes providing irrigation fluid from a lavage port of the endoscopic instrument that remains outside the flexible endoscope while the endoscopic instrument is disposed within the instrument channel. The lavage port is fluidly coupled to the outer cannula through a rotational coupler coupling the lavage port to an outer tubing connected to the outer cannula, the rotational coupler allowing the outer tubing and the outer cannula to rotate relative to the lavage port upon rotating a portion of the rotational coupler.

In some implementations, the method includes rotating, via rotation of the portion of the rotational coupler, the outer cannula to a position in which the opening of the outer cannula is viewable via a camera of the flexible endoscope.

In some implementations, disposing the endoscopic instrument within the instrument channel of the flexible endoscope includes inserting a distal end of the endoscopic instrument in the instrument channel of the flexible endoscope.

In some implementations, the method includes engaging a proximal connector that is coupled to the flexible torque component and positioned at a proximal end of the endoscopic instrument with a drive assembly configured to provide torque to the flexible torque component.

In some implementations, the method includes fluidly coupling a vacuum source to a distal end of the endoscopic instrument to remove, from the endoscopic instrument, cut portions of the lesion entering the endoscopic instrument via the opening of the outer cannula.

In some implementations, the flexible torque component includes a flexible torque coil having a plurality of layers of one or more threads, each of the plurality of layers is wound in a direction opposite to a direction in which one or more adjacent layers of the plurality of layers is wound and the aspiration channel is partially defined by an inner wall of the flexible torque coil.

In some implementations, actuating the flexible torque component and actuating a sample retrieval component of the endoscopic instrument includes actuating the flexible torque component and actuating the sample retrieval component of the endoscopic instrument simultaneously.

In some implementations, actuating the flexible torque component includes providing torque to the inner cannula that is sufficient to cut at least a portion of the lesion. In some implementations, actuating the flexible torque component includes actuating the flexible torque component to cause an inner cannula of the cutting assembly to rotate relative to the outer cannula via a foot pedal.

In some implementations, the lesion is a first lesion and the method further includes upon cutting at least a portion of the first lesion and without removing the endoscopic instrument from the flexible endoscope, positioning the opening of the outer cannula at a second lesion at another surgical site, actuating the flexible torque component to rotate the inner cannula relative to the outer cannula, the inner cannula cutting at least a portion of the second lesion, and actuating the sample retrieval component of the endoscopic instrument to remove the cut portion of the second lesion from within the patient.

According to another aspect, a method of resecting a lesion from within a mammalian cavity of a patient, includes inserting a flexible endoscope within an opening to a mammalian cavity of a patient, the flexible endoscope including a coupling component disposed within a distal end of the endoscope, the flexible endoscope inserted within the opening via the distal end. The method includes disposing a surgical cutting assembly within an instrument channel of the flexible endoscope. The surgical cutting assembly inserted into the instrument channel via an instrument channel opening to the instrument channel at a proximal end of the endoscope that remains outside the opening to the mammalian cavity. The surgical cutting assembly including a cutter assembly having an outer cannula, an inner cannula disposed within an outer cannula, and a cutting window defined along a portion of a radial wall of the outer cannula, a proximal end of the inner cannula coupled to a coupling member, the coupling member fluidly coupled to an aspiration tube that extends along a length of the flexible endoscope, the coupling member configured to rotatably couple with the coupling component of the flexible endoscope. The method includes positioning, by rotating the outer cannula of the surgical cutting assembly, the cutting window at the lesion within the mammalian cavity to be resected. The method includes providing torque to the coupling component of the endoscope. The torque provided by one of a torque generation component disposed within the distal end of the endoscope or via a flexible torque component extending from the proximal end of the endoscope to the distal end of the endoscope. The torque causing the coupling component of the endoscope to rotate and cause the coupling member of the surgical cutting assembly and the inner cannula to rotate relative to the outer cannula to resect at least a portion of the lesion at the cutting window of the outer cannula. The method includes actuating a sample retrieval component to provide suction to the aspiration tube to remove the resected portion of the lesion via an aspiration channel defined by an inner wall of the inner cannula, an inner wall of the coupling member and the aspiration tube.

In some implementations, the method includes actuating the torque generation component. In some implementations, actuating the torque generation component includes providing a fluid to the torque generation component via a fluid entry channel and removing the fluid from the torque generation component via a fluid exit channel. In some implementations, actuating the torque generation component includes providing an electric current to the torque generation component via an electrical wire that extends from the torque generation component to a current source outside the flexible endoscope.

In some implementations, the method includes actuating a rotary actuator positioned outside the endoscope and connected to the torque delivery component. The torque delivery component is configured to deliver the torque generated by the rotary actuator to the coupling component. The torque delivery component includes a flexible torque coil or flexible torque rope having a plurality of layers of one or more threads. Each of the plurality of layers is wound in a direction opposite to a direction in which one or more adjacent layers of the plurality of layers is wound.

In some implementations, the coupling component includes at least one magnet and the method further includes magnetically coupling the coupling component of the endoscope and the coupling member of the endoscope.

In some implementations, the method further includes providing irrigation fluid to the surgical cutting assembly via an irrigation fluid delivery channel defined within the endoscope, the irrigation fluid delivery channel including an entry port at a proximal end of the endoscope and a fluid exit port positioned towards the distal end of the endoscope and fluidly coupled to an irrigation entry opening of the surgical cutting assembly, the irrigation entry opening of the surgical cutting assembly fluidly coupled to an irrigation pathway defined between the outer cannula and the inner cannula of the cutter assembly.

In some implementations, a portion of the irrigation fluid delivery channel is positioned adjacent to at least one of the torque generation component, the coupling component or the torque delivery component to provide a cooling effect to the torque generation component, the coupling component or the torque delivery component.

In some implementations, positioning, by rotating the outer cannula of the surgical cutting assembly, the cutting window at the lesion within the mammalian cavity to be resected includes actuating an articulation assembly disposed at the distal end of the endoscope, the articular assembly configured to engage with the outer cannula and configured to cause the outer cannula to rotate relative to the endoscope.

In some implementations, positioning, by rotating the outer cannula of the surgical cutting assembly, the cutting window at the lesion within the mammalian cavity to be resected includes rotating an outer tubing coupled to the outer cannula, the outer tubing configured to cause the outer cannula to rotate relative to the endoscope based on rotating the outer tubing.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that offer any or all advantages or solve any or all state of the art problems.

BRIEF DESCRIPTION OF THE DRAWINGS

The present disclosure is illustratively shown and described in reference to the accompanying drawing in which:

FIG. 1A illustrates various types of polyps that can form within a body.

FIG. 16C illustrates a schematic view of an example engagement assembly of an example endoscopic instrument according to embodiments of the present disclosure.

FIG. 16D shows a cut-open view of the engagement assembly shown in FIG. 16C when the engagement assembly is disengaged according to embodiments of the present disclosure.

FIG. 16E shows a cut-open view of the engagement assembly shown in FIG. 16A when the engagement assembly is configured to engage with an instrument channel of an endoscope according to embodiments of the present disclosure.

FIG. 17A illustrates an exploded view of an example endoscopic instrument according to embodiments of the present disclosure.

FIG. 17B illustrates a cross-sectional view of the endoscopic instrument shown in FIG. 17A according to embodiments of the present disclosure.

FIG. 18A illustrates an exploded view of an example endoscopic instrument utilizing a tesla rotor according to embodiments of the present disclosure.

FIG. 18B illustrates a cross-sectional view of the endoscopic instrument shown in FIG. 18A according to embodiments of the present disclosure.

FIG. 19E shows a cut-open view of the engagement assembly shown in FIG. 19D in a disengaged position according to embodiments of the present disclosure.

FIG. 19F shows a cut-open view of the engagement assembly shown in FIG. 19D in an engaged position according to embodiments of the present disclosure.

FIGS. 23AA-23BB show an example implementation of a cutting tool according to embodiments of the present disclosure.

FIGS. 24A-24C illustrate various aspects of the drive shaft of the coupling component according to embodiments of the present disclosure.

FIG. 25 illustrates an example housing component according to embodiments of the present disclosure.

FIGS. 27A-27C show an example base plate that forms a portion of the casing according to embodiments of the present disclosure.

FIGS. 31AA-31AB and 31B-31C illustrate aspects of an endoscopic assembly in which the tip is press-fit according to embodiments of the present disclosure.

FIGS. 34A-34C are cross-sectional views of different configurations of the flexible portion region of one implementation of an endoscopic tool described herein.

FIGS. 35AA-AC show various views of portions of an endoscopic tool according to embodiments of the present disclosure.

FIGS. 40A-40B show a perspective view of an endoscopic tool and a portion of a drive assembly configured to drive the endoscopic tool according to embodiments of the present disclosure.

FIG. 41 shows a top view of the endoscopic tool and a top exposed view of the portion of the drive assembly shown in FIGS. 40A-40B according to embodiments of the present disclosure.

FIG. 42 shows a cross-sectional view of the endoscopic tool and the portion of the drive assembly across the section A-A shown in FIGS. 40A-40B according to embodiments of the present disclosure.

FIG. 47A and FIG. 47B show a top view and a cross-sectional view of the rotational coupler of the endoscopic tool according to embodiments of the present disclosure.

FIG. 50A is a side view of the endoscopic tool and drive assembly shown in FIG. 49 according to embodiments of the present disclosure.

FIG. 50B is a cross-sectional view of the endoscopic tool and drive assembly shown in FIG. 49 taken along the section A-A according to embodiments of the present disclosure.

FIG. 52B is a cross-sectional view of a portion of the endoscopic assembly along the reference line B-B shown in FIG. 52A.

FIG. 54B is an enlarged view of the torque generation component of the endoscope shown in FIG. 54A.

FIG. 55A is a perspective view of a portion of an endoscopic assembly including an endoscope and a surgical cutting assembly in which the endoscope includes an integrated torque delivery component according to embodiments of the present disclosure.

FIG. 63D is an enlarged view of a portion of FIG. 63B including the first coupler of the surgical cutting assembly shown in FIG. 63A.

FIG. 63G shows a perspective view of the surgical cutting assembly of FIG. 63A including the coupling member in a first position.

DETAILED DESCRIPTION

Figure 1B:
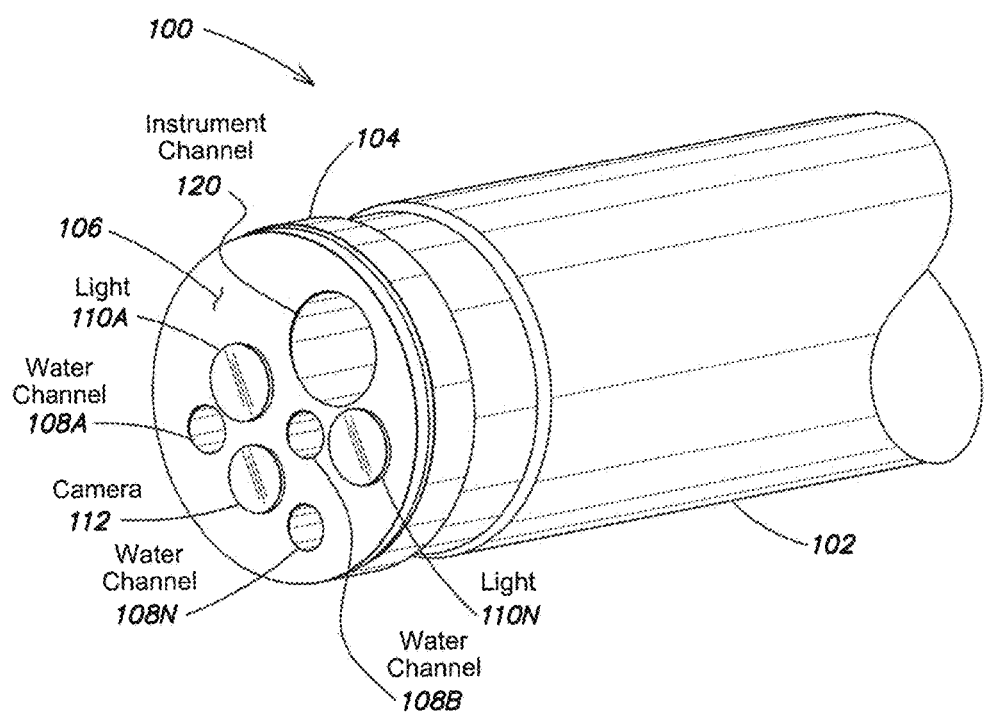
FIG. 1B illustrates a perspective partial view of an endoscope according to embodiments of the present disclosure.

Technologies provided herein are directed towards an improved flexible endoscopic instrument that can precisely and efficiently obtain samples of single and multiple polyps and neoplasms from a patient. In particular, the improved endoscopic instrument is capable of debriding samples from one or more polyps and retrieving the debrided samples without having to remove the endoscopic instrument from the treatment site within the patient's body.

FIG. 1A illustrates various types of polyps that can form within a body. Most polyps may be removed by snare polypectomy, though especially large polyps and/or sessile or flat polyps must be removed piecemeal with biopsy forceps or en bloc using endoscopic mucosal resection (EMR). A recent study has concluded that depressed sessile polyps had the highest rate for harboring a malignancy at 33%. The same study has also found that non-polypoid neoplastic lesions (sessile polyps) accounted for 22% of the patients with polyps or 10% of all patients undergoing colonoscopy. There are multiple roadblocks to resecting colon polyps, namely the difficulties in removing sessile polyps, the time involved in removing multiple polyps and the lack of reimbursement differential for resecting more than one polyp. Since resecting less accessible sessile polyps presents challenges and multiple polyps take more time per patient, most polyps are removed piece meal with tissue left behind as polyps increase in size, contributing to a sampling bias where the pathology of remaining tissue is unknown, leading to an increase in the false negative rate.

Colonoscopy is not a perfect screening tool. With current colonoscopy practices the endoscopist exposes the patient to sample bias through removal of the largest polyps (stalked polyps), leaving behind less detectable and accessible sessile/flat polyps. Sessile polyps are extremely difficult or impossible to remove endoscopically with current techniques and often are left alone. An estimated 28% of stalked polyps and 60% of sessile (flat) polyps are not detected, biopsied or removed under current practice, which contributes to sample bias and a 6% false-negative rate for colonoscopy screening. Current colonoscopy instruments for polyp resection are limited by their inability to adequately remove sessile polyps and inefficiency to completely remove multiple polyps. According to the clinical literature, sessile polyps greater than 10 mm have a greater risk of malignancy. Sessile polyp fragments that are left behind after incomplete resection will grow into new polyps and carry risks for malignancy.

In the recent past, endoscopic mucosal resection (EMR) has been adopted to remove sessile polyps. EMR involves the use of an injection to elevate surrounding mucosa followed by opening of a snare to cut the polyp and lastly use of biopsy forceps or a retrieval device to remove the polyp. The introduction and removal of the injection needle and snare through the length of the colonoscope, which is approximately 5.2 feet, must be repeated for the forceps.

The present disclosure relates to an endoscopic tool that is capable of delivering an innovative alternative to existing polyp removal tools, including snares, hot biopsy and EMR, by introducing a flexible powered instrument that that works with the current generation colonoscopes and can cut and remove any polyp. The endoscopic tool described herein can be designed to enable physicians to better address sessile or large polyps as well as remove multiple polyps in significantly less time. Through the adoption of the endoscopic tool described herein, physicians can become more efficient at early diagnosis of colorectal cancer.

The present disclosure will be more completely understood through the following description, which should be read in conjunction with the drawings. In this description, like numbers refer to similar elements within various embodiments of the present disclosure. Within this description, the claims will be explained with respect to embodiments. The skilled artisan will readily appreciate that the methods, apparatus and systems described herein are merely exemplary and that variations can be made without departing from the spirit and scope of the disclosure.

Referring back to the drawings, FIG. 1B illustrates a perspective partial view of an endoscope according to embodiments of the present disclosure. Although the present disclosure is directed towards endoscopic instruments adapted for use with any type of endoscope, for sake of convenience, the teachings of the present disclosure are directed towards endoscopic instruments used with a lower GI scope, such as a colonoscope. It should, however, be appreciated that the scope of the present disclosure is not limited to endoscopic instruments for use with GI scopes, but extends to any type of flexible endoscope, including but not limited to bronchoscopes, gastroscopes and laryngoscopes, or other medical devices that may be used to treat patients.

According to various embodiments, a typical lower GI scope 100 includes a substantially flexible member that extends from a first end or head portion 102 to a second end or handle portion. The head portion 102 may be configured to swivel so as to orient a tip 104 of the head portion 102 in any direction within a hemispherical space. The handle portion has controls that allows the operator of the endoscope 100 to steer the colonoscope towards an area of interest within the colon and turn the corners between colon segments with two steering wheels.

A series of instruments reside on the face 106 of the scope's tip 104, including but not limited to, one or more water channels 108A-108N, generally referred to as water channels 108, for irrigating the area with water, one or more light sources 110A-110N, generally referred to as light sources 110, a camera lens 112, and an instrument channel 120 through which an endoscopic instrument can be passed through to conduct a number of operations. The instrument channel 120 can vary in size based on the type of endoscope 100 being used. In various embodiments, the diameter of the instrument channel 120 can range from about 2 mm to 6 mm, or more specifically, from about 3.2 mm to 4.3 mm. Some larger scopes may have two instrument channels 120 so that two tools can be passed into the patient simultaneously. However, larger scopes may cause discomfort to the patient and may be too large to enter the patient's body through some of the smaller cavities.

Figure 1C:
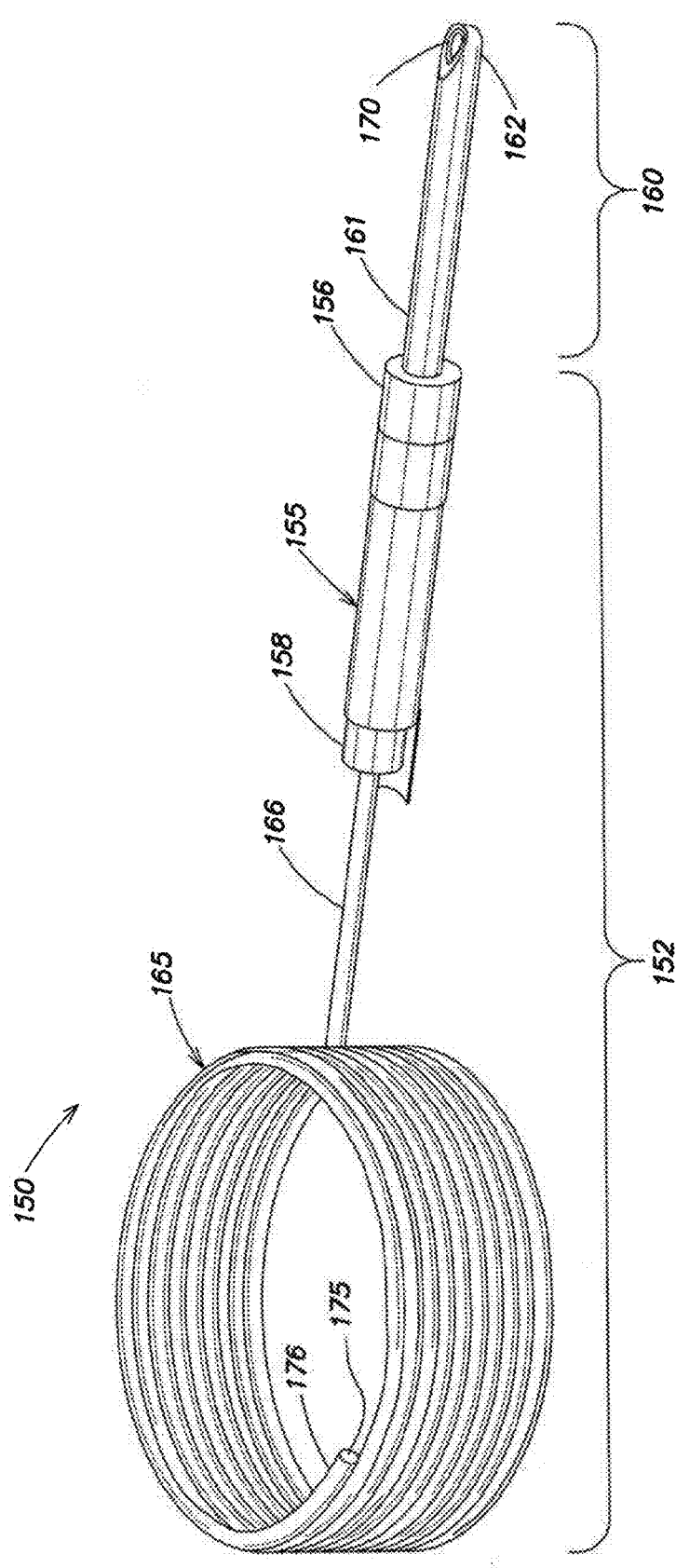
FIG. 1C illustrates a perspective view of an endoscopic instrument according to embodiments of the present disclosure.

FIG. 1C illustrates a perspective view of an endoscopic instrument 150 according to embodiments of the present disclosure. The endoscopic instrument 150 is configured to be fed through the instrument channel 120 of the endoscope 100 depicted in FIG. 1B. The endoscopic instrument 150 is configured to be inserted within an instrument channel of an endoscope, such as the instrument channel 120 of the endoscope 100 depicted in FIG. 1B. In some implementations, the portion of the endoscopic instrument 150 that is configured to be inserted within the instrument channel 120 may be sized to have an outer diameter that is smaller than the inner diameter of the instrument channel 120 of the endoscope. In some such implementations, the endoscopic instrument 150 can be sized to have an outer diameter that is sufficiently small to be slidably inserted within the instrument channel while the endoscope is coiled or bent. When the endoscope is coiled or bent, the instrument channel can form a tortuous path that includes one or more curves and bends. In one example implementations, an endoscope includes an instrument channel that has an inner diameter of about 4.3 mm when the endoscope is straightened. However, when the endoscope is coiled or bent, portions of the endoscope near the bends can have clearances that are smaller than the inner diameter of about 4.3 mm. In some implementations, the endoscope can have clearances that may be about 3.8 mm instead of the 4.3 mm achieved when the endoscope is straightened. In some implementations, the endoscope can have clearances that may be about 3.2 mm. As such, in some implementations, the endoscopic instrument 150 may be sized such that it can be slidably inserted within the instrument channel of the endoscope with which it is to be used even when the endoscope is coiled or bent.

In some implementations, the endoscopic instrument 150 includes a power-driven instrument head 160 configured to resect material at a site within a subject. The power-driven instrument head 160 has a distal end 162 and a proximal end 161. The distal end 162 of the power-driven instrument head 160 defines a material entry port 170 through which the resected material can enter the endoscopic instrument 150. The power-driven instrument head 160 can include a cutting section at the distal end 162 that is configured to cut tissue and other material. As used herein, a port can include any opening, aperture, or gap through which material can either enter or exit. In some implementations, the material entry port can be an opening through which resected material can enter the endoscopic instrument 150. In some implementations, material to be resected can be suctioned into the material entry port where the instrument head can then resect the material.

A body 152 includes a head portion 155 and a flexible portion 165. A distal end 156 of the head portion 155 of the body 152 is coupled to the proximal end 161 of the power-driven instrument head 160. In some implementations, the head portion 155 of the body 152 is configured to drive the power-driven instrument head 160. A proximal end 158 of the head portion 155 can be coupled to a distal end 166 of the flexible portion 165. A proximal end 176 of the flexible portion 165 defines a material exit port 175. The flexible portion 165 can include a hollow flexible tubular member.

The endoscopic instrument also includes an aspiration channel that extends from the material entry port 170 of the power-driven instrument head 160 to the material exit port 175 of the flexible portion 165. In some implementations, the aspiration channel is defined by the power-driven instrument head 160, the head portion 155 of the body 152 and the flexible portion 165 of the body. The proximal end 176 of the flexible portion 165 is configured to couple to a vacuum source such that the resected material entering the aspiration channel via the material entry port 170 is removed from the aspiration channel at the material exit port 175 while the endoscopic instrument 150 is disposed within an instrument channel of an endoscope.

The head portion 155 includes a housing that has an outer diameter that is configured such that the endoscopic instrument 150 can be slidably inserted into an instrument channel of an endoscope. In some implementations, the head portion 155 can include a powered actuator that is configured to drive the power-driven instrument head 160. In some implementations, the powered actuator is disposed within the head portion 155. In some implementations, the powered actuator is located external to the portion of the endoscopic instrument 150 that can be inserted into an instrument channel of an endoscope. In some implementations, the powered actuator is capable of driving the power-driven instrument head via a shaft that can translate motion generated by the power actuator to the power-driven instrument head. In some implementations, the powered actuator is not a part of the endoscopic instrument 150, but instead, is coupled to the power-driven instrument head 160. In some implementations, the shaft may be a flexible shaft. In some such implementations, the flexible shaft can be a flexible torque coil, additional details of which are provided below with respect to FIGS. 19A-19C.

The endoscopic instrument 150 can be sized to be insertable within an instrument channel of an endoscope. In some implementations, the endoscopic instrument 150 may be sized such that the endoscopic instrument can be inserted within the instrument channel of the endoscope while the endoscope is inserted within a subject. In some such implementations, the endoscope, for example, a colonoscope, may be curved or bent thereby requiring the endoscopic instrument 150 to be sized such that it can be inserted into a curved or bent endoscope.

In some implementations, the head portion 155 and the power-driven instrument head 160 of the endoscopic instrument 150 may be substantially stiff or rigid, while the flexible portion 165 may be relatively flexible or compliant. The head portion 155 and the power-driven instrument head 160 can be substantially rigid. As such, in some such implementations, the head portion 155 and the power-driven instrument head 160 may be sized, at least in thickness and in length, such that endoscopic instrument 150 can maneuver through sharp bends and curves during insertion of the endoscopic instrument 150 within the instrument channel of the endoscope. In some implementations, the length of the power-driven instrument head 160 may be between about 0.2"-2", about 0.2" and 1" or in some implementations, between 0.4" and 0.8". In some implementations, the outer diameter of the power-driven instrument head 160 may be between about 0.4"-1.5", 0.6" and 1.2" and 0.8" and 1". In some implementations, the length of the head portion 155 of the body may be between about 0.5"-3", about 0.8" and 2" and 1" and 1.5".

The length of the flexible portion 165 may be substantially and/or relatively longer than the length of the head portion and the power-driven instrument head 160. In some implementations, the flexible portion 165 can be sufficiently long such that the combined length of the endoscopic instrument exceeds the length of instrument channel of an endoscope in which the instrument can be inserted. As such, the length of the flexible portion 165 may have a length that exceeds about 36", about 45" or about 60". For endoscopic instruments configured for use with other types of endoscopes, the length of the flexible portion may be shorter than 36", but still sufficiently long to allow for the body of the endoscopic instrument to be approximately the same length or greater than the length of the endoscope with which the instrument is being used.

The outer diameter of the flexible portion 165 can also be configured such that the endoscopic instrument can be inserted into the instrument channel of the endoscope. In some implementations, the outer diameter of the flexible portion 165 can be sized smaller than a corresponding inner diameter of the instrument channel of the endoscope. In some such implementations, the endoscopic instrument can be sized to have an outer diameter that is sufficiently small to be slidably disposed within the endoscope while the endoscope is coiled or bent. For example, an endoscope can include an instrument channel that has an inner diameter of about 4.3 mm when the endoscope is straightened. However, when the endoscope is coiled or bent, portions of the endoscope near the bends can have clearances that are smaller than the inner diameter of about 4.3 mm. In some implementations, the endoscope can have clearances that may be as low as 3.2 mm. As such, in some implementations, the endoscopic instrument may be sized such that the endoscopic instrument can be slidably inserted within the instrument channel of the endoscope even when the endoscope is coiled or bent.

Figure 2B:
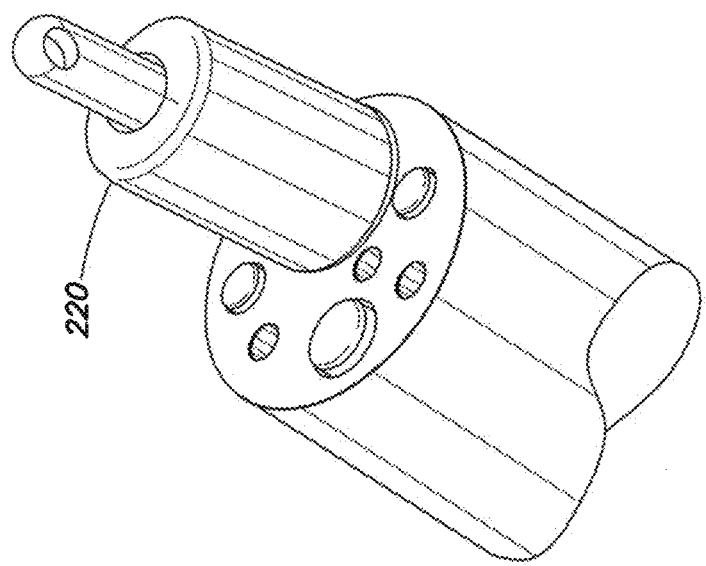
FIGS. 2A and 2B illustrate side perspective views of an endoscopic instrument coupled with the endoscope shown in FIG. 1 according to embodiments of the present disclosure.
Figure 2A:
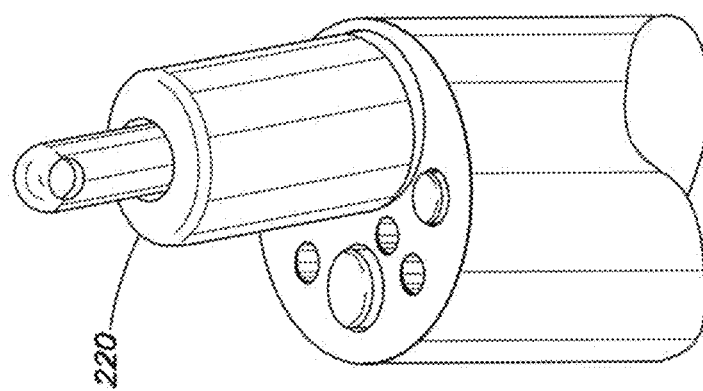
Figure 3B:
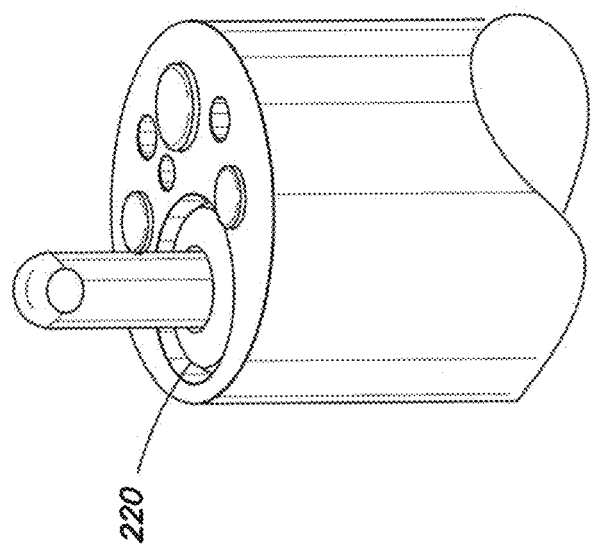
FIGS. 3A and 3B illustrate side perspective views of an example endoscopic instrument coupled with the endoscope shown in FIG. 1 according to embodiments of the present disclosure.
Figure 3A:
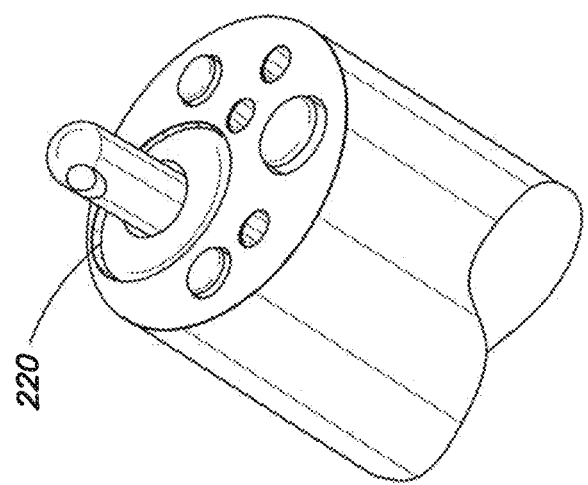

FIGS. 2A and 2B and 3A and 3B illustrate side perspective views of an endoscopic instrument coupled with the endoscope shown in FIG. 1B according to embodiments of the present disclosure. The endoscopic instrument 220 is configured to be fed through the instrument channel 120 of the endoscope 100. As shown in FIGS. 2A and 2B, the endoscopic instrument 220 is capable of extending outside the tip 104 of the endoscope 100, while FIGS. 3A and 3B show that the endoscope tool 220 can be retracted within the endoscope such that no part of the endoscopic instrument 220 is extending beyond the tip 104 of the endoscope 100. As will be described in further detail with respect to FIG. 4, the endoscopic instrument 220 is capable of cutting or debriding a polyp as well as obtaining the debrided polyp from the treatment site without having to remove the endoscopic instrument 220 from the endoscope 100.

Figure 4A:
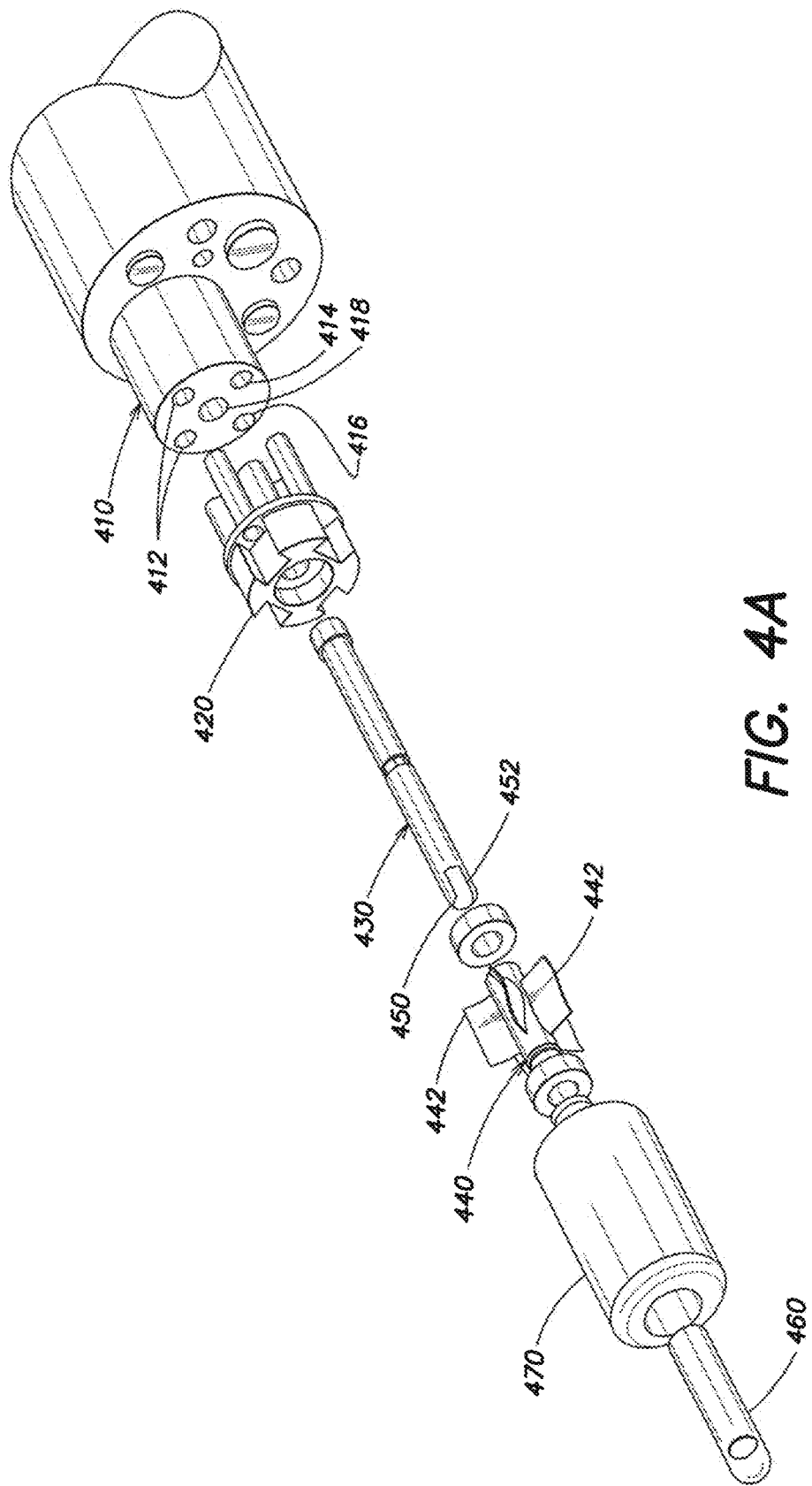
FIG. 4A illustrates an exploded view of the endoscopic instrument that can be coupled with the endoscope according to embodiments of the present disclosure.

FIG. 4A illustrates an exploded view of the endoscopic instrument 220 adapted for use with the endoscope 100 according to embodiments of the present disclosure. The endoscopic instrument 220 includes a debriding component for debriding polyps grown in the patient's body, and a sample retrieval component for retrieving the debrided polyps from the surgical site. The endoscopic instrument 220 includes a tubing 410 coupled to a cap 420. In various embodiments, the cap 420 may be sealingly engaged with the tubing 410. The cap can be aligned with a spindle 430 at a first portion of the spindle 430. In various embodiments, the spindle 430 may be substantially hollow. The spindle 430 can be coupled to a rotor 440, which is configured to rotate the spindle 430. A second portion of the spindle 430 includes an inner blade 450 that may be configured to interact with an outer blade 460. In some implementations, the outer blade 460 can be separated from the inner blade by a gap that forms an irrigation channel (not shown). A casing 470 is configured to encompass the cap 420 and the rotor 440, as shown above with respect to FIGS. 2A and 3A. It should be appreciated that other components, such as washers, bearings, seals, and the like, may be included in the endoscopic instrument 220.

Figure 4B:
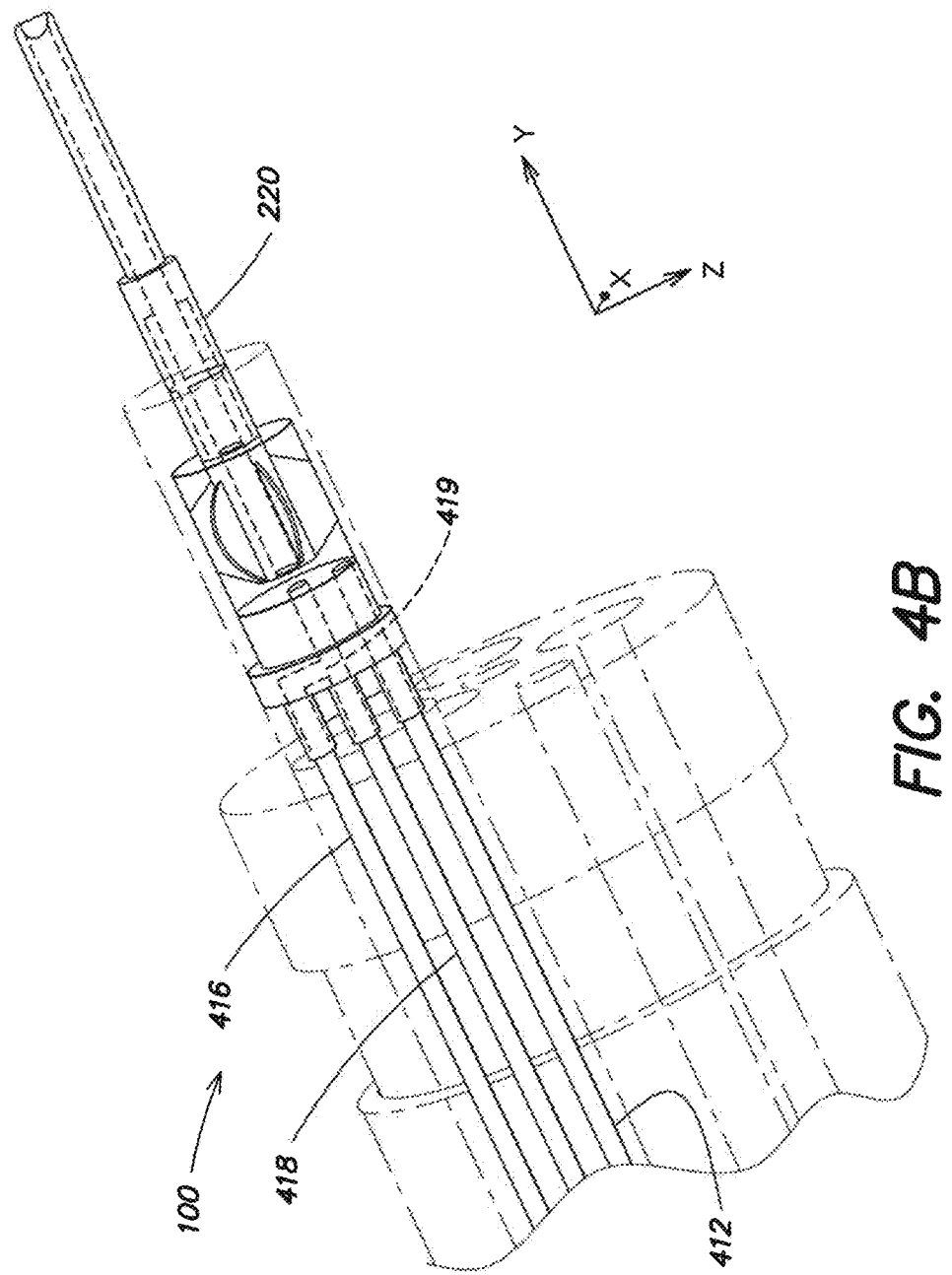
FIG. 4B illustrates a perspective view diagram of the endoscopic instrument coupled to the endoscope illustrating the various conduits associated with the endoscopic instrument.

FIG. 4B is a schematic diagram of an endoscopic instrument partially inserted within an instrument channel of an endoscope endoscopic instrument. In various embodiments, the cap, connector, rotor and casing may be made from injection molded plastic. The spindle and the cannula may be made from surgical grade steel, and the tubing may be made from silicone. However, it should be appreciated that these materials are merely examples of materials that can be used. Those skilled in the art will appreciate that other materials may be used instead of the ones described above.

The tubing 410 in FIG. 4A may be sized to pass through the instrument channel 120 of the endoscope 100 in FIGS. 4A and 4B. The tubing 410 may include one or more pneumatic fluid entry conduits 412, one or more pneumatic fluid exit conduits 414, one or more irrigation conduits 416, and one or more suction conduits 418. The pneumatic fluid entry conduits 412 are configured to supply pressurized air to pneumatically drive the rotor 440, while the pneumatic fluid exit conduits 414 remove the air supplied by the pneumatic fluid entry conduits 412 to prevent a large amount of air from entering the patient's body. The irrigation conduits 416 supply an irrigation fluid, such as water, between the inner blade 450 and the outer blade 460 to help lubricate the area between the inner blade 450 and the outer blade 460. In addition, the irrigation fluid then flows from the outside of the inner blade 450 to the inside portion of the inner blade 450. It should be appreciated that the inside portion of the inner blade 450 may be aligned with the suction conduit 418 of the tubing 410 via the cap 420 such that any fluid that enters the inner blade 450 can pass through the inner blade 450 into the suction conduit 418 of the tubing 410. The irrigation fluid that flows through the inside portion of the inner blade 450 and the suction conduit 418 helps lubricate the suction conduit 418, through which the debrided polyps and other waste from the patient's body are removed. As described above, the tubing 410 is coupled to the cap 420 at a first end, but is coupled to one or more components at a second end (not shown). For instance, at the second end, the pneumatic air entry conduits 412 may be coupled to a compressed air source, while the irrigation fluid conduit 416 may be coupled to a water supply source. In addition, the pneumatic fluid exit conduits 414 may be coupled to the compressed air source or simply left exposed outside the patient's body for venting.

In various embodiments, the suction conduit 418 may be coupled to a disposable cartridge that is configured to catch the cut polyps and store them for examination at a later time. In various embodiments, the disposable cartridge may include multiple collection bins. The operator may be capable of selecting the collection bin in which to collect a sample of a particular cut polyp. Upon selecting the collection bin, the suction conduit 418 supplies the collected material from within the patient's body to the particular collection bin. As such, the operator may be able to collect samples for each polyp in individual collection bins. In this way, the cancerous nature of individual polyps can be determined.

The cap 420 may be sized to fit within the first end of the tubing 410. In various embodiments, the first end of the tubing 410 may include a connector that is configured to couple with the cap 420. In various embodiments, the cap 420 may be press fitted into the connector of the tubing 410. As such, the cap 420 may include corresponding conduits that match the conduits of the tubing 410. Accordingly, compressed air from the compressed air source may be supplied through the pneumatic air entry conduits 412 of the tubing 410 and corresponding pneumatic air entry conduits of the cap 420 towards the rotor 440. The rotor 440 may include one or more rotor blades 442 on which the compressed air is impinged thereby causing the rotor 440 to rotate. The air impinging on the rotor blades 442 may then exit through the corresponding pneumatic air exit conduits of the cap and the pneumatic air entry conduits 414 of the tubing 410. The speed at which the rotor 440 can rotate depends on the amount of air and the pressure at which the air is supplied to the rotor 440. In various embodiments, the speed at which the rotor 440 rotates may be controlled by the operator of the endoscope 100. Although the present disclosure discloses pneumatic means for operating the rotor, some embodiments may include hydraulic means for operating the rotor. In such embodiments, a fluid, such as water, may be supplied in lieu of compressed air, in the pneumatic air entry conduit 412.

As described above, the spindle 430 is coupled to the rotor 440, such that when the rotor 440 rotates, the spindle 430 also rotates. In various embodiments, the first end of the spindle 430 includes the inner blade 450, which correspondingly, also rotates along with the rotor 440. The inner blade 450 may be sized to fit within the diameter of the outer blade 460. In various embodiments, irrigation fluid supplied from an irrigation fluid source may be supplied through the irrigation fluid conduit 416 of the tubing 410 and the corresponding conduit of the cap 420, along the space between the inner blade 450 and the outer blade 460, and into the suction conduit 418 defined by the inner diameter of the inner blade 450. It should be appreciated that since the suction conduit 418 is coupled to a vacuum source, fluids and other material may be suctioned through the suction conduit. In this way, the irrigation fluid is able to lubricate at least a substantial length of the suction conduit 418, from the tip 452 of the inner blade 450, through the spindle 430, cap 420, and tubing 410 into the disposable cartridge described above.

The inner blade 450 may rotate relative to the outer blade 460 such that the interaction between the inner blade 450 and the outer blade 460 causes polyps to be cut upon contact with the inner blade 450. In various embodiments, other mechanisms for cutting polyps may be utilized, which may or may not include the use of a rotor 440, inner blade 450 or outer blade 460.

The debriding component may generally be configured to debride a polyp. Debriding can, for example, include any action involving detaching the polyp or a portion of the polyp from a surface of the patient's body. Accordingly, actions, including but not limited to, cutting, snaring, shredding, slicing, shattering, either entirely or partially, are also examples of debriding. Accordingly, the debriding component may be a component that is capable of cutting, snaring, shredding, slicing, shattering, a polyp from a surface of the patient's body. As such, the debriding component may be implemented as a forceps, scissor, knife, snare, shredder, or any other component that can debride a polyp. In some embodiments, the debriding component may be manually actuated such that the debriding component may be operated through the translation of mechanical forces exerted by an operator or automatically actuated, using a turbine, electrical motor, or any other force generating component to actuate the debriding component. For instance, the debriding component may be actuated hydraulically, pneumatically, or electrically. In various embodiments, a separate conduit passing through the tubing or a channel of the endoscope may be configured to carry an electrical wire to provide power to the electrically powered actuator, such as an electrical motor.

According to various embodiments, the debriding component may include a turbine assembly, which is made up of the rotor 440, the rotor blades 442, and the spindle 430. The operator may actuate the debriding component of the endoscopic instrument by supplying compressed air to the turbine assembly. When the operator is ready to begin debriding the polyp, the operator actuates the turbine assembly causing the debriding component to be actuated. In embodiments, such as the embodiment disclosed in FIG. 4, actuating the debriding component may constitute causing the inner blade 450 to rotate relative to the outer blade 460. Upon actuation, the operator may bring the endoscopic instrument 220 towards the polyp to be debrided causing the inner blade 450 to debride the polyp, causing portions of the debrided polyp to lie in the vicinity around the area where the polyp had grown. The operator may then de-actuate the turbine assembly and actuate suction through the suction conduit 418. The operator may then bring the inner blade close to the cut polyp causing the cut polyp to be retrieved through the suction conduit 418. In various embodiments, the suction component of the endoscopic instrument may be actuated while the debriding component is actuated, thereby allowing any debrided material to be retrieved by the suction component.

Although the above embodiment houses a debriding component that utilizes a turbine assembly, the scope of the present disclosure is not limited to such embodiments. Rather, it should be appreciated by those skilled in the art that the debriding component may be manually operated or may utilize any other means of debriding a polyp such that the debrided polyps are capable of being retrieved from the surgical site via the suction conduit described above. Accordingly, examples of debriding components may include, but are not limited to, snips, blades, saws, or any other sharp tools that may or may not be driven by a turbine assembly. It should be appreciated that using a debriding component that is able to cut a polyp into small enough pieces may be desirable such that the cut pieces may be retrieved via the suction conduit without having to remove the endoscopic instrument from the endoscope.

The geometry and assembly of the turbine assembly for rotating at least one of the cutting tool blades may be based on fluid dynamics. Bernoulli's equation can be used to explain the conversion between fluid pressure and the fluid velocity. According to this equation, the fluid velocity is related to the initial fluid pressure by the equation:

$$V = \sqrt{2 * \frac{P}{D}}$$

where V is Velocity, P is Pressure, and D is Mass density.

In order for the fluid to reach the calculated velocity, the fluid can be developed at the point of exit such that the channel through which the fluid is flowing meets an empirically determined L/D ratio of 2, where 'D' is the wetted diameter of the flow and the 'L' is the length of the channel.

To further understand the interaction of the rotor blades and the fluid, it is assumed that the rotor blade is made so that the air jet impinges the rotor blade on a plane. The equation of linear momentum can be applied to find the forces generated:

$$\sum F = \frac{d}{dt}\left(\int\int\int Vp * dVol.\right) + \sum (\dot{m}V)_{out} - \sum (\dot{m}V)_{in}$$

where: $\dot{m}$ is the mass flow of the impinging air jet, and V is Volume.

Assuming that the control volume remains constant (volume between blades), the force created on the blade can be solved for:

$$\sum F = \dot{m}(V_{out} - V_{in})$$

The quantity $V_{out}$ and $V_{in}$ are the same in an impulse turbine, the momentum change being created by the changing direction of the fluid only. The mass flow in is defined by the pump that is to be specified. The actual numerical value also needs to account for the velocity of the rotor. So finally, the force generated by a single blade-air jet interaction is:

$$\Sigma F = \dot{m}(V_{jet}-V_{rotor})-(V_{jet}-V_{rotor})\cos\theta$$

$$\Sigma F = \dot{m}(V_{jet}-V_{rotor})(1-\cos\theta)$$

where 'θ' is the difference of the angle between the incoming air jet to that of the exiting air jet. Thought theoretically, the maximum amount of torque can be generated by a 'θ' value of 180°, but doing so will actually send the incoming jet onto the back of the following blade. Accordingly, the angle is best given a design value 15° to 20° below 180 to allow a fluid a clean exit. Finally, the force can be defined into a rotational torque:

$$\Sigma T = (\dot{m}/r)(V_{jet}-V_{rotor})(1-\cos\theta)$$

A second force that can be considered comes from redirecting the air jet from the nozzle into the turbine wheel. To power the turbine, the air jet can be turned 90° into the direction of the blades from the direction of the air jet. The turning of the air jet will create a force on the stationary housing that is a function of the jet velocity, which in turn is proportional to the applied pressure:

$$\Sigma F = \dot{m}V_{jet}$$

This force can be reacted by the connection between the housing and the endoscope, a failure to do so can result in the ejection of the turbine assembly during operation.

Computational analyses based on Finite Element Methods (FEM) reveal that the areas where the greatest stresses are found are located near the root of the blade where a sharp corner is located. The design of air input channel can be simplified by the existing air nozzle channel in endoscope. The air nozzle in existing endoscopes directs pressurized air across objective lens to remove moisture and also provides distension of a cavity being examined or directs pressurized water across objective lens to clear debris.

Referring now to FIG. 4B, a perspective view diagram of the endoscopic instrument coupled to the endoscope illustrating the various conduits associated with the endoscopic instrument is shown. In particular, the pneumatic air entry conduit 412 is shown supplying pressurized air to the rotor assembly, while the pneumatic air exit conduit 412 (not shown in this view) removes the air from the rotor assembly to outside the endoscope 100. The irrigation channel 416 is shown to carry irrigation fluid into the endoscopic instrument 220, where the irrigation fluid enters into the suction conduit 418, which carries material from within the patient's body to a collection component outside the endoscope. As shown in FIG. 4B, the irrigation fluid may enter the suction conduit 418 at an irrigation fluid entry opening 419. It should be appreciated that the placement of the irrigation fluid entry opening 419 may be placed anywhere along the suction conduit. Due to the suction force being applied to the suction conduit, irrigation fluid may be forced into the suction conduit without the risk of the materials flowing in the suction conduit from flowing outside the suction conduit through the irrigation fluid entry opening 419. Moreover, in some embodiments, the irrigation channel may only supply irrigation fluid to the endoscopic instrument while suction is being applied to the suction conduit.

Figure 5:
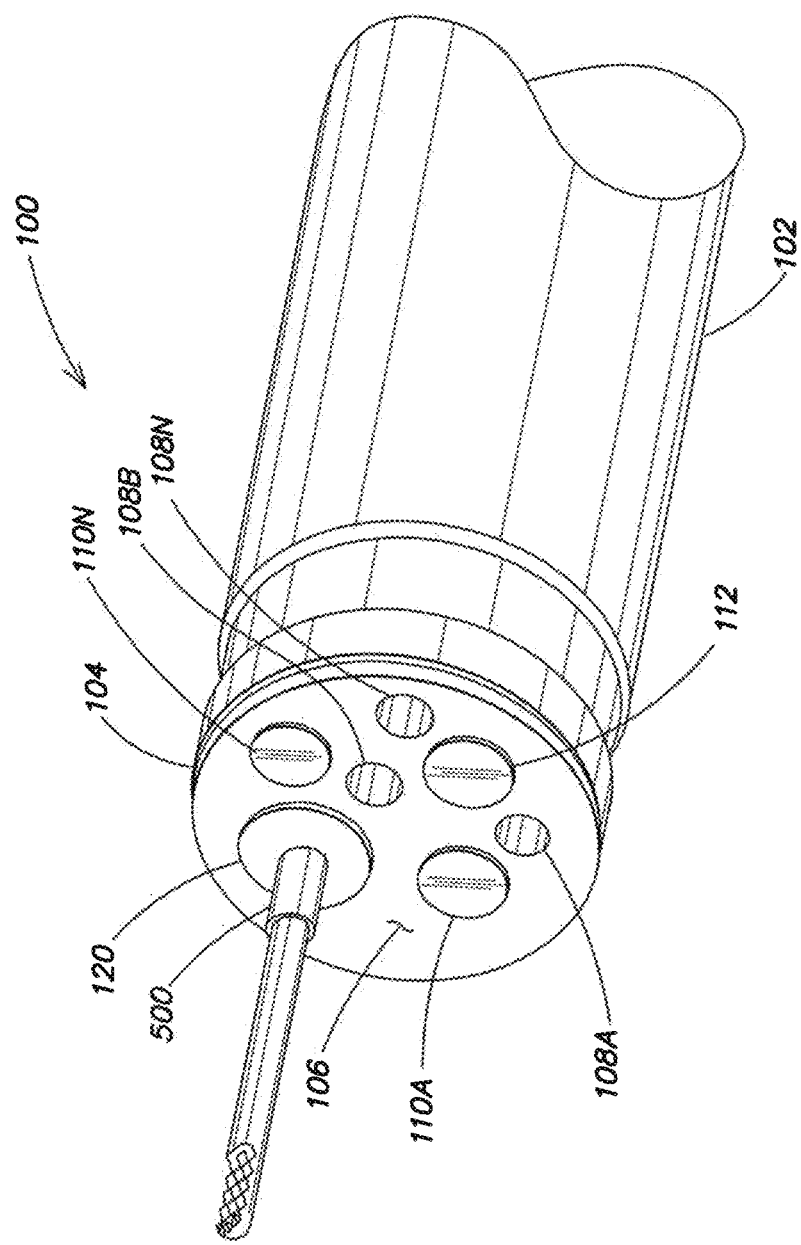
FIG. 5 illustrates a side perspective view of another example endoscopic instrument coupled with the endoscope shown in FIG. 1 according to embodiments of the present disclosure.

FIG. 5 illustrates a side perspective view of another endoscopic instrument coupled with the endoscope shown in FIG. 1 according to embodiments of the present disclosure. The add-on endoscopic instrument 500 is sized to couple with the walls defining the instrument channel 120 of the tip 104 of the endoscope 100. In various embodiments, the add-on endoscopic instrument 500 may be removably attached to the instrument channel 120 of the endoscope 100 at the tip 104 of the endoscope 104 by way of an interference fit or a press fit. In other embodiments, the add-on endoscopic instrument 500 may be coupled to the endoscope 100 using other attachment means known to those skilled in the art.

Figure 6:
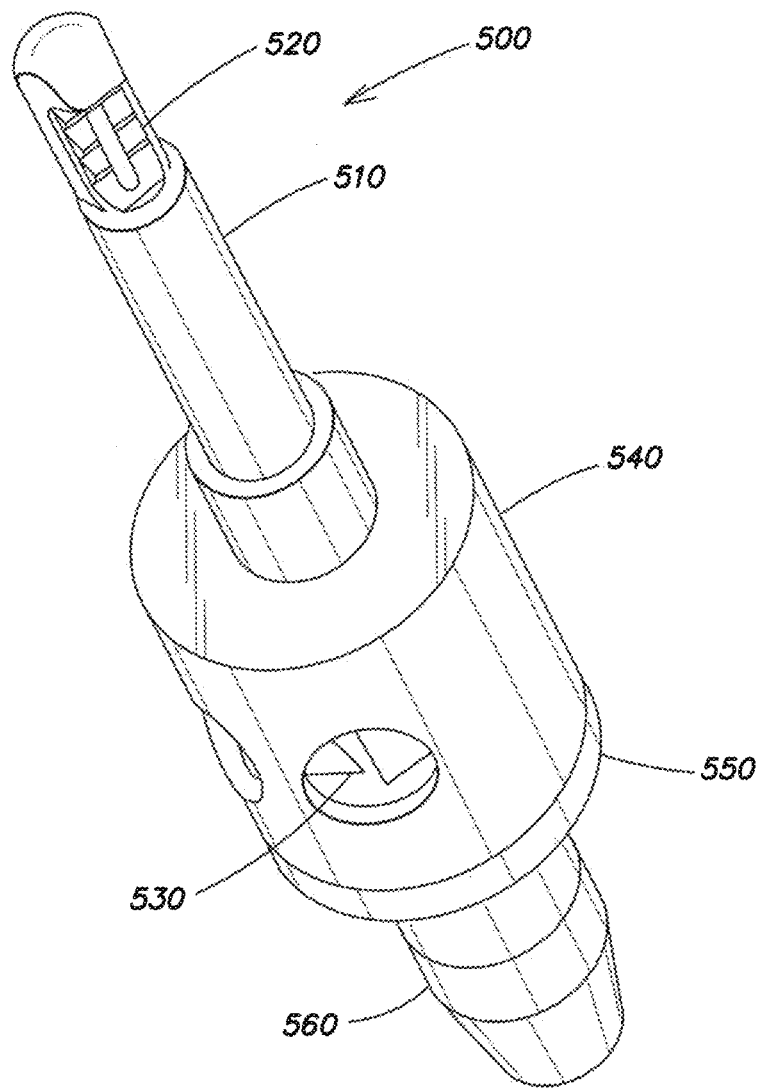
FIG. 6 illustrates an enlarged view of an example endoscopic instrument according to embodiments of the present disclosure.
Figure 7:
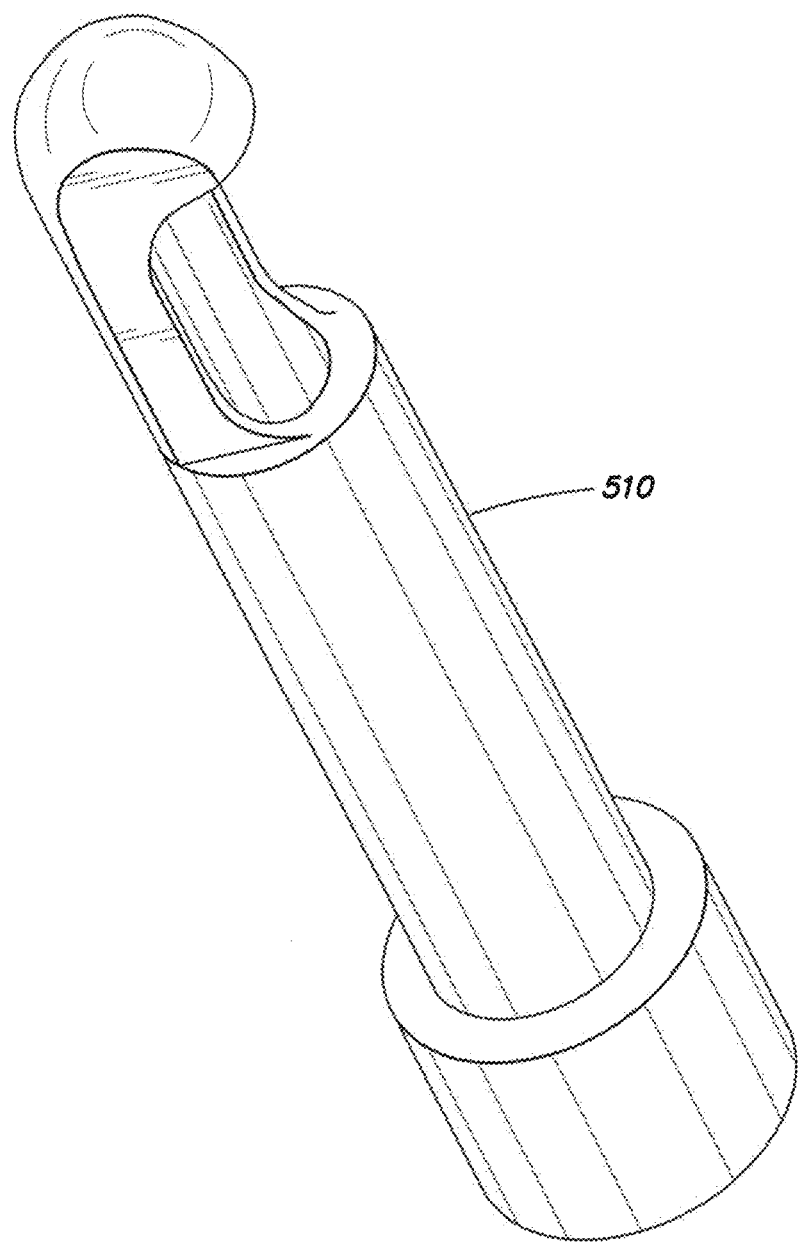
FIG. 7 illustrates a perspective view of an outer blade of a cutting tool of the endoscopic instrument shown in FIG. 6 according to embodiments of the present disclosure.
Figure 8:
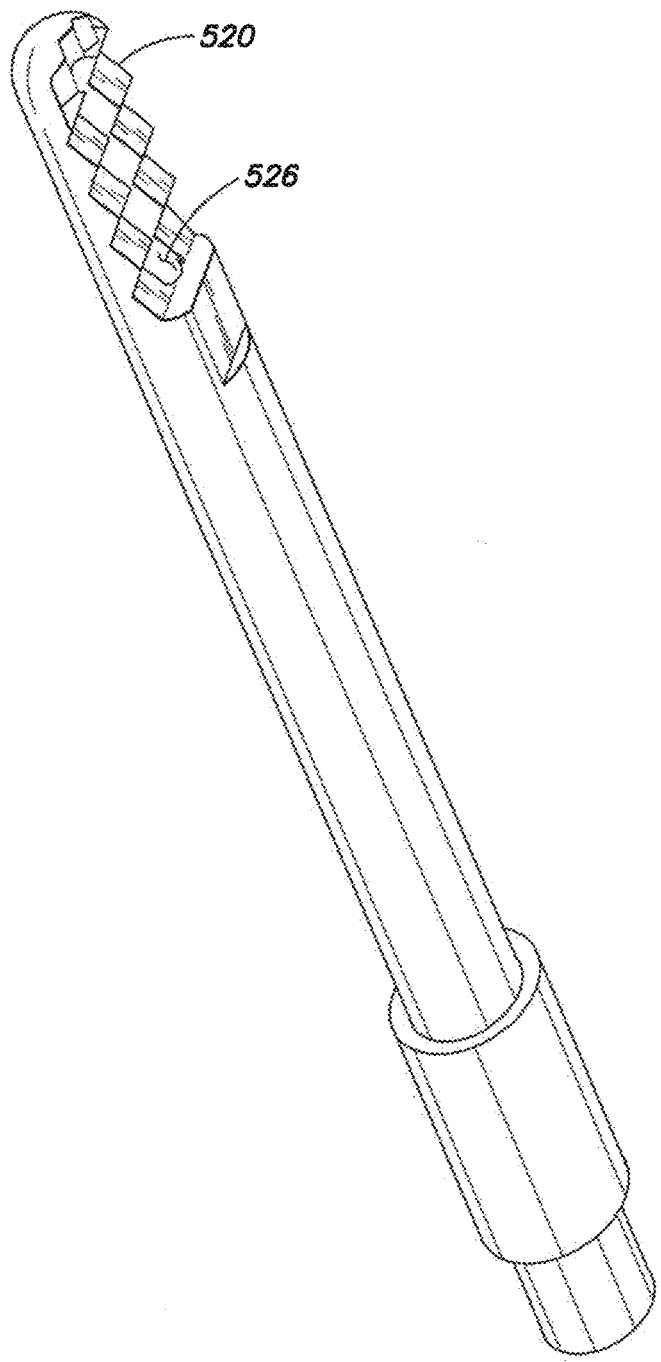
FIG. 8 illustrates a perspective view of an inner blade of the cutting tool of the endoscopic instrument shown in FIG. 6 according to embodiments of the present disclosure.
Figure 9:
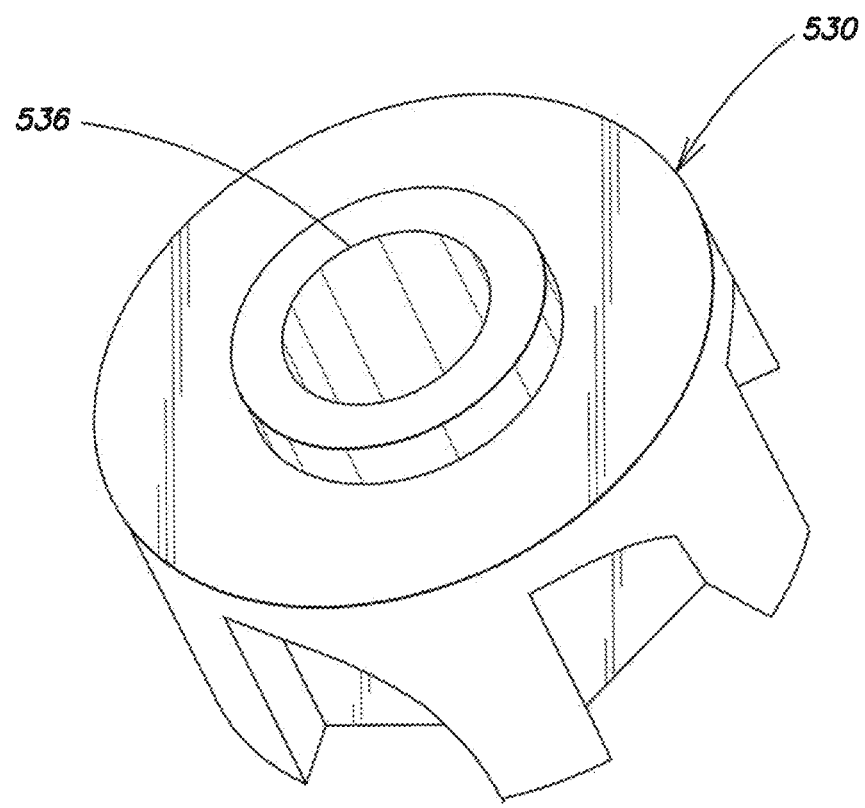
FIG. 9 illustrates a perspective view of a rotor of the endoscopic instrument shown in FIG. 6 according to embodiments of the present disclosure.

Referring now to FIG. 6, an enlarged view of the add-on endoscopic instrument 500 is shown. The add-on endoscopic instrument includes an outer blade or support member 510, an inner blade 520 disposed within the outer blade 510, a rotor 530 coupled to the inner blade 520 and encompassed by a casing 540. The casing is coupled to a cap 550, which is further coupled to a connector 560. In some embodiments, the connector 560 may be sized to engage with the inner diameter of the instrument channel 120 of the endoscope 100. In some embodiments, any other component of the endoscopic instrument may be configured to engage with the endoscope 100 in such a manner as to secure the endoscopic instrument to the instrument channel 120.

FIGS. 7-12 illustrate perspective views of the individual components of the add-on endoscopic instrument shown in FIG. 6 according to embodiments of the present disclosure. In contrast to the endoscopic instrument 220 disclosed with respect to FIGS. 1-4, the add-on endoscopic instrument 500 may be adapted to fit within a first end of instrument channel 120 of the endoscope 100.

In various embodiments, a second end of the instrument channel 120 may be coupled to a vacuum source, which causes material to be suctioned through the instrument channel 120. A suction conduit extends from the vacuum source through the instrument channel of the endoscope, and further through the connector 560, the cap 550, and the rotor 530, to a first end of the inner blade 520, which has an opening defined by the inner diameter of the inner blade 520. It should be appreciated that the connector 560, the cap 550, the casing 540, and the rotor 530 have respective center bores 566, 556, 546 and 536 that are aligned such that materials are allowed to flow from the opening of the inner blade 520 to the vacuum source via the second end of the instrument channel 120.

Figure 10:
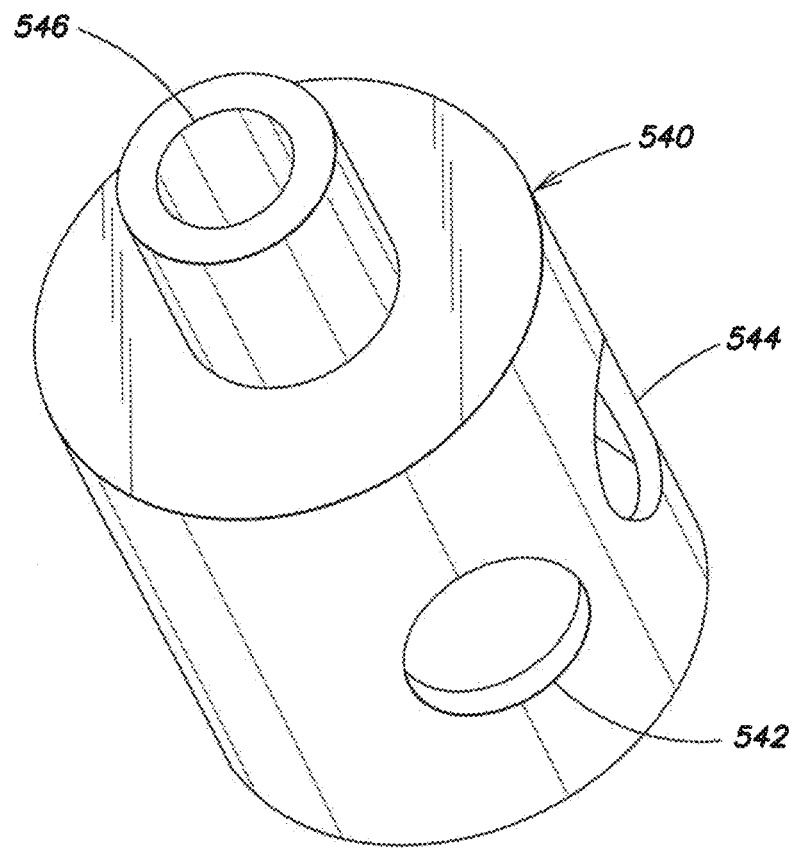
FIG. 10 illustrates a perspective view of a casing of the endoscopic instrument shown in FIG. 6 according to embodiments of the present disclosure.
Figure 11:
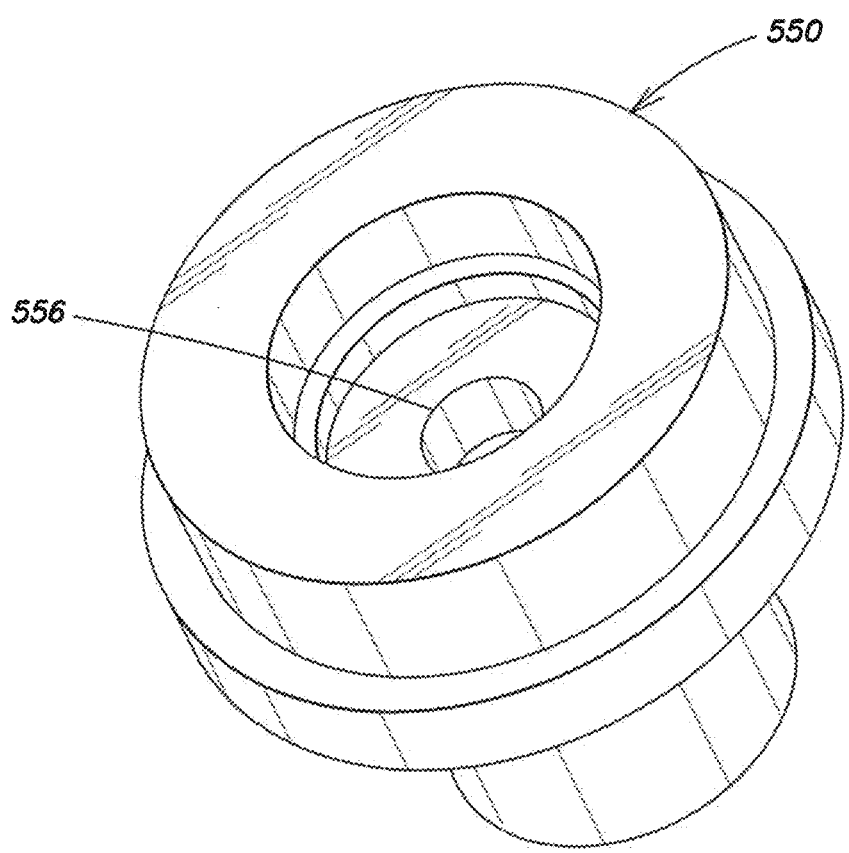
FIG. 11 illustrates a perspective view of a cap of the endoscopic instrument shown in FIG. 6 according to embodiments of the present disclosure.
Figure 12:
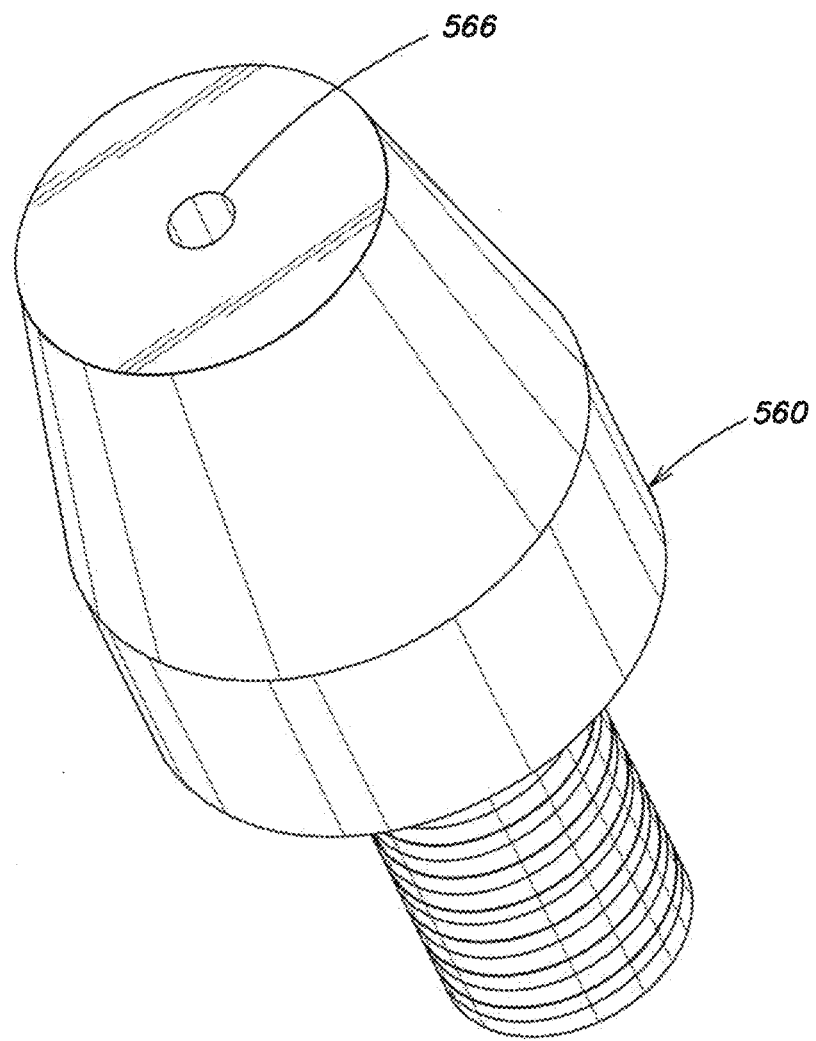
FIG. 12 illustrates a perspective view of a coupling member of the endoscopic instrument shown in FIG. 6 according to embodiments of the present disclosure.

In addition, the casing 540 of the add-on endoscopic instrument 500 includes a pneumatic air entry port 542 and a pneumatic air exit port 544 as shown in FIG. 10. The pneumatic air entry port 542 may be adapted to receive compressed air from a compressed air source through a pneumatic air entry conduit that passes along the length of the endoscope 100 to outside the patient's body, while the pneumatic air exit port 544 may be adapted to vent air that is impinged on the rotor 530 through a pneumatic air exit conduit that passes along the length of the endoscope 100 to outside the patient's body. In this way, the rotor may be actuated by supplying compressed air from the compressed air source, as described above with respect to FIGS. 1-4. It should be appreciated that although the rotor and associated components disclosed herein describe the use of pneumatic air, the rotor may be driven hydraulically. In such embodiments, the pneumatic air conduits may be configured to carry a liquid, such as water, to and from the area around the rotor.

Figure 13:
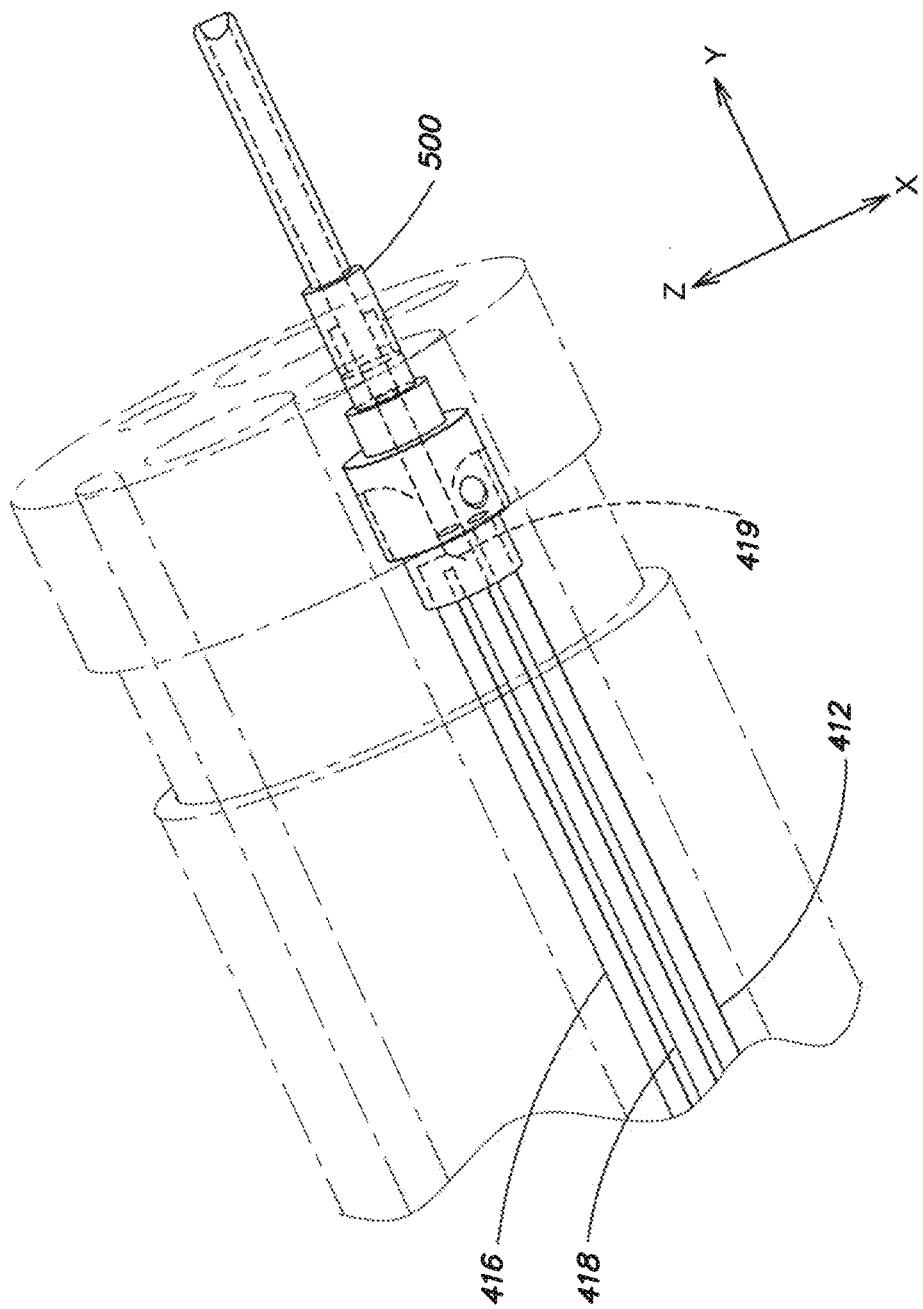
FIG. 13 illustrates a perspective view diagram of the endoscopic instrument coupled to the endoscope illustrating the various conduits associated with the endoscopic instrument.

Referring now also to FIG. 13, it should be appreciated that the pneumatic air entry and exit conduits may extend from the add-on endoscopic instrument to a pneumatic air source through the instrument channel 120 of the endoscope 100. In such embodiments, a tubing that includes separate conduits for the pneumatic air entry and exit conduits and the suction conduit may extend from outside the endoscope to the add-on endoscopic instrument within the endoscope. The tubing may be capable of being fed through the instrument channel of the endoscope and coupled to the add-on endoscopic instrument 500. In such embodiments, the add-on endoscopic instrument 500 may be configured with an additional component that has predefined channels that couple the respective channels of the tubing with the associated with the pneumatic air entry and exit openings of the add-on endoscopic instrument and the suction conduit formed within the add-on endoscopic instrument. In addition, an irrigation fluid channel may also be defined within the tubing such that irrigation fluid may be supplied to the add-on endoscopic instrument 500, from where the irrigation fluid is diverted into the suction conduit.

In various embodiments, the tip of the outer blade 510 may be sharp and may cause discomfort to the patient while entering a cavity of the patient's body. As such, a guard structure (not shown), such as a gel cap or other similar structure, may be attached to the outer blade prior to inserting the add-on endoscopic instrument into the patient's body to prevent injuries from the outer blade contacting a surface of the patient's body. Once the endoscopic instrument is inserted in the patient's body, the guard structure may be released from the outer blade 510. In various embodiments, the guard structure may dissolve upon entering the patient's body.

Figure 14:
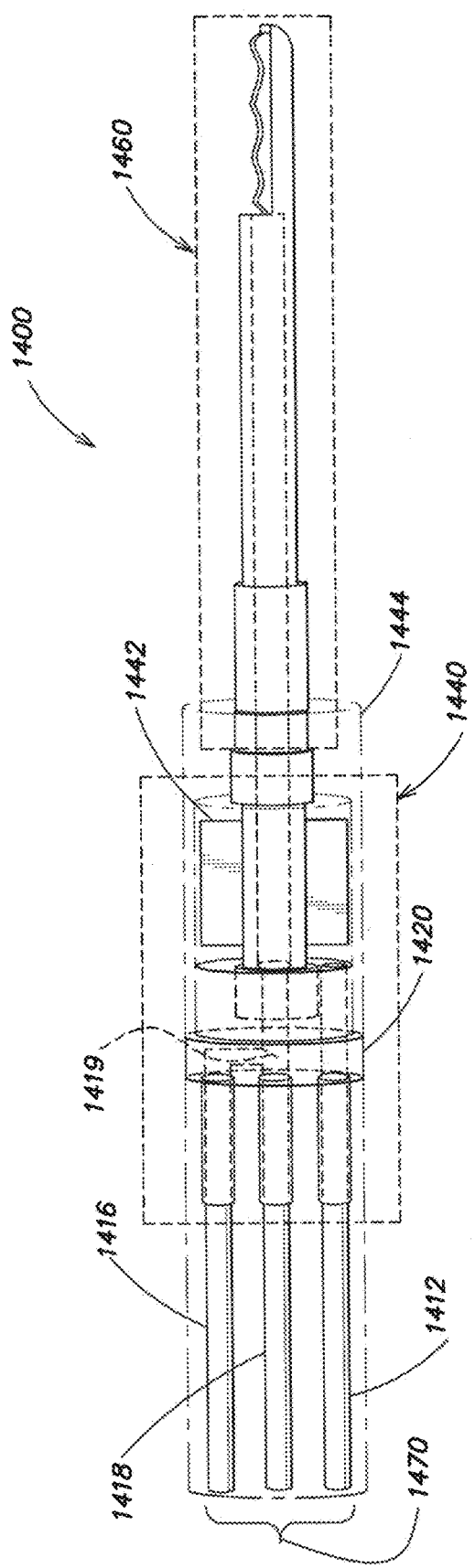
FIG. 14 illustrates another perspective view diagram of the endoscopic instrument coupled to the endoscope illustrating the various conduits associated with the endoscopic instrument.

Referring now to FIG. 14, an improved endoscope having a built in polyp removal assembly is shown according to embodiments of the present disclosure. The improved endoscope 1400 may be similar to conventional endoscopes in many aspects, but may differ in that the improved endoscope may include a built in polyp removal assembly 1440 within an instrument channel of the endoscope 1400. The polyp removal assembly 1440 may include a turbine assembly having a rotor 1442 with rotor blades sealed in a casing 1444 that has one or more inlet and outlet ports for allowing either pneumatic or hydraulic fluid to actuate the rotor 1442. The inlet ports may be designed such that the fluid may interact with the rotor blades at a suitable angle to ensure that the rotor can be driven at desired speeds.

In addition, the polyp removal assembly 1440 may be coupled to a connector 1420, which is configured to couple the polyp removal assembly 1440 to a tubing 1470. The tubing 1470 may include a pneumatic air entry conduit 1412, a pneumatic air exit conduit (not shown), an irrigation fluid conduit 1416 and a suction conduit 1418 that passes through the center of the turbine assembly. The tubing 1440 may be sized such that the tubing 1440 can be securely coupled to the connector 1420 such that one or more of the conduits of the tubing 1440 are coupled to corresponding conduits within the connector 1440. The connector 1420 may be designed to include an irrigation fluid entry opening 419, which allows irrigation fluid to pass into the suction conduit 1418 of the tubing 1440 when the tubing is coupled to the connector.

The turbine assembly of the endoscope 1400 may be configured to couple with a removable debriding assembly 1460, which includes a spindle and a cannula, in a manner that causes the debriding assembly to be operational when the turbine assembly is operating.

In other embodiments of the present disclosure, an endoscope may be designed to facilitate debriding one or more polyps and removing the debrided material associated with the polyps in a single operation. In various embodiments, the endoscope may include one or more separate channels for removing debrided material, supplying irrigation fluid, and supplying and removing at least one of pneumatic or hydraulic fluids. In addition, the endoscope may include a debriding component that may be fixedly or removably coupled to one end of the endoscope. In various embodiments, based on the operation of the debriding component, a separate debriding component channel may also be designed for the debriding component. In addition, the endoscope may include a light and a camera. In one embodiment, the endoscope may utilize existing channels to supply pneumatic or hydraulic fluids to the actuator of the endoscopic instrument for actuating the debriding component. For instance, in the endoscope shown in FIG. 1, the water channels 108A-N may be modified to supply fluids to the actuator pneumatically or hydraulically. In such embodiments, the endoscopic instrument may include a connector having a first end capable of being coupled to an opening associated with existing channels 108 of the endoscope, while another end of the connector is exposed to an opening at the actuator.

In various embodiments of the present disclosure, the endoscopic instrument may further be configured to detect the presence of certain layers of tissue. This may be useful for physicians to take extra precautions to prevent bowel perforations while debriding polyps. In some embodiments, the endoscopic instrument may be equipped with a sensor that can communicate with a sensor processing component outside the endoscope to determine the type of tissue. The sensor may gather temperature information as well as density information and provide signals corresponding to such information to the sensor processing unit, which can identify the type of tissue being sensed. In some implementations, the sensor may be an electrical sensor.

In addition, the endoscopic instrument may be equipped with an injectable dye component through which a physician may mark a particular region within the patient's body. In other embodiments, the physician may mark a particular region utilizing the debriding component, without the use of an injectable dye.

Although the present disclosure discloses various embodiments of an endoscopic instrument, including but not limited to a tool that may be attached to the tip of the endoscope, and a tool that may be fed through the length of the endoscope, the scope of the present disclosure is not intended to be limited to such embodiments or to endoscopic instruments in general. Rather, the scope of the present disclosure extends to any device that may debride and remove polyps from within a patient's body using a single tool. As such, the scope of the present disclosure extends to improved endoscopes that may be built with some or all of the components of the endoscopic instruments described herein. For instance, an improved endoscope with an integrated turbine assembly and configured to be coupled to a debriding component is also disclosed herein. Furthermore, the endoscope may also include predefined conduits that extend through the length of the endoscope such that only the suction conduit may be defined by a disposable tubing, while the air entry and exit conduits and the irrigation conduit are permanently defined within the improved endoscope. In other embodiments, the suction conduit is also predefined but made such that the suction conduit may be cleaned and purified for use with multiple patients. Similarly, the debriding component may also be a part of the endoscope, but also capable of being cleaned and purified for use with multiple patients. Furthermore, it should be understood by those skilled in the art that any or all of the components that constitute the endoscopic instrument may be built into an existing endoscope or into a newly designed endoscope for use in debriding and removing polyps from within the patient's body.

Figure 15:
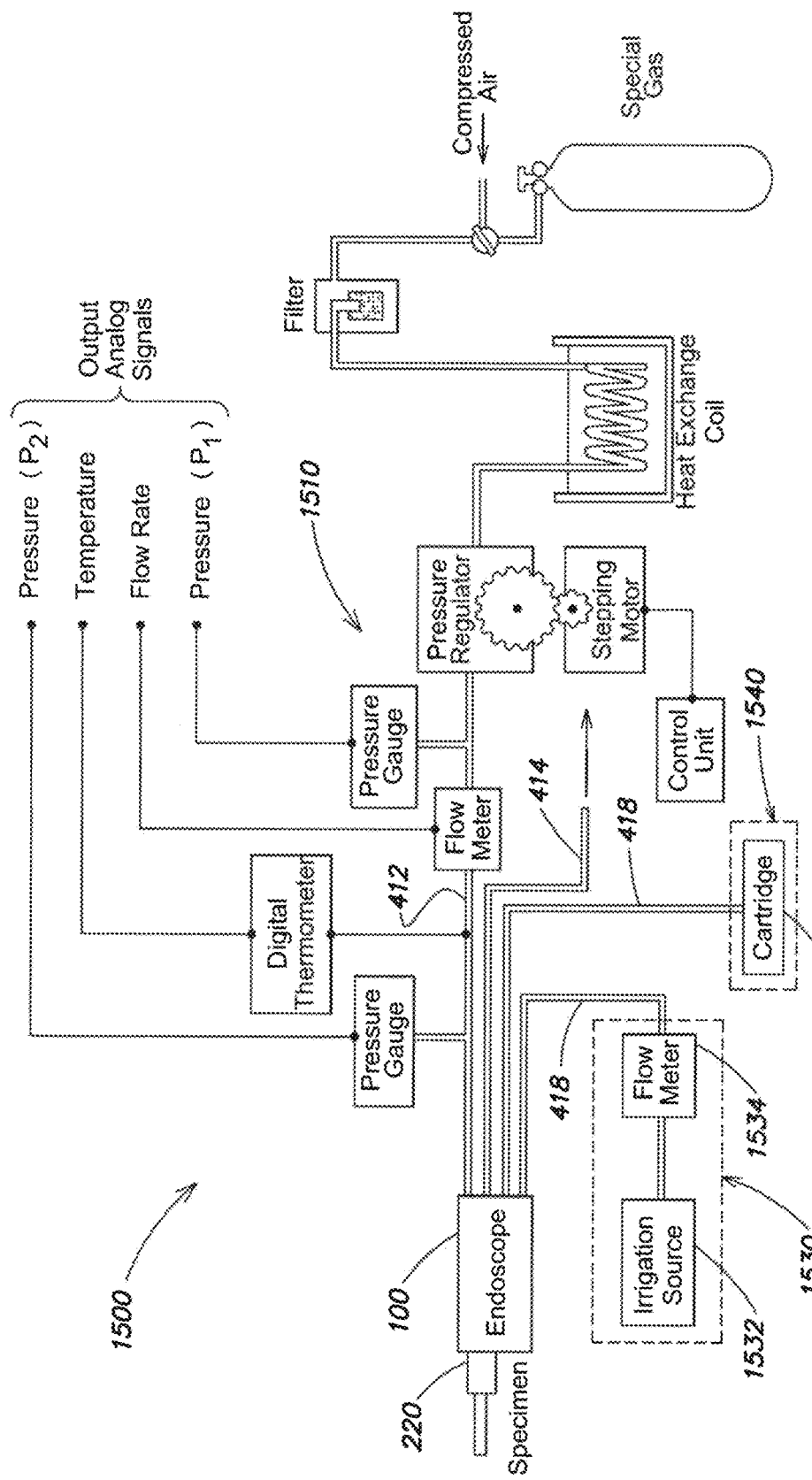
FIG. 15 is a conceptual system architecture diagram illustrating various components for operating the endoscopic instrument according to embodiments of the present disclosure.

Referring now to FIG. 15, a conceptual system architecture diagram illustrating various components for operating the endoscopic instrument according to embodiments of the present disclosure is shown. The endoscopic system 1500 includes an endoscope 100 fitted with an endoscopic instrument 220, and which may be coupled to an air supply measurement system 1510, an irrigation system 1530 and a polyp removal system 1540. As described above, the tubing that extends within the endoscope 100 may include one or more pneumatic air entry conduits 412 and one or more pneumatic air exit conduits 414. The pneumatic air entry conduits 412 are coupled to the air supply measurement system 1510, which includes one or more sensors, gauges, valves, and other components to control the amount of gas, such as air, being supplied to the endoscope 100 to drive the rotor 440. In some embodiments, the amount of air being supplied to the rotor 440 may be controlled using the air supply measurement system 1510. Furthermore, delivery of the air to actuate the rotor 440 may be manually controlled by the physician using the endoscope 100. In one embodiment, the physician may use a foot pedal or a hand-actuated lever to supply air to the rotor 440.

The pneumatic air exit conduit 414, however, may not be coupled to any component. As a result, air exiting from the rotor 440 may simply exit the endoscope via the pneumatic air exit conduit 414 into the atmosphere. In some embodiments, the pneumatic air exit conduit 414 may be coupled to the air supply measurement system 1510 such that the air exiting the pneumatic air exit conduit 414 is supplied back to the rotor via the pneumatic air entry conduit 412. It should be appreciated that a similar setup may be used for a hydraulically driven turbine system.

The endoscope 100 may also be coupled to the irrigation system 1530 via the irrigation fluid conduit 416. The irrigation system 1530 may include a flow meter 1534 coupled to an irrigation source 1532 for controlling the amount of fluid flowing from the irrigation source 1532 to the endoscope 100.

As described above, the endoscope 100 may also include a suction conduit 418 for removing polyps from within the patient's body. The suction conduit 418 may be coupled to the polyp removal system 1540, which may be configured to store the polyps. In various embodiments, the physician may be able to collect samples in one or more cartridges 1542 within the polyp removal system 1540 such that the removed polyps can be tested individually.

In various embodiments of the present disclosure, an endoscope, comprises a first end and a second end separated by a flexible housing, an instrument channel extending from the first end to the second end, and an endoscopic instrument comprising a debriding component and a sample retrieval conduit disposed within the instrument channel. The endoscopic instrument may further include a flexible tubing in which the sample retrieval conduit is partially disposed, the flexible tubing extending from the first end to the second end of the endoscope. The flexible tubing may also include a pneumatic air entry conduit and a fluid irrigation conduit. In various embodiments, the debriding component may include a turbine assembly and a cutting tool. In various embodiments in which the endoscope is configured to have a built in endoscopic instrument, the instrument channel may have a diameter that is larger than the instrument channels of existing endoscopes. In this way, larger portions of debrided material may be suctioned from within the patient's body without clogging the suction conduit.

In other embodiments, an endoscope may include a first end and a second end separated by a flexible housing; an instrument channel extending from the first end to the second end; and an endoscopic instrument coupled to the instrument channel at the first end of the endoscope, the endoscopic instrument comprising a debriding component and a sample retrieval conduit partially disposed within the instrument channel. In some embodiments, the endoscopic instrument may be removably attached to the endoscopic instrument.

In other embodiments of the present disclosure, an endoscopic system, includes an endoscope comprising a first end and a second end separated by a flexible housing and an instrument channel extending from the first end to the second end and an endoscopic instrument coupled to the instrument channel at the first end of the endoscope. The endoscopic instrument may include a debriding component and a flexible tubing having a length that is greater than the length of the endoscope. Moreover, the flexible tubing may include a sample retrieval conduit, an pneumatic air entry conduit, and a fluid irrigation conduit, a disposable cartridge configured to couple with the sample retrieval conduit proximal the second end of the endoscope, a pressurized air source configured to couple with the pneumatic air entry conduit proximal the second end of the endoscope, and a fluid irrigation source configured to couple with the fluid irrigation conduit proximal the second end of the endoscope. In various embodiments, the endoscope may also include at least one camera source and at least one light source. In some embodiments of the present disclosure, the pneumatic air entry conduit supplies pressurized air to a turbine assembly of the debriding component proximal the first end of the endoscope and the fluid irrigation conduit supplies irrigation fluid to the sample retrieval conduit proximal the first end of the endoscope.

Figure 16A:
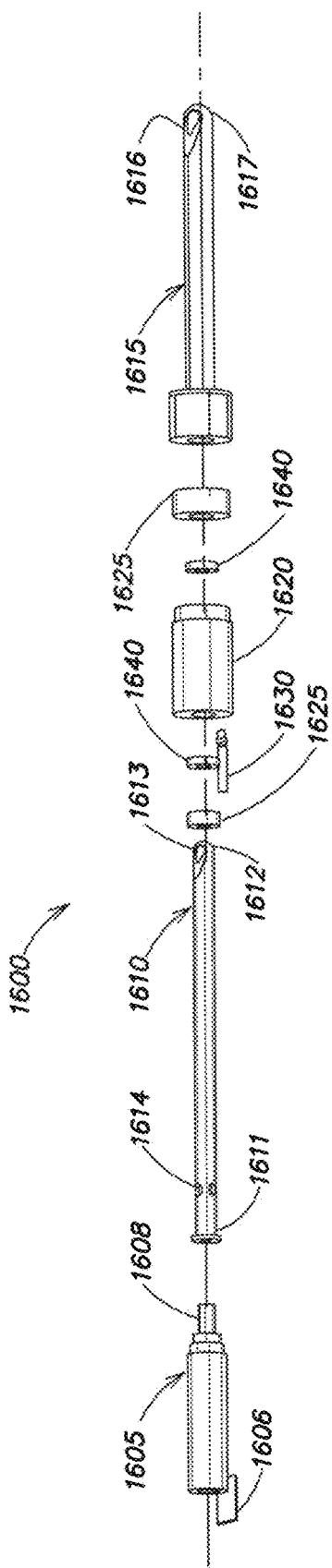
FIG. 16A illustrates an exploded view of an example endoscopic instrument according to embodiments of the present disclosure.
Figure 16B:
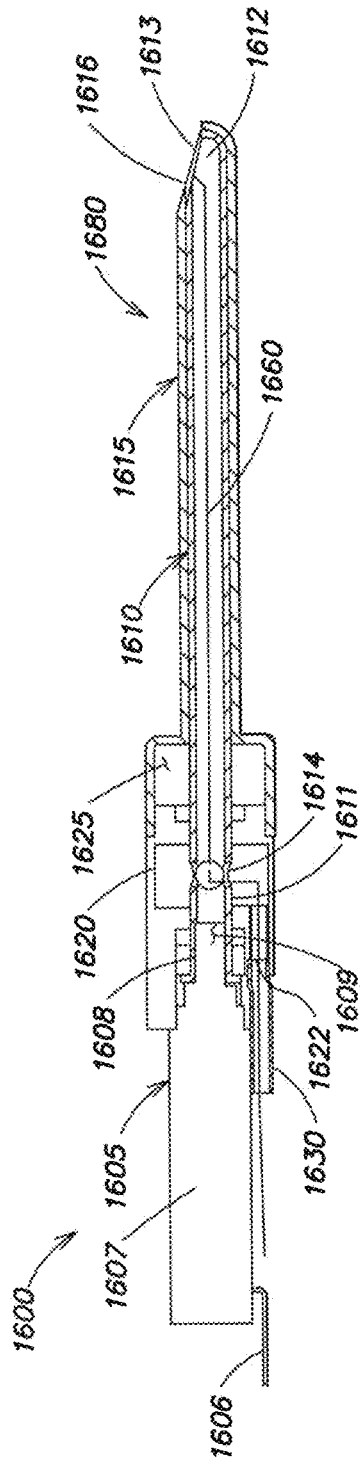
FIG. 16B illustrates a cross-sectional view of the endoscopic instrument shown in FIG. 16A according to embodiments of the present disclosure.

FIG. 16A illustrates an exploded partial view of an endoscopic instrument 1600, which is similar to the endoscopic instrument 150 depicted in FIG. 1C in that the endoscopic instrument 1600 is configured to be inserted within an instrument channel of an endoscope, such as the endoscope 100 depicted in FIG. 1B. FIG. 16B illustrates a cross-sectional partial view of the endoscopic instrument shown in FIG. 16A. As shown in FIGS. 16A and 16B, a head portion of the endoscopic instrument 1600 can include a powered actuator 1605, a power-driven instrument head 1680 including a cutting shaft 1610 and an outer structure 1615 and a feedthrough connector 1620 coupled to a distal end of a flexible tubular member 1630. The flexible tubular member 1630 forms the tail portion of the endoscopic instrument 1600. As such, FIGS. 16A and 16B illustrate the head portion of the endoscopic instrument 1600.

The endoscopic instrument 1600 is configured to define an aspiration channel 1660 that extends from a proximal end of the flexible tubular member 1630 to a distal tip 1614 of the power-driven instrument head 1680. In some implementations, the proximal end of the flexible tubular member 1630 may be configured to fluidly couple to a vacuum source. In this way, upon the application of a suction force at the proximal end of the flexible tubular member 1630, material at or around the distal tip 1614 of the power-driven instrument head 1680 can enter the endoscopic instrument 1600 at the distal tip and flow through the aspiration channel 1660 all the way to the proximal end of the flexible tubular member 1630.

The powered actuator 1605 can be configured to drive a power-driven instrument head 1680, which includes the cutting shaft 1610 disposed within the outer structure 1615. In some implementations, the powered actuator 1605 can include a drive shaft 1608 that is mechanically coupled to the cutting shaft 1610. In some implementations, one or more coupling elements may be used to couple the drive shaft 1608 to a proximal end 1611 of the cutting shaft 1610 such that the cutting shaft 1610 is driven by the drive shaft 1608. The powered actuator 1605 can be an electrically powered actuator. In some implementations, the electrically powered actuator can include an electrical terminal 1606 configured to receive an electrical conducting wire for providing electrical current to the electrically powered actuator 1605. In some implementations, the electrically powered actuator can include an electric motor. In some implementations, the electric motor can be a micro-sized motor, such that the motor has an outer diameter of less than a few millimeters. In some implementations, the powered actuator 1605 has an outer diameter that is smaller than about 3.8 mm. In addition to having a small footprint, the powered actuator 1605 may be configured to meet certain torque and rotation speed parameters. In some implementations, the powered actuator 1605 can be configured to generate enough torque and/or rotate at sufficient speeds to be able to cut tissue from within a subject. Examples of motors that meet these requirements include micromotors made by Maxon Precision Motors, Inc., located in Fall River, Mass., USA. Other examples of electrical motors include any type of electric motors, including AC motors, DC motors, piezoelectric motors, amongst others.

The power-driven instrument head 1680 is configured to couple to the powered actuator 1605 such that the powered actuator 1605 can drive the power-driven instrument head. As described above, the proximal end 1611 of the cutting shaft 1610 can be configured to couple to the drive shaft 1608 of the powered actuator 1605. The distal end 1614 of the cutting shaft 1610 opposite the proximal end 1611 can include a cutting tip 1612. The cutting tip 1612 can include one or more sharp surfaces capable of cutting tissue. In some implementations, the cutting shaft 1610 can be hollow and can define a material entry port 1613 at or around the cutting tip 1612 through which material that is cut can enter the endoscopic instrument 1610 via the material entry port 1613. In some implementations, the proximal end 1611 of the cutting shaft 1610 can include one or more outlet holes 1614 that are sized to allow material flowing from the material entry port 1613 to exit from the cutting shaft 1610. As shown in FIGS. 16A and 16B, the outlet holes 1614 are defined within the walls of the cutting shaft 1610. In some implementations, these outlet holes 1614 can be sized such that material entering the cutting shaft 1610 via the material entry port 1613 can flow out of the cutting shaft 1610 via the outlet holes 1614. In some implementations, the portion of the cutting shaft 1610 proximal the drive shaft 1608 may be solid such that all the material that enters the cutting shaft 1610 flows out of the cutting shaft 1610 via the outlet holes 1614.

The outer structure 1615 can be hollow and configured such that the cutting shaft can be disposed within the outer structure 1615. As such, the outer structure 1615 has an inner diameter that is larger than the outer diameter of the cutting shaft 1610. In some implementations, the outer structure 1615 is sized such that the cutting shaft 1610 can rotate freely within the outer structure 1615 without touching the inner walls of the outer structure 1615. The outer structure 1615 can include an opening 1616 at a distal end 1617 of the outer structure 1615 such that when the cutting shaft 1610 is disposed within the outer structure 1615, the cutting tip 1612 and the material entry port 1613 defined in the cutting shaft 1610 is exposed. In some implementations, the outer surface of the cutting shaft 1610 and the inner surface of the outer structure 1615 can be coated with a heat-resistant coating to help reduce the generation of heat when the cutting shaft 1610 is rotating within the outer structure 1615. A proximal end of the outer structure 1615 is configured to attach to the housing that houses the powered actuator 1605.

The feedthrough connector 1620 can be positioned concentrically around the portion of the cutting shaft 1610 that defines the outlet holes 1614. In some implementations, the feedthrough connector 1620 can be hollow and configured to enclose the area around the outlet holes 1614 of the cutting shaft 1610 such that material leaving the outlet holes 1614 of the cutting shaft 1610 is contained within the feedthrough connector 1620. The feedthrough connector 1620 can include an exit port 1622, which can be configured to receive the distal end of the tubular member 1630. In this way, any material within the feedthrough connector 1620 can flow into the distal end of the flexible tubular member 1630. The feedthrough connector 1620 can serve as a fluid coupler that allows fluid communication between the cutting shaft 1610 and the tubular member 1630.

The tubular member 1630 can be configured to couple to the exit port 1622 of the feedthrough connector 1620. By way of the cutting shaft 160, the feedthrough connector 1620 and the flexible tubular member 1630, the aspiration channel 1660 extends from the material entry port 1613 of the cutting shaft 1610 to the proximal end of the tubular member 1630. In some implementations, the tubular member 1630 can be configured to couple to a vacuum source at the proximal end of the tubular member 1630. As such, when a vacuum source applies suction at the proximal end of the tubular member 1630, material can enter the aspiration channel via the material entry port 1613 of the cutting shaft 1610 and flow through the aspiration channel 1660 towards the vacuum source and out of the endoscopic instrument 1600. In this way, the aspiration channel 1660 extends from one end of the endoscopic instrument to the other end of the endoscopic instrument 1600. In some implementations, a vacuum source can be applied to the tubular member 1630 such that the material at the treatment site can be suctioned from the treatment site, through the aspiration channel 1660 and withdrawn from the endoscopic instrument 1600, while the endoscopic instrument 1600 remains disposed within the instrument channel of the endoscope and inside the subject being treated. In some implementations, one or more of the surfaces of the cutting shaft 1610, the feedthrough connector 1620 or the tubular member 1630 can be treated to improve the flow of fluid. For example, the inner surfaces of the cutting shaft 1610, the feedthrough connector 1620 or the tubular member 1630 may be coated with a superhydrophobic material to reduce the risk of material removed from within the patient from clogging the suction conduit.

Examples of various types of instrument heads that can be coupled to the powered actuator 1605 are disclosed in U.S. Pat. No. 4,368,734, U.S. Pat. No. 3,618,611, U.S. Pat. No. 5,217,479, U.S. Pat. No. 5,931,848 and U.S. Pat. Publication 2011/0087260, amongst others. In some other implementations, the instrument head can include any type of cutting tip that is capable of being driven by a powered actuator, such as the powered actuator 1650, and capable of cutting tissue into small enough pieces such that the tissue can be removed from the treatment site via the aspiration channel defined within the endoscopic instrument 1600. In some implementations, the power-driven instrument head 1680 may be configured to include a portion through which material from the treatment site can be removed. In some implementations, the circumference of the aspiration channel can be in the order of a few micrometers to a few millimeters.

In some implementations, where the powered actuator 1620 utilizes an electric current for operation, the current can be supplied via one or more conductive wires that electrically couple the powered actuator to an electrical current source. In some implementations, the electrical current source can be external to the endoscopic instrument 1600. In some implementations, the endoscopic instrument 1600 can include an energy storage component, such as a battery that is configured to supply electrical energy to the electrical actuator. In some implementations, the energy storage component can be positioned within the endoscopic instrument. In some implementations, the energy storage component or other power source may be configured to supply sufficient current to the powered actuator that cause the powered actuator to generate the desired amount of torque and/or speed to enable the cutting shaft 1610 to cut tissue material. In some implementations, the amount of torque that may be sufficient to cut tissue can be greater than or equal to about 2.5 N mm. In some implementations, the speed of rotation of the cutting shaft can be between 1000 and 5000 rpm. However, these torque ranges and speed ranges are examples and are not intended to be limiting in any manner.

The endoscopic instrument 1600 can include other components or elements, such as seals 1640 and bearings 1625, which are shown. In some implementations, the endoscopic instrument 1600 can include other components that are not shown herein but may be included in the endoscopic instrument 1600. Examples of such components can include sensors, cables, wires, as well as other components, for example, components for engaging with the inner wall of the instrument channel of an endoscope within which the endoscopic instrument can be inserted. In addition, the endoscopic instrument can include a housing that encases one or more of the powered actuator, the feedthrough connector 1620, any other components of the endoscopic instrument 1600. In some implementations, the tail portion of the endoscopic instrument 1600 can also include a flexible housing, similar to the flexible portion 165 shown in FIG. 1C, that can carry one or more flexible tubular members, such as the flexible tubular member 1630, as well as any other wires, cables or other components.

In some implementations, the endoscopic instrument can be configured to engage with the instrument channel of an endoscope in which the instrument is inserted. In some implementations, an outer surface of the head portion of the endoscopic instrument can engage with an inner wall of the instrument channel of the endoscope such that the endoscopic instrument does not experience any unnecessary or undesirable movements that may occur if endoscopic instrument is not supported by the instrument channel. In some implementations, the head portion of the body of the endoscopic instrument can include a securing mechanism that secures the head portion of the body to the inner wall of the instrument channel. In some implementations, the securing mechanism can include deploying a frictional element that engages with the inner wall. The frictional element can be a seal, an o-ring, a clip, amongst others.

FIG. 16C illustrates a schematic view of an engagement assembly of an example endoscopic instrument. FIG. 16D shows a cut-open view of the engagement assembly when the engagement assembly is disengaged. FIG. 16E shows a cut-open view of the engagement assembly when the engagement assembly is configured to engage with an instrument channel of an endoscope. As shown in FIGS. 16C and 16D, the engagement assembly 1650 includes a housing portion 1652 that defines a cylindrical groove 1654 around an outer surface 1656 of the housing portion. The groove 1654 is sized such that a compliant seal component 1670 can be partially seated within the groove 1654. A cylindrical actuation member 1660 is configured to encompass the housing portion 1652. The cylindrical actuation member 1660 can slidably move along the length of the housing portion 1652. The cylindrical actuation member 1660 is configured to engage the securing member 1670 by pressing on the surface of the securing member 1670. The actuation member 1660 can apply a force on the securing member 1670 causing the securing member 1670 to deform such that the securing member 1670 becomes flatter and wider. The securing member 1670 is configured such that when the securing member 1670 widens, the outer surface of the securing member 1670 can engage with an inner surface of the instrument channel of an endoscope in which the endoscopic instrument is inserted. In this way, when the cylindrical actuation member 1660 is actuated, the endoscopic instrument 1600 can engage with the instrument channel thereby preventing the endoscopic instrument 1600 from moving relative to the instrument channel. This can help provide stability to the operator while treating the subject. In some implementations, more than one engagement assembly 1650 can be positioned along various portions of the endoscopic instrument 1600.

FIG. 17A illustrates an exploded view of an example endoscopic instrument 1700 according to embodiments of the present disclosure. FIG. 17B illustrates a cross-sectional view of the endoscopic instrument 1700. The endoscopic instrument 1700, similar to the endoscopic instrument 1600 shown in FIGS. 16A and 16B, can also be configured to be inserted within an instrument channel of an endoscope, such as the endoscope 100 depicted in FIG. 1B. The endoscopic instrument 1700, however, differs from the endoscopic instrument 1600 in that the endoscopic instrument 1700 defines an aspiration channel 1760 that extends through a powered actuator 1705. In this way, material entering a material entry port 1713 of the endoscopic instrument 1700 can flow through the endoscopic instrument 1700 and out of the endoscopic instrument in a straight line.

As shown in FIGS. 17A and 17B, the endoscopic instrument 1700 is similar to the endoscopic instrument 1600 except that the endoscopic instrument includes a different powered actuator 1705, a different cutting shaft 1710 and a different feedthrough connector 1720. The powered actuator 1705 is similar to the powered actuator 1605 shown in FIG. 16A but differs in that the powered actuator 1705 includes a drive shaft 1708 that is hollow and extends through the length of the powered actuator 1705. Since some of the components are different, the manner in which the endoscopic instrument is assembled is also different.

In some implementations, the powered actuator 1605 can be any actuator capable of having a hollow shaft that extends through the length of the motor. The distal end 1708*a* of the drive shaft 1708 includes a first opening and is coupled to the proximal end 1711 of the cutting shaft 1705. Unlike the cutting shaft 1610, the cutting shaft 1710 includes a fluid outlet hole 1714 at the bottom of the cutting shaft 1710. As a result, the entire length of the cutting shaft 1710 is hollow. The proximal end 1708*b* of the drive shaft 1708 is configured to couple to the feedthrough connector 1720, which differs from the feedthrough connector 1620 in that the feedthrough connector 1720 includes a hollow bore 1722 defining a channel in line with the proximal end of the drive shaft such that the drive shaft 1708 and the hollow bore 1722 are fluidly coupled. The hollow bore 1722 can be configured to couple to the flexible tubular member 1730, which like the flexible tubular member 1630, extends from the feedthrough connector at a distal end to a proximal end that is configured to couple to a vacuum source.

As shown in FIGS. 17A and 17B, the drive shaft 1708 can be hollow, such that the drive shaft 1708 defines a first opening at a distal end 1708*a* and a second opening at a proximal end 1708*b* of the drive shaft 1708. The cutting shaft 1710 is also hollow and defines an opening 1714 at the bottom end 1710*a* of the cutting shaft 1710. The distal end 1708*a* of the drive shaft 1708 is configured to couple to the bottom end 1710*a* of the cutting shaft 1710 such that the first opening of the drive shaft 1708 is aligned with the opening at the bottom end 1710*a* of the cutting shaft 1710. In this way, the drive shaft 1708 can be fluidly coupled to the cutting shaft 1710. A distal end 1710*b* of the cutting shaft 1710 includes a cutting tip 1712 and the material entry port 1713.

The proximal end 1708*a* of the drive shaft 1708 is fluidly coupled to a distal end of the flexible tubular member 1730 via the feedthrough connector 1720. In some implementations, the feedthrough connector 1720 couples the drive shaft and the flexible tubular member such that the flexible tubular member does not rotate with the drive shaft. The proximal end of the flexible tubular member can be configured to couple to a vacuum source.

As shown in FIG. 17B, the endoscopic instrument 1700 defines an aspiration channel 1760 that extends from the material entry port 1713 through the cutting shaft, the drive shaft, the feedthrough connector 1720 to the second end of the flexible tubular member 1730. In this way, material that enters the material entry port 1713 can flow through the length of the endoscopic instrument and exit from the endoscopic instrument at the second end of the endoscopic instrument.

Other components of the endoscopic instrument 1700 are similar to those shown in the endoscopic instrument 1600 depicted in FIGS. 16A and 16B. For example, the outer structure 1715, the encoding component 1606, the seals and the bearings may be substantially similar to the outer structure 1615, the encoding component 1606, the seals 1640 and the bearings 1625 depicted in FIG. 16. Other components, some of which are shown, may be included to construct the endoscopic instrument and for proper functioning of the instrument.

FIG. 18A illustrates an exploded view of an example endoscopic instrument 1800 according to embodiments of the present disclosure. FIG. 18B illustrates a cross-sectional view of the endoscopic instrument 1800. The endoscopic instrument 1800, similar to the endoscopic instrument 1700 shown in FIGS. 17A and 17B, can also be configured to be inserted within an instrument channel of an endoscope, such as the endoscope 100 depicted in FIG. 1B. The endoscopic instrument 1800, however, differs from the endoscopic instrument 1700 in that the endoscopic instrument 1800 includes a pneumatic or hydraulically powered actuator 1805.

In some implementations, the powered actuator 1802 includes a tesla turbine that includes a tesla rotor 1805, a housing 1806 and a connector 1830 that along with the housing 1806 encases the tesla rotor 1805. The tesla rotor 1805 can include a plurality of disks 1807 spaced apart and sized such that the tesla rotor 1805 fits within the housing.

In some implementations, the tesla rotor can include between 7 and 13 disks having a diameter between about 2.5 mm and 3.5 mm and thicknesses between 0.5 mm to 1.5 mm. In some implementations, the disks are separated by gaps that range from 0.2 mm to 1 mm. The tesla turbine 1802 also can include a hollow drive shaft 1808 that extends along a center of the tesla rotor 1805. In some implementations, a distal end 1808*a* of the drive shaft 1808 is configured to be coupled to a cutting shaft 1810 such that the cutting shaft 1810 is driven by the tesla rotor. That is, in some implementations, the cutting shaft 1810 rotates as the drive shaft 1808 of the tesla rotor 1805 is rotating. In some implementations, the cutting shaft 1810 can include outlet holes similar to the cutting shaft 1610 shown in FIG. 16A. In some such implementations, the feedthrough connector fluidly couples the cutting shaft and the flexible portion similar to the feedthrough connector 1630 shown in FIG. 16A.

The connector 1830 of the tesla turbine 1802 can include at least one fluid inlet port 1832 and at least one fluid outlet port 1834. In some implementations, the fluid inlet port 1832 and the fluid outlet port 1834 are configured such that fluid can enter the tesla turbine 1802 via the fluid inlet port 1832, cause the tesla rotor 1805 to rotate, and exit the tesla turbine 1802 via the fluid outlet port 1834. In some implementations, the fluid inlet port 1832 is fluidly coupled to a fluid inlet tubular member 1842 configured to supply fluid to the tesla rotor via the fluid inlet port 1832. The fluid outlet port 1834 is fluidly coupled to a fluid outlet tubular member 1844 and configured to remove the fluid supplied to the tesla turbine 1802. The amount of fluid being supplied and removed from the tesla turbine 1802 can be configured such that the tesla rotor 1805 can generate sufficient torque, while rotating at a sufficient speed to cause the cutting shaft 1810 to cut tissue at a treatment site. In some implementations, the fluid can be air or any other suitable gas. In some other implementations, the fluid can be any suitable liquid, such as water. Additional details related to how fluid can be supplied or removed from pneumatic or hydraulic actuators, such as the tesla turbine 1802 has been described above with respect to FIGS. 4A-15.

The connector 1830 also includes a suction port 1836 that is configured to couple to an opening defined at a proximal end 1808*b* of the hollow drive shaft 1808. The suction port 1836 is further configured to couple to a distal end of a flexible tubular member 1846, similar to the flexible tubular member 1730 shown in FIG. 17A, which is configured to couple to a vacuum source at a proximal end. In some implementations, a flexible tubular housing can include one or more of the fluid inlet tubular member 184, fluid outlet tubular member 1844 and the flexible tubular member 1846. In some implementations, the flexible tubular housing can include other tubular members and components that extend from the head portion of the endoscopic instrument to the proximal end of the tail portion of the endoscopic instrument 1800.

The cutting shaft 1810 and an outer structure 1815 are similar to the cutting shaft 1710 and the outer structure 1715 of the endoscopic instrument 1700 depicted in FIG. 17A. The cutting shaft 1810 is hollow and defines an opening at a proximal end 1810*b* of the cutting shaft 1810. The proximal end 1810*b* of the cutting shaft 1810 is configured to couple to a distal end 1808*a* of the drive shaft 1808 such that an opening at the distal end 1808*a* of the drive shaft 1808 is aligned with the opening defined at the proximal end 1808*b* of the cutting shaft 1810. In this way, the drive shaft 1808 can be fluidly coupled to the cutting shaft 1810. A distal end 1810*b* of the cutting shaft 1810 includes a cutting tip 1812 and a material entry port 1813 similar to the cutting shafts 1610 and 1710 shown in FIGS. 16A and 17A.

In some implementations, an irrigation opening 1852 can be formed in the housing 1806. The irrigation opening 1852 is configured to be fluidly coupled to the aspiration channel 1860. In some such implementations, the irrigation opening 1852 is configured to be fluidly coupled to a gap (not clearly visible) that separates the walls of outer structure 1815 and the cutting shaft 1810. In this way, fluid supplied to the tesla turbine 1802 can escape via the irrigation opening 1852 in to the gap. The fluid can flow towards the material entry port 1813 of the cutting shaft 1810, through which the fluid can enter the aspiration channel 1860. In some implementations, since the aspiration channel 1860 is fluidly coupled to a vacuum source, the fluid from the tesla turbine 1802 can be directed to flow through the aspiration channel 1860 as irrigation fluid along with any other material near the material entry port 1813. In this way, the irrigation fluid can irrigate the aspiration channel 1860 to reduce the risk of blockages.

In addition, as the irrigation fluid flows in the gap separating the outer structure 1815 and the cutting shaft 1810, the irrigation fluid can serve to reduce the generation of heat. In some implementations, one or both of the cutting shaft 1810 and the outer structure 1815 can be coated with a heat-resistant layer to prevent the cutting shaft and the outer structure from getting hot. In some implementations, one or both of the cutting shaft 1810 and the outer structure 1815 can be surrounded by a heat-resistant sleeve to prevent the cutting shaft 1810 and the outer structure 1815 from getting hot.

In some implementations, other types of hydraulically or pneumatically powered actuators can be utilized in place of the tesla turbine. In some implementations, a multi-vane rotor can be used. In some such implementations, the powered actuator can be configured to be fluidly coupled to a fluid inlet tubular member and a fluid outlet tubular member similar to the tubular members 1842 and 1844 shown in FIG. 18B.

As described above with respect to the endoscopic instruments 1600, 1700 and 1800 depicted in FIGS. 16A, 17A and 18A, an endoscopic instrument is configured to meet certain size requirements. In particular, the endoscopic instrument can be long enough such that when the endoscopic instrument is completely inserted into the endoscope, the power-driven instrument head can extend beyond the face of the endoscope at one end such that the cutting tip is exposed, while the tail portion of the endoscopic instrument can extend out of the other end of the endoscope such that the tail portion can be coupled to a vacuum source. As such, in some implementations, the endoscopic instrument may be configured to be longer than the endoscopes in to which the endoscopic instrument will be inserted. Further, since endoscopes have instrument channels that have different diameters, the endoscopic instrument may also be configured to have an outer diameter that is sufficiently small such that the endoscopic instrument can be inserted into the instrument channel of the endoscope in to which the endoscopic instrument will be inserted.

Some endoscopes, such as colonoscopes, can have instrument channels that have an inner diameter that can be as small as a few millimeters. In some implementations, the outer diameter of the endoscopic instrument can be less than about 3.2 mm. As such, powered actuators that are part of the endoscopic instrument may be configured to have an outer diameter than is less than the outer diameter of the endoscopic instrument. At the same time, the powered actuators may be configured to be able to generate sufficient amounts of torque, while rotating at speeds sufficient to cut tissue at a treatment site within a subject.

In some other implementations, the endoscopic instrument can be configured such that a powered actuator is not housed within the endoscopic instrument at all or at least within a portion of the endoscopic instrument that can be inserted within the instrument channel of an endoscope. Rather, the endoscopic instrument includes a flexible cable that is configured to couple a power-driven instrument head of the endoscopic instrument to a powered actuator that is located outside of the endoscope.

Figure 19A:
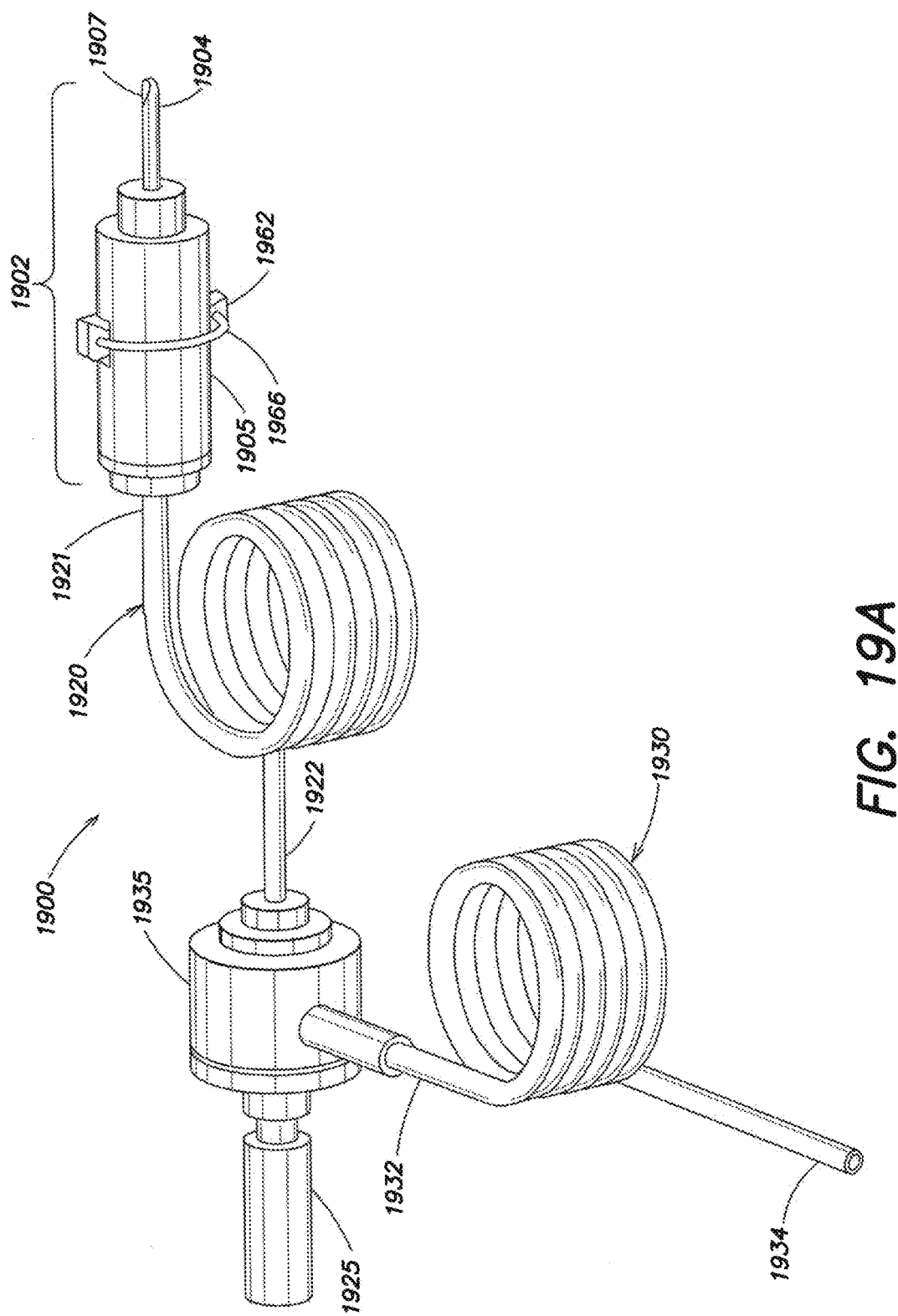
FIG. 19A illustrates an example endoscopic instrument that is coupled to a powered actuation and vacuum system according to embodiments of the present disclosure.

FIG. 19A illustrates an example endoscopic instrument 1900 that is coupled to a powered actuation and vacuum system 1980. The endoscopic instrument includes a head portion 1902 and a tail portion. The tail portion includes the flexible cable 1920, which can provide torque to the head portion 1902. The powered actuation and vacuum system 1980 includes a powered actuator 1925, a coupler 1935 and a vacuum tubing 1930 configured to couple to the couple 1935 at a first end 1932 and couple to a vacuum source at a second end 1934. In some implementations, the flexible cable 1920 can be hollow and configured to carry fluid from the head portion 1902 to the coupler 1935.

Figure 19B:
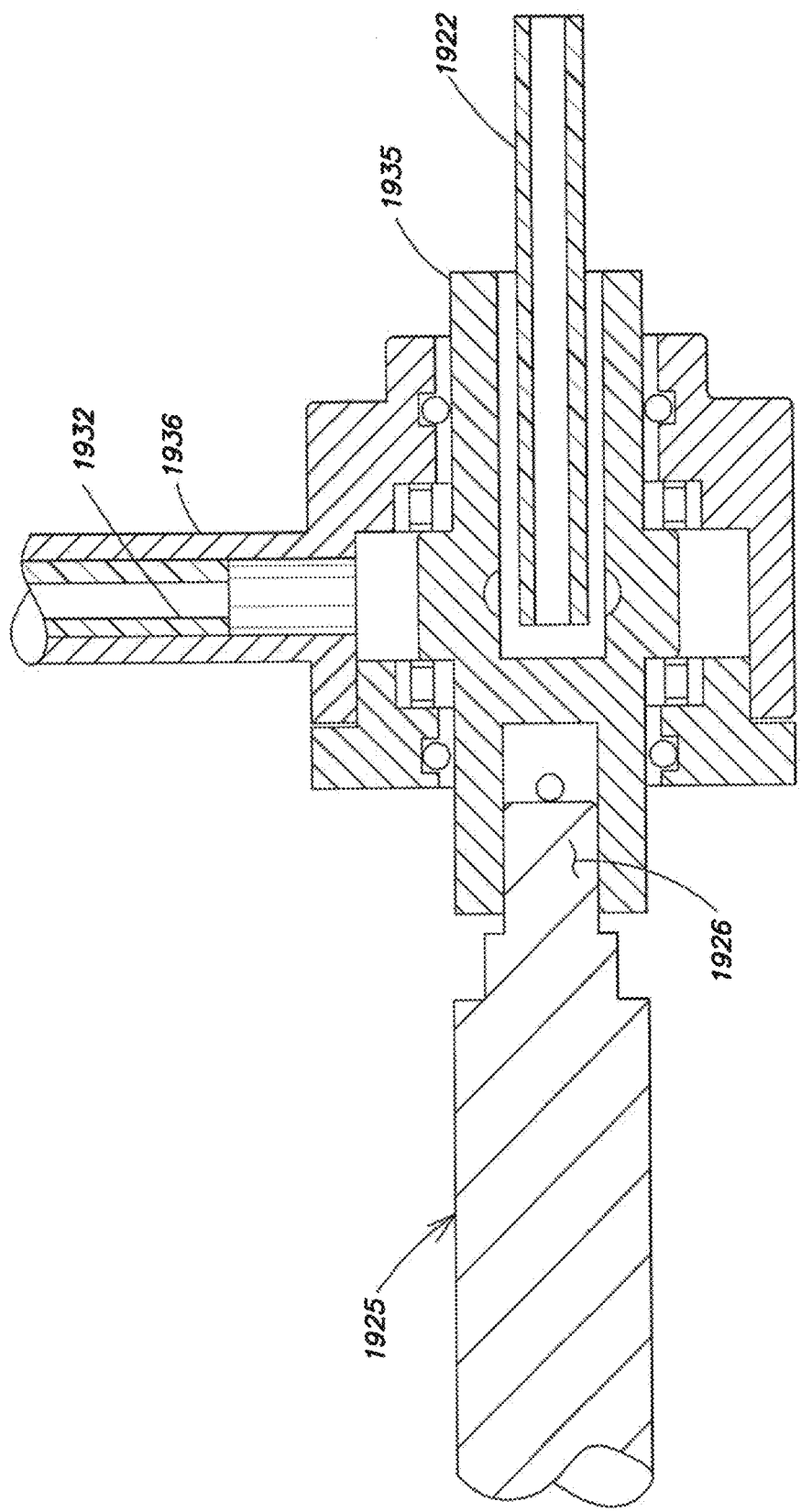
FIG. 19B illustrates a cross-section view of the powered actuation and vacuum system shown in FIG. 19A according to embodiments of the present disclosure.

FIG. 19B illustrates a cross-section view of the powered actuation and vacuum system 1980 of FIG. 19A. The powered actuator 1925 includes a drive shaft 1926 that is mechanically coupled to a proximal end 1922 of the flexible cable 1920. In some implementations, the drive shaft 1926 and the flexible cable 1920 are mechanically coupled via the coupler 1935. The coupler 1935 includes a vacuum port 1936 to which a first end 1932 of the vacuum tubing 1930 can be fluidly coupled. The coupler 1935 can be enclosed such that the vacuum tubing 1930 and the flexible cable are fluidly coupled. In this way, suction applied in the vacuum tubing 1930 can be applied all the way through the flexible cable 1920 to the head portion 1902 of the endoscopic instrument 1900. Further, any material that is in the flexible cable 1920 can flow through the flexible cable to the vacuum tubing 1930 via the coupler 1935. In some implementations, the coupling between the flexible cable and the vacuum tubing can occur within the head portion 1902. In such implementations, the coupler 1935 may be configured to be small enough to be positioned within the head portion 1902.

Figure 19C:
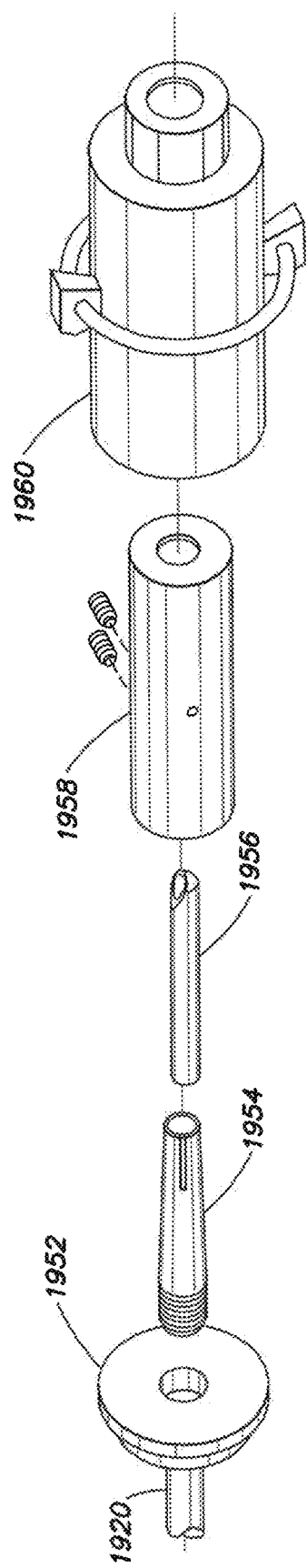
FIG. 19C illustrates an exploded view of an example head portion of the endoscopic instrument shown in FIG. 19A according to embodiments of the present disclosure.

FIG. 19C illustrates an exploded view of an example head portion of the endoscopic instrument 1900 shown in FIG. 19A. The head portion includes a housing cap 1952, a collet 1954, a cutting shaft 1956, a shaft coupler 1958 and a head portion housing 1960. In some implementations, the collet 1954 is slightly tapered towards a distal end such that the collet 1954 can couple with the cutting shaft 1956 that is disposed within the collet 1954. The shaft coupler 1958 is configured to couple the cutting shaft to the distal end of the flexible cable 1920. The head portion 1960 and the housing cap 1952 are configured to house the shaft coupler 1958.

Figure 19D:
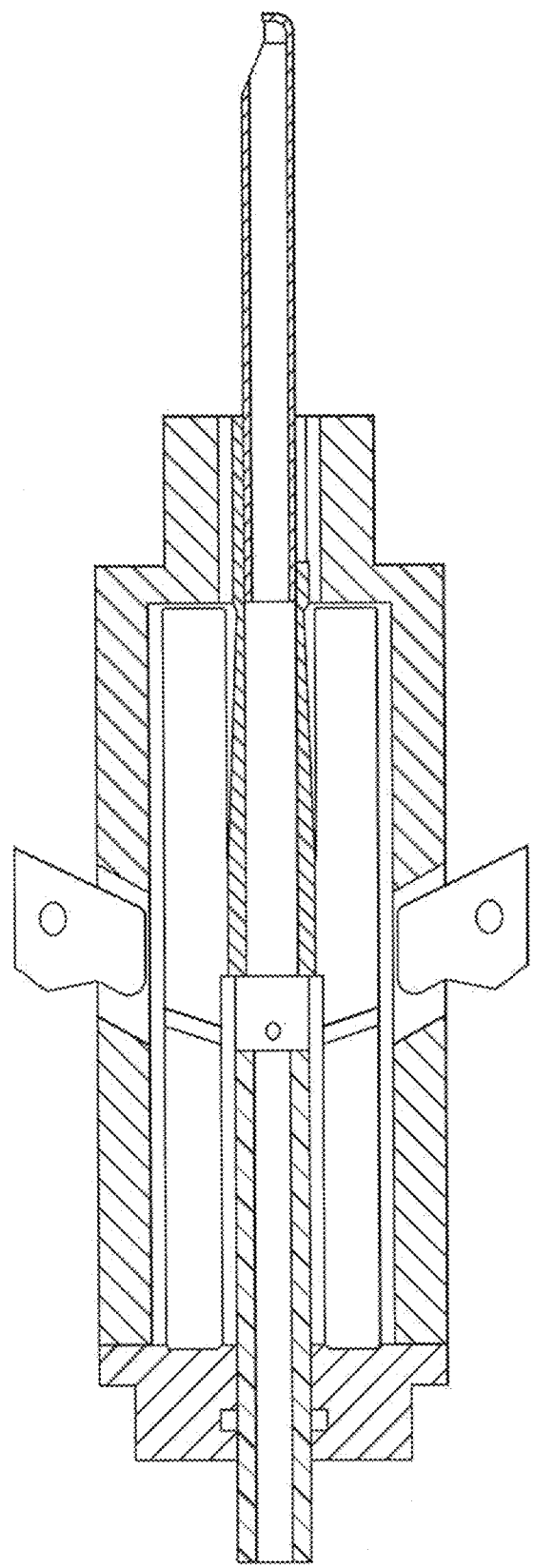
FIG. 19D illustrates a cut-open view of a portion of the endoscopic instrument having an engagement assembly according to embodiments of the present disclosure

FIG. 19D illustrates a cut-open view of a portion of the endoscopic instrument 1900 having an engagement assembly. In some implementations, the head portion housing 1960 can include an engagement assembly for engaging with the inner walls of an instrument channel. The engagement assembly can be similar to the engagement assembly 1650 shown in FIG. 16C. In some implementations, the engagement assembly can be actuated via a vacuum source. FIG. 19E shows a cut-open view of the engagement assembly shown in FIG. 19D in a disengaged position. FIG. 19F shows a cut-open view of the engagement assembly shown in FIG. 19D in an engaged position.

The engagement assembly can include a pair of vacuum actuated members 1962 that are configured to rotate between an extended position in which the members 1962 are extended outwardly to engage with a wall of the instrument channel 1990 and a retracted position in which the members 1962 are positioned such that they lie substantially parallel to the walls of the instrument channel 1990. The grooves 1964 are fluidly coupled to an aspiration channel 1970 defined within the flexible cable 1920. In some implementations, fluid channels 1966 fluidly couple the grooves 1964 to the aspiration channel 1970. When a vacuum source is applied to the aspiration channel 1970, a suction force is applied to the members 1962 causing them to move from a retracted position (as shown in FIG. 19E) to an extended position (as shown in FIG. 19F). In some implementations, the engagement assembly can also include an outer ring supported by the vacuum actuated members 1964. The outer ring 1966 can be configured to assist in guiding the endoscopic instrument through the instrument channel of the endoscope. In particular, the outer ring can prevent the endoscopic instrument from tilting to one side causing the power-driven instrument head from jarring against the instrument channel.

The endoscopic instrument 1900 is similar to the endoscopic instruments 1600, 1700 and 1800 depicted in FIGS. 16A-18A respectively but differs from them in that the endoscopic instrument 1900 does not include a powered actuator within the head portion 1902 of the endoscopic instrument 1900. Instead, the endoscopic instrument 1900 includes a flexible cable 1920 for providing torque to a power-driven instrument head 1904 of the endoscopic instrument 1900. In some implementations, the power-driven instrument head 1904 can be similar to the power-driven instrument heads depicted in FIGS. 16A-18A. In some implementations, the flexible cable 1920 can be hollow such that fluid can flow through the flexible cable 1920. In some such implementations, a proximal end 1922 of the flexible cable 1920 can be configured to couple to a vacuum source, while a distal end 1921 of the flexible cable 1920 can be coupled to the power-driven instrument head 1904. In this way, fluid that enters a material entry port 1907 can flow through the power-driven instrument head 1904 and into the flexible cable 1920, from which the fluid can flow through the flexible cable 1920 and be removed from the endoscopic instrument 1900 at the proximal end 1922 of the flexible cable 1920.

In some implementations, a flexible cable, such as the flexible cable 1920 can replace a powered actuator and drive shaft that are housed within an endoscopic instrument. For example, the endoscopic instruments 1600, 1700 and 1800 depicted in FIGS. 16A, 17A and 18A can be configured to utilize a flexible cable that is coupled to a cutting shaft of a power-driven instrument head at a distal end and coupled to a powered actuator located outside the endoscopic instrument at a proximal end. The powered actuator located outside the endoscopic instrument may be significantly larger than the powered actuators 1605, 1705 or 1805. As the powered actuator is actuated, torque generated by the powered actuator can be translated from the powered actuator to the power-driven instrument head via the flexible cable. The flexible cable 1920 is configured to translate torque from the powered actuator to the cutting shaft. In some implementations, the flexible cable 1920 is or includes a fine coil with multiple threads and multiple layers, which can transmit the rotation of one end of the flexible cable to an opposite end of the flexible cable. The flexibility of the cable allows the coil to maintain performance even in sections of the coil that are bent. Examples of the flexible cable 1920 include torque coils made by ASAHI INTECC USA, INC located in Santa Ana, Calif., USA. In some implementations, the flexible cable 1920 can be surrounded by a sheath to avoid frictional contact between the outer surface of the flexible cable and other surfaces. In some implementations, the flexible cable 1920 can be coated with Polytetrafluoroethylene (PFTE) to reduce frictional contact between the outer surface of the flexible cable and other surfaces.

Figure 20:
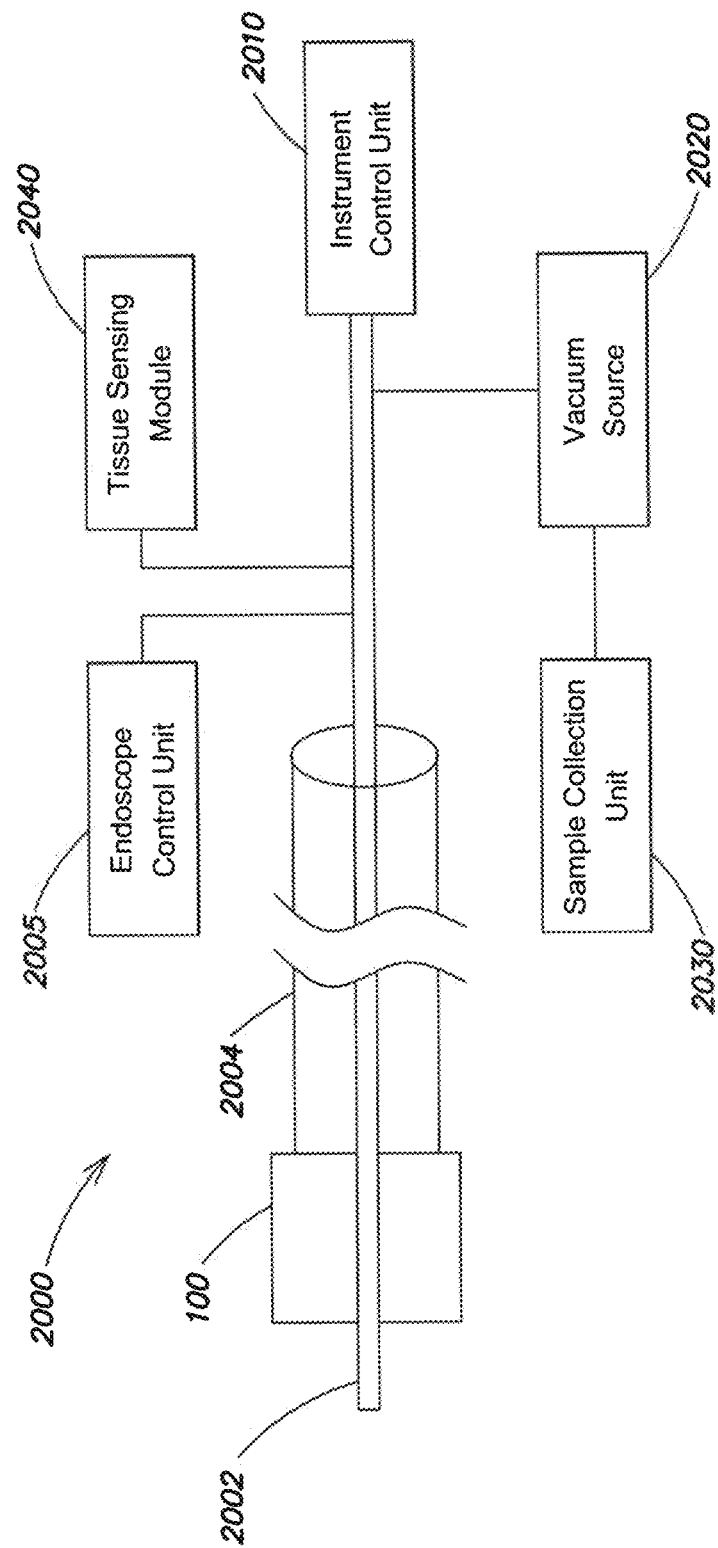
FIG. 20 is a conceptual system architecture diagram illustrating various components for operating the endoscopic instrument according to embodiments of the present disclosure.

FIG. 20 is a conceptual system architecture diagram illustrating various components for operating the endoscopic instrument according to embodiments of the present disclosure. The endoscopic system 2000 includes an endoscope 100 fitted with an endoscopic instrument 2002 that includes a flexible tail portion 2004. The endoscopic instrument can, for example, be the endoscopic instrument 220, 1600, 1700, 1800 or 1900 shown in FIGS. 4A-14, 16A, 17A, 18A and 19A. The system also includes an endoscope control unit 2005 that controls the operation of the endoscope 100 and an instrument control unit 2010 that controls the operation of the endoscopic instrument 2002.

In addition, the endoscopic instrument also includes a vacuum source 1990, a sample collection unit 2030 and a tissue sensing module 2040. The vacuum source 1990 is configured to fluidly couple to a flexible tubular member that forms a portion of the aspiration channel. In this way, material that flows from the endoscopic instrument through the aspiration channel towards the vacuum source 1990 can get collected at 2030 sample collection unit. The tissue sensing module can be communicatively coupled to a tissue sensor disposed at a distal tip of the endoscopic instrument 2000. In some such implementations, the tissue sensing module can also be configured to be communicatively coupled to the instrument control unit 2010 such that the tissue sensing module can send one or more signals instructing the control unit 2010 to stop the actuation of the powered actuator.

In some implementations in which the powered actuator is electrically actuated and disposed within the endoscopic instrument, the powered actuator can be electrically coupled to the instrument control unit 2010. In some such implementations, the powered actuator is coupled to the control unit via one or more electric cables. In some implementations, the powered actuator may be battery operated in which case, the tubing may include cables extending from the control unit to the powered actuator or the battery for actuating the powered actuator.

In some implementations in which the power-driven instrument head is coupled to a flexible torque coil that couples the power-driven instrument head to a powered actuator that resides outside of the endoscope, the powered actuator can be a part of the instrument control unit.

In various embodiments of the present disclosure, an endoscope, comprises a first end and a second end separated by a flexible housing, an instrument channel extending from the first end to the second end, and an endoscopic instrument comprising a debriding component and a sample retrieval conduit disposed within the instrument channel. The endoscopic instrument may further include a flexible tubing in which the sample retrieval conduit is partially disposed, the flexible tubing extending from the first end to the second end of the endoscope. The flexible tubing may also include a pneumatic air entry conduit and a fluid irrigation conduit. In various embodiments, the debriding component may include a turbine assembly and a cutting tool. In various embodiments in which the endoscope is configured to have a built in endoscopic instrument, the instrument channel may have a diameter that is larger than the instrument channels of existing endoscopes. In this way, larger portions of debrided material may be suctioned from within the patient's body without clogging the suction conduit.

In other embodiments, an endoscope may include a first end and a second end separated by a flexible housing; an instrument channel extending from the first end to the second end; and an endoscopic instrument coupled to the instrument channel at the first end of the endoscope, the endoscopic instrument comprising a debriding component and a sample retrieval conduit partially disposed within the instrument channel. In some embodiments, the endoscopic instrument may be removably attached to the endoscopic instrument.

In other embodiments of the present disclosure, an endoscopic system, includes an endoscope comprising a first end and a second end separated by a flexible housing and an instrument channel extending from the first end to the second end and an endoscopic instrument coupled to the instrument channel at the first end of the endoscope. The endoscopic instrument may include a debriding component and a flexible tubing having a length that is greater than the length of the endoscope. Moreover, the flexible tubing may include a sample retrieval conduit, a pneumatic air entry conduit, and a fluid irrigation conduit, a disposable cartridge configured to couple with the sample retrieval conduit proximal the second end of the endoscope, a pressurized air source configured to couple with the pneumatic air entry conduit proximal the second end of the endoscope, and a fluid irrigation source configured to couple with the fluid irrigation conduit proximal the second end of the endoscope. In various embodiments, the endoscope may also include at least one camera source and at least one light source. In some embodiments of the present disclosure, the pneumatic air entry conduit supplies pressurized air to a turbine assembly of the debriding component proximal the first end of the endoscope and the fluid irrigation conduit supplies irrigation fluid to the sample retrieval conduit proximal the first end of the endoscope.

As described above with respect to FIGS. 19A-19C, the endoscopic tool can include a flexible cable that can be configured to be driven by a powered actuator that resides outside the endoscopic tool itself. The flexible cable can be a torque coil or rope.

Figure 21B:
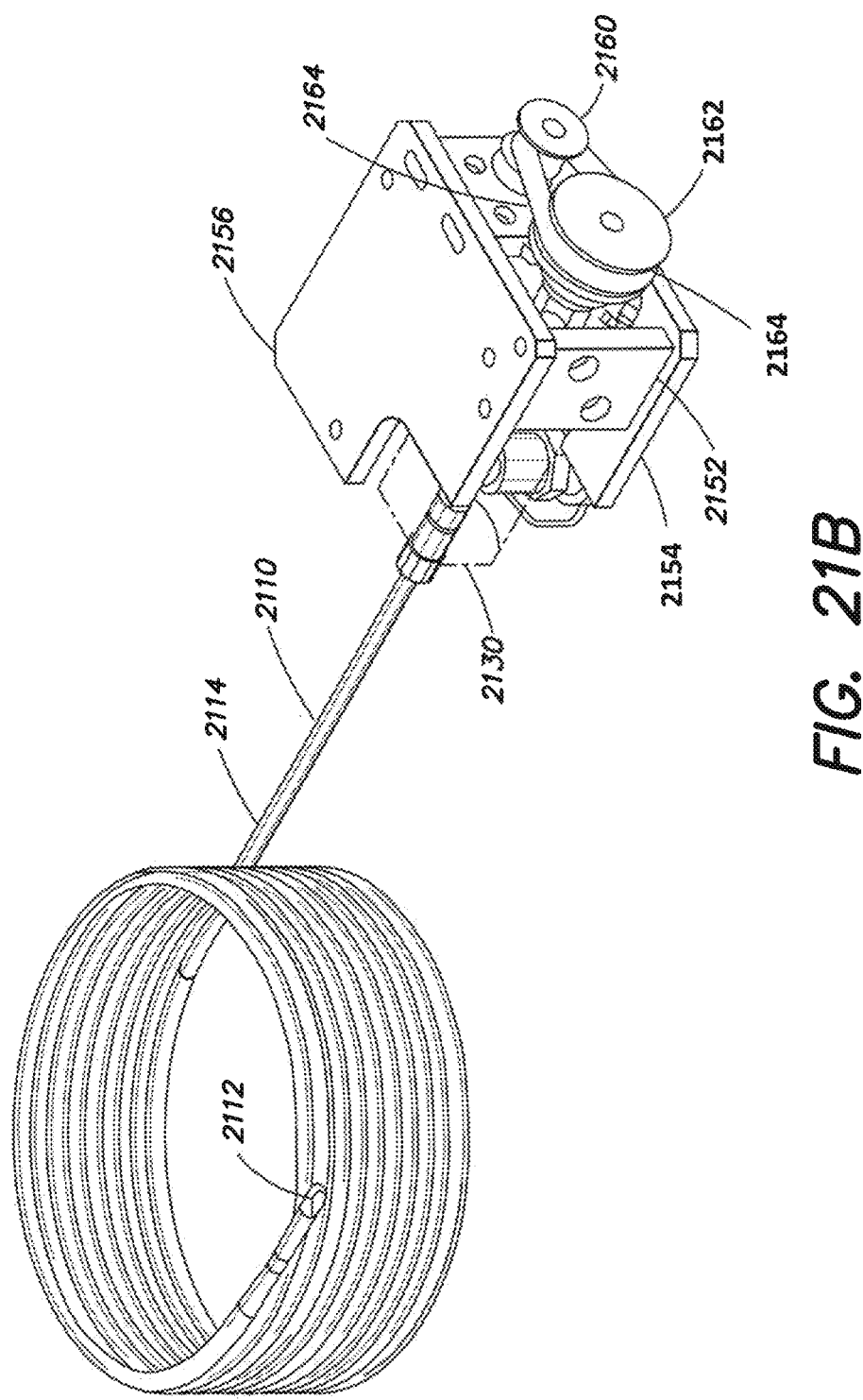
FIGS. 21AA-21F illustrate aspects of an endoscopic assembly according to embodiments of the present disclosure.
Figure 21C:
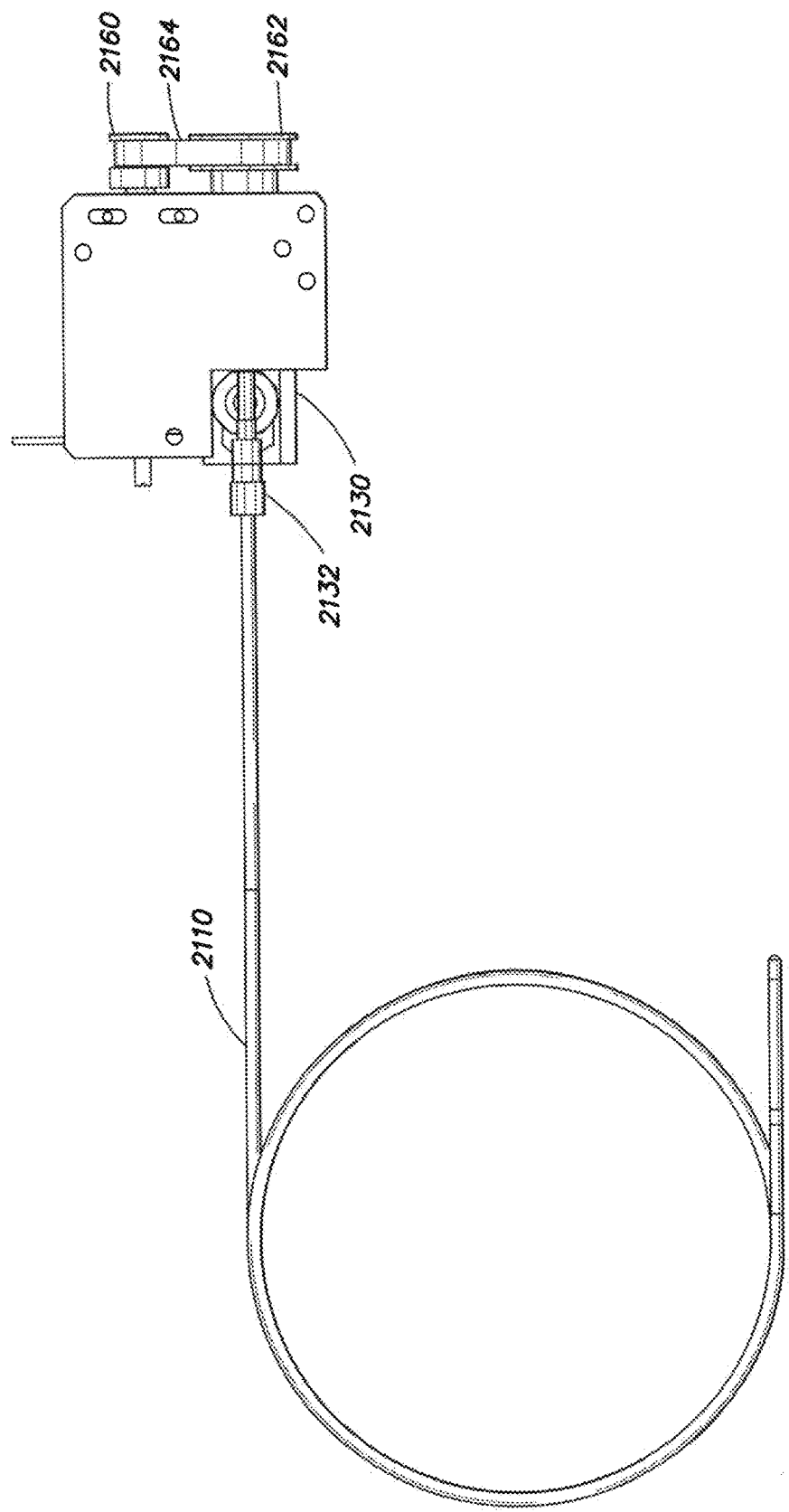
Figure 21D:
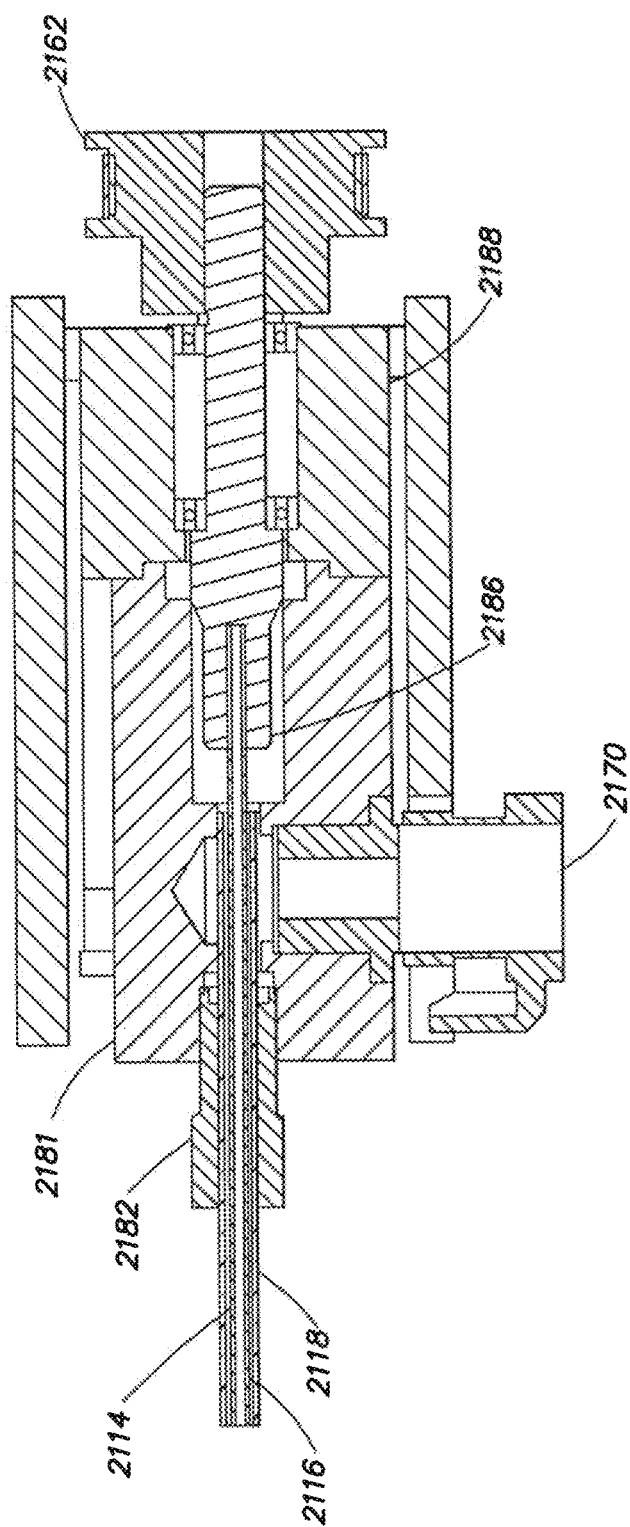
Figure 22B:
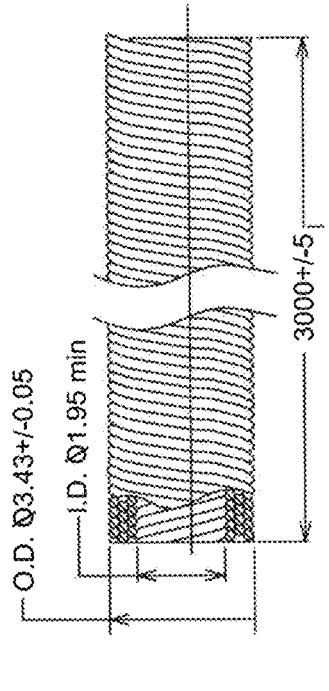
FIGS. 22A-22H show various implementations of example flexible cables according to embodiments of the present disclosure.
Figure 22D:
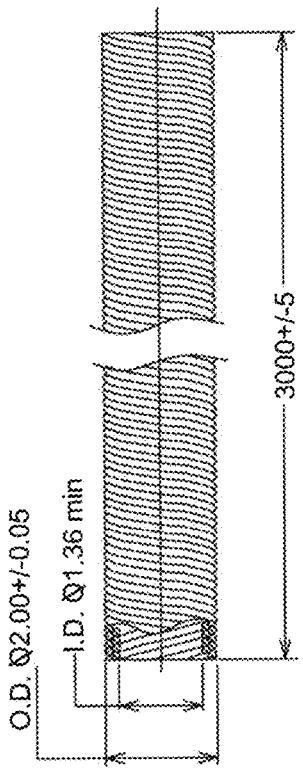
Figure 22A:
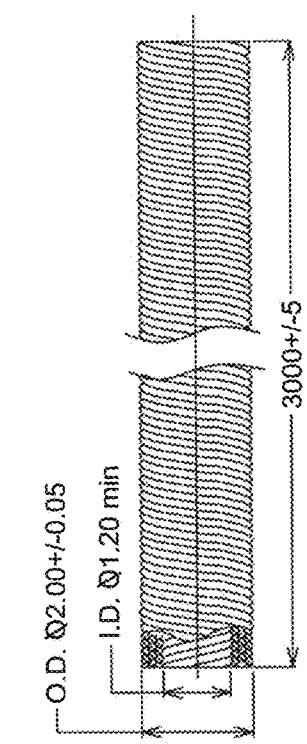
Figure 22C:
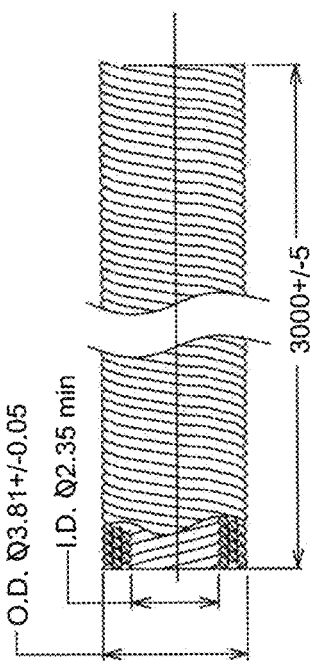
Figure 22E:
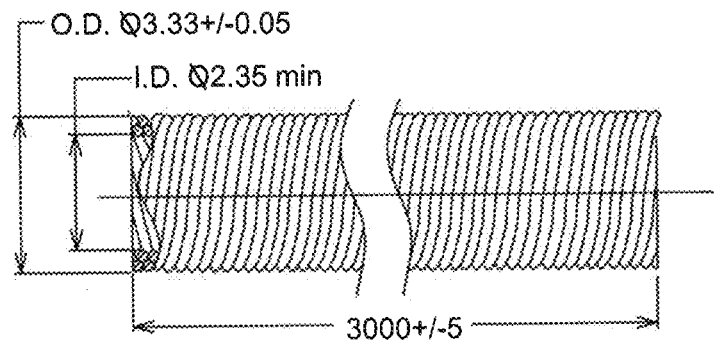
Figure 22F:
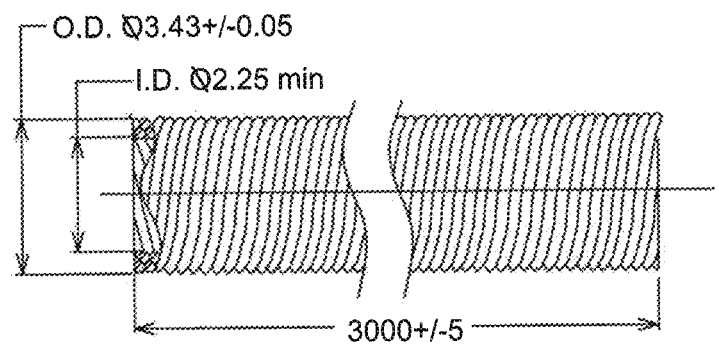
Figure 22G:
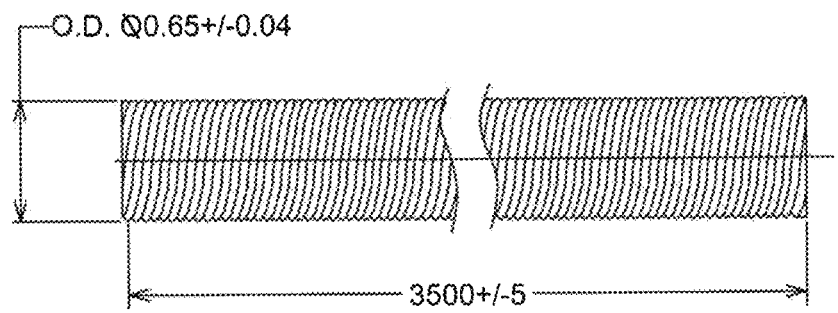
Figure 22H:
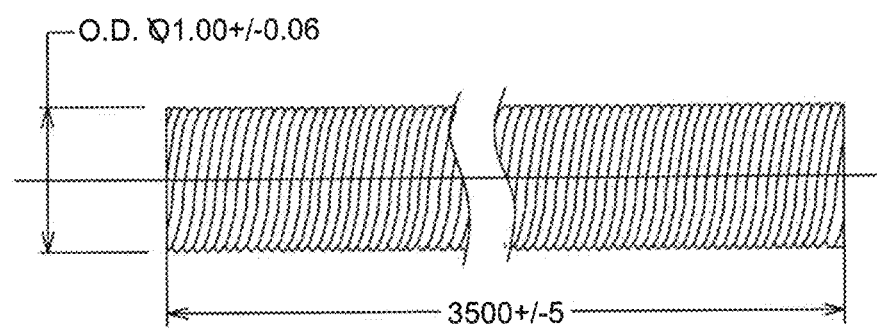
Figure 26A:
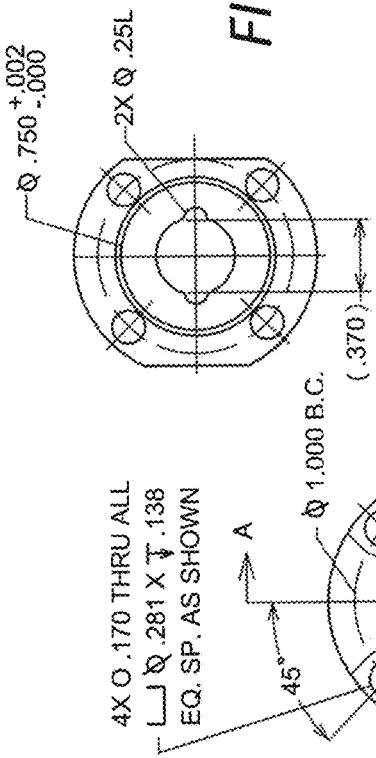
FIGS. 26A-26E show an example sleeve bearing according to embodiments of the present disclosure.
Figure 26B:
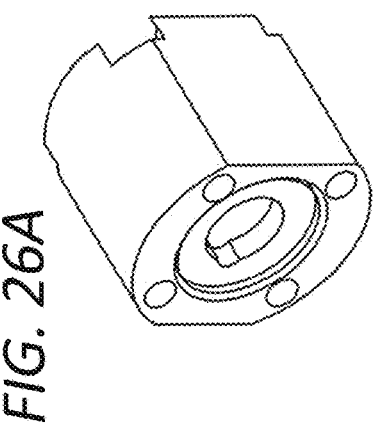
Figure 26C:
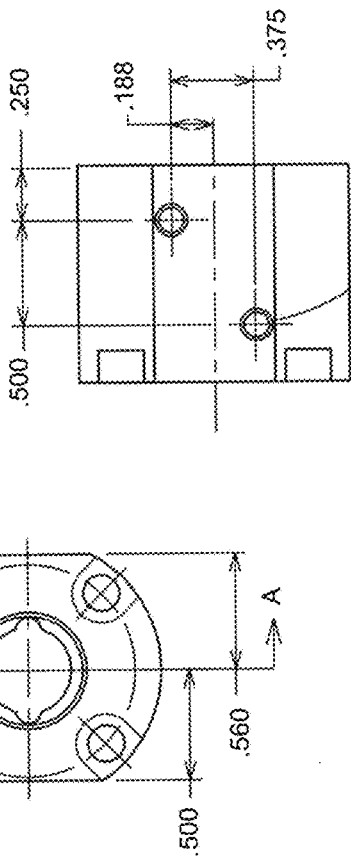
Figure 26D:
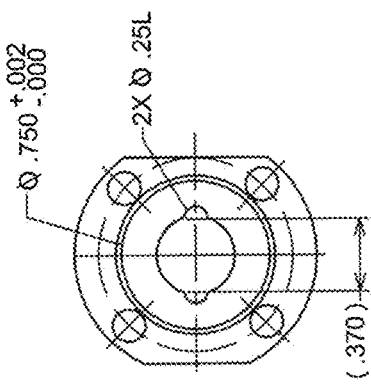
Figure 26E:
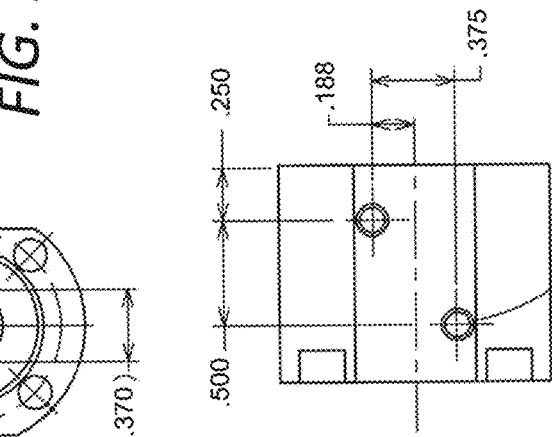
Figure 28B:
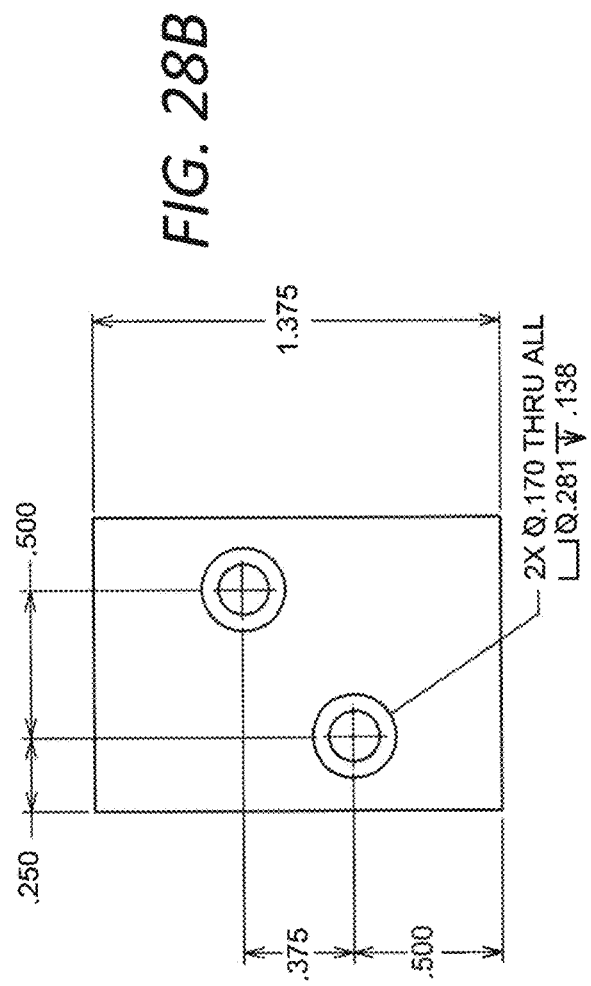
FIGS. 28A-28D show an example side plate that forms a portion of the casing according to embodiments of the present disclosure.
Figure 28D:
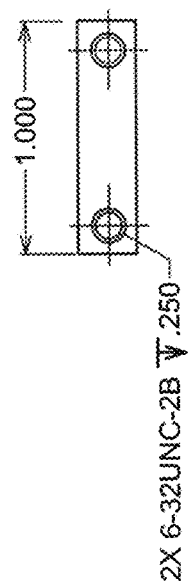
Figure 28A:
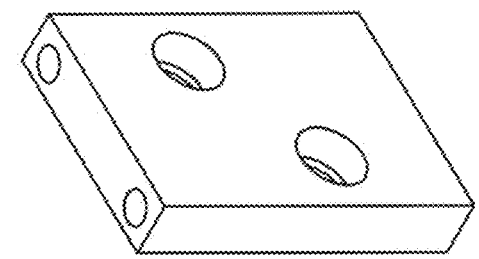
Figure 28C:
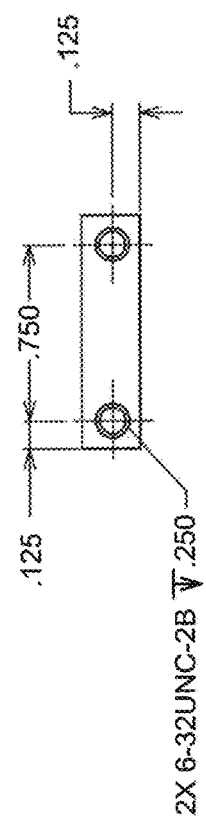

FIGS. 21AA-21F illustrate aspects of an endoscopic assembly. In particular, FIGS. 21AA-21F illustrate various views of an endoscopic tool 2110 coupled to a powered actuator 2120 encased in a housing 2150. As shown in FIG. 21, the powered actuator 2120 can be a motor that is operatively coupled to a flexible cable via a pulley system. A casing 2150 including one or more structures, such as a base plate 2152, one or more side plates 2154 and a top plate 2156 can encase the motor 2120. A coupling component 2130 can be configured to couple the flexible cable 2114 to the motor 2120, while providing a suction mechanism to remove any fluids passing through the endoscopic tool 2110. The coupling component 2130 can include a suction port 2170 through which fluid within the endoscopic tool 2110 can be removed and collected. In FIG. 21B, a pair of pulleys 2160 and 2162 coupled to a timing belt 2164 are configured such that rotational energy from the motor is transferred to one end of the flexible cable 2114. The other end of the flexible cable 2114 can be coupled to a cutting member 2112. Additional details regarding the flexible cable 2114 are described herein with respect to FIGS. 22A-22H.

FIGS. 22A-22H show various implementations of example flexible cables. In some implementations, the flexible cable can be made of three separate threads or wires. An inner wire can have a left-hand wound, a middle wire can have a right-hand wound and the outer wire can have a left-hand wound. In some implementations, the inner wire can have a right-hand wound, a middle wire can have a left-hand wound and the outer wire can have a right-hand wound. In some implementations, the flexible cable can be made of two separate threads or wires. In some such implementations, the inner wire can have a left-hand wound and the outer wire can have a right-hand wound. In some other implementations, the inner wire can have a right-hand wound and the outer wire can have a left-hand wound. In some implementations, the wirerope strands can be twisted in either Z-lay or S-lay. Examples of flexible cables include wireropes and torque coils manufactured by ASAHI INTECC. In some implementations, the outer diameter of the torque rope or coil is limited by the size of the working channel of the endoscope with which the endoscopic tool will be used. Other size considerations that need to be taken into account include providing enough space for the aspiration channel, irrigation channel, amongst others. In some implementations, the outer diameter of the torque coil or torque rope can range between 0.1 mm and 4 mm. In some implementations, the torque coil or rope can have an outer diameter of 0.5 mm to 2.0 mm.

Referring back to FIG. 21D, a cross-sectional view of the coupling component 2130 is shown. The coupling component 2130 couples one end of the endoscopic tool to the powered actuator 2120 via the pulleys 2160 and 2162 and to the suction port 2170. The coupling component includes a collection chamber 2181, which is where fluid within the aspirating tube 2118 of the endoscopic tool 2110 can be collected before being suctioned out from the coupling component 2130. The coupling component includes a collection chamber 2181 can also include a drive shaft 2186 that is configured to engage with the pulley 2162. The flexible cable or torque rope 2114 can be coupled to one end of the drive shaft 2186. An opposite end of the drive shaft 2186 is coupled to the pulley 2162, such that the drive shaft is operatively coupled with the motor 2120. In this way, as the motor rotates, the pulleys and the timing belt 2164 are configured to rotate the drive shaft 2186, and in turn, the torque rope 2114. FIGS. 24A-24C illustrate various aspects of the drive shaft of the coupling component 2130. As shown in FIGS. 24A-24C, the drive shaft 2186 can be configured to receive one end of the flexible cable via an opening 2406. A pair of holes 2402a and 2402b can be configured to receive set screws or other securing members for securing the flexible cable to the drive shaft 2186.

The coupling component 2130 also includes a housing component 2500 that couples a flexible portion of the endoscopic tool to the suction port 2170 via an opening 2502. FIG. 25 illustrates an example housing component 2500.

FIGS. 26A-26E show an example sleeve bearing.

FIGS. 27A-27C show an example base plate 2152 that forms a portion of the casing. FIGS. 28A-28D show an example side plate that forms a portion of the casing. The side plate can also serve as a feedthrough mount.

In some implementations, the coupling component is a part of the endoscopic tool. In some implementations, the coupling component is coupled to a flexible portion of the endoscopic tool via a compression fitting component 2182.

The flexible portion of the endoscopic tool includes an outer tubing, which includes an aspiration tube 2118, the torque rope 2114 and a sheath 2116 that surrounds the outer circumference of the torque rope 2114. The sheath can help reduce friction or the formation of kinks. The aspiration tube 2118 is configured to couple to a cutting tool 2190 such that material that enters into the cutting tool 2190 via an opening 2193 can pass through the length of the endoscopic tool 2110 via the aspiration tube 2118.

As shown in FIGS. 21E-21F, the torque rope is configured to be coupled to an inner cannula 2192 that forms a portion of the cutting tool. The inner cannula 2192 can be surrounded by or disposed within the outer cannula 2191. The opening 2193 is formed within the outer cannula 2191 at one end of the cutting tool 2190. Details of the cutting tool 2190 have been provided herein. FIGS. 23AA-23BB show an example implementation of a cutting tool. The cutting tool can be any type of cutting tool used in existing medical devices. The cutting tool shown in FIGS. 23AA-23BB are shown only for the sake of example and the present disclosure is not intended to be limited to such sizes, shapes, or dimension. Commercially available cutting tools can be used. In some implementations, the cutting tools can be modified in length. In some implementations, the inner cannula can be bonded to the ferrule, while the outer cannula can be coupled to the outer aspirating tube. In some implementations, the connection between the outer cannula and the aspiration channel may be sealed to prevent material from leaking through the connection.

Figure 29C:
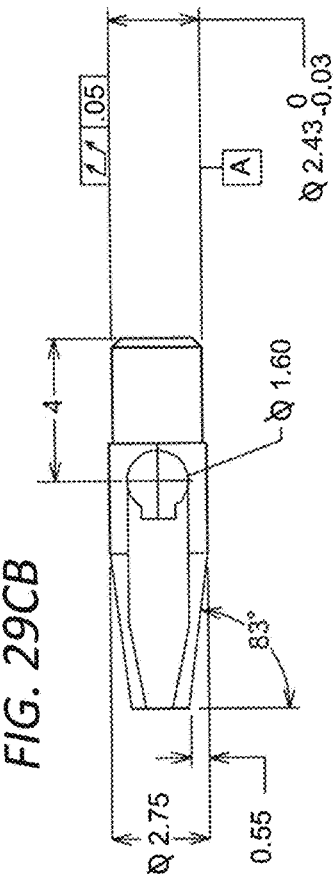
FIGS. 29AA-29EE show various aspects of ferrules according to embodiments of the present disclosure FIGS. 30AA-30C illustrate aspects of an endoscopic assembly in which the tip is press-fit according to embodiments of the present disclosure.
Figure 29C:
Figure 29C:
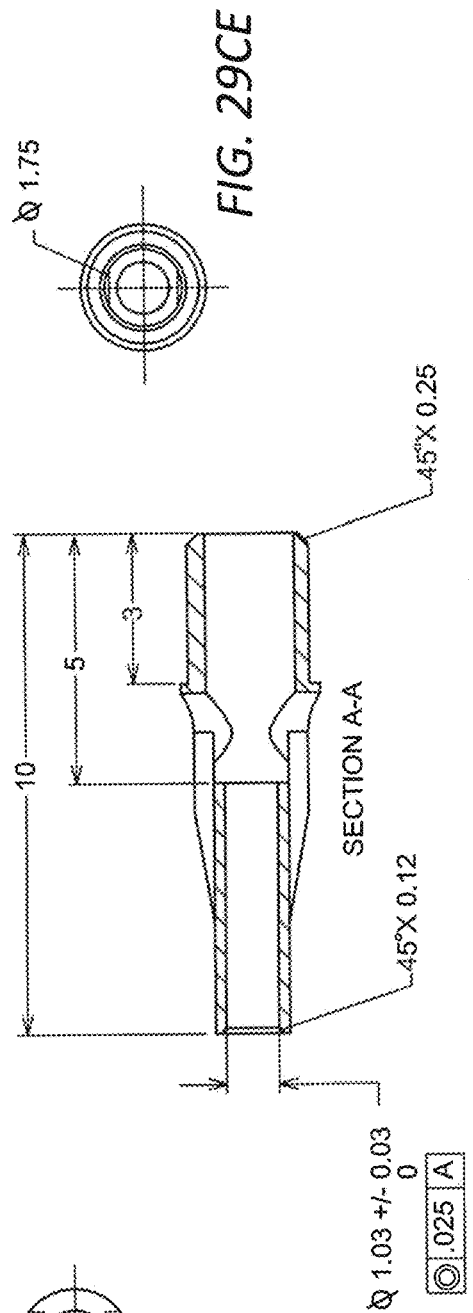
Figure 29C:
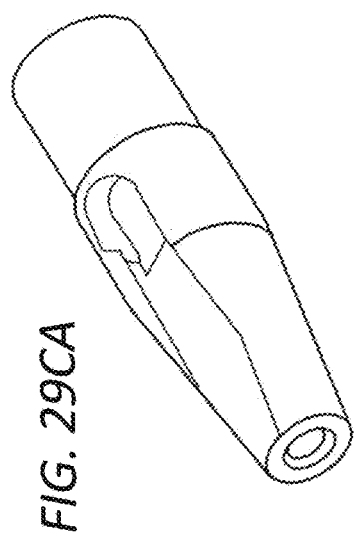
Figure 29C:
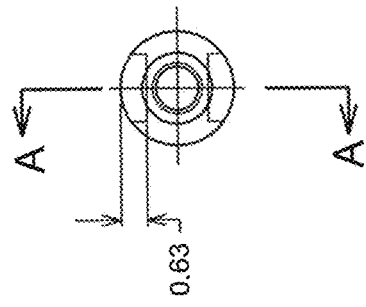

In some implementations, the torque rope 2114 is coupled to the inner cannula 2192 via a ferrule 2194. The ferrule can be a component that couples the torque rope to the inner cannula such that rotational energy within the torque rope is transferred to the inner cannula. Additional details regarding the shape, size and dimensions of the ferrule are shown in FIGS. 29AA-29EE. Depending on the size of the torque rope or flexible cable used in the endoscopic tool 2110, the shape and size of the ferrule may vary. Further, the ferrules shown in FIGS. 29AA-29EE are merely shown for the sake of example and are not intended to be limited to the particular size, shape, or dimensions shown in the Figures. In some implementations, the ends of the torque rope can be inserted into and bonded to short lengths of hypodermic tubing. Doing so can make it easier to attach the ferrule to the distal end, and to clamp onto on the proximal end (towards the drive shaft). In some implementations, a graphite filled cyanoacrylate, such as loctite black max, can be used. Other similar types of materials can also be used instead.

FIGS. 30AA-30C illustrate aspects of an endoscopic assembly in which the tip is press-fit. In some implementations, the flexible portion of the endoscopic tool can include a balloon structure that can be deployed such that the balloon structure can engage with the inner walls of the endoscope. The balloon structure can be coupled to an air supply line 3006 that is coupled to an air supply source, such that when air is supplied, the balloon can expand and engage with the inner wall of the endoscope. In some implementations, the balloon structure can expand asymmetrically, as shown in FIG. 30AA-30AB. In some implementations, the air supply source can be actuated via a foot pedal. An irrigation line 3002 can be configured to supply an irrigation fluid. The irrigation fluid can flow towards the cutting tool, where the irrigation fluid can then flow through the suction channels 3004. The irrigation fluid can prevent the suction channels from blockages. As shown in FIG. 30C, the flexible cable or torque rope can be press fit into a button at one end of the cutting tool.

FIGS. 31AA-31AB and 31B-31C illustrate aspects of an endoscopic assembly in which the tip is press-fit. In some implementations, the flexible portion of the endoscopic tool can include a balloon structure that can be deployed such that the balloon structure can engage with the inner walls of the endoscope. The balloon structure can be coupled to an air supply source such that when air is supplied, the balloon can expand and engage with the inner wall of the endoscope. In some implementations, the balloon structure can expand symmetrically, as shown in FIGS. 31AA and 31AB. An irrigation line can be configured to supply an irrigation fluid. The irrigation fluid can flow towards the cutting tool, where the irrigation fluid can then flow through the suction channels. The irrigation fluid can prevent the suction channels from blockages. As shown in FIG. 31C, the flexible cable or torque rope can be welded to one end of the cutting tool.

Figure 32:
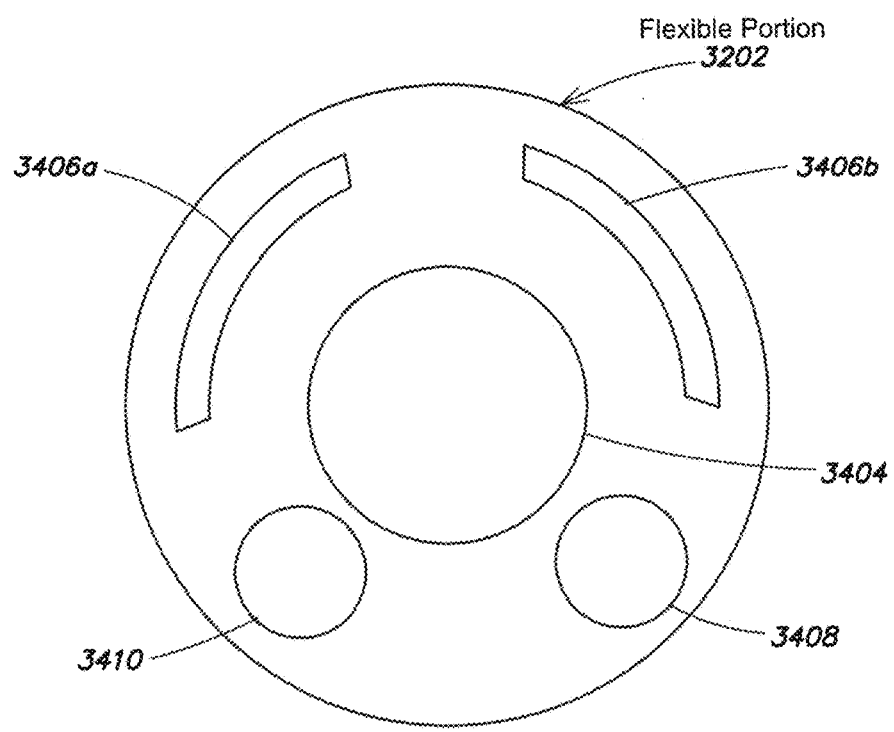
FIG. 32 shows a top view of an example flexible portion of an endoscopic tool according to embodiments of the present disclosure.

FIG. 32 shows a top view of an example flexible portion of an endoscopic tool. In some implementations, the flexible portion shown in FIG. 32 can be used with the implementations shown in FIGS. 30AA-30C and 31AA-31AB and 31B-31C. The flexible portion 3202 includes a center channel 3204 through which the flexible cable passes through. The flexible portion 3202 also includes two aspiration channels 3406a and 3406b, an irrigation channel 3408 and an air supply channel 3410.

In some implementations, the operating speed of the torque rope can vary. In some example implementations, the torque rope can have an operating speed within the range of 0.5 k RPM to 20 k RPM. In some implementations, the torque rope can have an operating speed within the range of 1 k RPM and 4 k RPM. In some implementations, the operating speed of the torque rope can vary. In some example implementations, the torque rope can operate with a torque of 5 to 100 mN*m (milliNewton Meters). In some implementations, the torque rope can operate with a torque of 20 to 50 mN*m (milliNewton Meters). However, it should be appreciated by those skilled in the art that the torque and running speed of the flexible cable can be altered based on the performance of the endoscopic tool. In some implementations, various factors contribute to the performance of the endoscopic tool, including the amount of suction, the type of cutter, the size of the opening in the cutter, amongst others. As such, the torque and running speed at which to operate the flexible cable can be dependent on a plurality of factors.

Figure 33:
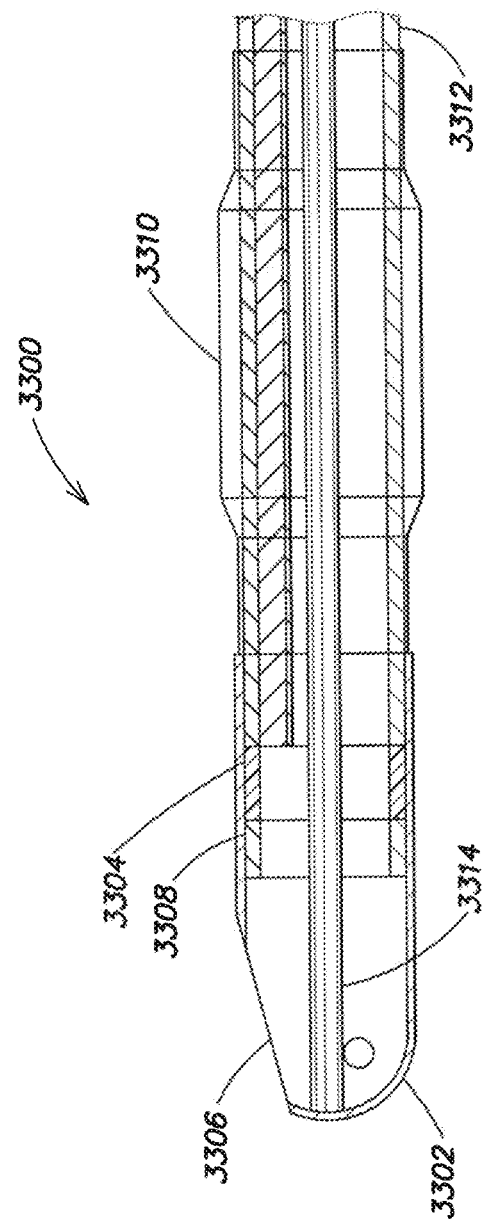
FIG. 33 is a cross-sectional view of an example cutting assembly of an endoscopic tool using a torque rope according to embodiments of the present disclosure.

FIG. 33 is a cross-sectional view of an example cutting assembly of an endoscopic tool using a torque rope. The cutting assembly 3300 includes an outer cannula 3302, an inner cannula 3304 including an inner cutter 3306 disposed within the outer cannula 3302, a PTFE bearing 3308, a semi-compliant balloon 3310, and a multilumen extrusion 3312. A torque rope 3314 can be coupled to the inner cutter 3306. The diameter of the outer cannula can be between 0.05 inches to a size suitable to pass through an instrument channel of an endoscope.

FIGS. 34A-34C are cross-sectional views of different configurations of the flexible portion region of one implementation of an endoscopic tool described herein. The flexible portion region can include an aspiration lumen 3402, an inflation lumen 3404, a lavage or irrigation lumen 3406 and a torque rope.

FIGS. 35AA-35AC show various views of portions of an endoscopic tool. The endoscopic tool can include an outer cannula 1, an inner cutter 2, an inner cannula 3, a torque rope 4, a trilumen extrusion 5, a balloon 6, a PTFE washer 7, two sidearms 8, a proximal plug 9, an PTFE gasket 10 and a gasket cap 11.

Figure 36:
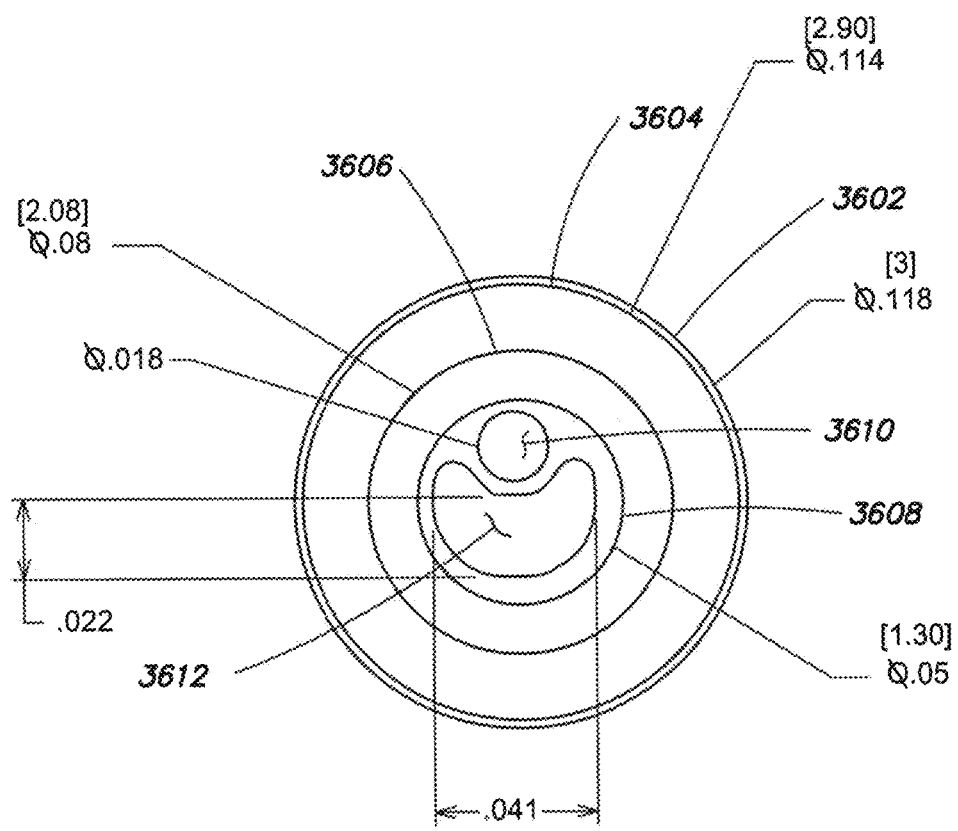
FIG. 36 shows a cross-sectional view of the flexible portion region of one implementation of an endoscopic tool according to embodiments of the present disclosure.

FIG. 36 shows a cross-sectional view of the flexible portion region of one implementation of an endoscopic tool described herein. The flexible portion region can include an outer inflation jacket 3602, an outer coil 3604, a torque coil 3606, a multi-lumen extrusion 3608 disposed within the torque coil. The multi-lumen extrusion 3608 can include a lavage lumen 3610 and an aspiration lumen 3612.

Figure 37:
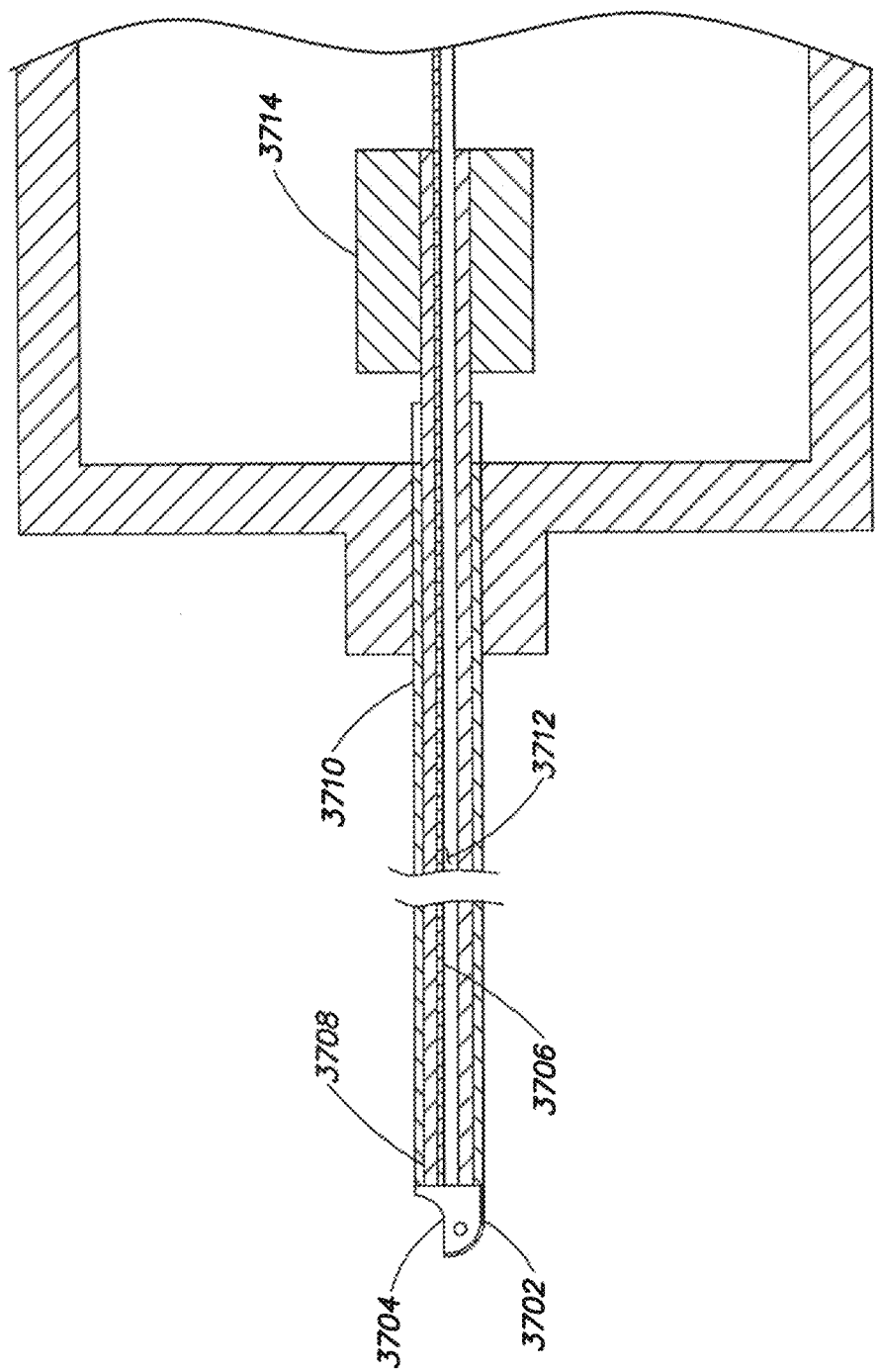
FIG. 37 shows a cross-section view of one implementation of the endoscopic tool according to embodiments of the present disclosure.

FIG. 37 shows a cross-section view of one implementation of the endoscopic tool described herein. The endoscopic tool includes an outer cannula 3702, an inner cutter 3704, an inner torque coil 3706, an outer coil 3708, an outer inflation jacket and balloon 3710, and a multi-lumen extrusion 3712. A gear 3714, such as a worm gear can engage with the torque coil to drive the inner cutter.

Figure 38A:
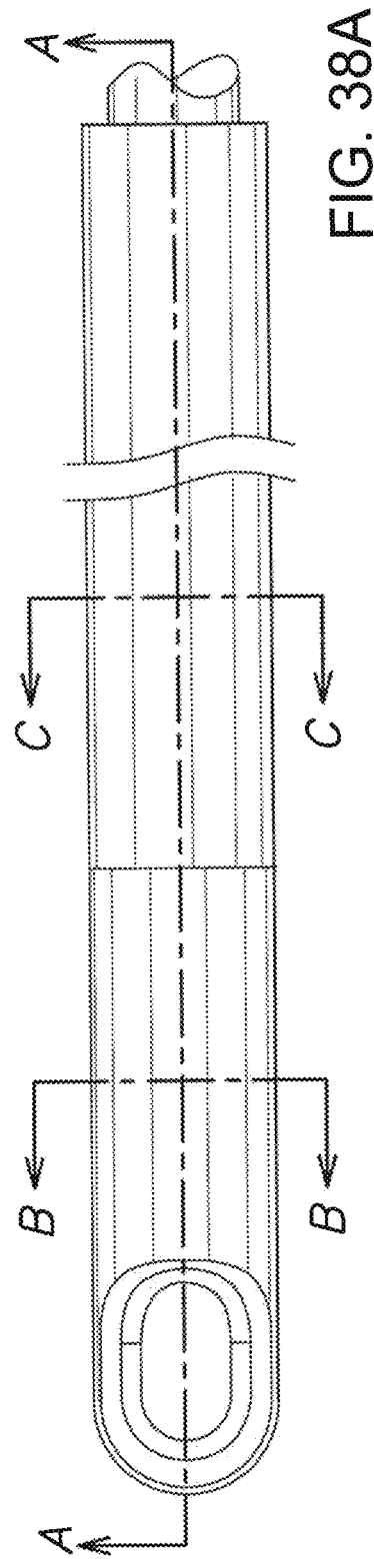
FIGS. 38A and 38B show various views of a distal portion of one implementation of an endoscopic tool according to embodiments of the present disclosure.
Figure 38B:
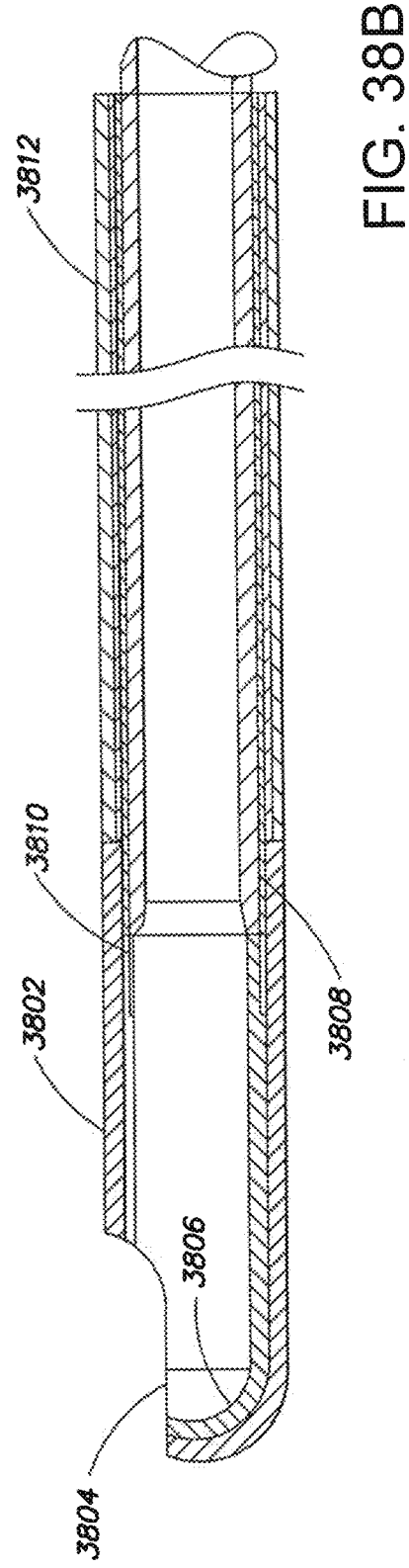

FIGS. 38A and 38B show various views of a distal portion of one implementation of an endoscopic tool described herein. The endoscopic tool includes an outer cutter 3802 that defines an opening 3804. The endoscopic tool also includes an inner cutter 3806 disposed within the outer cutter. The inner cutter is coupled to a torque coil 3808. The torque coil is disposed within a PET heat shrink 3810 or other type of tubing. The outer cutter is coupled to a braided shaft 3812 to allow the outer cutter 3802 to rotate relative to the inner cutter 3806.

Figure 39B:
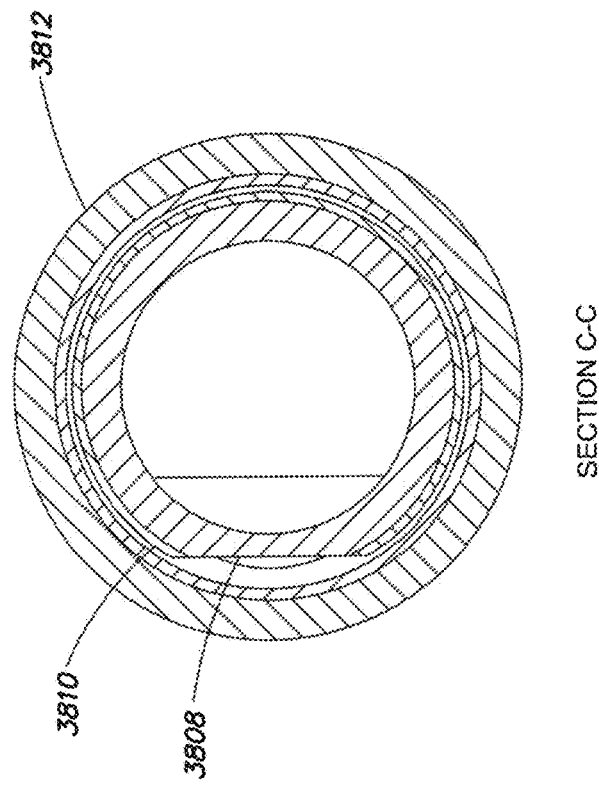
FIGS. 39A and 39B show cross-sectional views of the distal portion of the endoscopic tool shown in FIGS. 38A and 38B along the sections B-B and sections C-C according to embodiments of the present disclosure.
Figure 39A:
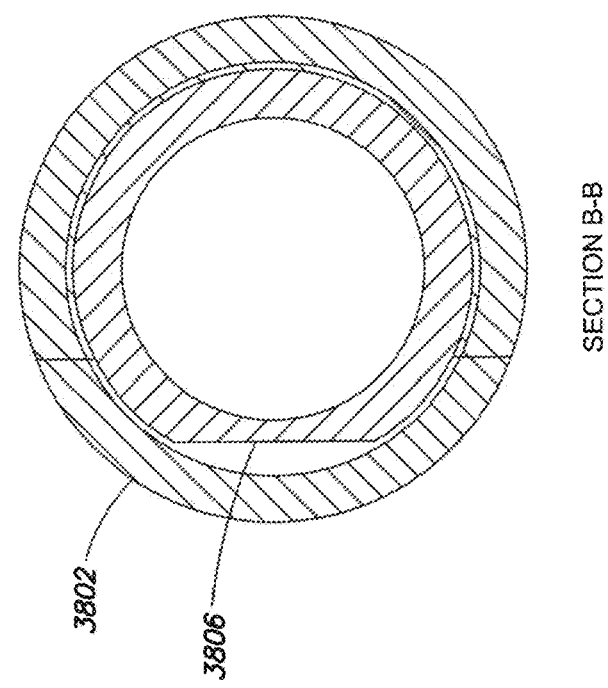

FIGS. 39A and 39B show cross-sectional views of the distal portion of the endoscopic tool shown in FIGS. 38A and 38B along the sections B-B and sections C-C.

In some implementations, an endoscopic instrument insertable within a single instrument channel of an endoscope can include a power driven instrument head or cutting assembly that is configured to resect material at a site within a subject. The cutting assembly includes an outer cannula and an inner cannula disposed within the outer cannula. The outer cannula defines an opening through which material to be resected enters the cutting assembly. The endoscopic instrument also includes a flexible outer tubing coupled to the outer cannula and configured to cause the outer cannula to rotate relative to the inner cannula. The flexible outer tubing can have an outer diameter that is smaller than the instrument channel in which the endoscopic instrument is insertable. The endoscopic instrument also includes a flexible torque coil having a portion disposed within the flexible outer tubing. The flexible torque coil having a distal end coupled to the inner cannula. The flexible torque coil is configured to cause the inner cannula to rotate relative to the outer cannula. The endoscopic instrument also includes a proximal connector coupled to a proximal end of the flexible torque coil and configured to engage with a drive assembly that is configured to cause the proximal connector, the flexible torque coil and the inner cannula to rotate upon actuation. The endoscopic instrument also includes an aspiration channel having an aspiration port configured to engage with a vacuum source. The aspiration channel is partially defined by an inner wall of the flexible torque coil and an inner wall of the inner cannula and extends from an opening defined in the inner cannula to the aspiration port. The endoscopic instrument also includes an irrigation channel having a first portion defined between an outer wall of the flexible torque coil and an inner wall of the flexible outer tubing and configured to carry irrigation fluid to the aspiration channel.

In some implementations, the proximal connector is hollow and an inner wall of the proximal connector defines a portion of the aspiration channel. In some implementations, the proximal connector is a rigid cylindrical structure and is configured to be positioned within a drive receptacle of the drive assembly. The proximal connector can include a coupler configured to engage with the drive assembly and a tensioning spring configured to bias the inner cannula towards a distal end of the outer cannula. In some implementations, the tensioning spring is sized and biased such that the tensioning spring causes a cutting portion of the inner cannula to be positioned adjacent to the opening of the outer cannula. In some implementations, the proximal connector is rotationally and fluidly coupled to the flexible torque coil. In some implementations, the tensioning spring can be sized and biased such that the distal tip of the inner cannula can contact the inner distal wall of the outer cannula. This may limit any lateral or undesired movement generated due to whip at the distal end of the inner cannula caused by the rotation of the flexible torque coil.

In some implementations, the endoscopic instrument also includes a lavage connector including an irrigation entry port and a tubular member coupled to the lavage connector and the flexible outer tubing. An inner wall of the tubular member and the outer wall of the flexible torque coil can define a second portion of the irrigation channel that is fluidly coupled to the first portion of the irrigation channel. In some implementations, the endoscopic instrument also includes a rotational coupler coupling the flexible outer tubing to the tubular member and configured to cause the flexible outer tubing to rotate relative to the tubular member and cause the opening defined in the outer cannula to rotate relative to the inner cannula. In some implementations, the lavage connector defines an inner bore within which the flexible torque coil is disposed.

In some implementations, the endoscopic instrument also includes a lining within which the flexible torque coil is disposed, the outer wall of the lining configured to define a portion of the irrigation channel. In some implementations, the inner cannula is configured to rotate about a longitudinal axis of the inner cannula and relative to the outer cannula and the aspiration channel is configured to provide a suction force at the opening of the inner cannula.

In some implementations, the flexible torque coil includes a plurality of threads. Each of the plurality of threads can be wound in a direction opposite to a direction in which one or more adjacent threads of the plurality of threads is wound. In some implementations, the flexible torque coil includes a plurality of layers. Each of the plurality of layers can be wound in a direction opposite to a direction in which one or more adjacent layers of the plurality of layers is wound. In some implementations, each layer can include one or more threads. Additional details regarding the flexible torque coil are described above in regard to the discussion of the flexible cable with respect to at least FIGS. 22A-22H.

In some implementations, the flexible outer tubing has a length that exceeds the length of the endoscope in which the endoscopic instrument is insertable. In some implementations, the flexible outer tubing has a length that is at least 100 times larger than an outer diameter of the flexible outer tubing. In some implementations, the flexible portion is at least 40 times as long as the cutting assembly.

Figure 40A:
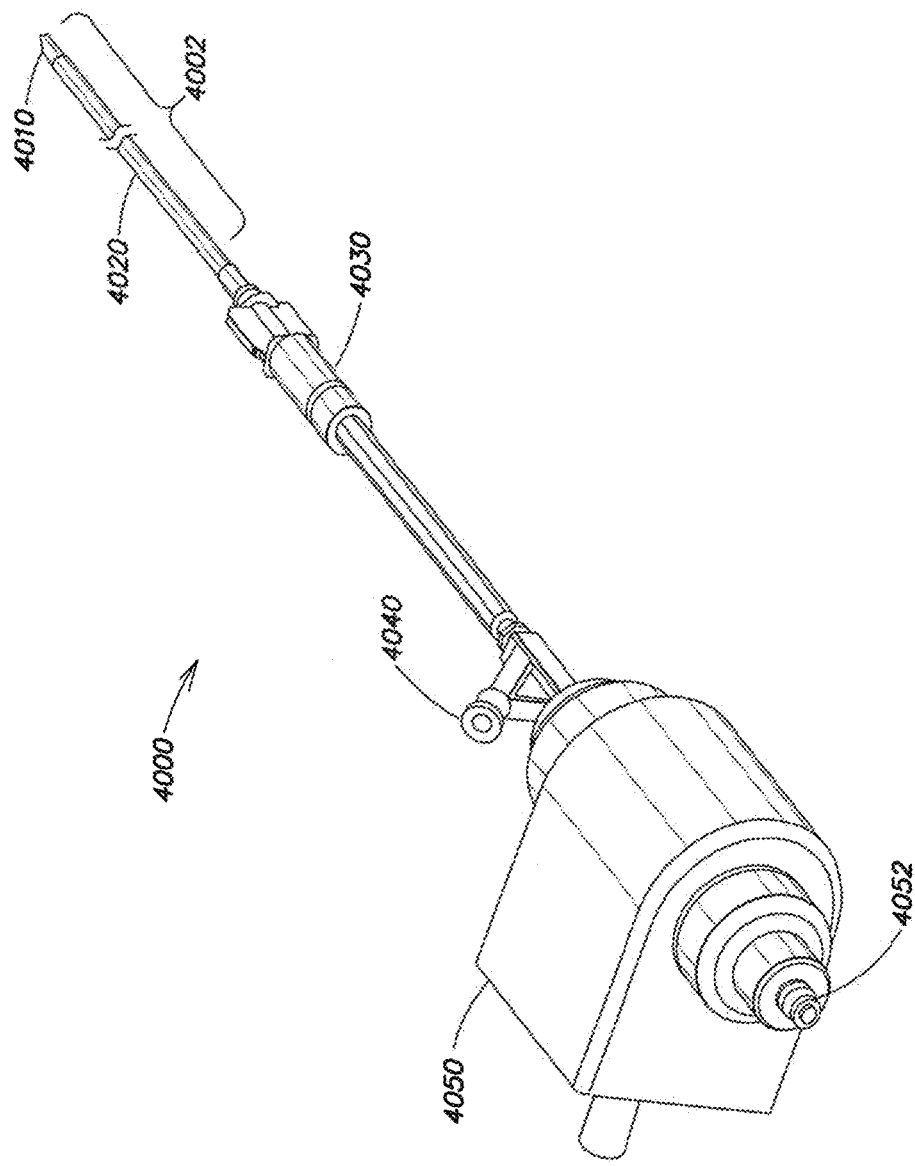
Figure 43:
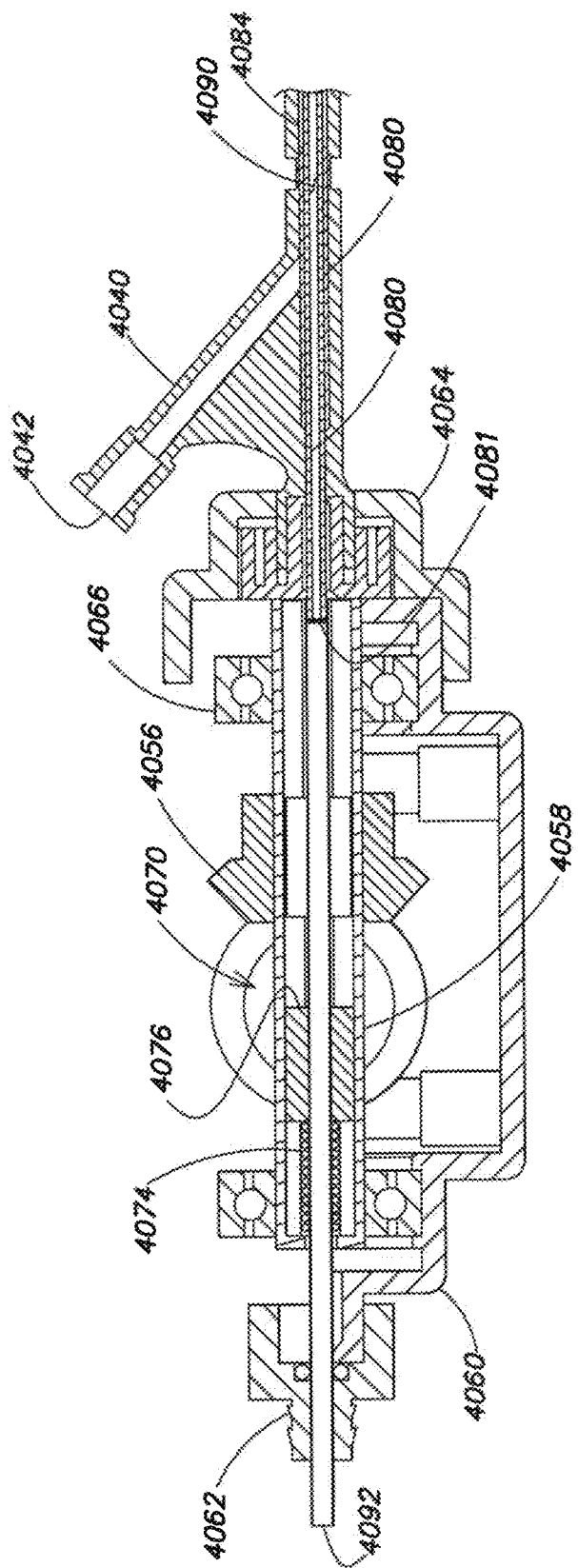
FIG. 43 shows an enlarged view of the drive connector of the endoscope and the portion of the drive assembly shown in FIGS. 40A-40B according to embodiments of the present disclosure.
Figure 44:
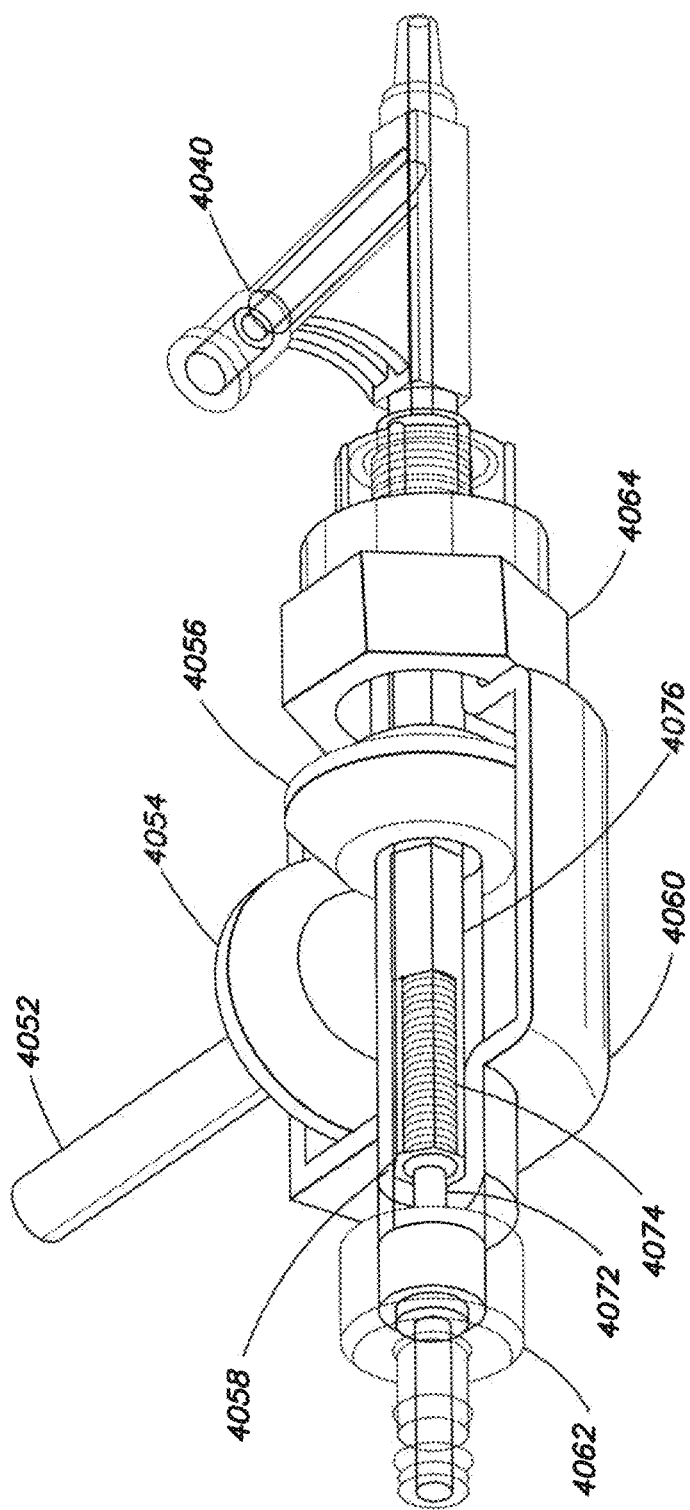
FIG. 44 shows a perspective view of the endoscopic tool and a portion of the drive assembly shown in FIGS. 40A-40B according to embodiments of the present disclosure.
Figure 45:
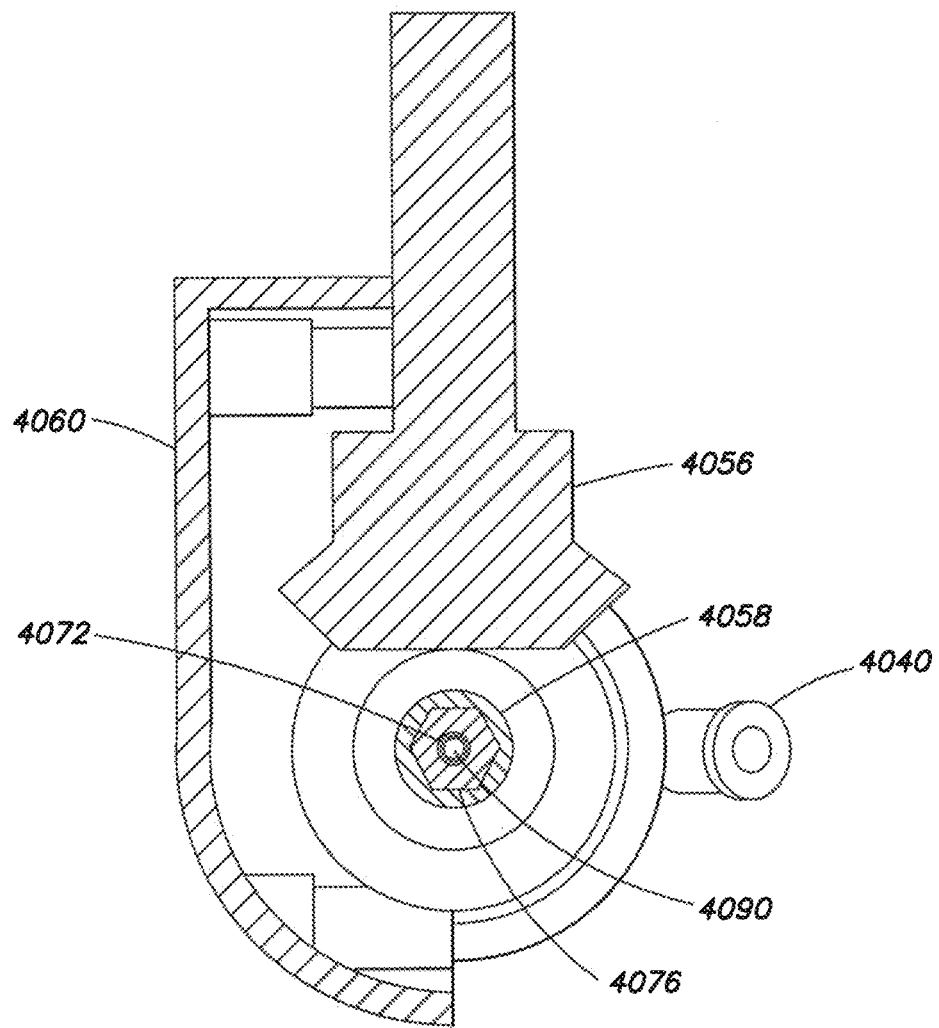
FIG. 45 shows a cross-sectional view of the endoscopic tool and the portion of the drive assembly across the section B-B according to embodiments of the present disclosure.
Figure 46:
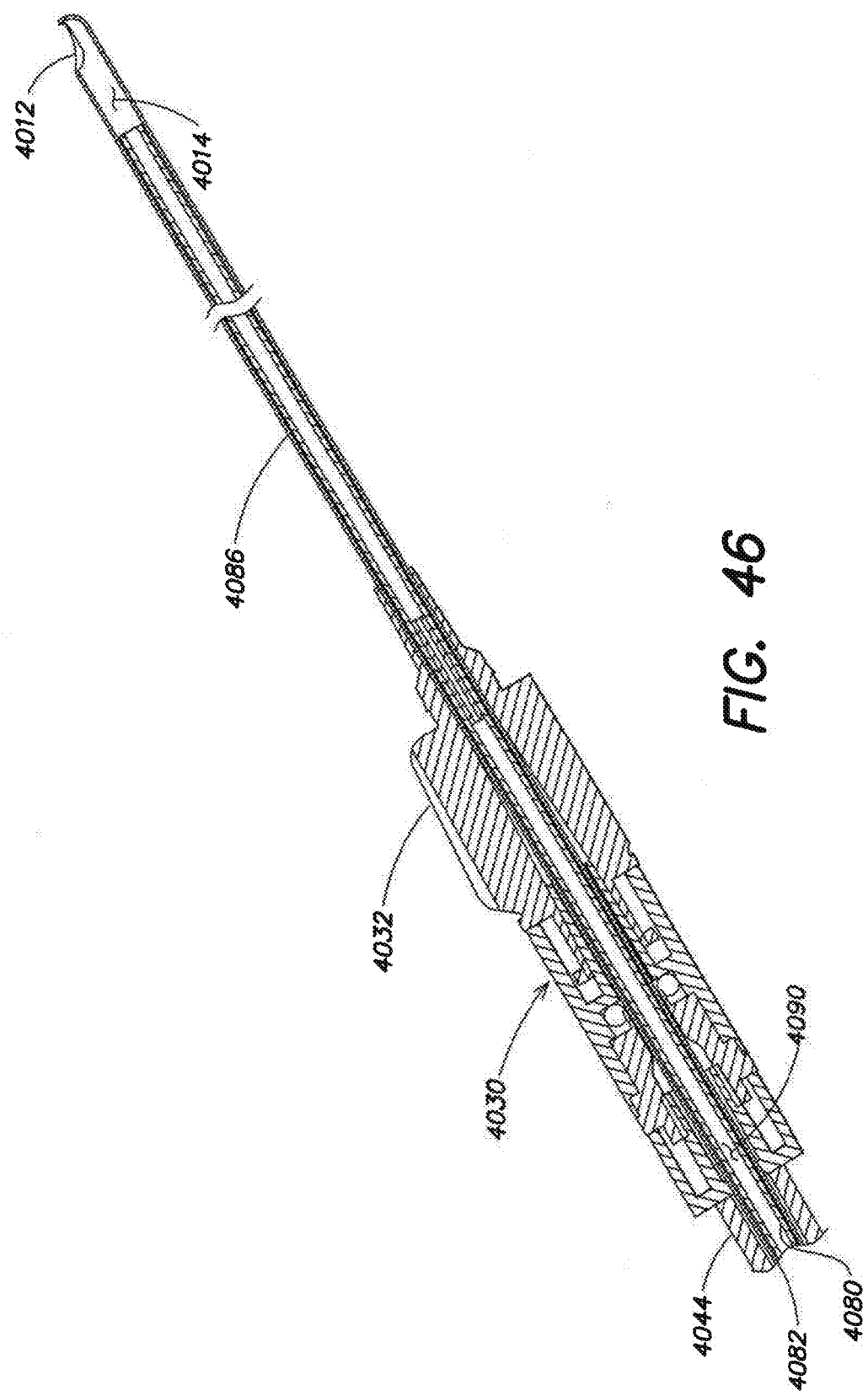
FIG. 46 shows an enlarged cross-sectional view of the rotational coupler section of the endoscopic tool according to embodiments of the present disclosure.

FIGS. 40A-40B show a perspective view of an endoscopic tool 4000 and a portion of a drive assembly 4050 configured to drive the endoscopic tool. Referring now also to FIGS. 41, 42 and 43, FIG. 41 shows a top view of the endoscopic tool 4000 and a top exposed view of the portion of the drive assembly 4050 shown in FIGS. 40A-40B. FIG. 42 shows a cross-sectional view of the endoscopic tool 4000 and the portion of the drive assembly 4050 across the section A-A. FIG. 43 shows an enlarged view of the drive connector of the endoscope and the portion of the drive assembly 4050. FIG. 44 shows a perspective view of the endoscopic tool 4000 and a portion of the drive assembly shown in FIGS. 40A-40B. FIG. 45 shows a cross-sectional view of the endoscopic tool and the portion of the drive assembly across the section B-B. FIG. 46 shows an enlarged cross-sectional view of the rotational coupler section of the endoscopic tool. FIG. 47A and FIG. 47B show a top view and a cross-sectional view of the rotational coupler of the endoscopic tool.

The endoscopic tool 4000, as shown in FIGS. 40A-47B, may be configured to be inserted within an instrument channel of an endoscope. Examples of the endoscope can include a gastroscope, such as a colonoscope, a laryngoscope, or any other flexible endoscope. The endoscopic tool can include a flexible portion 4002 that is shaped, sized and configured to be inserted within the instrument channel, while a remaining portion of the endoscopic tool 4000 can be configured to remain outside the instrument channel of the endoscope. The flexile portion 4002 can be shaped and sized to fit within the instrument channel and be configured to navigate through a tortuous path defined by the instrument channel while the endoscope is inserted within the patient. In the case of colonoscopes, the endoscope can form a series of bends of over at least 60 degrees and in some situations, over 90 degrees.

The endoscopic tool 4000 can include a cutting assembly 4010 configured to resect material at a site within a subject. The cutting assembly 4010 can be similar to the cutting assembly 160 described in FIG. 1C and elsewhere in the description and figures. In some implementations, the cutting assembly 4010 can include an outer cannula and an inner cannula disposed within the outer cannula. The outer cannula can define an opening 4012 through which material to be resected can enter the cutting assembly 4010. In some implementations, the opening 4012 is defines through a portion of the radial wall of the outer cannula. In some implementations, the opening may extend around only a portion of the radius of the outer cannula, for example, up to one third of the circumference of the radial wall. As the aspiration channel 4090 extends between the aspiration port 4092 and the opening 4012, any suction applied at the aspiration port 4092 causes a suction force to be exerted at the opening 4012. The suction force causes material to be introduced into the opening of the outer cannula, which can then be cut by the inner cannula of the cutting assembly.

The inner cannula can include a cutting section that is configured to be positioned adjacent to the opening 4012 such that material to be resected that enters the cutting assembly via the opening 4012 can be resected by the cutting section of the inner cannula. The inner cannula may be hollow and an inner wall of the inner cannula may define a portion of an aspiration channel that may extend through the length of the endoscopic tool. A distal end of the inner cannula can include the cutting section while a proximal end of the inner cannula can be open such that material entering the distal end of the inner cannula via the cutting section can pass through the proximal end of the inner cannula. In some implementations, the distal end of the inner cannula can come into contact with an inner surface of a distal end of the outer cannula. In some implementations, this can allow the inner cannula to rotate relative to the outer cannula along a generally longitudinal axis, providing more stability to the inner cannula while the inner cannula is rotating. In some implementations, the size of the opening can dictate the size of the materials being cut or resected by the inner cannula. As such, the size of the opening may be determined based in part on the size of the aspiration channel defined by the inner circumference of the flexible torque coil.

The endoscopic instrument 4000 can include a flexible torque coil 4080 that is configured to couple to the proximal end of the inner cannula at a distal end of the flexible torque coil 4080. The flexible torque coil can include a fine coil with multiple threads and multiple layers, which can transmit the rotation of one end of the flexible torque coil to an opposite end of the flexible torque coil. Each of the layer of thread of the flexible torque coil can be wound in a direction opposite to a direction in which each of the layer of thread adjacent to the layer of thread is wound. In some implementations, the flexible torque coil can include a first layer of thread wound in a clockwise direction, a second layer of thread wound in a counter-clockwise direction and a third layer of thread wound in a clockwise direction. In some implementations, the first layer of thread is separated from the third layer of thread by the second layer of thread. In some implementations, each of the layers of thread can include one or more threads. In some implementations, the layers of thread can be made from different materials or have different characteristics, such as thickness, length, among others.

The flexibility of the torque coil 4080 allows the coil to maintain performance even in sections of the torque coil 4080 that are bent. Examples of the flexible torque coil 4080 include torque coils made by ASAHI INTECC USA, INC located in Santa Ana, Calif., USA. In some implementations, the flexible torque coil 4080 can be surrounded by a sheath or lining to avoid frictional contact between the outer surface of the flexible torque coil 4080 and other surfaces. In some implementations, the flexible torque coil 4080 can be coated with Polytetrafluoroethylene (PFTE) to reduce frictional contact between the outer surface of the flexible torque coil 4080 and other surfaces. The flexible torque coil 4080 can be sized, shaped or configured to have an outer diameter that is smaller than the diameter of the instrument channel of the endoscope in which the endoscopic tool is to be inserted. For example, in some implementations, the outer diameter of the flexible torque coil can be within the range of 1-4 millimeters. The length of the flexible torque coil can be sized to exceed the length of the endoscope. In some implementations, the inner wall of the flexible torque coil 4080 can be configured to define another portion of the aspiration channel that is fluidly coupled to the portion of the aspiration channel defined by the inner wall of the inner cannula of the cutting assembly 4010. A proximal end of the flexible torque coil 4080 can be coupled to a proximal connector assembly 4070, details of which are provided below.

The endoscopic instrument 4000 can include a flexible outer tubing 4086 that can be coupled to the proximal end of the outer cannula. In some implementations, a distal end of the flexible outer tubing 4086 can be coupled to the proximal end of the outer cannula using a coupling component. In some implementations, the outer cannula can be configured to rotate responsive to rotating the flexible outer tubing. In some implementations, the flexible outer tubing 4086 can be a hollow, braided tubing that has an outer diameter that is smaller than the instrument channel of the endoscope in which the endoscopic instrument 4000 is to be inserted. In some implementations, the length of the flexible outer tubing 4086 can be sized to exceed the length of the endoscope. The flexible outer tubing 4086 can define a bore through which a portion of the flexible outer tubing 4086 extends. The flexible outer tubing 4086 can include braids, threads, or other features that facilitate the rotation of the flexible outer tubing 4086 relative to the flexible torque coil, which is partially disposed within the flexible outer tubing 4086.

The endoscopic instrument 4000 can include a rotational coupler 4030 configured to be coupled to a proximal end of the flexible outer tubing 4086. The rotational coupler 4030 may be configured to allow an operator of the endoscopic tool to rotate the flexible outer tubing 4086 via a rotational tab 4032 coupled to or being an integral part of the rotational coupler 4030. By rotating the rotational tab 4032, the operator can rotate the flexible outer tubing and the outer cannula along a longitudinal axis of the endoscope and relative to the endoscope and the inner cannula of the cutting assembly 4010. In some implementations, the operator may want to rotate the outer cannula while the endoscopic instrument is inserted within the endoscope while the endoscope is within the patient. The operator may desire to rotate the outer cannula to position the opening of the outer cannula to a position where the portion of the radial wall of the outer cannula within which the opening is defined may aligned with the camera of the endoscope such that the operator can view the material entering the endoscopic instrument for resection via the opening. This is possible in part because the opening is defined along a radial wall extending on a side of the outer cannula as opposed to an opening formed on the axial wall of the outer cannula.

In some implementations, a proximal end 4034 of the rotational coupler 4030 can be coupled to a lavage connector 4040. In some implementations, the rotational coupler 4030 can be a rotating luer component that allows a distal end 4036 of the rotational coupler 4030 rotate relative to the proximal end 4034 of the rotational coupler 4030. In this way, when the flexible outer tubing 4086 is rotated, the component to which the proximal end of the rotational coupler 4030 is coupled, is not caused to rotate. In some implementations, the proximal end 4034 of the rotational coupler 4030 can be coupled to an outer tubular member 4044 configured to couple the proximal end 4034 of the rotational coupler 4030 to the lavage connector 4040. The rotational coupler 4030 can define a bore along a central portion of the rotational coupler 4030 through which a portion of the flexible torque coil 4080 extends. In some implementations, the rotational coupler 4030 can be a male to male rotating luer connector. In some implementations, the rotational coupler can be configured to handle pressures up to 1200 psi.

The lavage connector 4040 can be configured to introduce irrigation fluid into the endoscopic tool 4000. The lavage connector 4040 includes a lavage port 4042 configured to engage with an irrigation source, such as a water container. In some implementations, the lavage connector 4040 can be a Y port used in fluid delivery systems that complies with medical device industry standards and is sized to couple to the flexible outer tubing 4086 or the outer tubular member 4044 that serves to couple a distal end 4048 of the lavage connector 4040 to the proximal end 4034 of the rotational coupler 4030. In some implementations, the lavage connector can define a hollow channel between the proximal end 4046 and the distal end 4048 of the lavage connector 4040 that is sized to allow the flexible torque coil 4080 to pass through the hollow channel defined through the lavage connector 4040.

As described above, the proximal connector assembly 4070 is configured to be coupled to a proximal end of the flexible torque coil 4080. The proximal connector assembly 4070 can be configured to engage with the drive assembly 4050 that is configured to provide torque to the inner cannula via the proximal connector assembly 4070 and the flexible torque coil 4080. The proximal connector assembly 4070 can further define a portion of the aspiration channel and be configured to fluidly couple the aspiration channel to a vacuum source to facilitate the removal of material entering the aspiration channel. In some implementations, a proximal end of the proximal connector assembly 4070 can include an aspiration port 4092 through which the material that enters the endoscopic tool 4000 can be withdrawn from the endoscopic tool 4000.

In some implementations, the endoscopic tool 4000 can be configured to be driven by the drive assembly 4050. The drive assembly 4050 is configured to provide rotational energy from an energy source to the endoscopic tool 4000. The drive assembly 4050 can include a housing 4060 that may house a first beveled gear 4054 and a second beveled gear 4056 that are positioned such that the rotation of the first beveled gear 4054 causes a rotation of the second beveled gear 4056. The second beveled gear 4056 can be coupled to a drive receptacle that is sized and shaped to receive and engage with the proximal connector assembly 4070 of the endoscopic tool 4000. In some implementations, the first beveled gear 4054 can be coupled to a motor (not shown) or other rotational source via a rotational input shaft 4052.

The proximal connector assembly 4070 can include a hollow drive shaft 4072, a coupler 4076 through which the hollow drive shaft 4072 passes and a tensioning spring 4074 coupled to the hollow drive shaft 4072. A distal end of the drive shaft 4072 can be coupled to the proximal end of the flexible torque coil 4080. In some implementations, the drive shaft 4072 and the flexible torque coil 4080 can be permanently coupled to one another. In some implementations, the drive shaft 4072 and flexible torque coil 4080 can be coupled using a coupler, a press fit, a weld, such as a butt weld, or any other attachment means that allows the flexible torque coil 4080 to rotate when the drive shaft 4072 rotates and to allow material passing through the flexible torque coil 4080 to flow through the drive shaft 4072. A proximal end of the drive shaft 4072 can define the aspiration port 4092. In some implementations, the aspiration port 4092 can be configured to engage with a vacuum source causing material entering the opening 4012 to flow through the aspiration channel 4090 and out of the endoscopic tool through the aspiration port 4092.

A coupler 4076, such as a hex-shaped coupler, can be configured to couple with the hollow drive shaft. In some implementations, the hex-shaped coupler is a part of the hollow drive shaft. The coupler 4076 can include an outer wall that is configured to engage with an inner wall of a drive receptacle 4058. The drive receptacle 4058 is coupled to the second beveled gear 4056 and is configured to rotate when the second beveled gear 4056 rotates. In some implementations, the drive receptacle 4058 can be a hollow cylindrical tube. In some implementations, a proximal end 4059 of the drive receptacle 4058 can include an opening defined by an inner wall of the proximal end of the drive receptacle 4058 that has a diameter that smaller than the inner diameter of the remaining portion of the drive receptacle 4058. In some implementations, the diameter of the opening through the proximal end 4059 of the drive receptacle 4058 can be large enough to receive the drift shaft 4072 but small enough to prevent the tensioning spring 4074 coupled to the drive shaft 4072 from passing through the opening. In some implementations, the inner diameter of the remaining portion of the drive receptacle is sized to engage with the coupler 4076.

The tensioning spring 4074 can be biased in such a way that, during operation of the endoscopic tool 4000, the tensioning spring 4074 may prevent the drive shaft 4072, the flexible torque coil 4080 and the inner cannula from sliding towards the proximal end of the endoscopic tool 4000. In some implementations, without the tensioning spring 4074, the inner cannula may slide away from the distal end of the endoscopic tool 4000. This may be due to a force applied by the material to be resected at the opening 4012. In some implementations, the tensioning spring 4074 provides a countering force that prevents the inner cannula from sliding away from the distal end when the inner cannula comes into contact with the material to be resected at the opening 4012. In some implementations, the tensioning spring 4074 can be configured to bias the distal end of the inner cannula to contact an inner wall of the distal end of the outer cannula. In some implementations, the tensioning spring 4074 can be sized and biased such that the distal tip of the inner cannula can contact the inner distal wall of the outer cannula. This may limit any lateral or undesired movement generated due to whip at the distal end of the inner cannula caused by the rotation of the flexible torque coil.

The housing 4060 can be configured to engage with an aspiration end cap 4062 and a locking collar 4064. In some implementations, the aspiration end cap 4062 can be configured to allow a vacuum source to maintain a secure connection with the aspiration port 4092 of the drive shaft 4072. In some implementations, the aspiration end cap 4062 can be configured to allow the drive shaft 4072 to rotate while maintaining a secure connection between the vacuum source and the aspiration port 4092 of the drive shaft 4072. In some implementations, the aspiration end cap 4062 can be configured to be secured to a portion of the housing 4060 in such a way that the aspiration port of the drive shaft 4072 is accessible via an opening of the aspiration end cap 4062. In some implementations, the vacuum source can be coupled to the end cap 4062 such that the vacuum source does not rotate along with the proximal end of the drive shaft 4072. In some implementations, one or more bearings or bushings can be used to allow facilitate a fluid connection between the aspiration port 4092 of the drive shaft 4072 and the vacuum source without causing the vacuum source to rotate with the drive shaft 4072.

The locking collar 4064 can be configured to secure the lavage connector 4040 to the proximal connector assembly 4070. In some implementations, the locking collar 4064 can be configured to secure a proximal end 4046 of the lavage connector 4040 to the housing 4060 of the drive assembly 4050. The locking collar 4064 can further be configured to prevent the proximal connector assembly 4070 from disengaging with the drive receptacle 4058 and moving towards the distal end of the endoscopic tool 4000. In some implementations, the locking collar 4064 can be configured to secure a lining 4082 within which the flexible torque coil 4080 is disposed to the flexible torque coil 4080, the drive shaft 4072 or the housing 4060. In some implementations, the lining 4082 can serve as a heat shrink to reduce the dissipation of heat generated in the flexible torque coil to other components of the endoscopic tool. In some implementations, the outer wall of the lining 4082 can define a portion of the irrigation channel, while the inner wall of the lining 4082 can serve to prevent any material passing through the aspiration channel from escaping through the walls of the flexible torque coil. In some implementations, the lining 4082 can also prevent the irrigation fluid passing through the irrigation channel to flow into the aspiration channel 4090 through the walls of the flexible torque coil 4080.

The distal end 4048 of the lavage connector 4040 can be configured to engage with an inner wall of the outer tubing 4044. In some implementations, the distal end 4048 of the lavage connector 4040 can be press fit into a proximal end of the outer tubing 4044. In some implementations, a connector connecting the distal end 4048 of the lavage connector 4040 and the outer tubing can be used. The inner wall of the outer tubing 4044 and the outer wall of the lining 4082 can define a portion of the irrigation channel 4096. The outer tubing 4044 can extend from the distal end 4048 of the lavage connector 4040 to a proximal end 4034 of the rotational coupler 4030. The distal end of the outer tubing 4044 can be configured to engage with the proximal end 4034 of the rotational coupler 4030.

In some implementations, the irrigation channel can extend from the irrigation entry port to the opening of the outer cannula. The irrigation channel can be defined by the inner wall of the outer tubular member, the rotational coupler, the inner wall of the outer tubing and the inner wall of outer cannula. In some implementations, the irrigation channel can also be defined by the outer wall of the inner cannula and the outer wall of the flexible torque coil 4080. In some implementations, the endoscopic instrument 4000 can also include the hollow lining 4082 that is sized to fit around the flexible torque coil 4080. In some implementations, the hollow lining 4082 can serve as a barrier between the irrigation channel 4096 and the aspiration channel 4090. In some implementations, the hollow lining 4082 can prevent air or other fluids to seep through the threads of the flexible torque coil 4080. In addition, the hollow lining can allow the aspiration channel to maintain a suction force throughout the length of the aspiration channel by preventing air to escape or enter through the threads of the flexible torque coil 4080.

As described above, the cutting assembly 4010 includes the outer cannula. The braided tubing 4086 is coupled to the outer cannula such that rotating the rotational tab 4032 of the rotational coupler 4030 results in rotating the outer cannula. The outer cannula includes the opening 4012 at a distal end of the outer cannula. The opening is defined within a portion of the radial wall of the outer cannula and may only extend around a portion of the radius of the outer cannula. As the aspiration channel 4090 extends between the aspiration port 4092 and the opening 4012, any suction applied at the aspiration port 4092 causes a suction force to be exerted at the opening 4012. The suction force causes material to be introduced into the opening of the outer cannula, which can then be cut by the inner cannula of the cutting assembly. In some implementations, the aspirated material can be collected in a collection cartridge. In some implementations, the collection cartridge can be fluidly coupled to the proximal end of the aspiration channel.

The inner cannula is disposed within the outer cannula and configured to resect any material that is sucked into or otherwise enters the opening 4012 due to the suction force in the aspiration channel 4090. The inner cannula can cut, resect, excise, debride or shave the material at the opening 4012 based in part on the interaction between the cutting surface and the wall of the outer cannula that defines the opening. In some implementations, the rotational movement of the cutting surface relative to the opening 4012 can cause the material to be cut, resected, excised, or shaved. The flexible torque coil is coupled to the inner cannula and causes the inner cannula to rotate along the longitudinal axis of the inner cannula. As the outer cannula is coupled to the outer tubing and is not rotationally coupled to the inner cannula or flexible torque coil, the inner cannula rotates relative to the outer cannula. A gap between an outer wall of the inner cannula and the inner wall of the outer cannula defines a portion of the irrigation channel through which irrigation fluid can flow from the lavage connector 4040 through the irrigation channel portion defined in part by the outer tubing 4044, the rotational coupler 4030, and the flexible outer tubing 4086 towards the cutting surface of the inner cannula. The inner cannula may define a portion of the aspiration channel through which excised or resected material and the irrigation fluid can flow from the cutting surface of the inner cannula towards the aspiration port 4092.

The length of the cutting assembly 4010 may be sized to allow the endoscopic instrument 4000 to traverse through the length of the endoscope while the endoscope is inserted inside a patient. In some implementations, the endoscope may be disposed within the patient and the endoscope may include bends that exceed 60 degrees. As such, the length of the cutting assembly 4010 may not exceed a few centimeters. In some implementations, the length of the cutting assembly 4010 may be less than 1% of the length of the endoscopic tool 4000, or the length of the flexible portion of the endoscope within which the endoscopic tool can be inserted. As described above, tissue sensing capabilities can be implemented with the cutting assembly serving as a portion of the tissue sensor.

It should be appreciated that one or more seals, bearings, and other components may be used. Seals may be used to maintain pressure, prevent fluid leaks, or to securely engage components to one another. In some implementations, bearings may be used to allow components to rotate relative to one another without adversely affecting the components or the performance of the endoscopic tool.

FIG. 45 shows a cross-sectional view of the endoscopic tool and the portion of the drive assembly across the section B-B. As shown in FIG. 45, the second beveled gear 4056 may be configured to engage with the drive receptacle 4058 of the drive assembly 4050. The proximal connector 4070 of the endoscopic tool 4000, which includes the coupler 4076 and the drive shaft 4072, can be inserted disposed within the drive receptacle 4058. The outer wall of the coupler 4076 is sized to engage with the inner wall of the drive receptacle 4058 such that when the drive receptacle 4058 rotates, the coupler 4076 also rotates. Because the coupler 4076 is coupled to the drive shaft 4072, the drive shaft 4072 may also rotate when the drive receptacle 4058 rotates. The inner wall of the drive shaft defines a portion of the aspiration channel 4090.

FIG. 46 shows an enlarged cross-sectional view of the rotational coupler section of the endoscopic tool. FIG. 47A and FIG. 47B show a top view and a cross-sectional view of the rotational coupler of the endoscopic tool.

As shown in FIGS. 46-47B, the outer tubing 4044 is configured to engage with the rotational coupler 4030. The outer tubing 4044 surrounds the lining 4082, which in turn surrounds the flexible torque coil 4080. The inner wall of the flexible torque coil 4080 may define a portion of the aspiration channel 4090. The space between the inner wall of the outer tubing 4044 and the outer wall or surface of the lining 4082 defines a portion of the irrigation channel. The tab 4032 can be configured to be rotated by an operator of the endoscopic tool. In some implementations, the operator can rotate the tab 4032 while the endoscopic tool is inserted within the instrument channel of the endoscope and cause the outer cannula to rotate relative to the inner cannula and the endoscope. In this way, the operator can position the opening defined through the outer cannula by rotating the outer cannula to a desired position. In some implementations, by providing a mechanism through which the outer cannula can be rotated relative to the endoscope, an operator does not have to be concerned about the position of the opening when the endoscopic tool is inserted within the instrument channel of the endoscope as the operator may be able to adjust the position of the opening by causing the outer cannula to rotate while the endoscopic tool is inserted within the endoscope.

Figure 48:
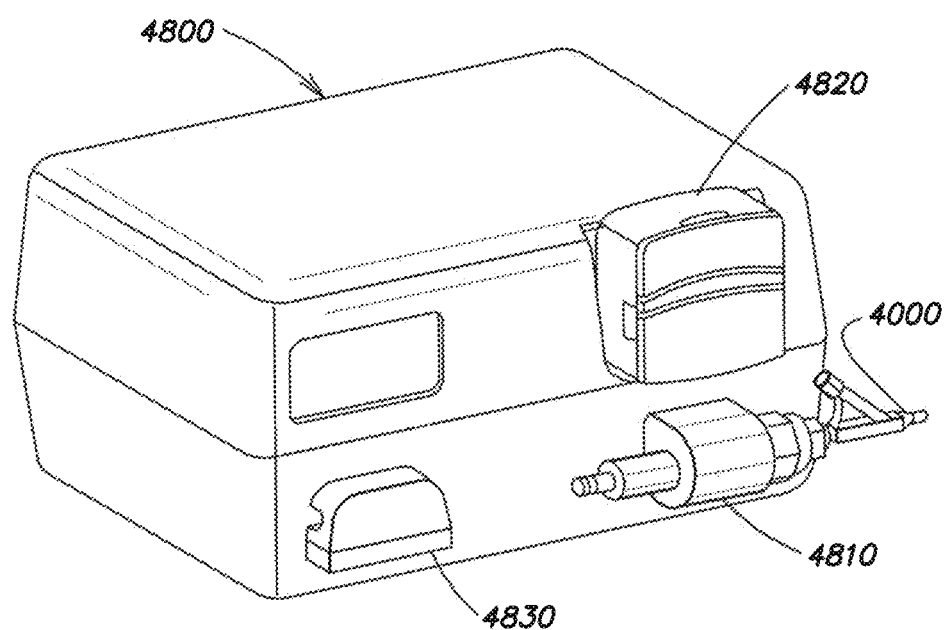
FIG. 48 is a perspective view of a portion of the endoscopic tool inserted for operation within a drive assembly according to embodiments of the present disclosure.

FIG. 48 is a perspective view of a portion of the endoscopic tool inserted for operation within a drive assembly. The drive assembly 4800 includes a drive interface 4810 configured to receive the proximal connector 4070 of the endoscopic tool 4000. The proximal connector 4070 can engage with the drive receptacle of the drive interface 4810 to translate rotational energy generated by the drive assembly 4800 to the cutting assembly of the endoscopic tool 4000. The drive assembly 4800 may include a pump 4820 or other fluid displacement device to control the flow of irrigation fluid into the lavage port 4042 of the endoscopic tool 4000. In some implementations, the pump 4820 can be a peristaltic pump. In some implementations, the pump can be any positive displacement fluid pump. In some implementations, a valve between the pump 4820 and the lavage port 4042 can be placed to control an amount of irrigation fluid entering the endoscopic tool. In some implementations, the speed at which the pump 4820 operates can dictate the rate at which irrigation fluid enters the endoscopic tool. The drive assembly can also include a pinch valve 4830. In some implementations, the pinch valve can be configured to control the application of a suction force applied to the aspiration channel.

In some implementations, an actuator, such as a control switch can be used to actuate the drive assembly 4800. In some implementations, the actuator can be a foot pedal, a hand switch, or any other actuation means for controlling the drive assembly 4800. In some implementations, the actuator can be coupled to the drive means, such as the pump 4820 such that when the actuator is actuated, the pump 4820 begins to rotate, generating torque, which is translated to the proximal connector of the endoscopic tool via the drive interface 4810. The torque applied to the proximal connector can be translated via the flexible torque coil to the inner cannula, thereby causing the inner cannula to rotate relative to the outer cannula. In some implementations, the actuator can be coupled to a pinch valve, such as the pinch valve 4830 to control the amount of suction applied to the aspiration channel. In some implementations, the actuator can be configured to actuate both the drive means and the pinch valve simultaneously, such that the inner cannula is rotating while suction is applied through the aspiration channel. In some implementations, the actuator can also be coupled to an irrigation control switch or valve that controls the flow of irrigation fluid into the endoscopic tool via the irrigation entry port 4042. In some implementations, the actuator can be configured to actuate the drive means, the pinch valve for aspiration and the irrigation control switch for irrigation simultaneously, such that the inner cannula is rotating while suction is applied through the aspiration channel and irrigation fluid is supplied to the endoscopic tool.

In some implementations, a separate irrigation control switch can be configured to control the flow of irrigation fluid through the irrigation channel of the endoscopic tool. An operator can control the volume of irrigation fluid provided to the irrigation channel via the irrigation control switch.

The drive assembly configuration shown in FIGS. 40-48 is one example configuration of a drive assembly. It should be appreciated that the endoscopic tool 4000 can be configured to be driven by other drive assembly configurations. In some implementations, the proximal connector portion of the endoscopic tool 4000 can be modified to engage with other drive assembly configurations. In some implementations, the endoscopic tool 400 can be configured to be packaged as one or more different components that can be assembled prior to inserting the endoscopic tool within the instrument channel of the endoscope. In some implementations, the proximal connector of the endoscopic tool 4000 can be assembled together by an operator of the endoscopic tool after one or more components of the endoscopic tool are caused to engage with components of the drive assembly.

Figure 49:
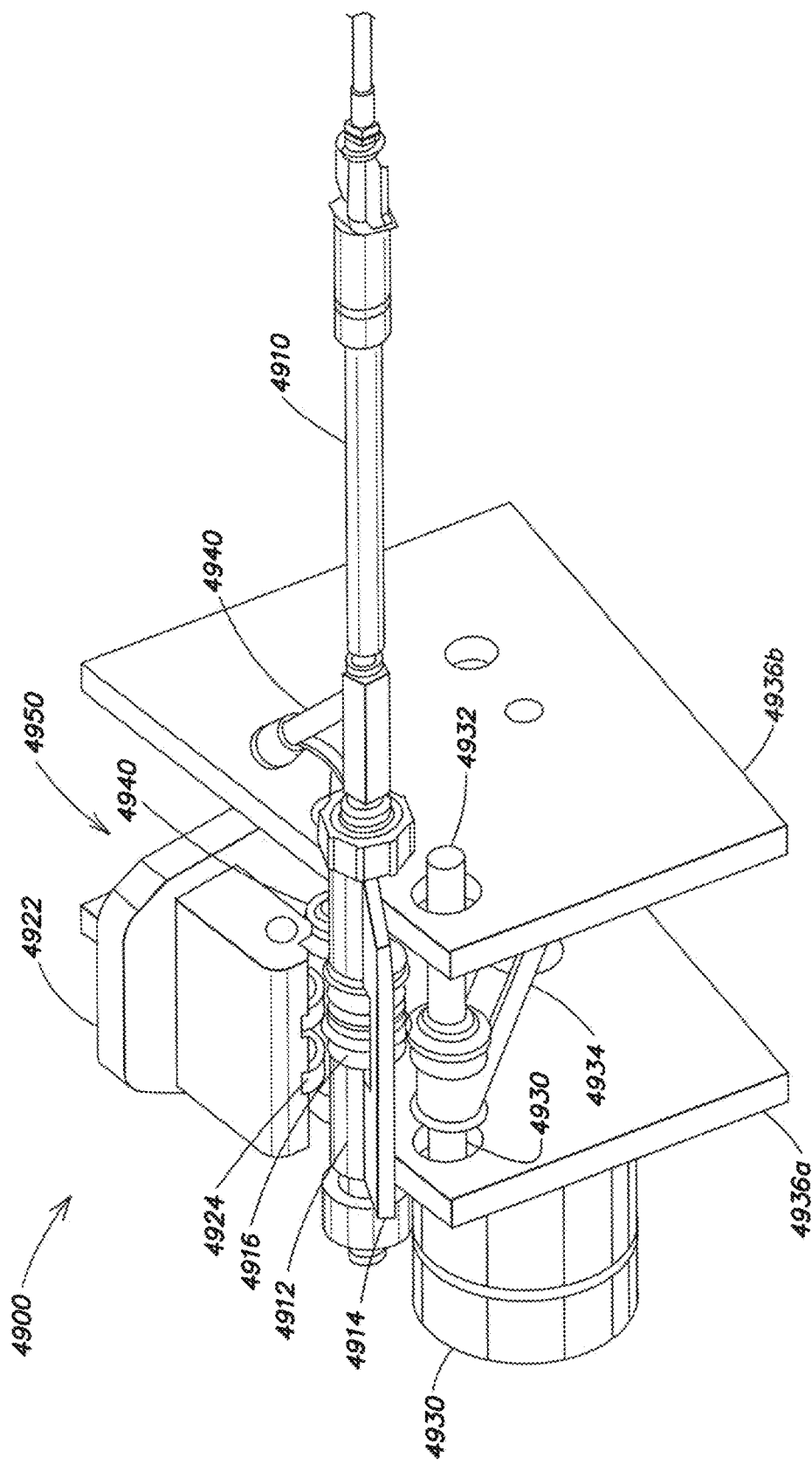
FIG. 49 illustrates another implementation of the endoscopic tool and a drive assembly configured to drive the endoscopic tool according to embodiments of the present disclosure.

FIG. 49 illustrates another implementation of the endoscopic tool and a drive assembly configured to drive the endoscopic tool. FIG. 50A is a side view of the endoscopic tool and drive assembly shown in FIG. 49. FIG. 50B is a cross-sectional view of the endoscopic tool and drive assembly shown in FIG. 49 taken along the section A-A. The endoscopic tool 4910 is similar to the endoscopic tool 4000 but differs from the endoscopic tool 4000 in that the endoscopic tool 4910 has a different proximal connector 4912. In this implementation, the proximal connector 4912 can be coupled to a flexible torque coil, similar to the flexible torque coil of the flexible torque coil 4000 shown in FIGS. 40-43, and include a proximal connector engagement structure 4914 that is configured to engage with a drive assembly 4950. The proximal connector engagement structure can be sized to engage with the drive assembly 4950 and include one or more engagement surfaces configured to engage with the drive assembly 4950. The engagement surfaces can be coupled to the drive shaft included within the proximal connector 4912 such that when the drive assembly 4950 applies a rotating force to the engagement surfaces, the drive shaft rotates, which in turn causes the flexible torque coil and cutting assembly of the endoscopic tool 4900 to rotate. In some implementations, the engagement surfaces 4914 can be cylindrical objects having an outer wall configured to engage with the drive assembly 4950 and an inner wall configured to engage with an outer wall of the drive shaft. In some implementations, the proximal connector 4910 can also include a fin 4916 or other structure that prevents the proximal connector 4910 and endoscopic tool 4910 from rotating relative to the drive assembly 4950. In some implementations, a side of the fin 4916 can rest on or engage with a mounting structure 4936a and 4936b. In this way, when a rotating force is applied by the drive assembly on the engagement surfaces, the fin 4916 prevents the proximal connector 4910 from rotating relative to the drive assembly 4950. The mounting structures 4936 can be configured such that various components of the drive assembly 4950 can be mounted on or receive support from the mounting structures 4936.

The drive assembly 4950 can include a retractable arm 4922, one or more spring loaded bearings 4924, a drive belt 4932 and a drive wheel 4936 and one or more stationary bearings 4940. The retractable arm 4922 can be configured to rotate between a first position and a second position. The spring loaded bearings 4924 can be mounted to the retractable arm 4922 and positioned such that when the retractable arm 4922 is in the first position as shown in FIGS. 49 and 50A-B, the spring loaded bearings 4924 can apply a force on the proximal connector 4912 causing the proximal connector to remain in place while the drive assembly 4950 is actuated. The spring loaded bearings 4924 can be positioned such that when the proximal connector 4912 of the endoscopic tool 4910 is engaged with the drive assembly 4950, the spring loaded bearings 4924 engage with an engagement component 4916 of a drive shaft (not shown) disposed within the proximal connector 4912. The engagement component 4916 can be strategically located on the proximal connector 4912 such that when the retractable arm 4922 is in the first position, the spring loaded bearings 4924 come into contact with the engagement component 4916. The engagement component 4916 can be cylindrical in shape and surround the drive shaft disposed within the proximal connector 4912. The engagement component 4916 can form a portion of the outer wall of the proximal connector 4912. In some implementations, the engagement component 4916 can rotate along a longitudinal axis of the proximal connector 4912 and rotate relative to the proximal connector 4912. In some implementations, the drive wheel 4936 can be an elastomeric friction drive wheel.

A drive means, such as a motor or other driving source, can drive the drive wheel 4936 mounted on a mounting shaft 4930 via the drive belt 4934 that moves when the drive means is actuated. The drive belt 4934 can cause the drive wheel 4936 to rotate. The engagement component 4916 of the proximal connector 4912 can be configured to contact the drive wheel 4936 when the endoscopic tool is positioned within the drive assembly 4950. A stationary bearing 4940 of the drive assembly 4950 can be positioned to hold the proximal connector 4912 in place while the rotation of the drive wheel 4936 causes the engagement component 4916 to rotate. The stationary bearing 4940 can also provide a force causing the drive wheel 4936 and the engagement component 4916 to maintain contact.

As shown in FIG. 50B, when the retractable arm is in the first position, or engaged position, the spring loaded bearings 4924 are in contact with the one or more engagement components 4916 at a first side and the drive wheel 4936 is in contact with the engagement components 4916 at a second side. The spring loaded bearings may allow the engagement components 4916 to rotate when the drive wheel is rotating. The fin 4914 rests against the mounting structures of the drive assembly preventing the endoscopic tool from rotating. When the retractable arm is in a second position, or disengaged position, the spring loaded bearings 4924 are not in contact with the one or more engagement components 4916. As such, the endoscopic tool is not securely positioned within the drive assembly, and as such, actuating the drive means may not cause the flexible torque coil within the endoscopic tool to rotate.

It should be appreciated that the outer diameter of the endoscopic instrument may be sized to be inserted within the instrument channel of an endoscope while the endoscope is inserted within a patient. In addition, the endoscopic instrument may be sized to be large enough that the endoscopic tool comes into contact with the inner walls of the instrument channel at various portions of the instrument channel to maintain stability of the endoscopic instrument. If the outer diameter of the endoscopic instrument is much smaller than the inner diameter of the instrument channel, there may be a large amount of space between the endoscopic instrument and the inner wall of the instrument channel, which may allow the endoscopic instrument to move, vibrate or otherwise experience some instability during operation.

It should be appreciated that the FIGs. shown herein are intended to be for illustrative purposes only and are not intended to limit the scope of the application in any way. In addition, it should be appreciated that the dimensions provided herein are only example dimensions and can vary based on specific requirements. For example, the dimensions may change to alter the aspiration rate, irrigation flow, amount of torque being provided, cutting speed, cutting efficiency, amongst others. Moreover, it should be appreciated that details within the drawings are part of the disclosure. Moreover, it should be appreciated that the shape, materials, sizes, configurations and other details are merely illustrated for the sake of examples and persons having ordinary skill in the art should appreciate that design choices can alter any of the shape, materials, sizes and configurations disclosed herein. For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

Although the present disclosure is directed towards endoscopic instruments adapted for use with any type of endoscope, for sake of convenience, the teachings of the present disclosure are directed towards endoscopic instruments used with a lower GI scope, such as a colonoscope. It should, however, be appreciated that the scope of the present disclosure is not limited to endoscopic instruments for use with GI scopes, but extends to any type of flexible or rigid endoscope, including but not limited to bronchoscopes, gastroscopes and laryngoscopes, hysteroscopes, or other medical devices that may be used to treat patients.

Integrated Torque Generation Component

Aspects of the present disclosure are related to endoscopes configured to include a torque generation component formed within an insertable portion of the endoscope that is insertable within a mammalian cavity of a patient. The torque generation component can be configured to generate torque and provide the generated torque to a surgical cutting assembly removably insertable within the endoscope that is configured, designed or otherwise constructed to be used with such endoscopes. FIGS. 52A-53C and 54A-54B and their corresponding description provided herein relate to endoscopes including an integrated torque generation component, while FIGS. 53D-53F and their corresponding description provided herein relate to a surgical cutting assembly insertable within the endoscope shown in FIG. 53A. Other aspects of the present disclosure relate to endoscopes configured to include a torque delivery component formed within the insertable portion of the endoscope that is configured to deliver torque to a surgical cutting assembly removable insertable within the endoscope. FIGS. 55A-55B and their corresponding description provided herein relate to endoscopes including an integrated torque delivery component. Further, aspects of the present disclosure are related to endoscopes that include either a torque generation component or a torque delivery component and are configured to convert rotational energy to linear motion to provide a surgical cutting assembly that utilizes a reciprocating motion to cut and remove tissue. FIGS. 56A-57C and their corresponding description provided herein relate to endoscopic assemblies that include an endoscope configured to convert rotational energy to linear motion to provide a surgical cutting assembly that utilizes a reciprocating motion to cut and remove tissue. Additional aspects of the present disclosure are related to endoscopic assemblies including an endoscope and a surgical cutting assembly in which the endoscope is configured to rotate an outer cannula of the surgical cutting assembly using a rotary actuator. FIGS. 58A-59B and their corresponding description provided herein relate to such endoscope assemblies. Additional aspects of the present disclosure are related to surgical cutting assemblies which include an outer coupler and an inner coupler magnetically or otherwise coupled to one another. FIGS. 60A-60B and their corresponding description provided herein relate to such surgical cutting assemblies.

The surgical cutting assemblies described herein may be substantially similar to the endoscopic instrument or tool described with respect to FIGS. 40A and 40B. The surgical cutting assemblies described below, however, do not include a flexible torque coil that extends from outside the endoscope to the inner cannula of the surgical cutting assembly to deliver torque. Rather, the surgical cutting assemblies can include a coupling member connected to the inner cannula or cutting assembly and is configured to couple to a coupling component of the endoscope itself. The coupling component of the endoscope is configured to provide the torque to the coupling member of the surgical cutting assembly from a torque generation component integrated within the endoscope or from a torque delivery component, such as flexible torque coil as described above with respect to FIGS. 40A and 40B, that is included in the endoscope but is not part of the surgical cutting assembly.

As previously described with respect to FIG. 14, FIG. 14 shows an implementation of an improved endoscope 1400 including a built in polyp removal assembly 1440. The improved endoscope 1400 may be configured to include a torque generation component, such as a rotary actuator configured to drive a removable surgical cutting assembly.

Figure 51:
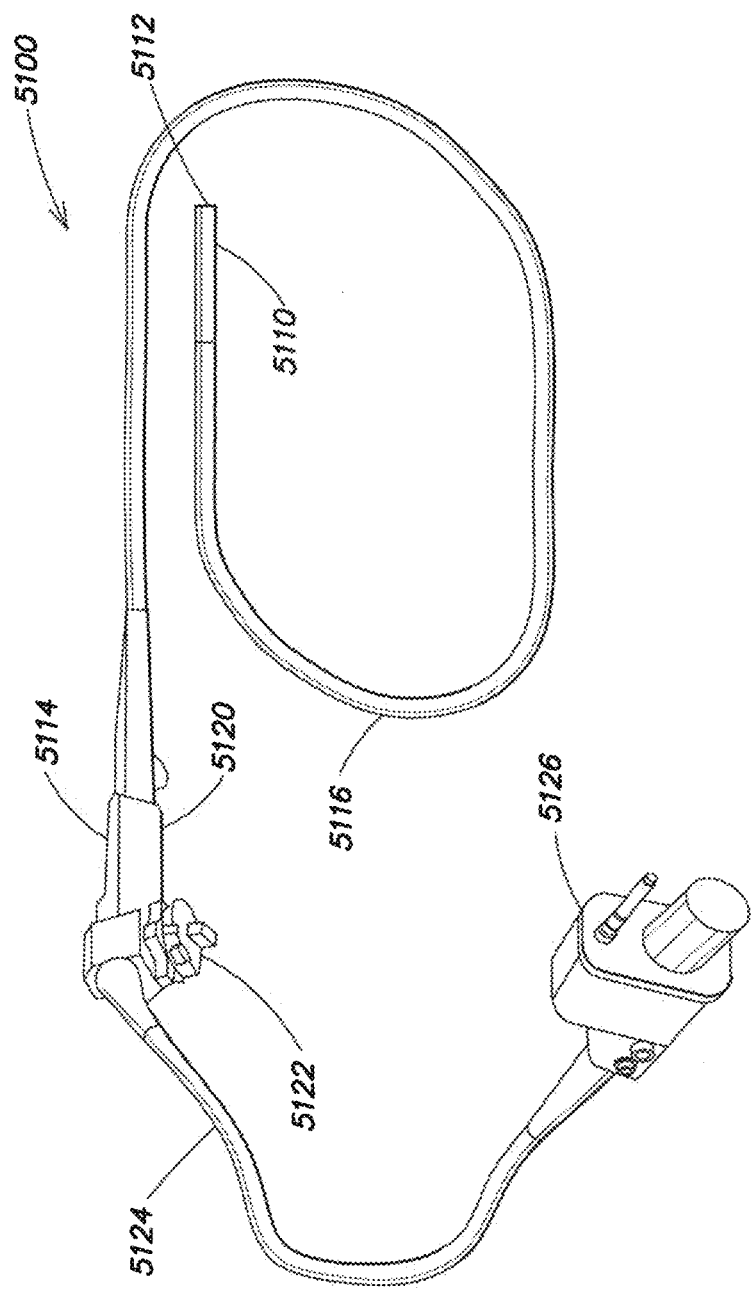
FIG. 51 is perspective view of an endoscope including an integrated torque generation component or a torque delivery component according to embodiments of the present disclosure.

FIG. 51 is perspective view of an endoscope including an integrated torque generation component or a torque delivery component according to embodiments of the present disclosure. The endoscope 5100 can be sized and shaped to fit within one or more mammalian cavities of a patient. In some implementations, the endoscope 5100 can be sized and shaped to fit within a particular mammalian cavity of the patient. For example, the endoscope 5100 is a flexible endoscope insertable within a colon of a patient. However, the present disclosure is not limited to colonoscopes. As such, the endoscope may be a laryngoscope, a bronchoscope, a lower GI scope, a hysteroscope, among others. In some implementations, the endoscope can be a flexible endoscope that is capable of navigating a tortuous path defined by the mammalian cavity of the patient within which the endoscope is being inserted.

The endoscope 5100 can include a distal end 5110 and a proximal end 5114. The distal end 5110 of the endoscope 5100 includes a distal tip 5112 that is first inserted within the mammalian cavity of the patient when the endoscope 5100 is being inserted into the patient. The proximal end 5114 can be sized to not be inserted within the mammalian cavity of the patient. The distal end 5110 can be connected to the proximal end 5114 via an elongated tubular body 5016. The elongated tubular body can be flexible such that both the distal end and a portion of the elongated tubular body 5016 is insertable within a mammalian cavity, such as a colon or other cavity that forms a tortuous path, of the patient. In some implementations, the endoscope 5100 may have dimensions that are similar to existing colonoscopes. In some implementations, the proximal end 5114 may be coupled to or otherwise positioned closer to a handle 5120 or other component by which a medical professional or user of the endoscope can control the endoscope and one or more features of the endoscope. In some implementations, the endoscope can include one or more steering controls 5122 to steer the distal tip 5112 of the endoscope 5100. In addition, the endoscope 5100 can include a connection housing and one or more ports, sockets, plugs or other connection mechanisms for providing one or more functionality to the endoscope, including but not limited to irrigation fluid, camera capabilities, one or more lighting components, among others.

Figure 52A:
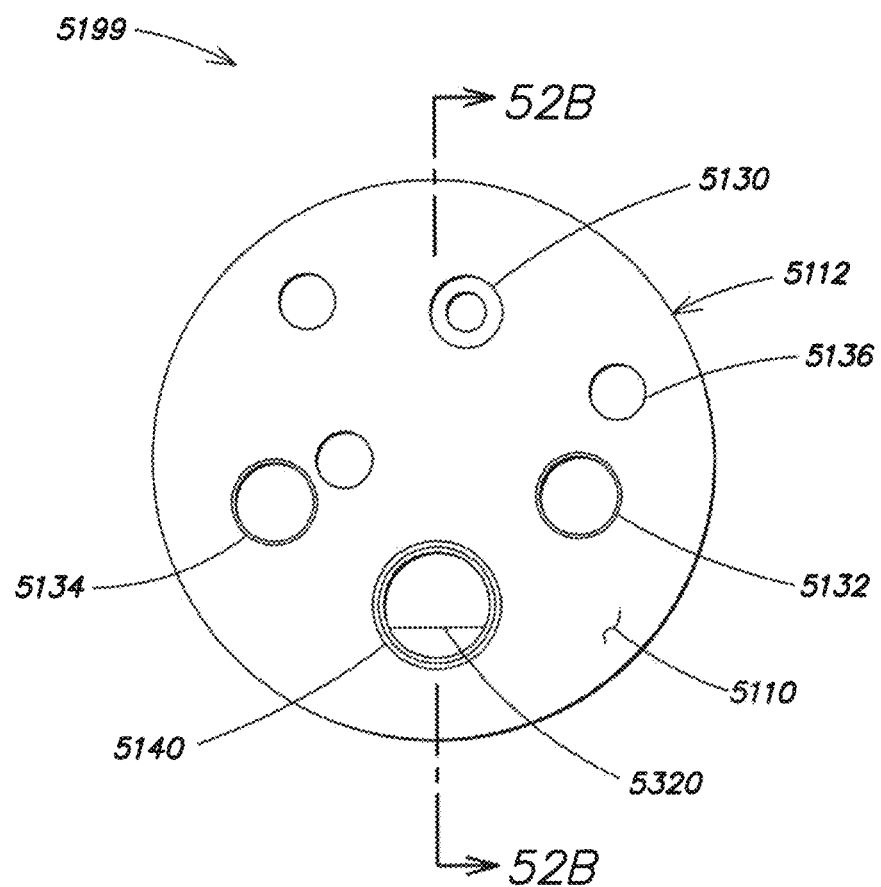
FIG. 52A is a top view of a distal end of an endoscopic assembly including the endoscope shown in FIG. 51 and a surgical cutting assembly inserted within an instrument channel of the endoscope according to embodiments of the present disclosure.

Referring now to FIG. 52A is a top view of the distal end of an endoscopic assembly 5199 including the endoscope 5100 shown in FIG. 51 and a surgical cutting assembly 5320 inserted within an instrument channel 5140 of the endoscope 5100 is shown. The distal tip 5112 of the endoscope 5100 includes a camera 5130, two light sources 5132 and 5134, one or more irrigation channels 5136 and the instrument channel 5140. In some implementations, the endoscope 5100 can include more than one instrument channel.

FIG. 52B is a cross-sectional view of a portion of the endoscopic assembly along the reference line B-B shown in FIG. 52A. The endoscopic assembly 5199 includes the endoscope 5100 and the surgical cutting assembly 5320. Additional details of the surgical cutting assembly 5320 are provided below with respect to at least FIGS. 53A-53F. The elongated tubular body 5116 and the distal tip 5112 of the distal end 5110 of the endoscope 5100 define a portion of the instrument channel 5140 through which one or more instruments, such as the surgical cutting assembly, can be inserted via the proximal end of the endoscope 5100. The instrument channel 5140 can be a bore defined within the endoscope and extending between a first opening defined in the distal tip 5112 of the endoscope 5100 and a second opening defined at the proximal end 5114 of the endoscope. The instrument channel 5140 extends along the length of the tubular body 5116 of the endoscope 5100. In some implementations, the instrument channel 5140 can be cylindrical and can have a diameter that is sized to be large enough to receive a surgical cutting assembly, but small enough to be defined within the endoscope 5100 while providing sufficient space within the endoscope to include other components and channels, such as the camera, light source, irrigation channels, among others. In addition, the instrument channel 5140 may be sized to also provide sufficient space for a torque generation component or a torque delivery component to be inserted within or formed within the endoscope 5100 as will be described in further detail below.

In some implementations, the instruments can be inserted via the distal end 5110 of the endoscope but can only be done so before the endoscope 5100 is inserted within the mammalian cavity of the patient as an opening of the instrument channel at the distal end is no longer accessible once the endoscope is inserted in the mammalian cavity.

The endoscope 5100 can include a coupling component 5150. The coupling component can be positioned at or near the distal end of the endoscope 5100. In some implementations, the coupling component can be positioned at the distal tip 5112 of the endoscope 5100.

In some implementations, the coupling component 5150 can be configured to be positioned around a portion of the instrument channel 5140. The coupling component 5150 can be configured to define a bore through which a portion of the instrument channel 5140 is defined. The diameter of the bore defined by an inner wall of the coupling component 5150 can be greater than a diameter of the instrument channel 5140. In this way, the outer diameter of the portion of the instrument channel 5140 is disposed within the bore of the coupling component 5150. In some implementations, the coupling component 5150 can be cylindrical. In some implementations, the inner bore of the coupling component 5150 can be cylindrical in shape, while an outer wall of the coupling component 5150 can include one or more sides or surfaces. The coupling component 5150 can be aligned with the instrument channel 5140. That is, a longitudinal axis of the bore through which a portion of the instrument channel 5140 is defined can be parallel to a corresponding longitudinal axis of the instrument channel 5140. Moreover, each of the longitudinal axes corresponding to the coupling component 5150, the instrument channel 5140 and the endoscope 5100, respectively can be parallel to one another.

The instrument channel 5140 of the endoscope 5100 can include an engagement portion of the instrument channel 5140. The engagement portion of the instrument channel 5140 is a portion of the instrument channel 5140 where a surgical cutting assembly 5320 inserted within the endoscope is configured to engage with the coupling component 5150 of the endoscope such that the torque generated by the torque generation component or the torque delivered by the torque delivery component can be transferred, transmitted, or otherwise provided to the surgical cutting assembly 5320. In some implementations, the engagement portion of the instrument channel 5140 can be positioned, located or otherwise defined near the distal tip of the endoscope. In some implementations, the engagement portion of the instrument channel can be positioned, located or otherwise defined near the distal tip of the endoscope such that a component of the surgical cutting assembly 5320 configured to engage with the engagement portion of the instrument channel 5140 is able to cause a rigid cutter of the surgical cutting assembly 5320 to cut tissue. Conversely, if the engagement portion of the instrument channel 5140 is positioned away from the distal end of the endoscope such that one or more bends are formed between the engagement portion and the distal tip, the surgical cutting assembly 5320 may be designed to include a flexible torque delivery component configured to provide torque to the cutter to cut tissue. Although the description provided herein refers to torque and providing torque to the surgical cutting assembly 5320, the torque is particularly pertinent to surgical cutting assemblies that utilize rotational motion to cut tissue. The description, however, is not limited to rotational motion based cutting assemblies and the teachings provided herein can be applied to reciprocating motion based cutting assemblies. Details of reciprocating motion based cutting assemblies are provided below.

In some implementations, the coupling component 5150 of the endoscope 5100 can be a cylindrical ring structure that includes an inner wall and an outer wall. The coupling component 5150 can be positioned around the engagement portion of the instrument channel 5140 such that the inner wall of the coupling component forms a portion of the wall of the endoscope 5100 that defines the instrument channel 5140.

In some implementations, the coupling component 5150 can be sized and positioned such that the coupling component allows the endoscope to pass through a tortuous path of the mammalian cavity of the patient within which the endoscope was designed to be inserted. In some implementations, the dimensions of the coupling component can be based on a bending radius of the endoscope. In some implementations, the dimensions of the coupling component, in particular the height of the coupling component may be sized to allow the endoscope to be inserted within a mammalian cavity of the patient and to navigate a tortuous path defined by the mammalian cavity. If the height of the coupling component is too large, the coupling component 5150 may prevent the elongated tubular body within which the coupling component 5150 is formed, disposed or otherwise positioned to navigate past bends defined by the mammalian cavity. In some implementations, the coupling component 5150 may be made from a material that takes the shape of the elongated tubular body. In some such implementations, the coupling component can have a height that is greater than a height that would otherwise prevent the elongated tubular body from navigating past bends of the mammalian cavity.

The coupling component 5150 can be configured to provide torque from the endoscope 5100 to the surgical cutting assembly 5320 by coupling with a corresponding component of the surgical cutting assembly 5320. The coupling component 5150 can receive the torque to provide to the surgical cutting assembly 5320 from a torque generation component, such as a rotary actuator, or from a torque delivery component, such as a torque coil or torque rope configured to deliver torque from a torque generation component to which the torque delivery component is coupled. Additional details of the torque generation component or torque delivery component from which the coupling component is configured to receive torque are provided below.

In some implementations, the coupling component 5150 is or can include a magnetic coupler. The coupling component 5150 can be a magnet that has a magnetic field. In some implementations, the coupling component 5150 can be positioned such that a force of the magnetic field is sufficiently strong to magnetically couple with a coupling member of the surgical cutting assembly 5320 configured to be inserted within the instrument channel of the endoscope. The coupling component 5150 can be configured to magnetically couple with the coupling member of the surgical cutting assembly 5320 such that when the coupling component 5150 is rotated, the coupling member of the surgical cutting assembly 5320 also rotates due to the magnetic field of the coupling component 5150 acting on the coupling member of the surgical cutting assembly 5320.

Figure 53A:
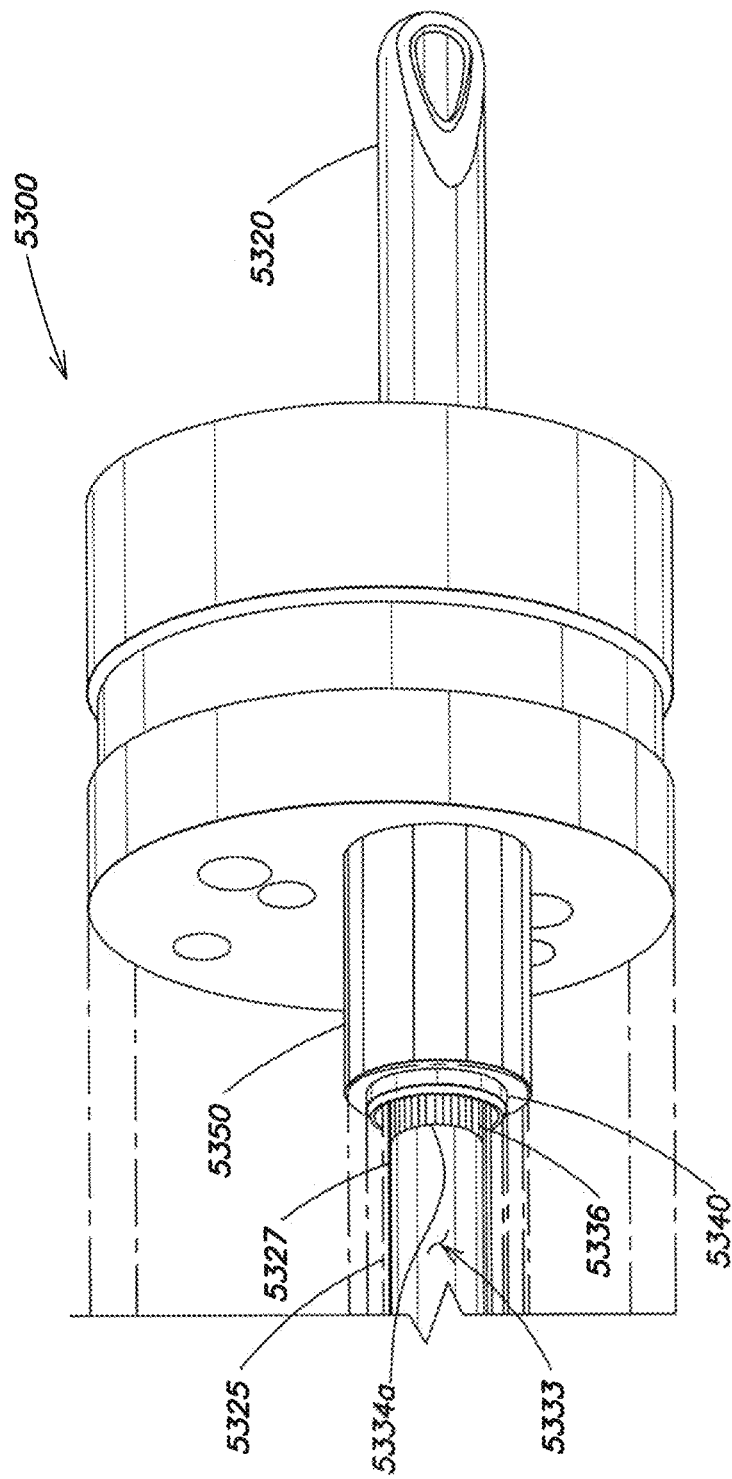
FIG. 53A is a perspective view of the portion of the endoscopic assembly shown in FIG. 51.
Figure 53B:
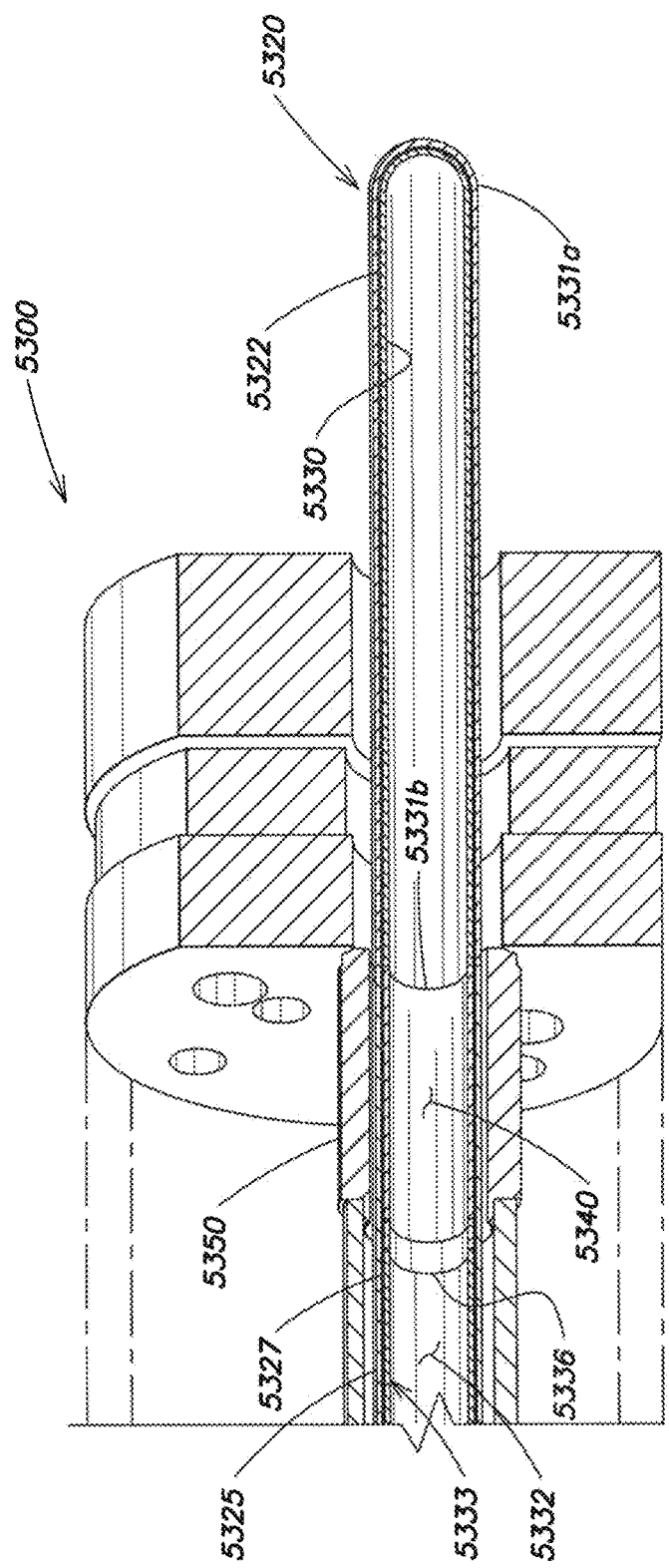
FIG. 53B is a cross-sectional view of the portion of the endoscopic assembly shown in FIG. 53A.
Figure 53C:
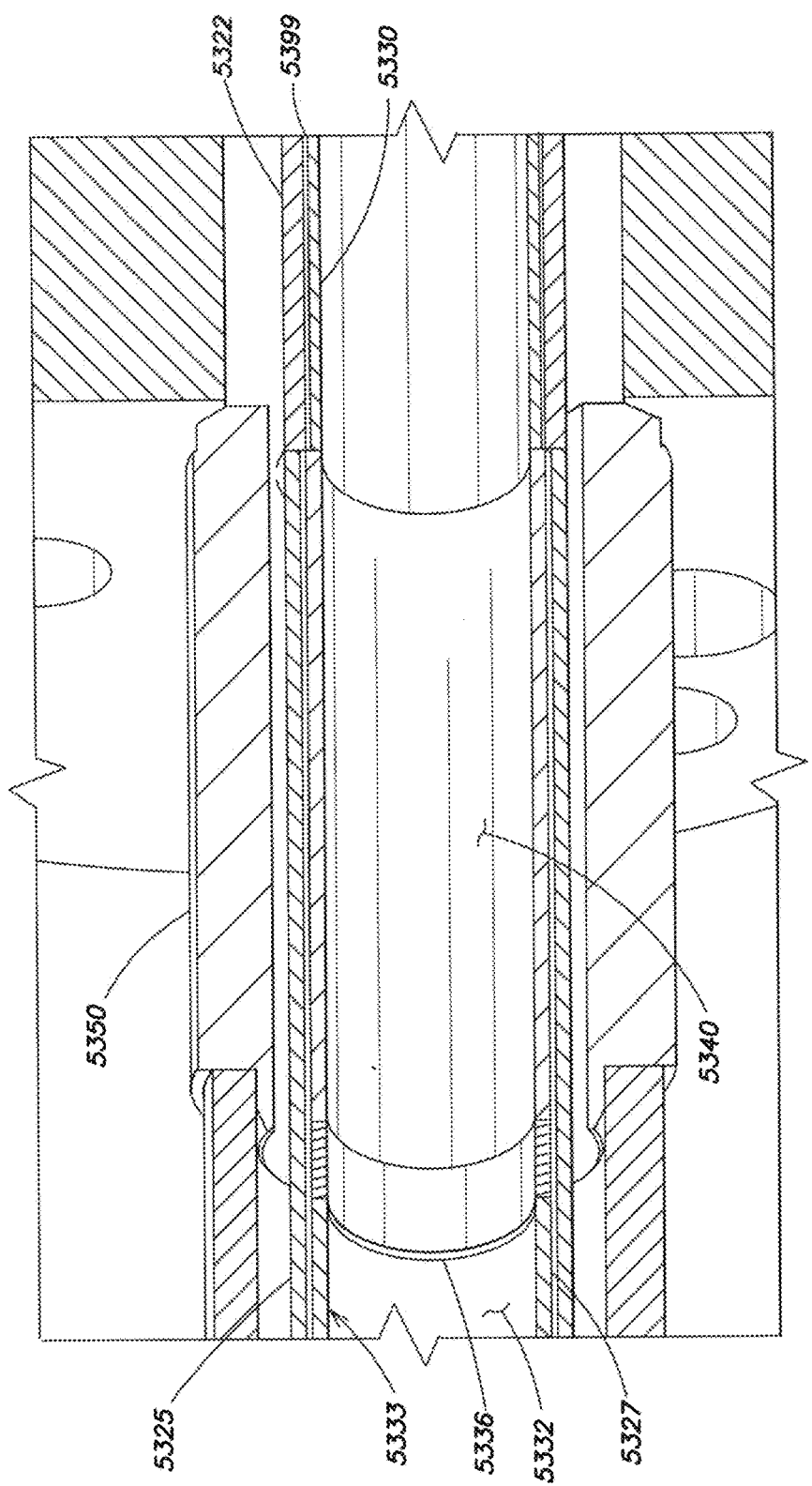
FIG. 53C is an enlarged cross-sectional view of the portion of the endoscopic assembly shown in FIG. 53A.

FIG. 53A is a perspective view of the portion of the endoscopic assembly shown in FIG. 51. FIG. 53B is a cross-sectional view of the portion of the endoscopic assembly shown in FIG. 53A. FIG. 53C is an enlarged cross-sectional view of the portion of the endoscopic assembly shown in FIG. 53A. Referring now to FIGS. 53A-53C as well as FIG. 52B, the surgical cutting assembly 5320 is disposed within the instrument channel 5140 of the endoscope 5100.

The surgical cutting assembly 5320 is configured to be inserted within the instrument channel 5140 of the endoscope 5100. As such, the surgical cutting assembly 5320 can be sized and shaped to correspond to the dimensions of the instrument channel 5140. The surgical cutting assembly 5320 can have an outer diameter or dimension that is smaller than an inner diameter or other corresponding dimension of the instrument channel. Further, in some implementations, the surgical cutting assembly 5320 may have a length that is longer than a corresponding length of the instrument channel, which may be the length between the opening of the instrument channel at the distal tip 5112 of the endoscope 5100 and the opening of the instrument channel 5140 at the proximal end 5114 of the endoscope 5100.

Figure 53D:
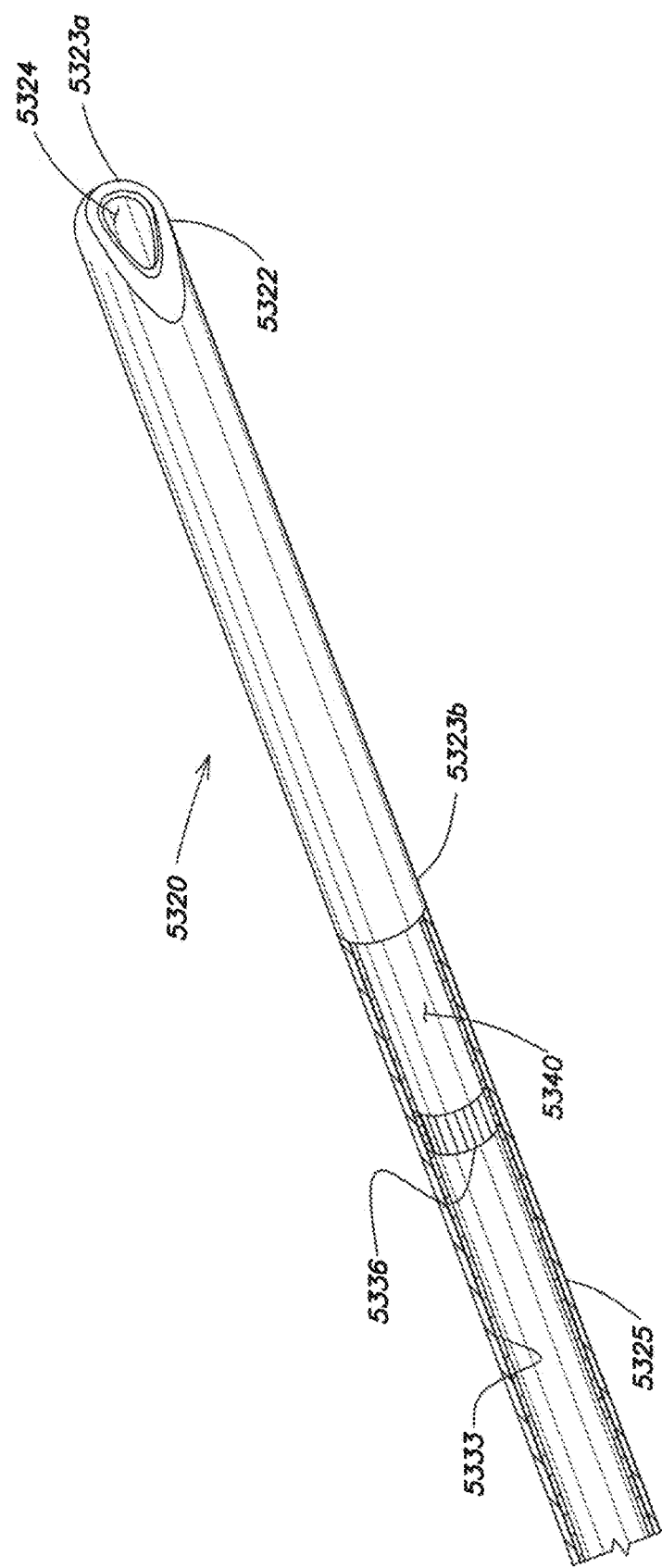
FIG. 53D is a perspective view of a surgical cutting assembly inserted in the endoscope shown in FIG. 53A.
Figure 53E:
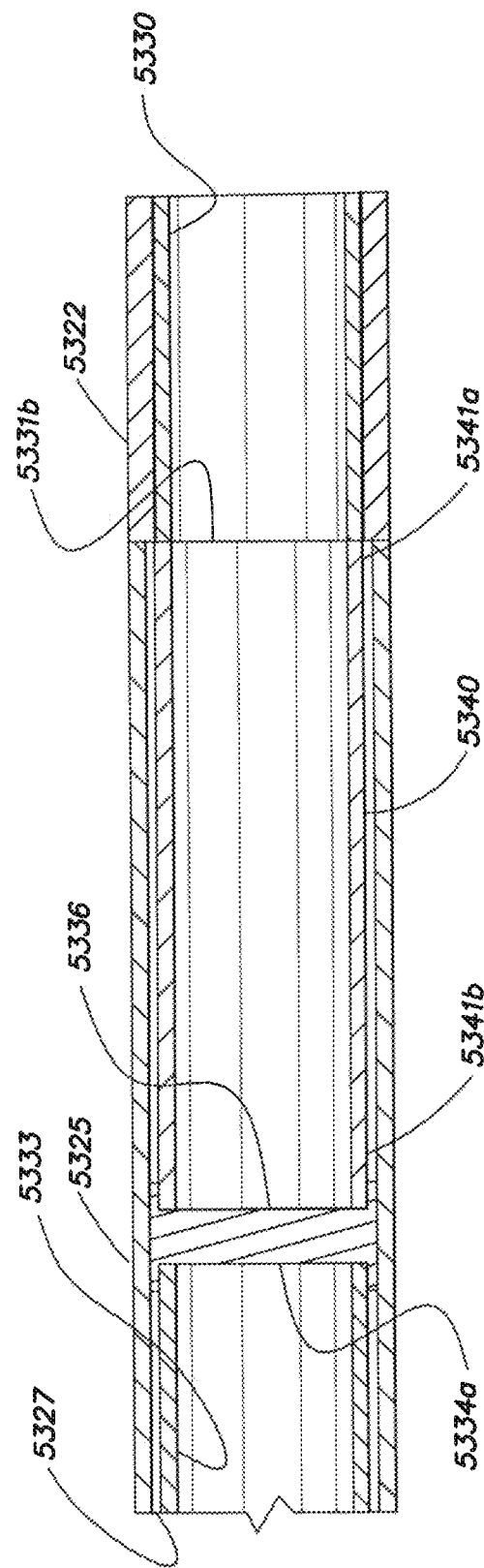
FIG. 53E is a cross-sectional view of a portion of the surgical cutting assembly shown in FIG. 53D.
Figure 53F:
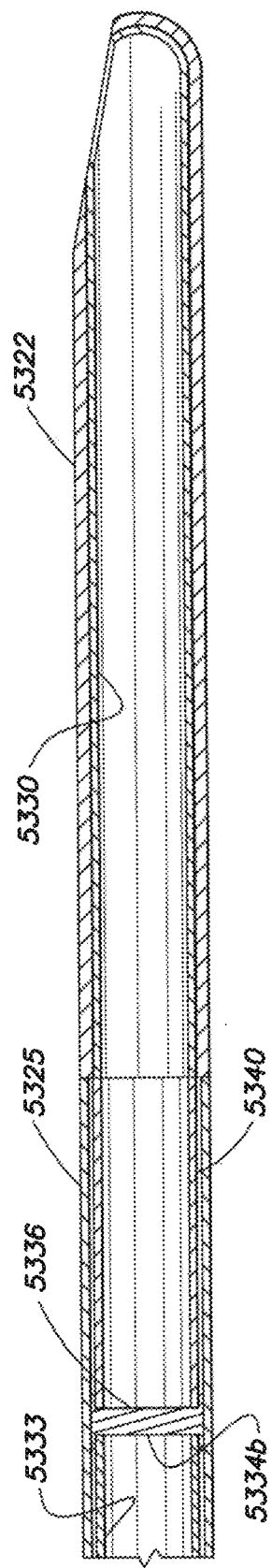
FIG. 53F is a side cross-sectional view of the surgical cutting assembly shown in FIG. 53D.

FIG. 53D is a perspective view of a surgical cutting assembly inserted in the endoscope shown in FIG. 53A. FIG. 53E is a cross-sectional view of a portion of the surgical cutting assembly shown in FIG. 53D. FIG. 53F is a side cross-sectional view of the surgical cutting assembly shown in FIG. 53D. Referring now also to FIG. 53D-53F, the surgical cutting assembly 5320 can include a cutter section including an outer cannula 5322 and an inner cannula 5330 at a distal end of the surgical cutting assembly 5320, a coupling member 5336 and an elongated flexible tubing portion (shown as including the braided tubing 5325 and an aspiration tube 5333 described below) extending from the cutter section to the proximal end of the surgical cutting assembly 5320. The outer cannula 5322 can include a distal tip 5323a and can define an opening 5324 along a radial wall of the distal tip 5323a of the outer cannula 5322. The inner cannula 5330 can be disposed within the outer cannula 5322 such that the inner cannula 5330 can rotate about or translate along a longitudinal axis extending through a length of the surgical cutting assembly 5320 within the outer cannula 5322. The inner cannula 5330 can include a cutting edge at a distal tip 5333 of the inner cannula 5330 that is configured to cut tissue entering the opening 5324 of the outer cannula 5322. The outer cannula 5322 can have an outer diameter that is smaller than the diameter of the instrument channel 5140 and the inner cannula 5330 can have an outer diameter that is smaller than the inner diameter of the outer cannula 5322. A gap 5399 between the inner wall of the outer cannula 5322 and the outer wall of the inner cannula 5330 can define a portion of an irrigation channel of the surgical cutting assembly 5320.

A proximal end 5323b of the outer cannula 5322 can be coupled to an elongated braided tubing 5325. The braided tubing 5325 can extend from the outer cannula 5322 to the proximal end of the surgical cutting assembly 5320. The braided tubing 5325 can be configured to allow rotation provided at a portion of the proximal end of the elongated braided tubing 5325 to be transmitted to the outer cannula 5322. In this way, by rotating the portion of the elongated braided tubing 5325 at the proximal end, the opening 5324 of the outer cannula 5322 can be rotated relative to the endoscope 5100 within which the surgical cutting assembly 5320 is inserted. The inner wall of the braided tubing 5325 may also define another portion of the irrigation channel that is fluidly coupled to the gap 5399 extending between the outer cannula 5322 and the inner cannula 5330.

A proximal end 5333b of the inner cannula 5330 can be configured to be coupled to a distal end 5341a of a coupling member 5340. The coupling member 5340 may be coupled to the inner cannula such that when the coupling member 5340 rotates, the inner cannula 5130 also rotates. Moreover, the bore of the inner cannula 5130 defines a portion of an aspiration channel 5332 through which tissue cut by the inner cannula 5330 can be aspirated through the surgical cutting assembly 5120. The coupling member 5340 can be configured to define a bore that is fluidly coupled to the portion of the aspiration channel 5332 defined by the inner cannula 5330 such that material entering the aspiration channel 5332 via a cutting tip of the inner cannula 5330 is allowed to flow through the coupling member 5340. A proximal end 5341b of the coupling member 5340 may be fluidly coupled to an aspiration tube 5333. The aspiration tube 5333 can be an elongated tube that may extend from the proximal end 5341a of the coupling member 5340 to the proximal end of the surgical cutting assembly 5320. The aspiration tube 5333 may be disposed within the elongated braided tubing 5325 and an outer wall of the aspiration tube 5333, together with the inner wall of the elongated braided tubing 5325 may define a portion of the irrigation channel 5327. In some implementations, the aspiration tube 5333 and the braided tubing 5325 may be made from a material that is configured to bend sufficiently to pass through tortuous paths defined by the instrument channel 5140 once the endoscope 5100 is inserted within a mammalian cavity of the patient.

The surgical cutting assembly 5320 can include a rotary seal 5336 that is configured to couple the proximal end 5341a of the coupling member 5340 to a distal end 5334a of the aspiration tube 5333. The rotary seal 5336 can be designed and configured such that the rotary seal 5336 prevents the aspiration tube 5333 from rotating when the coupling member 5340 is rotated. In some implementations, the rotary seal 5336 may also be configured to couple the inner cannula 5330, coupling member 5340 and the aspiration tube 5333 to the braided tubing 5325 and outer cannula 5322. In some implementations, an outer ring of the rotary seal 5336 can connect the proximal end 5323*b* of the outer cannula 5322 to the distal end of the braided tubing 5325. In some implementations, an outer surface of the outer ring of the rotary seal 5336 can include frictional elements to allow the outer ring to frictionally engage with a portion of the outer cannula or inner wall of the braided tubing such that the outer cannula and the inner cannula can move laterally together without be rotationally coupled. The rotary seal 5336 can also include an inner ring connected to the outer ring. In some implementations, the inner ring can rotate independently of the outer ring and vice versa. The inner ring may have a rotational portion and a stationary portion. The rotational portion may be coupled to the proximal end 5341*b* of the coupling member 5340, while the stationary portion may be coupled to the distal end 5334*a* of the aspiration tube 5333. The rotational portion and the stationary portion may be fluidly coupled such that fluid passing through the inner cannula 5330 and the coupling member 5340 can flow through the aspiration tube 5333. The outer ring and the inner ring may be fluidly disconnected or uncoupled such that fluid passing in the aspiration channel 5332 cannot flow into the irrigation channel via the rotary seal 5336 and fluid from the irrigation channel 5327 cannot flow into the aspiration channel 5332 via the rotary seal 5336. Although rotary seals are described herein to couple the coupling member to the aspiration tube, any component capable of isolating rotation of the coupling member from the aspiration tube, while allowing the coupling member to be fluidly coupled to the aspiration tube may be used. Additional details as well as other aspects of the surgical cutting assembly are provided below.

In some implementations, the surgical cutting assembly may be similar to the endoscopic tool 4000 described above in that both the surgical cutting assembly and the endoscopic tool can include an outer cannula, an inner cannula, an outer braided tubing coupled to the outer cannula, an irrigation channel defined between the inner walls of the outer cannula and outer braided tubing and the outer walls of the inner cannula and the aspiration tube (defined in the endoscopic tool by the flexible torque coil). The surgical cutting assembly is different in that it does not include the flexible torque coil or rope, but rather includes a flexible aspiration tube that is coupled to the inner cannula via a coupling member capable of being magnetically coupled to a coupling component of the endoscope.

The surgical cutting assembly can include a rotational coupler (similar to the rotational coupler 4030) configured to be coupled to a proximal end of the outer braided tubing 5325. The rotational coupler may be configured to allow an operator of the surgical cutting assembly to rotate the outer braided tubing 5325 via a rotational tab (similar to the rotational tab 4032) coupled to or being an integral part of the rotational coupler. By rotating the rotational tab, the operator can rotate the outer braided tubing 5325 and the outer cannula 5322 along a longitudinal axis of the endoscope and relative to the endoscope and the inner cannula 5330 of the surgical cutting assembly 5320. In some implementations, the operator may want to rotate the outer cannula while the endoscopic instrument is inserted within the endoscope while the endoscope is within the patient. The operator may desire to rotate the outer cannula to position the opening of the outer cannula to a position where the portion of the radial wall of the outer cannula within which the opening or cutting window is defined may be aligned with the camera of the endoscope such that the operator can view the material entering the endoscopic instrument for resection via the opening. This is possible in part because the opening is defined along a radial wall extending on a side of the outer cannula as opposed to an opening formed on the axial wall of the outer cannula.

In some implementations, a proximal end (similar to the proximal end 4034) of the rotational coupler can be coupled to a lavage connector (similar to the lavage connector 4040). In some implementations, the rotational coupler can be a rotating luer component that allows a distal end of the rotational coupler to rotate relative to the proximal end of the rotational coupler. In this way, when the outer braided tubing 5325 is rotated, the component to which the proximal end of the rotational coupler is coupled, is not caused to rotate. In some implementations, the proximal end of the rotational coupler can be coupled to an outer tubular member (similar to the outer tubular member 4044) configured to couple the proximal end of the rotational coupler to the lavage connector. The rotational coupler can define a bore along a central portion of the rotational coupler through which a portion of the aspiration tube 5333 extends. In some implementations, the rotational coupler can be a male to male rotating luer connector. In some implementations, the rotational coupler can be configured to handle pressures up to 1200 psi.

The lavage connector (similar to the lavage connector 4040) can be configured to introduce irrigation fluid into the surgical cutting assembly 5320. The lavage connector includes a lavage port (similar to the lavage port 4042) configured to engage with an irrigation source, such as a water container. In some implementations, the lavage connector can be a Y port used in fluid delivery systems that complies with medical device industry standards and is sized to couple to the outer braided tubing 5325 or the outer tubular member that serves to couple a distal end of the lavage connector to the proximal end of the rotational coupler. In some implementations, the lavage connector can define a hollow channel between the proximal end and the distal end of the lavage connector that is sized to allow the aspiration tube 5333 to pass through the hollow channel defined through the lavage connector.

Figure 54A:
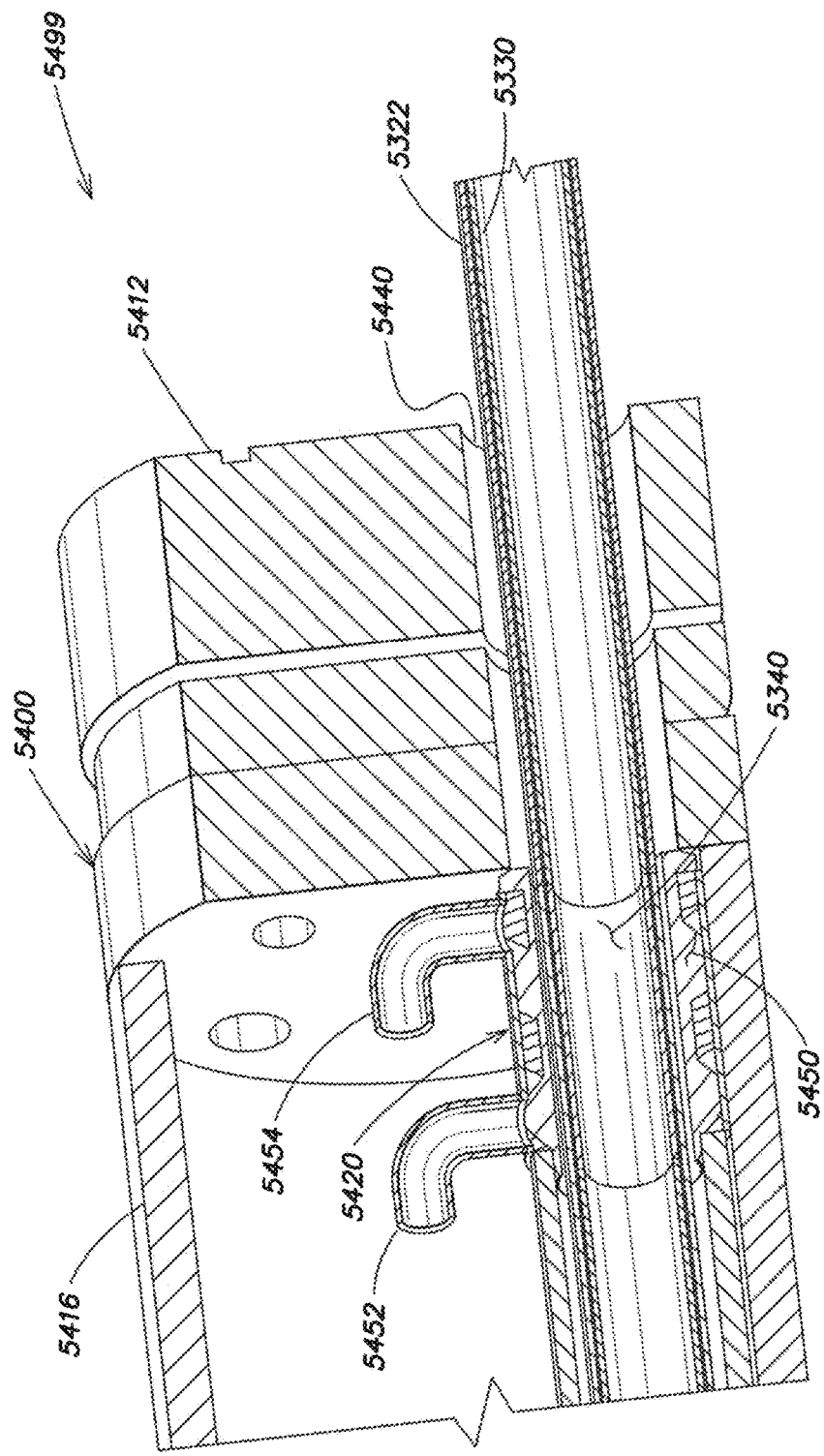
FIG. 54A is a cross-sectional perspective view of a portion of an endoscopic assembly including an endoscope and a surgical cutting assembly in which an endoscope includes an integrated torque generation component according to embodiments of the present disclosure.
Figure 55B:
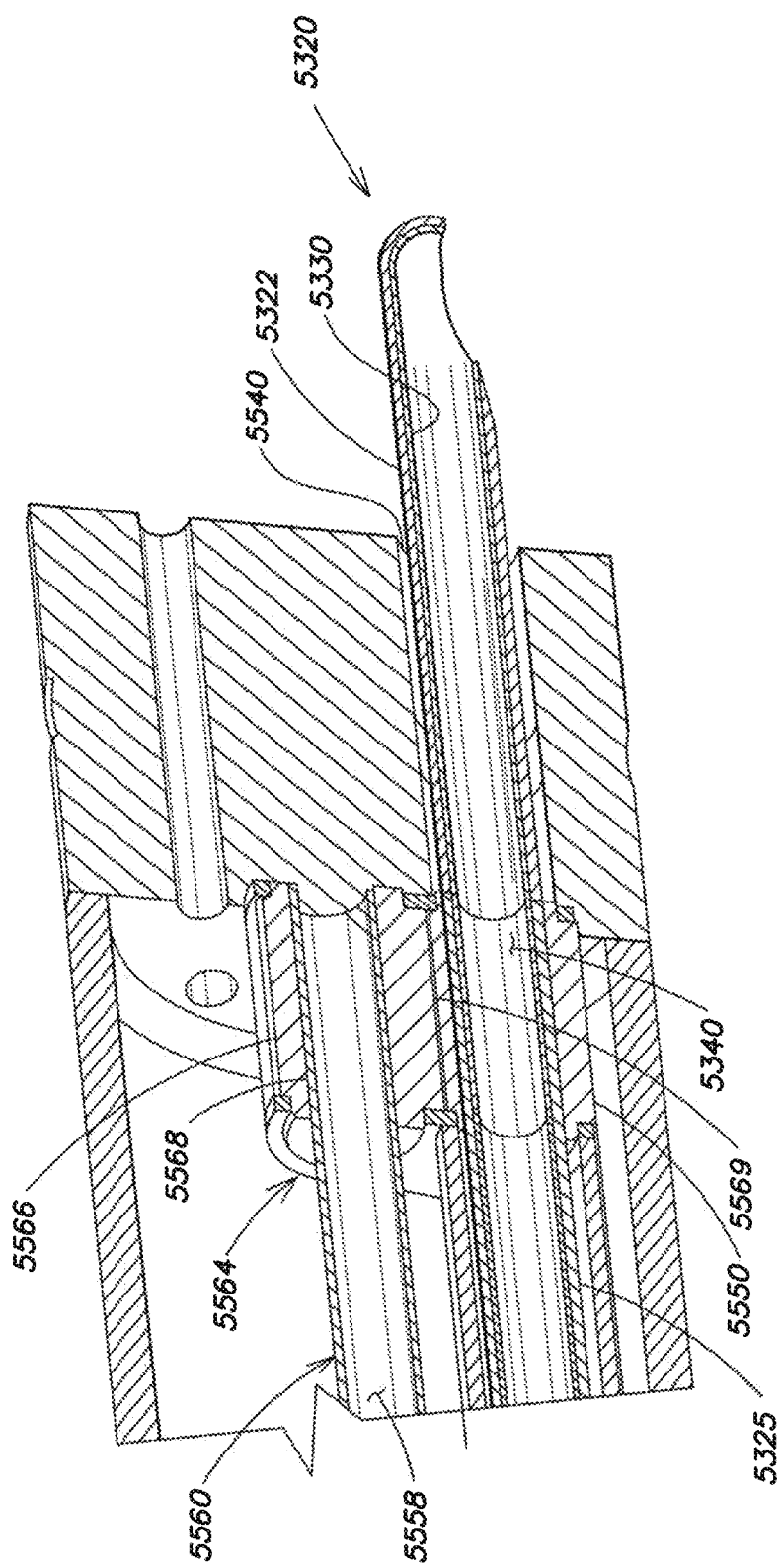
FIG. 55B is a cross-sectional perspective view of the portion of the endoscope shown in FIG. 55A and a surgical cutting assembly inserted in the endoscope according to embodiments of the present disclosure.

FIG. 54A is a cross-sectional perspective view of a portion of an endoscopic assembly including an endoscope and a surgical cutting assembly in which an endoscope includes an integrated torque generation component according to embodiments of the present disclosure. The endoscopic assembly 5499 shown in FIG. 54A can be the endoscopic assembly 5100 shown in FIGS. 51-53A. FIG. 54B is an enlarged view of the torque generation component of the endoscope shown in FIG. 54A. Referring now to FIGS. 54A-54B, the endoscopic assembly includes an endoscope 5400 and the surgical cutting assembly 5320 shown in FIGS. 53A-53F. The endoscope 5400 includes a distal tip 5412 coupled to a distal portion of a flexible elongated tubular body 5416. The elongated tubular body 5416 can include a torque generation component 5420 configured to generate torque that can be provided to the surgical cutting assembly 5320 insertable within the instrument channel 5440 of the endoscope 5400 via a coupling component 5450.

In some implementations, the torque generation component 5420 can be a rotary actuator configured to generate torque or rotational energy. In some implementations, the torque generation component 5420 can be a hydraulic or pneumatic rotary actuator. In some implementations, the hydraulic or pneumatic rotary actuator can include a rotor configured to rotate by supplying a fluid to the rotary actuator. In some implementations, the rotary actuator can be actuated using a vacuum source. The rotary actuator can be sized to fit within the elongated tubular body. Moreover, the rotary actuator can be sized to fit within the elongated tubular body while allowing the elongated tubular body to navigate bends in the mammalian cavity of the patient. In some implementations, the rotary actuator can be configured to include the coupling component 5450. In some such implementations, the coupling component 5450 may form a portion of the torque generation component. In some implementations, the coupling component 5150 shown in FIGS. 53A-53C may form an inner portion of the rotary actuator 5420 that is configured to rotate. In some implementations, the coupling component 5450 may be coupled to a shaft of the rotary actuator such that when the shaft of the rotary actuator is rotated, the coupling component 5450 also rotates. An example of hydraulic or pneumatic rotary actuators that can be used as the torque generation component can include the vane type rotary actuators provided by Kuroda Pneumatics, Ltd. Of Tokyo, Japan. The rotary actuator 5420 may include one or more features that are similar to the features of the rotor 440 described in FIG. 4A. As described with respect to FIG. 4A, the rotor 440 was formed within the endoscopic instrument insertable within an endoscope. In contrast, however, the rotary actuator 5420 is configured to be formed within the endoscope itself and configured to generate torque to provide to an endoscopic instrument, such as the surgical cutting assembly 5320, that does not include a torque generation component but rather receives the torque generated by the rotary actuator 5420 via the coupling component 5150.

In some implementations, the elongated tubular body 5416 can include at least one fluid delivery channel 5452 configured to deliver fluid to the torque generation component 5420 and at least one fluid removal channel 5454 configured to remove the fluid from the torque generation component 5420. The fluid delivery channels 5452 and the fluid removal channels 5452 can be defined within the elongated tubular body and may extend parallel to one another as well as one or more other channels defined within the endoscope 5400. In some implementations, the fluid delivery channels 5452 and the fluid removal channels 5454 can be defined within the elongated tubular body 5416 such that the fluid delivery channels 5452 and the fluid removal channels 5454 do not intersect other channels defined within the elongated tubular body 5416. In some implementations, each of the fluid delivery channels 5452 and the fluid removal channels 5452 may include a corresponding opening defined at the proximal end of the elongated tubular body 5416. The fluid delivery channels 5452 can be fluidly coupled to a fluid source configured to provide a fluid to drive the torque generation component 5420. In some such implementations, the fluid removal channels 5454 can be configured to remove the fluid from the torque generation component 5420 supplied by the fluid delivery channels 5452. In some implementations, the fluid can be a liquid, such as water or other fluid suitable for use in driving a hydraulic rotary actuator. In some implementations, the fluid delivery channels 5452 can be configured to supply pressurized air to a pneumatic rotary actuator to drive the pneumatic rotary actuator. In some such implementations, the fluid removal channels 5454 can be configured to remove the air from the pneumatic rotary actuator previously supplied by the fluid delivery channels.

In some implementations, the torque generation component 5420 can be a piezoelectric rotary actuator configured to generate torque. In some implementations, the torque generation component can be an electric motor, including but not limited to stepper motors, servo motors, among others. In some such implementations, one or more channels for electrical wires to power the electric motor may be defined within the elongated tubular body. In some implementations, the electric motor may be battery powered such that the elongated tubular body may include one or more energy storage components, such as cells, batteries or other components capable of storing electrical charge. In some such implementations, the endoscope may include a battery charging port or be constructed such that the energy storage components are removable from the endoscope. An example of motors that can be used as the torque generation component can include DC motors manufactured by Maxon Precision Motors, Inc., of Fall River, Mass., USA. These DC motors can have sizes that can range from less than 4 mm to greater than 12 mm. As the elongated tubular bodies of typical colonoscopes can have an outer diameter of about 13 mm, these motors can be integrated within the elongated tubular bodies, while still providing space to provide channels of other features. In some implementations, the SQUIGGLE micromotor and M3-R motors manufactured by New Scale Technologies of Victor, N.Y., USA may also be used. In some implementations, the SQUIGGLE micromotor can be used to generate linear motion, which is described above with respect to FIGS. 56-57C.

In some implementations, the coupling component 5450 can form a portion of the torque generation component. The torque generation component can be a frameless motor that includes a stator and a rotor. In some implementations, the coupling component 5450 can form the stator portion of the frameless rotor. The coupling component 5450 can be sized to fit within the endoscope and positioned such that the coupling component 5450 surrounds a portion of the instrument channel towards the distal tip of the endoscope. The coupling component 5450 can be configured to engage with the coupling member 5340 of the surgical cutting assembly 5320 such that the coupling member 5340 rotates when the coupling component 5450 is actuated. The coupling component may be actuated by an electric current, which can be provided via an electrical connection to a power source. In some implementations, the electrical connection can be from a power source outside the endoscope. In some implementations, the electrical connection can be from a battery or other power source disposed within the endoscope.

In some implementations, the elongated tubular body 5416 of the endoscope 5400 may define a cavity positioned near the distal tip of the endoscope 5400. The cavity may be sized and shaped to contain the torque generation component. The cavity may include openings that are fluidly coupled to the fluid delivery channels 5452 and the fluid removal channels 5454. The torque generation component can be positioned such that the openings of the fluid delivery channels 5452 and the fluid removal channels 5454 are fluidly coupled to the torque generation component to cause the torque generation component 5420 to generate torque upon supplying and removing the fluid to the torque generation component 5420.

The torque generation component 5420 or the cavity within which the torque generation component is disposed may be sized such that the endoscope is capable of passing through tortuous paths defined by a mammalian cavity of a patient within which the endoscope is configured to be inserted. Moreover, the torque generation component may be disposed in the endoscope at a location that is close to the distal tip such that the coupling component 5450 that is part of or coupled to the torque generation component can provide the torque generated by the torque generation component 5420 to the surgical cutting assembly such that a distal end of the inner cannula of the surgical cutting assembly can extend beyond the distal tip 5412 of the endoscope 5400, while a proximal end of the inner cannula 5330 is rotationally coupled to the coupling component 5450 of the endoscope 5400 and the surgical cutting assembly does not include a torque delivery component that may be configured to deliver the torque generated by the torque generation component 5420.

FIG. 55A is a perspective view of a portion of an endoscopic assembly including an endoscope and a surgical cutting assembly in which the endoscope includes an integrated torque delivery component according to embodiments of the present disclosure. FIG. 55B is a cross-sectional perspective view of the portion of the endoscope shown in FIG. 55A and a surgical cutting assembly inserted in the endoscope according to embodiments of the present disclosure. Referring now to FIGS. 55A and 55B, the endoscopic assembly 5599 includes an endoscope 5500 and a surgical cutting assembly, such as the surgical cutting assembly 5320. The endoscope 5500 is similar to the endoscope 5400 but different in that the endoscope 5500 does not include a torque generation component 5400, but instead, includes a torque delivery component 5560 that is coupled to a coupling component 5550 that is configured to provide the torque from the torque delivery component to the surgical cutting assembly 5320.

The torque delivery component 5560 can be a flexible torque coil or torque rope capable of delivering torque applied at a proximal end of the torque delivery component that extends outside a proximal end of the endoscope 5500 to a distal end of the torque delivery component disposed within the endoscope 5500. The torque delivery component can be similar to the flexible cable 1920 described above to FIGS. 19A-19C and the torque coil 4080 described above with respect to FIG. 40. The torque delivery component 5560 can include a plurality of layers of threads. Each layer of threads can be wound in a direction opposite to a direction in which an adjacent layer of threads is wound. The torque delivery component 5560 can be configured to provide rotation in a first direction based on the way the layers of threads are wound. In some implementations, the torque delivery component 5560 may be designed to deliver rotational energy in a preferred direction but may be capable of delivering rotational energy in a direction opposite the preferred direction. Although the torque delivery component 5560 can similar to the flexible cable 1920 or the torque coil 4080, the torque delivery component 5560 can be any type of torque delivery component capable of delivering rotational energy that is provided at a proximal end of the torque delivery component that extends outside a proximal end of the endoscope 5500 to a distal end of the torque delivery component that is disposed within the elongated tubular body 5516 of the endoscope 5500.

The proximal end of the torque delivery component 5560 can be configured to couple to a torque generation component configured to generate rotational energy. The torque generation component can be any rotary actuator capable of providing rotational energy to the torque delivery component 5560 to deliver to the distal end of the torque delivery component. The size and shape of the torque delivery component 5560 can be such that the torque delivery component 5560 is capable of delivering sufficient rotational energy to cause the inner cannula 5330 of the surgical cutting assembly 5320 insertable within the endoscope 5500 to rotate at a sufficient speed to cut tissue from a surgical site within the mammalian cavity of the patient.

The endoscope 5500 includes a torque delivery channel 5558 configured to dispose the torque delivery component. The torque delivery channel can be sized to have an inner diameter that is slightly larger than an outer diameter of the torque delivery component. In some implementations, the torque delivery channel 5558 can be lined with a heat-absorbing material or other such material, such as PTFE, that absorbs heat generated by the torque delivery component 5560 when the torque delivery component 5560 is operating. The torque delivery channel can extend from the distal end of the endoscope to an opening defined at the proximal end of the endoscope. The torque delivery channel can have a longitudinal axis that extends parallel to a longitudinal axis of the instrument channel 5540. In some implementations, the torque delivery channel 5558 may be defined within the endoscope such that the torque delivery channel does not intersect or otherwise interfere with any other components in the endoscope. The distal end of the torque delivery channel can include an opening that is configured to allow the distal end of the torque delivery component 5558 to couple to a torque transferring assembly 5564.

The torque transferring assembly 5564 can include the coupling component 5550 and a second coupler 5566. In some implementations, the distal end of the torque delivery component 5560 can be coupled to the second coupler 5566, such that torque from the torque delivery component 5560 is transferred to the second coupler 5566, causing the second coupler 5566 to rotate. In some implementations, the torque delivery component 5560 can be coupled to the second coupler 5566 with a friction based fit, such as a press fit or using some adhesive or other coupling mechanism. In some implementations, the outer wall of the torque delivery component 5560 is attached to an inner wall 5568 of the second coupler 5566. In some implementations, the coupling component 5550 and the second coupler 5566 can be cylindrical ring structures. In some implementations, the outer portions of the radial wall of the coupling component 5550 and the radial wall 5569 of the second coupler 5566 may include grooves, raised edges, or other engagement members configured to provide rotational energy from the second coupler 5566 to the coupling component 5550 and from the coupling component 5550 to the second coupler 5566. In this way, torque from the torque delivery component 5560 can cause the second coupler 5566 to rotate, which in turn, can cause the coupling component 5500 to rotate, which in turn can cause the inner cannula 5330 of the surgical cutting assembly 5320 disposed within the instrument channel 5540 of the endoscope 5500 to rotate.

The surgical cutting assembly 5320 includes the outer cannula 5522, the inner cannula 5530, a coupling member 5340 coupled to the inner cannula 5330, an aspiration tube 5333 coupled to a proximal end of the coupling member and a braided tubing 5325 that is coupled to a proximal end 5323b of the outer cannula 5322 and within which the aspiration tube 5531 and the coupling member 5340 are disposed. In some implementations, the inner cannula 5530 can have a length that is greater than the outer cannula 5522 such that a portion of the inner cannula 5530, the coupling member 5340 and the aspiration tubing 5333 are disposed within the braided tubing 5325 of the surgical cutting assembly 5320. This can allow the coupling member 5340 to be adjacent to but separated from the coupling component 5550 of the endoscope 5500 by the braided tubing 5325 of the surgical cutting assembly 5320 instead of the outer cannula 5322. In some implementations, the length of the inner cannula 5330 and the coupling member 5340 may be greater than the length of the outer cannula 5322 to ensure that a portion of the coupling member 5340 is separated from the coupling member 5550 by the braided tubing 5525.

In operation, when the torque delivery component 5560 is actuated by a torque generation component, the torque delivery component 5560 can receive the torque generated by the torque generation component at the proximal end of the torque generation component 5560 and translate that torque to the distal end of the torque delivery component 5560. The torque delivery component 5560 is rotationally coupled to the second coupler 5566 such that the torque from the torque delivery component 5560 is transferred to the second coupler 5566. The second coupler 5566 can be rotationally coupled to the coupling component 5550, which can be positioned around a portion of the instrument channel of the endoscope. The torque of the second coupler 5566 can be transferred to the coupling component 5500. The coupling component can rotate creating a magnetic field due to the coupling component including magnets in an inner portion of the coupling component. The inner portion of the coupling component 5550 can surround a portion of the instrument channel and be positioned such that the coupling component rotates along a longitudinal axis that extends substantially parallel to an axis of the portion of the instrument channel of the endoscope adjacent to the coupling component 5550. When the surgical cutting assembly is inserted within the instrument channel, the surgical cutting assembly can be inserted far enough in the instrument channel such that the distal tip of the outer cannula is extending outside the distal tip of the endoscope and the coupling member attached to the inner cannula is disposed within the portion of the instrument channel is that adjacent to the coupling component 5550. The coupling member attached to the inner cannula can be made from or include a material on an outer radial wall of the coupling member that is capable of being influenced by the magnetic field of the coupling component. In some implementations, the coupling member can be made from a ferromagnetic material capable of being magnetized, such as a metal or metal alloy, for example, annealed iron. When the coupling member 5340 of the surgical assembly is positioned adjacent to the coupling component 5550, a magnetic coupling effect takes place such that the coupling component and the coupling member 5340 are magnetically coupled. As described above, during operation, when the coupling component is rotated due to the torque being transferred via the torque delivery component, the rotation of the coupling component rotates the coupling member, which thereby causes the inner cannula to rotate.

The lengths of the outer cannula, the inner cannula and the coupling member of the surgical cutting assembly, the length of the coupling component and the position of the coupling component relative to the opening of the instrument channel at the distal tip of the endoscope are features that can affect the operability and performance of the endoscopic assembly. One constraint when selecting a length of the coupling component is the bend radii of the endoscope. The coupling component may be sized to have a length that does not prevent the endoscope from having a bend radii that is greater than a threshold amount. The threshold amount may be specific to the type of endoscope. For instance, a colonoscope may have a bend radii that is less than a hysteroscope as the bends formed by the colon as much sharper than bends in the uterine canal of patients. In some implementations, the colonoscope can be configured to bend about 180 degrees in the vertical (y) axis and about 160 degrees in the horizontal (x) axis. The colonoscope can be configured to make bend angles that are less than 180 degrees in the y axis and less than 160 degrees in the x axis but this may adversely affect the endoscope's ability to traverse through the tortuous path defined by the colon, especially at the junction connecting the sigmoid to the rectum. As such, the length of the coupling component should be sized such that the colonoscope is capable of bending at least the threshold amount along the vertical and horizontal axes. Further, the length of the outer cannula and the combined length of the inner cannula and coupling member should be sufficiently small that the surgical cutting assembly is insertable within the endoscope while the endoscope is inserted within the mammalian cavity of the patient. The length of the inner cannula and coupling member, however, should be large enough that the coupling member is positioned adjacent to the coupling component of the endoscope to allow the coupling member to magnetically couple to the coupling component.

Figure 56A:
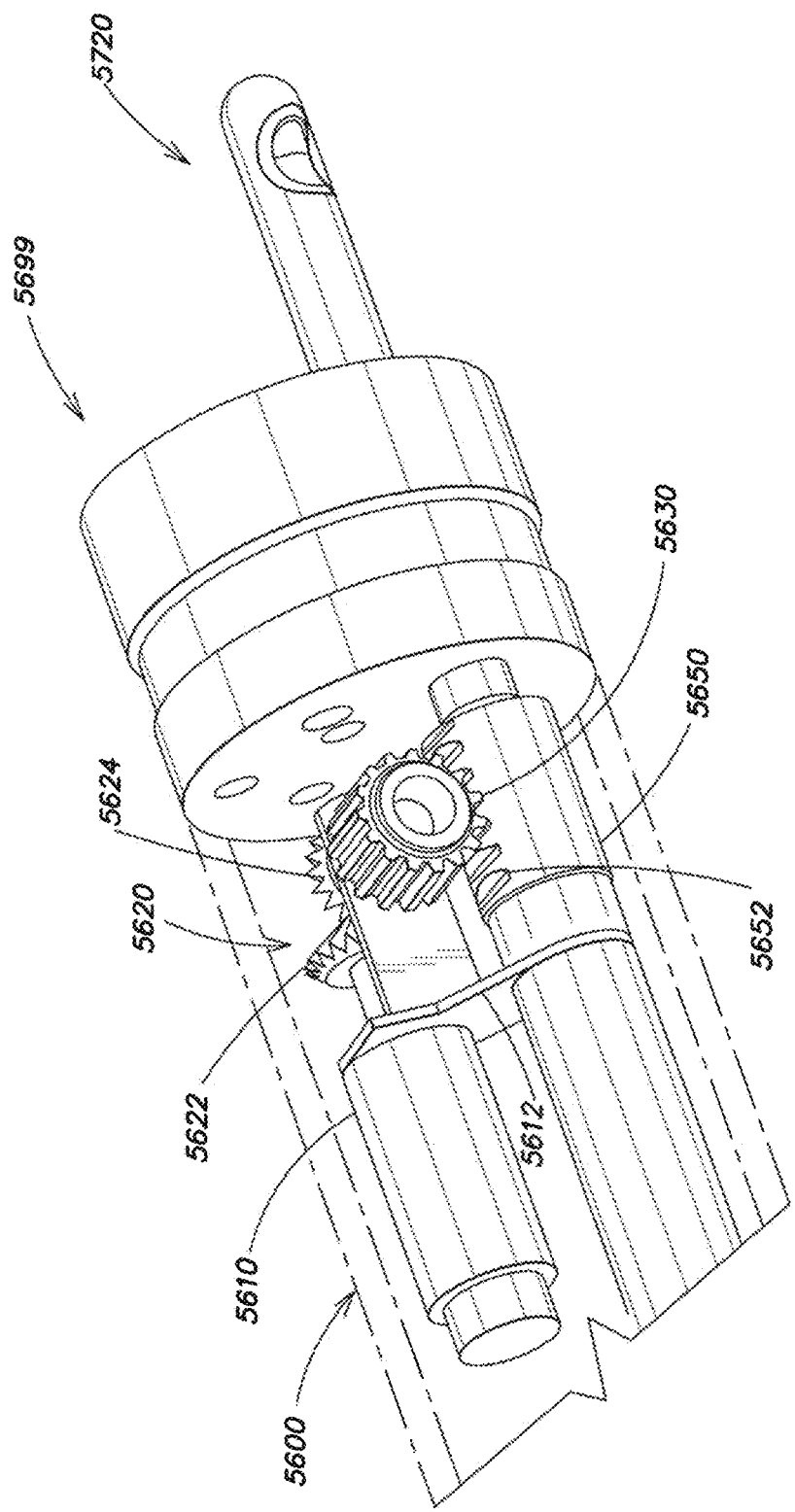
FIG. 56A is a perspective view of a portion of an endoscopic assembly including an endoscope having an integrated torque generation assembly capable of causing a surgical cutting assembly inserted within the endoscope to cut tissue in a reciprocating motion according to embodiments of the present disclosure.
Figure 56B:
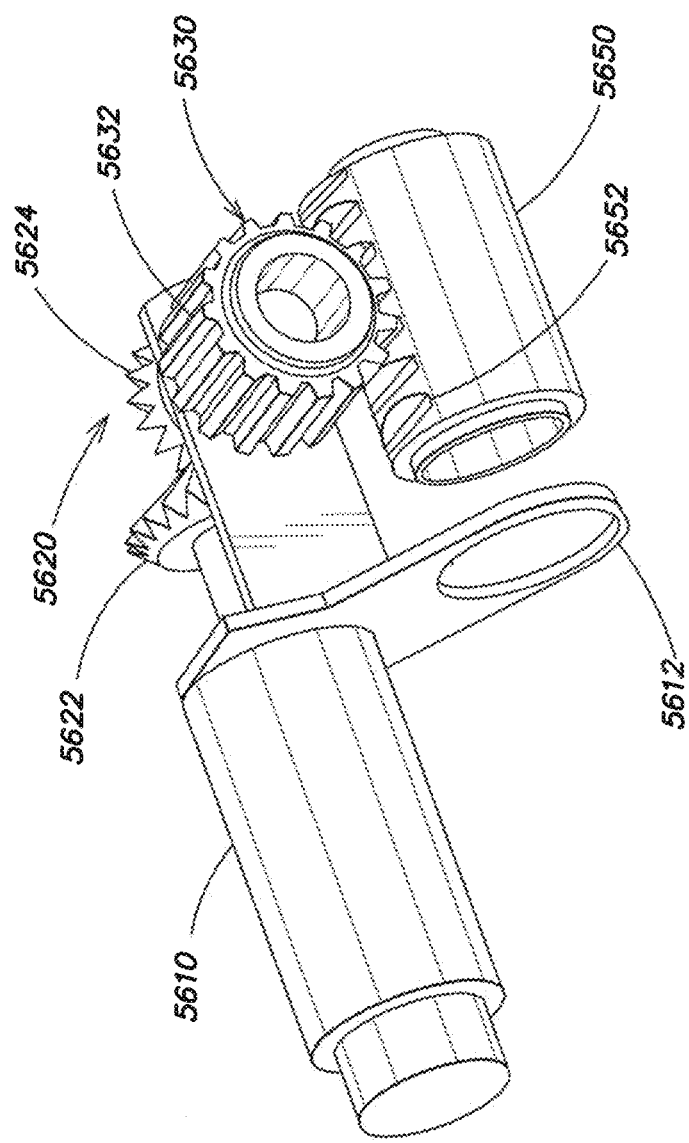
FIG. 56B is an enlarged perspective view of the torque generation assembly shown in FIG. 56A.

FIG. 56A is a perspective view of a portion of an endoscopic assembly including an endoscope having an integrated torque generation assembly capable of causing a surgical cutting assembly inserted within the endoscope to cut tissue in a reciprocating motion according to embodiments of the present disclosure. FIG. 56B is an enlarged perspective view of the torque generation assembly shown in FIG. 56A. The endoscopic assembly 5699 includes an endoscope 5600 and the surgical cutting assembly 5720. The endoscope is similar to the other endoscopes, such as the endoscope 5500 but differs in that the endoscope includes a linear motion generation assembly that includes a rotary actuator 5610, a rotary to linear motion converting assembly 5620 configured to convert rotational motion to linear motion, and a coupling component 5650 having an outer surface configured to engage with the rotary to linear motion converting assembly 5620. The rotary actuator 5610 can be a hydraulic or pneumatic rotary actuator or an electric rotary actuator, similar to ones described herein. In some implementations, the rotary actuator includes a shaft that is coupled to the rotary to linear motion converting assembly 5620.

The rotary to linear motion converting assembly 5620 can include a first gear 5622 coupled to the shaft of the rotary actuator 5610. The first gear 5622 can include engagement elements configured to engage with corresponding engagement elements of a second gear 5624. The orientation of the first gear is transverse to the axis of rotation of the shaft of the rotary actuator. The orientation of the second gear 5624 is transverse to the orientation of the first gear such that a gear coupler 5630 coupled to the second gear 5624 is configured to rotate along an axis that is transverse to a longitudinal axis of the coupling component and the instrument channel around which the coupling component is positioned. The gear coupler 5630 can include one or more structures 5632 on an outer wall of the gear coupler 5630 that are configured to engage with corresponding structures 5652 formed on an outer wall of the component coupler 5650. The structures 5632 are configured to frictionally engage with the structures 5652 such that when the gear coupler 5630 rotates, the structures 5632 and the structures 5652 engage with one another to cause the coupling component to move along the longitudinal axis extending through the length of the instrument channel and the coupling component 5650. The direction in which the rotary actuator 5610 rotates dictates the direction in which the coupling component 5650 moves along the longitudinal axis. In some implementations, the rotary actuator is configured to rotate in a first direction to cause the coupling component to move from a first position to a second position and then rotate in a second direction opposite to the first direction to cause the coupling component to move from the second position back the first position. In some implementations, the rotary to linear motion converting assembly 5620 may also include a support structure 5612 configured to keep the rotary actuator 5610 and the first and second gears 5622 and 5624 in place.

It should be appreciated that the rotary to linear motion converting assembly 5620 shown in FIG. 56A is one implementation of a rotary to linear motion converting assembly. The rotary to linear motion converting assembly 5620 can include any number of components that collectively are configured to convert rotary motion generated by a rotary actuator to linear motion that can cause the coupling component of the endoscope to repeatedly move between a first position to a second position such that an inner cannula can cut or resect material entering a cutting window or opening of an outer cannula of a surgical cutting assembly inserted within the instrument channel of the endoscope.

In some implementations, instead of using a rotary actuator and a rotary to linear motion converting assembly, the endoscope can include an actuator configured to generate linear motion. For example, a SQUIGGLE micromotor manufactured by New Scale Technologies of Victor, N.Y., USA or the principles on which the SQUIGGLE motor works can be employed to cause the coupling component to move linearly along a longitudinal axis of the instrument channel. As the coupling member of the surgical cutting assembly 5320 can be magnetically coupled to the coupling component, as the coupling component moves linearly along the longitudinal axis, the coupling member and the inner cannula coupled thereto will move linearly along the longitudinal axis as well.

Figure 57A:
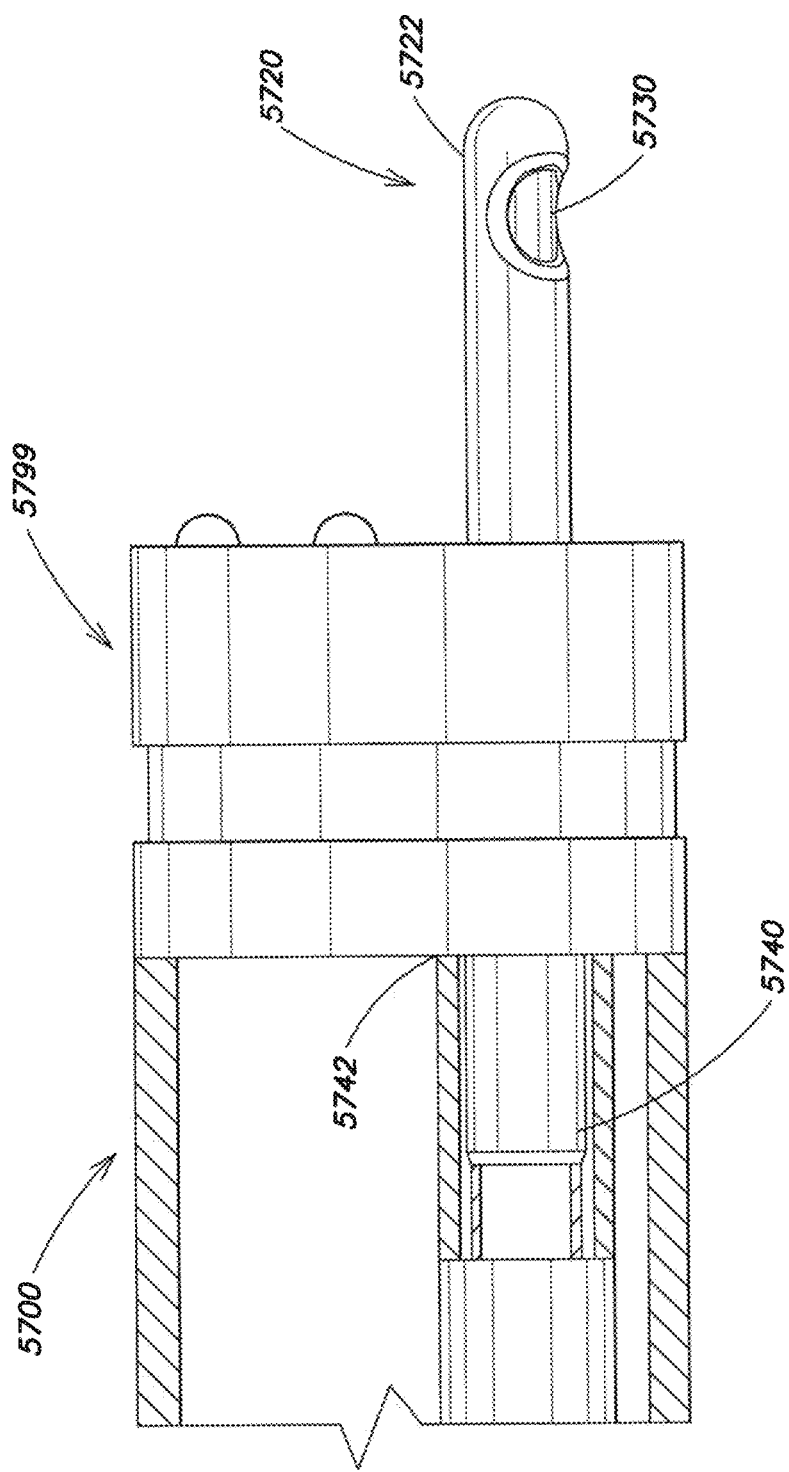
FIGS. 57A-57C is a side perspective view of a portion of an endoscopic assembly including an endoscope and a surgical cutting assembly inserted within the endoscope to cut tissue in a reciprocating motion according to embodiments of the present disclosure.
Figure 57B:
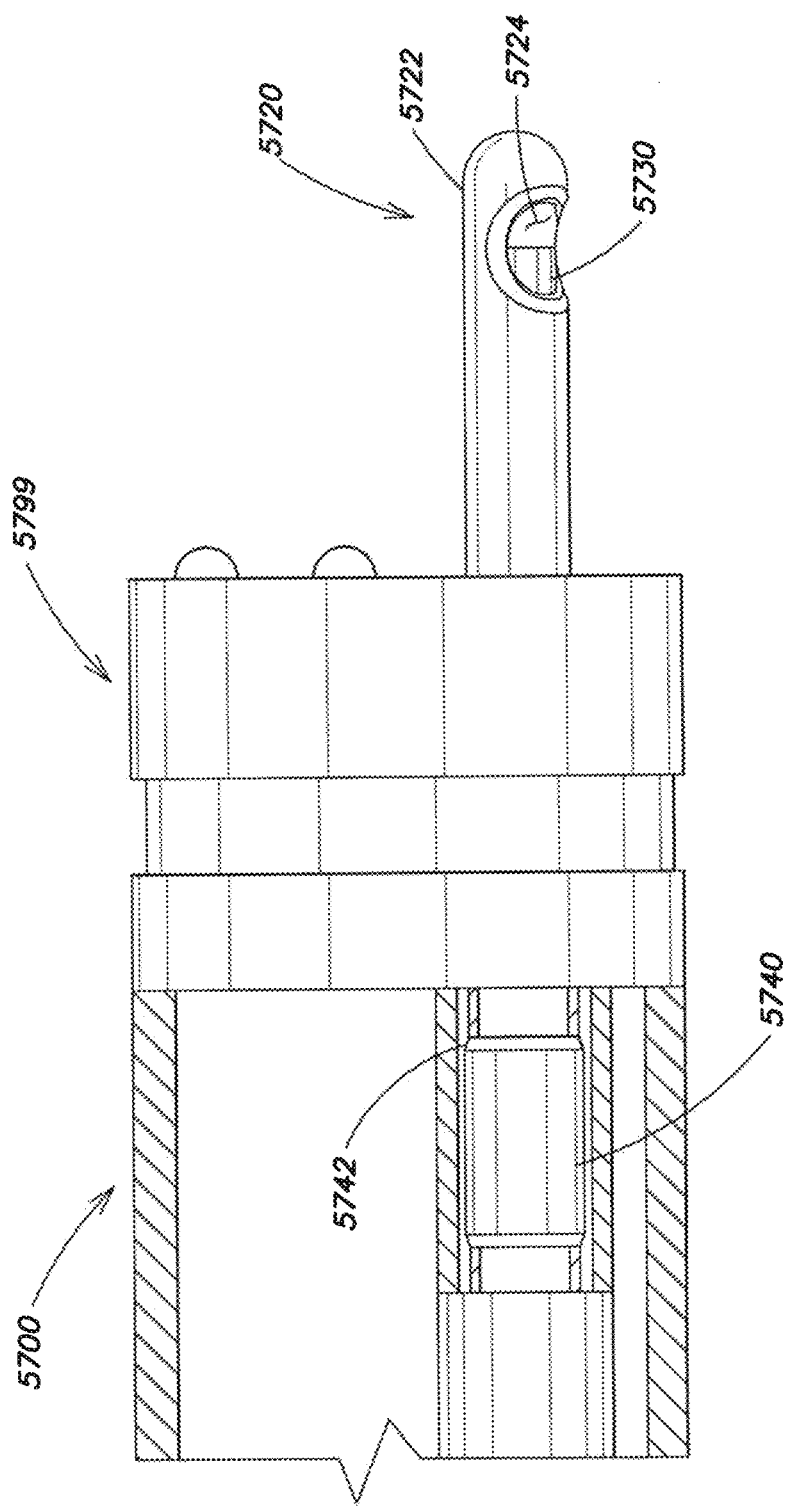
Figure 57C:
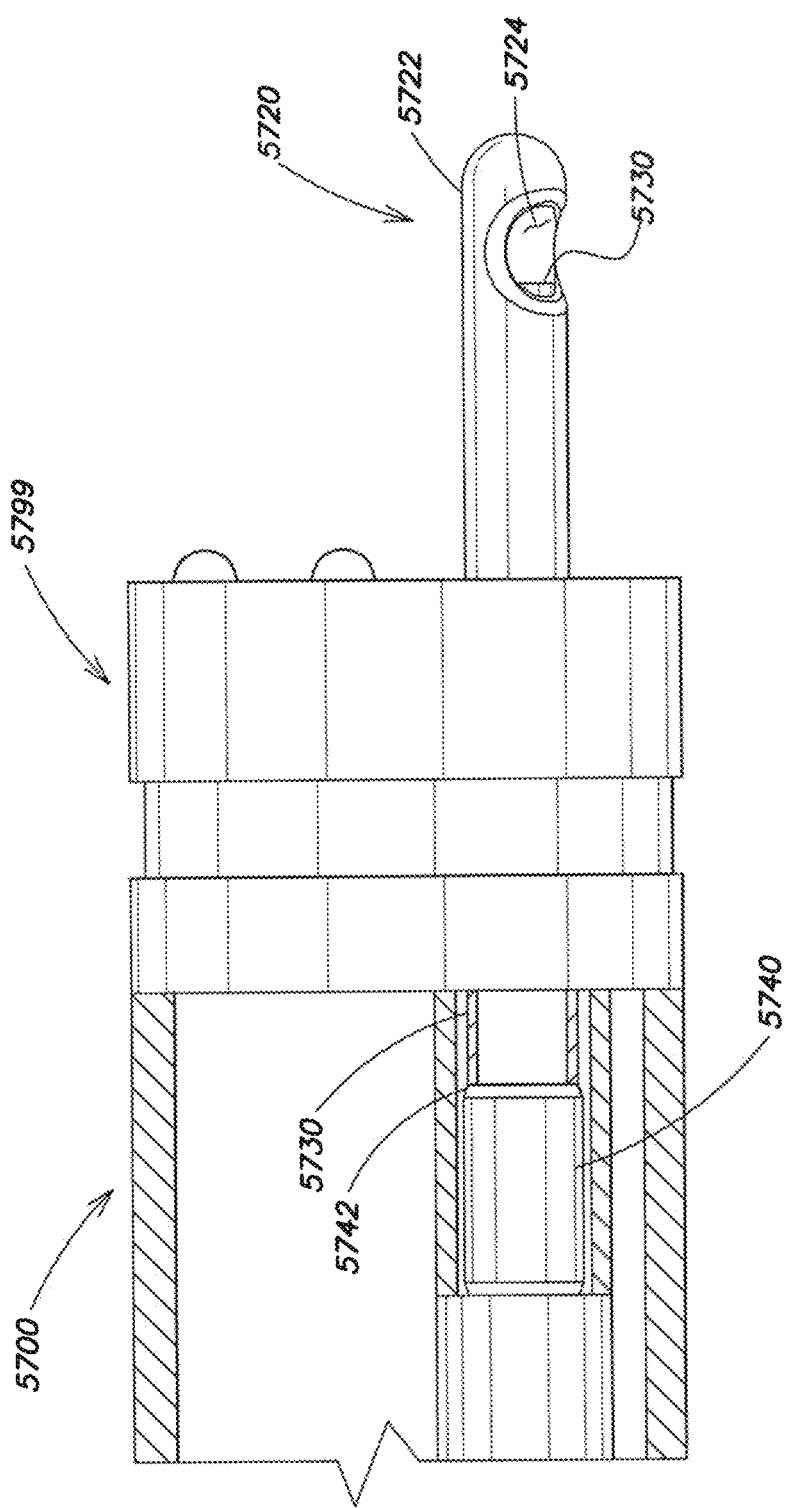

FIGS. 57A-57C is a side perspective view of a portion of an endoscopic assembly including an endoscope and a surgical cutting assembly inserted within the endoscope to cut tissue in a reciprocating motion according to embodiments of the present disclosure. FIG. 57A shows an endoscopic assembly 5799 that includes an endoscope 5700 and a surgical cutting assembly 5720. The surgical cutting assembly 5720 is similar to the surgical cutting assembly 5320 but differs in that the inner cannula is configured to move linearly relative to the outer cannula in contrast with rotating along a longitudinal axis relative to the outer cannula. Various components of the endoscopic assembly 5799 are not shown. In FIG. 57A, the coupling member 5740 of the surgical cutting assembly 5720 is shown to be positioned in a first position. In this position, a distal end 5742 of the coupling member 5740 is positioned close to the distal tip. When the coupling member 5740 is in the first position, the inner cannula 5730 of the surgical cutting assembly 5720 is in a closed position. In the closed position, a distal tip of the inner cannula 5730 is either in contact with or close to the inner wall of a distal end of the outer cannula 5722 such that the inner cannula 5730 blocks the opening 5724 of the outer cannula 2722 as shown.

In FIG. 57B, the coupling member 5740 of the surgical cutting assembly 5720 is shown to be positioned in a second position. In this position, a distal end 5742 of the coupling member 5740 is positioned farther away from the distal tip when compared to when the coupling member 5740 was in the first position as shown in FIG. 57A. When the coupling member 5740 is in the second position, the inner cannula 5730 of the surgical cutting assembly 5720 is in a half closed position. In the half-closed position, a distal tip of the inner cannula 5730 is positioned such that the inner cannula 5730 blocks a portion of the opening 5724 of the outer cannula 2722 as shown.

In FIG. 57C, the coupling member 5740 of the surgical cutting assembly 5720 is shown to be positioned in a third position. In this position, a distal end 5742 of the coupling member 5740 is positioned farther away from the distal tip when compared to when the coupling member 5740 was in the second position as shown in FIG. 57C. When the coupling member 5740 is in the third position, the inner cannula 5730 of the surgical cutting assembly 5720 is in an open position. In the open position, a distal tip of the inner cannula 5730 is positioned such that the inner cannula 5730 does not block the opening 5724 of the outer cannula 2722 as shown.

Figure 58A:
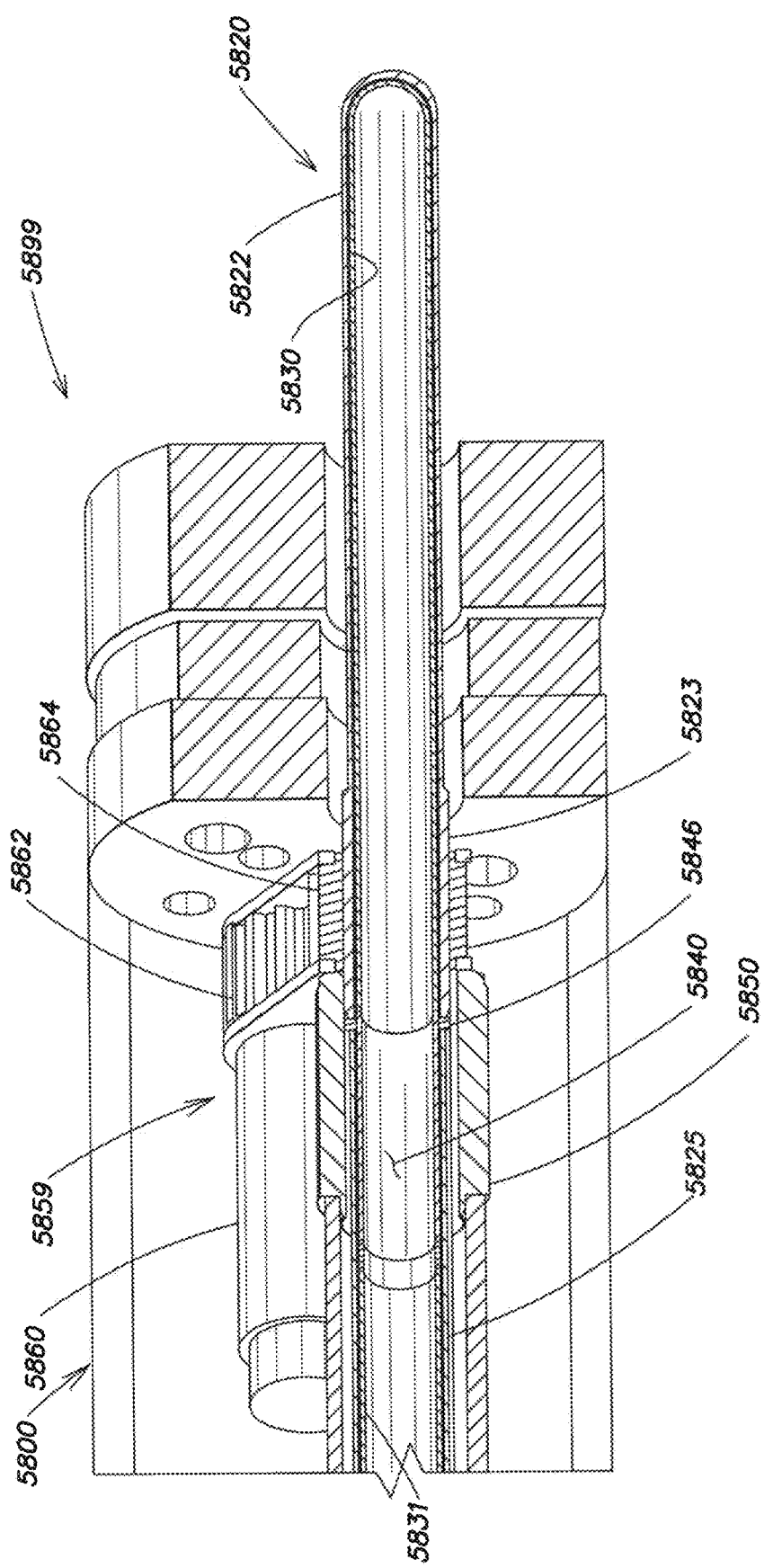
FIG. 58A is a perspective cross-sectional view of an endoscopic assembly including an endoscope and a surgical cutting assembly in which the endoscope is configured to rotate an outer cannula of the surgical cutting assembly using an actuator according to embodiments of the present disclosure.
Figure 58B:
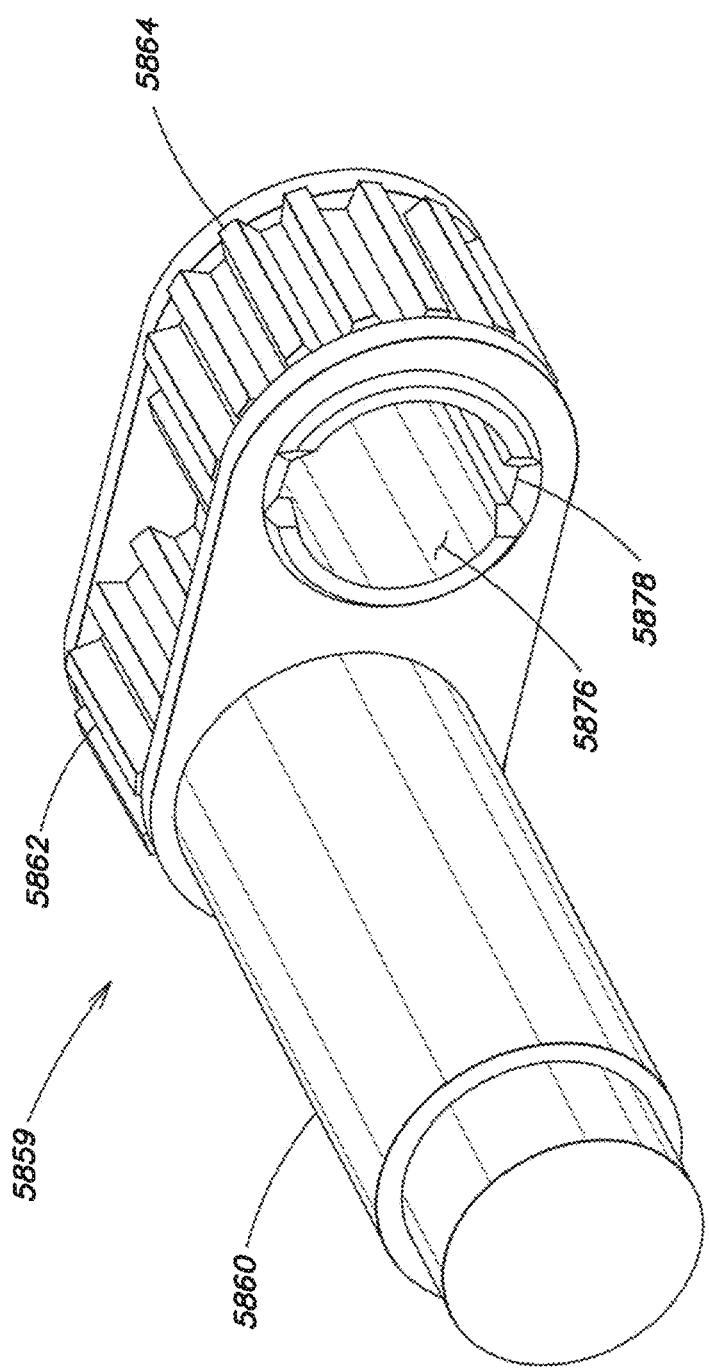
FIG. 58B is a perspective view of a component of the endoscope for rotating the outer cannula of the surgical cutting assembly shown in FIG. 58A.

FIG. 58A is a perspective cross-sectional view of an endoscopic assembly including an endoscope and a surgical cutting assembly in which the endoscope is configured to rotate an outer cannula of the surgical cutting assembly using an actuator according to embodiments of the present disclosure. FIG. 58B is a perspective view of a component of the endoscope for rotating the outer cannula of the surgical cutting assembly shown in FIG. 58A. The endoscopic assembly 5899 includes an endoscope 5800 and a surgical cutting assembly 5820. The endoscope 5800 can be similar to any of the endoscopes shown in FIGS. 51-57 but differs in that the endoscope 5800 includes an articulation assembly 5859 configured to articulate an outer cannula 5822 of the surgical cutting assembly 5820 relative to a longitudinal axis of the outer cannula extending through the length of the outer cannula. The articulation assembly 5859 is disposed within the distal end of the endoscope 5800 and can include a torque generation component 5860, a first gear 5862 coupled to the torque generation component and a second gear 5864 coupled to the first gear 5862. The second gear can include an inner radial wall 5876 within which one or more engagement elements 5878 are defined. These engagement elements 5878 can include grooves or ribs that are configured to engage with complementary engagement elements 5823 defined on the outer cannula 5822. In some implementations, the complementary engagement elements can be ribs or grooves.

The torque generation component 5860 can be a rotary actuator configured to rotate in one or both directions. In some implementations, the rotary actuator can be an electric motor configured to generate sufficient torque to rotate the outer cannula 5822. In some implementations, the rotary actuator can be controlled by a switch or other input mechanism that allows an operator of the endoscope to actuate the rotary actuator. In some implementations, the rotary actuator 5860 is configured to rotate the outer cannula 5822 to one or more predefined positions. In some implementations, the predefined positions may be relative to a position of a camera of the endoscope 5800. For example, one position may orient the cutting window or opening 5824 of the outer cannula such that the camera can capture an image that shows the cutting window. In some implementations, the articulation assembly 5859 can be defined within a distal tip of the endoscope 5800. In some implementations, the articulation assembly 5859 can be positioned within the endoscope such that the articulation assembly 5859 does not interfere with other components of the endoscope, including the torque generation component or torque delivery components configured to rotate the coupling component 5850 configured to rotate the inner cannula 5830 of the surgical cutting assembly 5820 disposed within the endoscope 5800. The coupling component 5850 can be similar to other coupling components shown in FIGS. 51A-57B.

It should be appreciated that to rotate the outer cannula 5822 via the articulation assembly 5859, care must be taken to not rotate the outer tubing 5825 that is coupled to the outer cannula and configured to define a portion of the irrigation channel as described herein. In some implementations, a rotary seal 5846 may couple the outer tubing 5825 to the outer cannula 5822. The rotary seal 5846 can allow the outer cannula 5822 to rotate about its longitudinal axis while preventing the outer tubing from rotating along with the outer cannula 5822.

In some implementations, the endoscope 5800 can include a dedicated irrigation channel defined within the endoscope 5800 that is configured to provide irrigation fluid to the surgical cutting assembly insertable within the endoscope. In some implementations, the dedicated irrigation channel can extend between an irrigation fluid entry opening defined in a proximal end of the elongated tubular body of the endoscope and an irrigation fluid exit opening defined within the body of the tubular body. The irrigation fluid exit opening can be positioned such that the irrigation fluid exit opening is capable of fluidly coupling to the surgical cutting assembly insertable within the instrument channel of the endoscope. In some implementations, the irrigation fluid exit opening can be configured to engage with an opening to an irrigation pathway defined in the surgical cutting assembly. In some implementations, the irrigation fluid exit opening can be defined in a radial wall defining the instrument channel. In some implementations, the irrigation fluid exit opening can be defined close to or within the articulation assembly 5859. In some implementations, the irrigation fluid exit opening can fluidly connect to an opening defined near or within an opening of the outer cannula such that when the outer cannula engages with the articulation assembly 5859, the irrigation fluid exit opening can be fluidly coupled to the irrigation pathway defined by the inner wall of the outer cannula and the outer wall of the inner cannula of the surgical assembly. In some implementations, the irrigation fluid from the irrigation channel defined within the endoscope can be configured to enter the surgical cutting assembly due to a suction force applied to the aspiration channel of the surgical cutting assembly. In some implementations in which the aspiration channel is fluidly coupled to the irrigation fluid exit opening, the irrigation fluid can flow from the irrigation fluid exit opening of the endoscope to an opening within the surgical cutting assembly. In some implementations, the opening within the surgical cutting assembly may be fluidly coupled to the aspiration channel, such that the suction force applied to the aspiration channel can cause the irrigation fluid to enter the opening of the surgical cutting assembly and into the aspiration channel via the cutting window of the outer cannula. The surgical cutting assembly can include the irrigation fluid opening at a location near the outer cannula. In some implementations, the irrigation fluid opening can be located at a location where the outer cannula is coupled to the outer tubing of the surgical cutting assembly.

In some implementations, one or more seals can be positioned to prevent the fluid from escaping from the opening of the instrument channel defined at the distal end of the endoscope. In some implementations, one or more seals can further be positioned to prevent the irrigation fluid from escaping from the opening of the instrument channel defined at the proximal end of the endoscope. The irrigation channel can be configured to carry irrigation fluid to irrigate the aspiration channel of the surgical cutting assembly. In some implementations, the irrigation channel can be configured to also provide topical medication as will be described below. In some implementations, a control mechanism can control an amount of fluid being provided to the irrigation channel. The control mechanism can be controlled by an operator of the endoscope. In some implementations, the control mechanism can be an actuator.

Figure 59A:
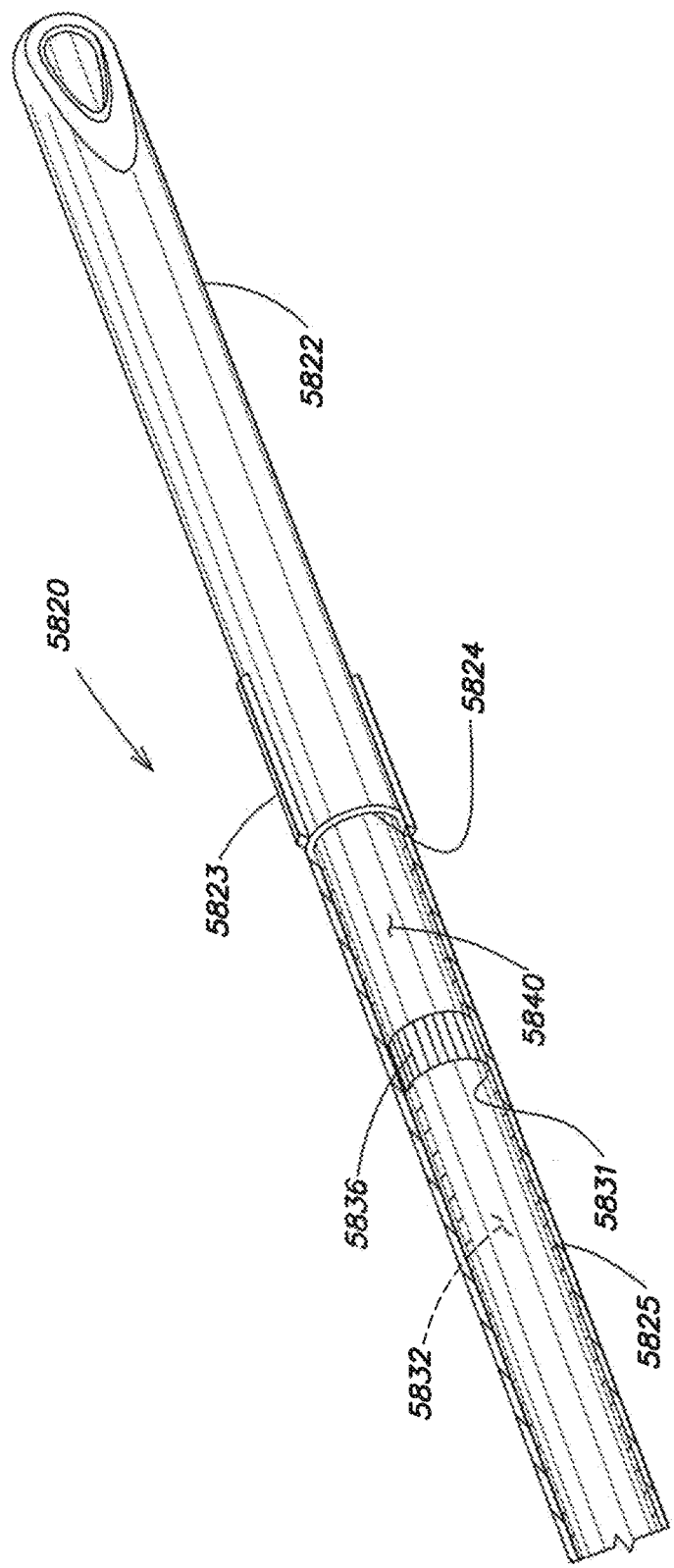
FIG. 59A is a perspective view of the surgical cutting assembly shown in FIG. 58A.
Figure 59B:
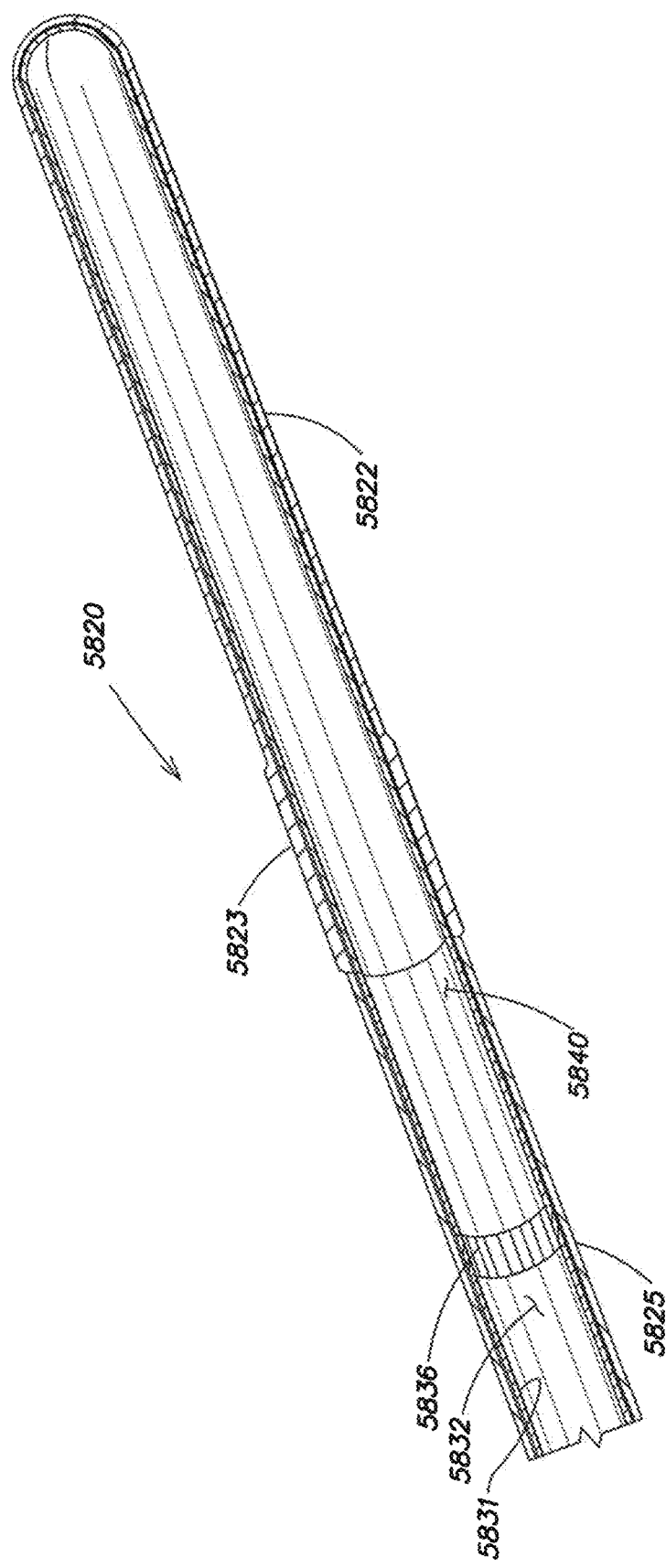
FIG. 59B is a perspective cross-sectional view of the surgical cutting assembly shown in FIG. 58A.
Figure 60A:
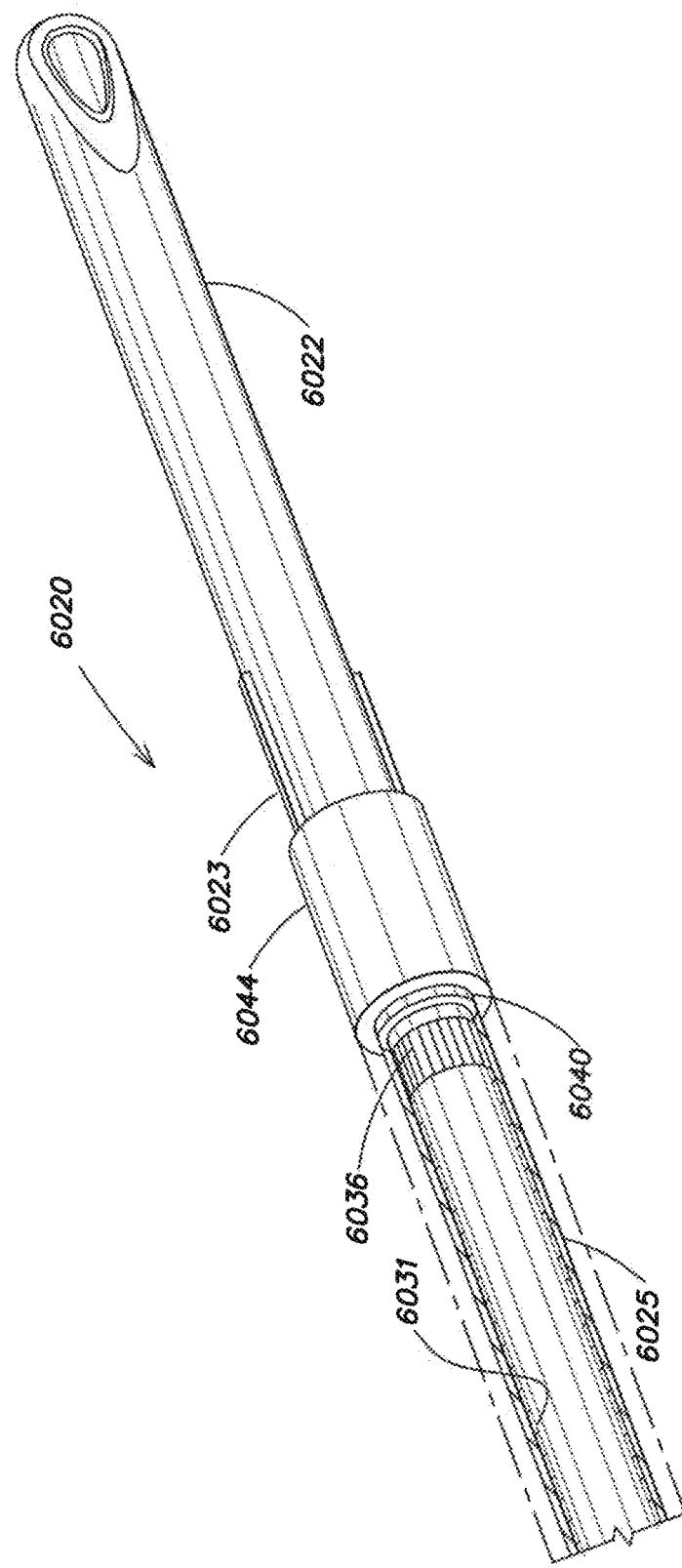
FIG. 60A is a perspective view of a surgical cutting assembly according to embodiments of the present disclosure.
Figure 60B:
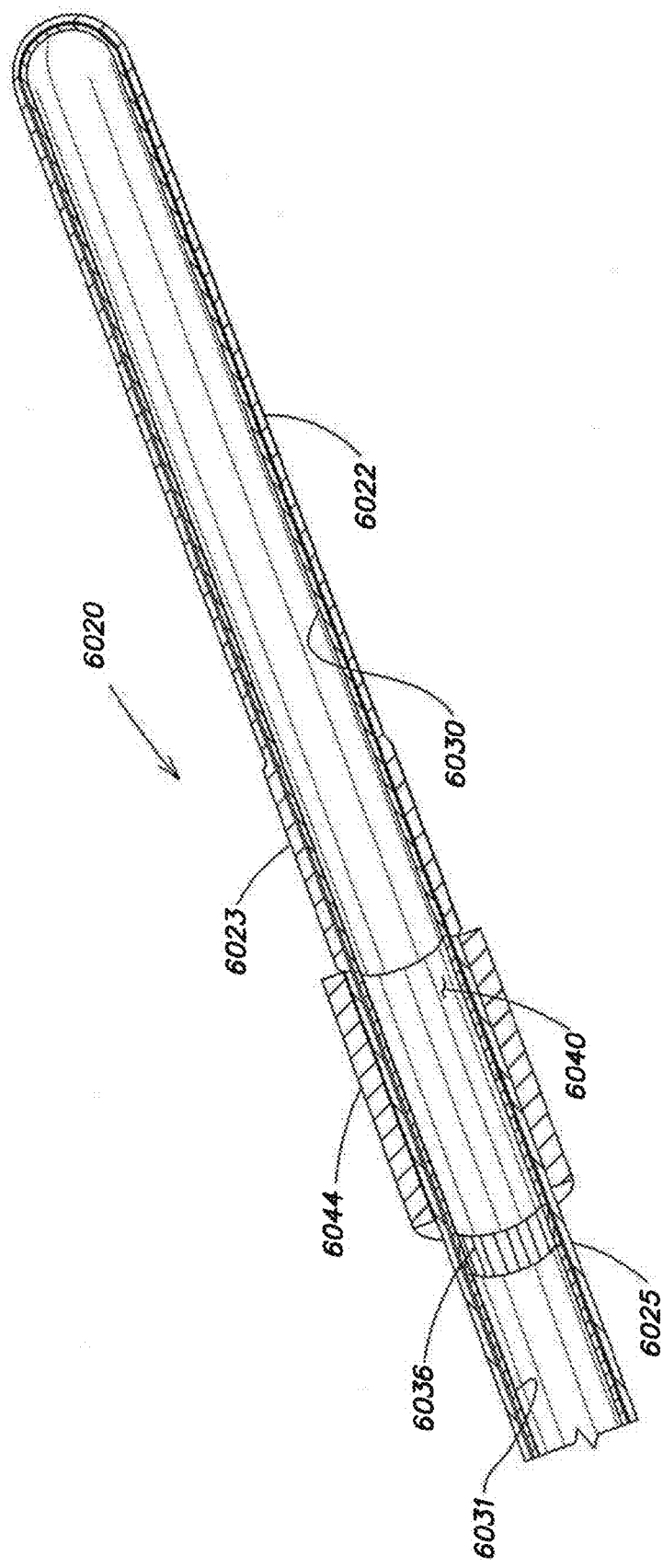
FIG. 60B is a perspective cross-sectional view of the surgical cutting assembly shown in FIG. 60A.

FIG. 59A is a perspective view of the surgical cutting assembly shown in FIG. 58A. FIG. 59B is a perspective cross-sectional view of the surgical cutting assembly shown in FIG. 58A. The surgical cutting assembly 5820 can include an outer cannula 5822, an inner cannula disposed within the outer cannula, a coupling member 5840 that is coupled to the inner cannula and configured to rotate when the coupling member 5840 is positioned adjacent a rotating coupling component of the endoscope within which the surgical cutting assembly is inserted. The surgical cutting assembly can also include a rotary seal 5836 that is configured to fluidly couple the coupling member 5840 to an aspiration tube 5831 having an inner wall that defines a portion of an aspiration channel 5832. The outer cannula can include one or more engagement elements 5823 configured to engage with complementary engagement elements of the articulation assembly of the endoscope 5800. Further, the outer cannula 5822 can be coupled to an outer tubing 5825 via a rotary seal (not shown in FIGS. 59A and 59B) that is configured to allow the outer cannula to rotate relative to the outer tubing 5825. An inner wall of the outer tubing 5825 and the outer wall of the aspiration tube 5831 can define a first portion of an irrigation channel configured to deliver irrigation fluid to the opening of the outer cannula that defines one end of the aspiration channel. An inner wall of the outer cannula 582 and an outer wall of the inner cannula 5830 defines a second portion of the irrigation channel that is fluidly coupled to the first portion.

FIG. 60A is a perspective view of a surgical cutting assembly according to embodiments of the present disclosure. FIG. 60B is a perspective cross-sectional view of the surgical cutting assembly shown in FIG. 60A. The surgical cutting assembly 6020 is similar to the surgical cutting assembly 5820 shown in FIG. 59A but differs in that the surgical cutting assembly 6020 includes an outer coupling component 6044. The outer coupling component can have an outer diameter that is less than an inner diameter of the instrument channel of an endoscope within which the surgical cutting assembly is configured to be inserted. Moreover, the outer coupling component 6040 can be configured to engage with a complementary coupling component that can provide torque to the outer coupling component.

The outer coupling component 6044 can include a hollow bore within which other components of the surgical cutting assembly 6020 can be disposed. For instance, a portion of the outer braided tubing 6029 can be coupled to the outer coupling component via a rotary seal or other component that allows the outer coupling component to rotate while maintaining the braided tubing stationary relative to the outer coupling component.

Similar to the surgical cutting assembly 5820, the outer braided tubing 6025 can be coupled to an outer cannula 6022, while an inner cannula 6030 disposed within the outer cannula can be coupled to an aspiration tube 6031 via an inner coupling member 6040. The inner coupling member 6040 can be coupled to the outer coupling component 6044 such that the inner coupling member 6040 moves with the outer coupling component 6044. The inner coupling member 6040 can be coupled to the outer coupling component 6044 such that when the outer coupling component rotates, the inner coupling member 6040 also rotates. In some implementations, the inner coupling member 6040 can be magnetically coupled to the outer coupling component 6044. To do so, the inner portion of the outer coupling component 6044 may be configured to include one or more magnets to create a magnetic force on the inner coupling member 6040.

The inner coupling member 6040 can be aligned with the outer coupling component 6044 such that the inner coupling member 6040 is positioned adjacent to the outer coupling component 6044. In some implementations, the inner coupling member and the inner cannula can be sized relative to the outer cannula and the outer coupling component such that when the distal tip of the inner cannula is adjacent the cutting window or opening of the outer cannula, the inner coupling member is adjacent to the outer coupling component but separated from the outer coupling component by the outer tubing that is coupled to the outer cannula. In some implementations, the rotary seal 6036 that fluidly couples the inner coupling member to the aspiration tube but maintains the inner coupling member rotationally decoupled from the aspiration tube can be configured to include an outer ring or radial surface that is As the inner coupling member 6040 and the outer coupling component 6044 are assembled so that they remain in alignment with one another, the inner coupling member 6040 can be more responsive to rotational energy provided to the outer coupling component 6044 relative to when the inner coupling member 6040 is magnetically coupled to an outer coupling member that is not a part of the surgical cutting assembly 6020, but rather a part of the endoscope within which the surgical cutting assembly is inserted.

The endoscope within which the surgical cutting assembly 6020 can be inserted can include the complementary coupling component from which the outer coupling component 6044 is configured to receive rotational energy or torque. The complementary coupling component can be the stator of a frameless motor in which the outer coupling component 6044 serves as the rotor. In some implementations, the complementary coupling component can be a rotating portion of a torque generation component or a rotating member configured to provide torque from a torque generation component or torque delivery component of the endoscope. In some implementations, the complementary coupling component can be capable of transmitting torque to the outer coupling component via friction or other physical contact. In some implementations, the complementary coupling component does not need to be positioned around the instrument channel. Instead, the complementary coupling component can be designed and positioned within the endoscope to transfer rotational energy from a torque generation component or torque delivery component to the outer coupling component 6044. The complementary coupling component can be a wheel or rotary component that has an outer surface capable of contacting the outer radial wall of the outer coupling component 6044.

As described herein, the surgical cutting assemblies, such as the surgical cutting assemblies shown in FIGS. 52A-60B can include or define an irrigation channel through which irrigation fluid is provided from outside the endoscope to the distal tip of the endoscope. The irrigation fluid at the distal tip can enter the opening or cutting window defined in the outer cannula and pass through the aspiration channel defined in part by the inner wall of the inner cannula and an aspiration tube. For the irrigation fluid to enter the inner cannula via the opening defined in the outer cannula, a suction force is generally applied at the proximal end of the aspiration tube to create a pressure difference that causes the irrigation fluid to enter the aspiration channel. In some implementations, the irrigation channel can be used as a drug delivery channel. To do so, the irrigation fluid, which is generally water, can be replaced with a drug solution that is to be administered at a site, such as the surgical site, within the mammalian cavity of the patient. To prevent the drug from being suctioned into the aspiration channel when the drug solution approaches the distal tip of the outer cannula, the suction force applied to the aspiration channel may be switched off or reduced. Moreover, the pressure or flow rate at which the drug solution is delivered may be increased to a much higher rate such that the drug solution can exit from the gap defined between the inner cannula and the outer cannula with a large enough force or pressure to be squirted, sprayed or otherwise directed towards the site within the mammalian cavity at which to deliver the drug solution. In some implementations, the drug solution can exit the surgical cutting assembly in a direction based on the position of the opening of the outer cannula. As described above, the outer cannula can be rotated via an outer braided tubing that is coupled to the outer cannula at a distal end and has a proximal end that extends out of the opening of the instrument channel at the proximal end of the endoscope. In some implementations, the irrigation channel can be configured to receive the fluid at a first flow rate to provide irrigation fluid to facilitate aspiration and at a second flow rate to spray the irrigation fluid via an opening or cutting window of the outer cannula at a site within the mammalian cavity.

As described above, the endoscope may include a dedicated irrigation channel defined within the elongated body of the endoscope. In some implementations, the surgical cutting assembly can include an irrigation fluid opening to receive irrigation fluid from the irrigation channel defined within the endoscope. In some implementations, the irrigation fluid opening can be located at a location near the outer cannula. In some implementations, the irrigation fluid opening can be located at a location where the outer cannula is coupled to the outer tubing of the surgical cutting assembly. In some implementations, the irrigation fluid can be configured to enter an irrigation pathway of the surgical cutting assembly that is partially defined by the inner wall of the outer cannula and the outer wall of the inner cannula. In some implementations, the beginning of the irrigation pathway is the irrigation fluid opening that is fluidly coupled to the irrigation fluid exit opening defined within the endoscope.

In some implementations, the instrument channel of an endoscope can configured to include at least one groove configured to engage with a corresponding key of a surgical cutting assembly insertable within the endoscope to ensure that an orientation of an opening of an outer cannula of the surgical cutting assembly is aligned with respect to a camera lens of the endoscope. In some implementations, the proximal end of the outer tubing can include markings indicating a length of a portion of the surgical cutting assembly that has been inserted into the instrument channel as well as an orientation of the cutting window of the outer cannula. In this way, the medical professional inserting the surgical cutting assembly may rotate the proximal end of the outer tubing to position the cutting window of the outer cannula to a desired position.

It should further be appreciated that the surgical cutting assembly can be similar to the endoscopic tool 4000 previously described with respect to FIGS. 40A-49B. In some implementations, the surgical cutting assemblies described with respect to FIGS. 51-60B may differ from the endoscopic tool 4000 in that the surgical cutting assemblies replace a flexible torque coil with an aspiration tube. As described herein, the aspiration tube can be fluidly coupled to a coupling member that is coupled to the inner cannula. In some implementations, a seal or other coupling component can be included in the surgical cutting assemblies that fluidly couple the coupling member to the aspiration tube but allow the coupling member to be rotationally decoupled from the aspiration tube. Further, the proximal end of the aspiration tube can be configured to be connected to a suction source without having to couple to a proximal connector that is configured to drive the flexible torque coil similar to the proximal connector described with respect to FIGS. 40A-49B.

In some implementations, the endoscopes described with respect to FIGS. 50A-60B describe inserting the surgical cutting assembly from an opening at a proximal end of the endoscope. However, in some other implementations, a surgical cutting assembly can be configured to be inserted into the endoscope via an opening of the instrument channel at the distal end of the endoscope. In some implementations, the surgical cutting assembly may not include an aspiration tube or an outer tubing. Rather, the surgical cutting assembly may include an outer cannula, an inner cannula and a coupling member configured to move (translate or rotate, among others) the inner cannula relative to the outer cannula. In some implementations, the outer cannula can be configured to engage with an articulation assembly configured to rotate the outer cannula relative to the endoscope. The articulation assembly can be controlled or actuated by the operator of the endoscope via a control mechanism. The operator can rotate or articulate the orientation of the outer cannula and as such, the cutting window of the outer cannula. The surgical cutting assembly can be configured to engage with a deployment component of the endoscope configured to be actuated by an actuator. The deployment component can be configured to bias the surgical cutting assembly in a retracted position. In some implementations, the operator may load the surgical cutting assembly in a retracted position within the endoscope prior to inserting the endoscope in the mammalian cavity of the patient. The deployment component can be configured to maintain the surgical cutting assembly disposed within the tubular body in a undeployed or retracted position. The deployment component can further be configured to deploy the surgical cutting assembly from the undeployed position to a deployed position upon actuation of the deployment component. In some implementations, the deployment component is configured to move between a closed state in which the surgical cutting assembly is maintained in the undeployed position and an opened state in which the surgical cutting assembly is deployed to the second deployed position. In some implementations, the deployment component can be a slidable cover that covers the distal end of the endoscope. In some implementations, the deployment component can be a spring that can move between a biased state and a relaxed state.

In some implementations, when the surgical cutting assembly is in the deployed position, the outer cannula of the surgical cutting assembly extends outwardly along a longitudinal axis of the endoscope from the distal end of the endoscope such that the cutting window can be viewed in an image captured by the camera.

Figure 61:
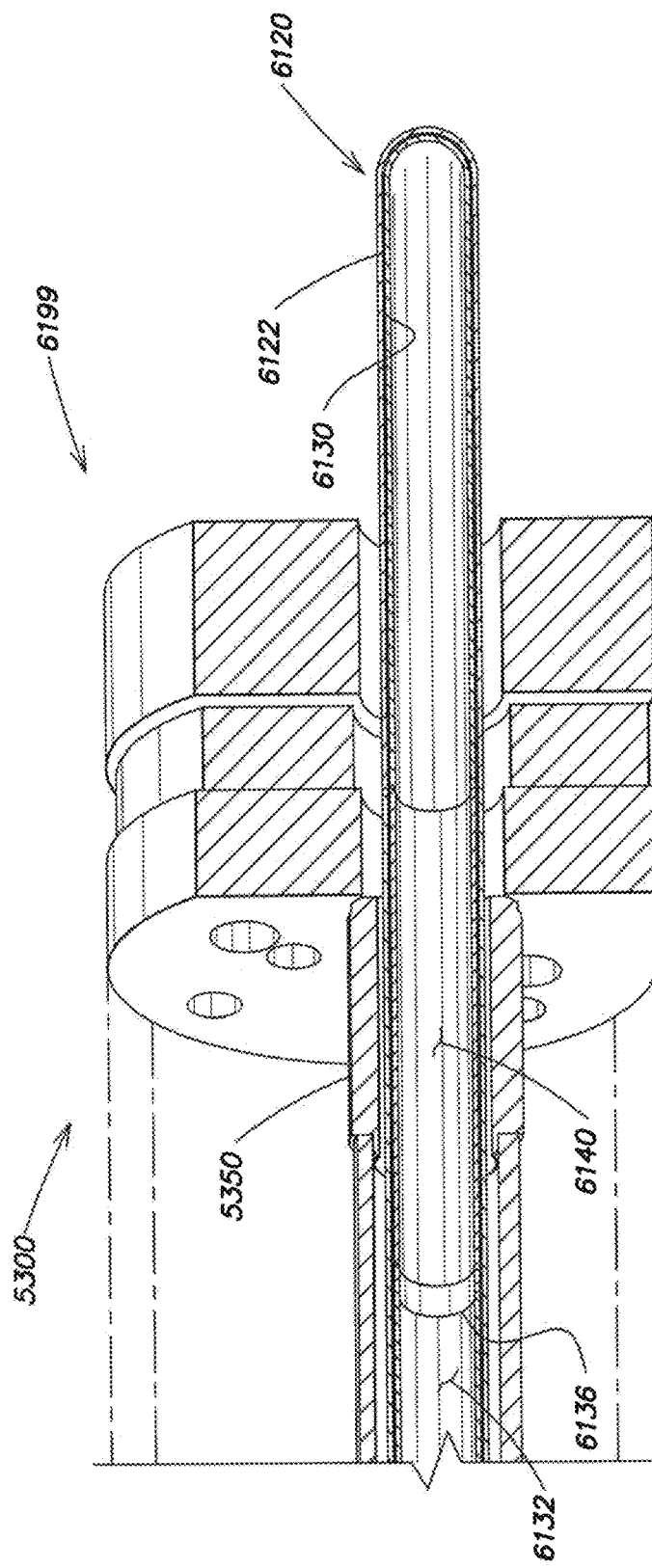
FIG. 61 shows an endoscopic assembly that includes the endoscope shown in FIG. 53B and a surgical cutting assembly similar to the surgical cutting assembly shown in FIG. 53B.

FIG. 61 shows an endoscopic assembly 6199 that includes the endoscope 5300 shown in FIG. 53B and a surgical cutting assembly 6120 similar to the surgical cutting assembly shown in FIG. 53B. As shown in FIG. 61, the length of a coupling member 6140 of the surgical cutting assembly 6120 is greater than the length of the corresponding coupling component 5350 of the endoscope 5300. Although the dimensions of both the coupling component 5350 and the coupling member 6140 are constrained because both the endoscope and the surgical cutting assembly have to be sized to be insertable within a mammalian cavity of the patient, by having the length of the coupling member 6140 exceed the length of the coupling component 5350, the operator of the surgical cutting assembly may be able to move the surgical cutting assembly 6120 along the longitudinal axis of the instrument channel of the endoscope over a distance that is based on the length of the coupling member 6140. As long as a portion of the coupling member 6140 is positioned adjacent to the coupling component 5350, the coupling member 6140 can be configured to be magnetically coupled to the coupling member 5350. This can allow an operator more freedom and a larger distance of movement of the surgical cutting assembly along the longitudinal axis of the instrument channel of the endoscope while still being able to cause the inner cannula to rotate relative to the outer cannula 6122.

In some implementations, the coupling member of the surgical cutting assembly 6120 has a first length that extends from a first end coupled to the inner cannula to a second end coupled to the aspiration tube. In some implementations, the first length can be greater than a corresponding length of the coupling component of the endoscope within which the surgical cutting assembly is insertable. The coupling member 6140 can be configured to rotatably couple to the coupling component of the endoscope 5300 over a distance that extends from a first position where the first end of the inner cannula is adjacent to a proximal end of the coupling component to a second position where the second end of the coupling member is adjacent to a distal end of the coupling component.

In some implementations, the coupling member of the surgical cutting assembly can have a first length extending from a first end coupled to the inner cannula 6130 and a second end coupled to the aspiration tube 6132 that is less than a corresponding length of the coupling component of the endoscope within which the surgical cutting assembly is insertable. In some such implementations, the coupling member 6140 is configured to be rotatably coupled to the coupling component 5350 over a distance that extends from a first position where the distal end of the inner cannula is adjacent to a proximal end of the coupling component to a second position where the second end of the coupling member is adjacent to a distal end of the coupling component 5350.

It should be appreciated that by providing an coupling member 6140 of the surgical cutting assembly that is longer than the corresponding coupling component 5350 of the endoscope, an operator of the surgical cutting assembly will have more maneuverability to perform surgical resection. As the length of the coupling member 6140 is limited by the space within which the surgical cutting assembly has to be inserted and the tortuous paths that can be taken by the endoscope when being inserted within the mammalian cavity, in some implementations, telescoping tubes or couplers may be used. A surgeon may increase the length of the coupling member or the surgical cutting assembly telescopically to allow for an increased reach. In addition, the use of telescoping tubes can provide for variable exposure giving the surgeon more control.

Generally, the size and dimensions of the endoscope may vary based on the type of endoscope and the size and shape of the mammalian cavity of the patient within which the endoscope is to be inserted. For example, the endoscope can be a colonoscope configured to pass through the colon of a patient. The colonoscope can have an outer diameter that is sized to be insertable inside an orifice through which the colon is accessed. Moreover, the colonoscope may be pliable or flexible enough to be inserted along a length of the colon and capable of navigating through a tortuous path defined by the colon. It should be appreciated that the colon can include several bends, some of which exceed 90 degrees. The length of the colonoscope may be sized to be substantially equal to or longer than the length of a colon of a patient. In some implementations, the length of the colonoscope can be between 3 feet and 8 feet long. Although the present disclosure described herein provides details relating to a colonoscope, one having ordinary skill in the art should appreciate that the endoscope may be a bronchoscope, a laryngoscope, a hysteroscope, any gastroentrology scope or other type of scope insertable within a mammalian cavity of a patient.

Figure 62:
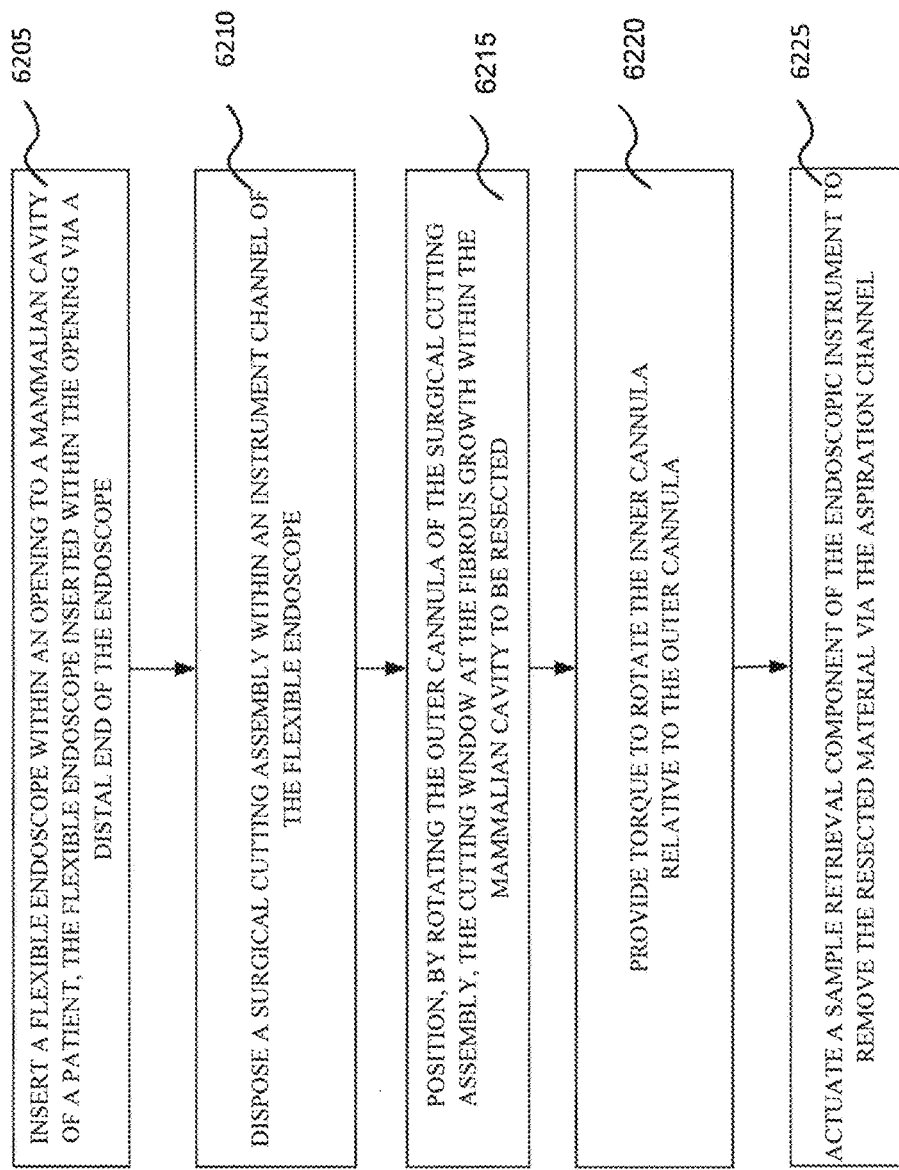
FIG. 62 is a flow chart depicting a method for resecting material from within a mammalian cavity of a patient.

Referring now to FIG. 62, a flow chart depicting a method for resecting material from within a mammalian cavity of a patient is shown. In brief summary, a flexible endoscope is inserted within an opening to a mammalian cavity of a patient, the flexible endoscope inserted within the opening via a distal end of the endoscope (BLOCK 6205). A surgical cutting assembly is disposed within an instrument channel of the flexible endoscope (BLOCK 6210). A cutting window of an outer cannula of the surgical cutting assembly is positioned at the material within the mammalian cavity to be resected (BLOCK 6215). Torque is then provided to rotate the inner cannula relative to the outer cannula (BLOCK 6220). A sample retrieval component of the surgical cutting assembly is then actuated to remove the resected material via the aspiration channel (BLOCK 6225).

In further detail, the method includes inserting a flexible endoscope within an opening to a mammalian cavity of a patient, the flexible endoscope inserted within the opening via a distal end of the endoscope (BLOCK 6205). The flexible endoscope can be inserted within the opening via a distal end of the endoscope. A medical professional may insert the endoscope. In some implementations, the mammalian cavity can be a colon of the patient, a larynx of the patient, a uterus of the patient, a lung of the patient, a stomach, an esophagus or a duodenum of the patient or any other region in the gastro-intestinal tract, among other mammalian cavities.

The method includes disposing a surgical cutting assembly within an instrument channel of the flexible endoscope (BLOCK 6210). The instrument channel of the endoscope can extend between an opening at the proximal end of the endoscope and another opening at the distal end of the endoscope. The surgical cutting assembly can be inserted into the instrument channel via the instrument channel opening at the proximal end of the endoscope. This end of the endoscope remains outside the opening to the mammalian cavity even after the endoscope has been inserted within the mammalian cavity. As described above, the surgical cutting assembly can be any of the surgical cutting assemblies described above with respect to FIGS. 51A-61B. In some implementations, the surgical cutting assembly can be an endoscopic instrument described above with respect to FIGS. 40A-50B. The surgical cutting assembly can include a cutter assembly having an outer cannula, an inner cannula disposed within an outer cannula, and a cutting window defined along a portion of a radial wall of the outer cannula. The proximal end of the inner cannula can be fluidly coupled to an aspiration channel that extends along a length of the flexible endoscope. The inner cannula can be configured to rotate relative to the outer cannula to cut material entering the cutting window of the outer cannula.

The method includes positioning, by rotating the outer cannula of the surgical cutting assembly, the cutting window at the material within the mammalian cavity to be resected (BLOCK 6215). In some implementations, the outer cannula can be coupled to a distal end of an outer tubing. The outer tubing can be a braided tubing or any other tube or coil configured to rotate the outer cannula by rotating a proximal end of the outer tubing. In some implementations, the outer tubing can be a flexible torque coil.

The method includes providing torque to rotate the inner cannula relative to the outer cannula via a flexible torque component (BLOCK 6220). The torque can be provided by one of a torque generation component disposed within the distal end of the endoscope or via a flexible torque component extending from the proximal end of the endoscope to the distal end of the endoscope. The torque causing the coupling component of the endoscope to rotate and cause the coupling member of the surgical cutting assembly and the inner cannula to rotate relative to the outer cannula to resect at least a portion of the material at the cutting window of the outer cannula. In some implementations, the material can be a lesion, fibrous tissue, or any other growth or appearance formed within the mammalian cavity.

In some implementations, the method includes actuating the torque generation component. In some implementations, actuating the torque generation component includes providing a fluid to the torque generation component via a fluid entry channel and removing the fluid from the torque generation component via a fluid exit channel. In some implementations, actuating the torque generation component includes providing an electric current to the torque generation component via an electrical wire that extends from the torque generation component to a current source outside the flexible endoscope.

In some implementations, the method includes actuating a rotary actuator positioned outside the endoscope and connected to the torque delivery component. The torque delivery component is configured to deliver the torque generated by the rotary actuator to the coupling component. The torque delivery component includes a flexible torque coil or flexible torque rope having a plurality of layers of one or more threads, each of the plurality of layers is wound in a direction opposite to a direction in which one or more adjacent layers of the plurality of layers is wound.

In some implementations, the flexible endoscope includes a coupling component disposed within a distal end of the endoscope. The coupling component can include at least one magnet and the method further includes magnetically coupling the coupling component of the endoscope and the coupling member of the endoscope. In some implementations, the torque generated by the rotary actuator or delivered by the torque delivery component can be provided to the coupling component, which causes the coupling component to rotate. The coupling member can be magnetically coupled to a coupling member of the surgical cutting assembly. The coupling member is coupled to the inner cannula and as such, rotation of the coupling component can cause the inner cannula to rotate.

The method includes actuating a sample retrieval component of the surgical cutting assembly to remove the resected material via the aspiration channel (BLOCK 6225).

A suction source may be applied to a proximal end of the aspiration channel that causes material entering the endoscope via the cutting window of the outer cannula and being resected by the inner cannula to be aspirated through the surgical cutting assembly within the aspiration channel. In some implementations, the aspiration channel can be defined by an inner wall of the inner cutter, an inner wall of the coupling member and an inner wall of the aspiration tube. In some implementations in which the inner cannula is rotated via the flexible torque delivery component of the surgical cutting assembly, the aspiration channel can be defined by the inner wall of the inner cutter and the inner wall of the flexible torque delivery component.

In some implementations, a method of resecting a lesion from within a mammalian cavity of a patient includes inserting a flexible endoscope within an opening to a mammalian cavity of a patient, the flexible endoscope including a coupling component disposed within a distal end of the endoscope, the flexible endoscope inserted within the opening via the distal end. The method includes disposing a surgical cutting assembly within an instrument channel of the flexible endoscope. The surgical cutting assembly inserted into the instrument channel via an instrument channel opening to the instrument channel at a proximal end of the endoscope that remains outside the opening to the mammalian cavity. The surgical cutting assembly including a cutter assembly having an outer cannula, an inner cannula disposed within an outer cannula, and a cutting window defined along a portion of a radial wall of the outer cannula, a proximal end of the inner cannula coupled to a coupling member, the coupling member fluidly coupled to an aspiration tube that extends along a length of the flexible endoscope, the coupling member configured to rotatably couple with the coupling component of the flexible endoscope. The method includes positioning, by rotating the outer cannula of the surgical cutting assembly, the cutting window at the lesion within the mammalian cavity to be resected. The method includes providing torque to the coupling component of the endoscope. The torque provided by one of a torque generation component disposed within the distal end of the endoscope or via a flexible torque component extending from the proximal end of the endoscope to the distal end of the endoscope. The torque causing the coupling component of the endoscope to rotate and cause the coupling member of the surgical cutting assembly and the inner cannula to rotate relative to the outer cannula to resect at least a portion of the lesion at the cutting window of the outer cannula. The method includes actuating a sample retrieval component to provide suction to the aspiration tube to remove the resected portion of the lesion via an aspiration channel defined by an inner wall of the inner cannula, an inner wall of the coupling member and the aspiration tube.

In some implementations, the method includes actuating the torque generation component. In some implementations, actuating the torque generation component includes providing a fluid to the torque generation component via a fluid entry channel and removing the fluid from the torque generation component via a fluid exit channel. In some implementations, actuating the torque generation component includes providing an electric current to the torque generation component via an electrical wire that extends from the torque generation component to a current source outside the flexible endoscope.

In some implementations, the method includes actuating a rotary actuator positioned outside the endoscope and connected to the torque delivery component. The torque delivery component is configured to deliver the torque generated by the rotary actuator to the coupling component. The torque delivery component includes a flexible torque coil or flexible torque rope having a plurality of layers of one or more threads, each of the plurality of layers is wound in a direction opposite to a direction in which one or more adjacent layers of the plurality of layers is wound.

In some implementations, the coupling component includes at least one magnet and the method further includes magnetically coupling the coupling component of the endoscope and the coupling member of the endoscope.

In some implementations, the method further includes providing irrigation fluid to the surgical cutting assembly via an irrigation fluid delivery channel defined within the endoscope, the irrigation fluid delivery channel including an entry port at a proximal end of the endoscope and a fluid exit port positioned towards the distal end of the endoscope and fluidly coupled to an irrigation entry opening of the surgical cutting assembly, the irrigation entry opening of the surgical cutting assembly fluidly coupled to an irrigation pathway defined between the outer cannula and the inner cannula of the cutter assembly.

In some implementations, a portion of the irrigation fluid delivery channel is positioned adjacent to at least one of the torque generation component, the coupling component or the torque delivery component to provide a cooling effect to the torque generation component, the coupling component or the torque delivery component.

In some implementations, positioning, by rotating the outer cannula of the surgical cutting assembly, the cutting window at the lesion within the mammalian cavity to be resected includes actuating an articulation assembly disposed at the distal end of the endoscope, the articular assembly configured to engage with the outer cannula and configured to cause the outer cannula to rotate relative to the endoscope.

In some implementations, positioning, by rotating the outer cannula of the surgical cutting assembly, the cutting window at the lesion within the mammalian cavity to be resected includes rotating an outer tubing coupled to the outer cannula, the outer tubing configured to cause the outer cannula to rotate relative to the endoscope based on rotating the outer tubing.

In some implementations, a method of retrieving polyps from a mammalian cavity of a patient includes inserting a flexible endoscope within an opening to a mammalian cavity of a patient. An endoscopic instrument is disposed or inserted within an instrument channel of the flexible endoscope to resect at least a portion of lesion from within the mammalian cavity. The endoscopic instrument including a cutting assembly having an outer cannula, an inner cannula disposed within an outer cannula, and a cutting window defined along a portion of a radial wall of the outer cannula, the inner cannula rotatably coupled to a flexible torque component having a length that extends along a length of the flexible endoscope, the flexible torque component, upon actuation, providing torque to the inner cannula to rotate relative to the outer cannula to resect the portion of the lesion. Irrigation fluid is then provided from a lavage port of the endoscopic instrument that remains outside the flexible endoscope while the endoscopic instrument is disposed within the instrument channel. The lavage port is fluidly coupled to the outer cannula through a rotational coupler coupling the lavage port to an outer tubing connected to the outer cannula. The rotational coupler allowing the outer tubing and the outer cannula to rotate relative to the lavage port upon rotating a portion of the rotational coupler. The outer cannula is then rotated, via rotation of the portion of the rotational coupler, to a position in which the opening of the outer cannula is viewable via a camera of the flexible endoscope. The cutting window of the outer cannula is then positioned at the lesion of the mammalian cavity. The flexible torque component is then actuated to rotate the inner cannula relative to the outer cannula, the inner cannula cutting the portion of the lesion as the inner cannula rotates adjacent to the cutting window. A sample retrieval component of the endoscopic instrument is actuated to remove the cut portions of the lesion from within the mammalian cavity via an aspiration channel defined by an inner wall of the inner cannula and the flexible torque component.

In some implementations, disposing the endoscopic instrument within the instrument channel of the flexible endoscope includes inserting a distal end of the endoscopic instrument in the instrument channel of the flexible endoscope.

In some implementations, a proximal connector that is coupled to the flexible torque component and positioned at a proximal end of the endoscopic instrument is engaged with a drive assembly configured to provide torque to the flexible torque component.

In some implementations, a vacuum source is fluidly coupled to a distal end of the endoscopic instrument to remove, from the endoscopic instrument, portions of the polyp entering the endoscopic instrument via the opening of the outer cannula.

In some implementations, the flexible torque component includes a flexible torque coil having a plurality of layers of one or more threads, each of the plurality of layers is wound in a direction opposite to a direction in which one or more adjacent layers of the plurality of layers is wound and the aspiration channel is partially defined by an inner wall of the flexible torque coil.

In some implementations, actuating the flexible torque component and actuating the sample retrieval component of the endoscopic instrument includes actuating the flexible torque component and actuating the sample retrieval component of the endoscopic instrument simultaneously.

In some implementations, actuating the flexible torque component includes providing torque to the inner cannula that is sufficient to cut at least a portion of the polyp. In some implementations, actuating the flexible torque component includes actuating the flexible torque component to cause an inner cannula of the cutting assembly to rotate relative to the outer cannula via a foot pedal.

In some implementations, the lesion is a first polyp and the mammalian cavity is a colon. Upon cutting at least a portion of the first polyp and without removing the endoscopic instrument from the flexible endoscope, the opening of the outer cannula is positioned at a second polyp within the colon. The flexible torque component is actuated to rotate the inner cannula relative to the outer cannula, the inner cannula cutting at least a portion of the second polyp. The sample retrieval component of the endoscopic instrument is actuated to remove the cut portion of the second polyp from within the colon.

In some implementations, a method of removing polyps from within a patient can include inserting a flexible endoscope within an opening of a patient, disposing an endoscopic instrument within an instrument channel of the flexible endoscope to remove a polyp from the surgical site, the endoscopic instrument including a cutting assembly having an outer cannula, an inner cannula disposed within an outer cannula, and an opening defined along a portion of a radial wall of the outer cannula, the inner cannula rotatably coupled to a flexible torque component having a length that extends along a length of the flexible endoscope, the flexible torque component, upon actuation, providing torque to the inner cannula, positioning the opening of the outer cannula at the polyp, actuating the flexible torque component to rotate the inner cannula relative to the outer cannula, the inner cannula cutting a portion of the polyp as the inner cannula rotates adjacent to the opening, and actuating a sample retrieval component of the endoscopic instrument to remove the cut portions of the polyp from within the patient via an aspiration channel defined by an inner wall of the inner cannula and the flexible torque component.

In some implementations, the method includes providing irrigation fluid from a lavage port of the endoscopic instrument that remains outside the flexible endoscope while the endoscopic instrument is disposed within the instrument channel. The lavage port is fluidly coupled to the outer cannula through a rotational coupler coupling the lavage port to an outer tubing connected to the outer cannula, the rotational coupler allowing the outer tubing and the outer cannula to rotate relative to the lavage port upon rotating a portion of the rotational coupler.

In some implementations, the method includes rotating, via rotation of the portion of the rotational coupler, the outer cannula to a position in which the opening of the outer cannula is viewable via a camera of the flexible endoscope.

In some implementations, disposing the endoscopic instrument within the instrument channel of the flexible endoscope includes inserting a distal end of the endoscopic instrument in the instrument channel of the flexible endoscope.

In some implementations, the method includes engaging a proximal connector that is coupled to the flexible torque component and positioned at a proximal end of the endoscopic instrument with a drive assembly configured to provide torque to the flexible torque component.

In some implementations, the method includes fluidly coupling a vacuum source to a distal end of the endoscopic instrument to remove, from the endoscopic instrument, cut portions of the polyp entering the endoscopic instrument via the opening of the outer cannula.

In some implementations, the flexible torque component includes a flexible torque coil having a plurality of layers of one or more threads, each of the plurality of layers is wound in a direction opposite to a direction in which one or more adjacent layers of the plurality of layers is wound and the aspiration channel is partially defined by an inner wall of the flexible torque coil.

In some implementations, actuating the flexible torque component and actuating a sample retrieval component of the endoscopic instrument includes actuating the flexible torque component and actuating the sample retrieval component of the endoscopic instrument simultaneously.

In some implementations, actuating the flexible torque component includes providing torque to the inner cannula that is sufficient to cut at least a portion of the polyp. In some implementations, actuating the flexible torque component includes actuating the flexible torque component to cause an inner cannula of the cutting assembly to rotate relative to the outer cannula via a foot pedal.

In some implementations, the polyp is a first polyp and the method further includes upon cutting at least a portion of the first polyp and without removing the endoscopic instrument from the flexible endoscope, positioning the opening of the outer cannula at a second polyp at another surgical site, actuating the flexible torque component to rotate the inner cannula relative to the outer cannula, the inner cannula cutting at least a portion of the second polyp, and actuating the sample retrieval component of the endoscopic instrument to remove the cut portion of the second polyp from within the patient.

In some implementations, a method of resecting lesion from within a mammalian cavity of a patient includes inserting a flexible endoscope within an opening to a mammalian cavity of a patient, the flexible endoscope including a coupling component disposed within a distal end of the endoscope, the flexible endoscope inserted within the opening via the distal end. The method includes disposing a surgical cutting assembly within an instrument channel of the flexible endoscope. The surgical cutting assembly inserted into the instrument channel via an instrument channel opening to the instrument channel at a proximal end of the endoscope that remains outside the opening to the mammalian cavity. The surgical cutting assembly including a cutter assembly having an outer cannula, an inner cannula disposed within an outer cannula, and a cutting window defined along a portion of a radial wall of the outer cannula, a proximal end of the inner cannula coupled to a coupling member, the coupling member fluidly coupled to an aspiration tube that extends along a length of the flexible endoscope, the coupling member configured to rotatably couple with the coupling component of the flexible endoscope. The method includes positioning, by rotating the outer cannula of the surgical cutting assembly, the cutting window at the lesion within the mammalian cavity to be resected. The method includes providing torque to the coupling component of the endoscope. The torque provided by one of a torque generation component disposed within the distal end of the endoscope or via a flexible torque component extending from the proximal end of the endoscope to the distal end of the endoscope. The torque causing the coupling component of the endoscope to rotate and cause the coupling member of the surgical cutting assembly and the inner cannula to rotate relative to the outer cannula to resect at least a portion of the lesion at the cutting window of the outer cannula. The method includes actuating a sample retrieval component to provide suction to the aspiration tube to remove the resected portion of the lesion via an aspiration channel defined by an inner wall of the inner cannula, an inner wall of the coupling member and the aspiration tube.

In some implementations, the method includes actuating the torque generation component. In some implementations, actuating the torque generation component includes providing a fluid to the torque generation component via a fluid entry channel and removing the fluid from the torque generation component via a fluid exit channel. In some implementations, actuating the torque generation component includes providing an electric current to the torque generation component via an electrical wire that extends from the torque generation component to a current source outside the flexible endoscope.

In some implementations, the method includes actuating a rotary actuator positioned outside the endoscope and connected to the torque delivery component. The torque delivery component is configured to deliver the torque generated by the rotary actuator to the coupling component. The torque delivery component includes a flexible torque coil or flexible torque rope having a plurality of layers of one or more threads, each of the plurality of layers is wound in a direction opposite to a direction in which one or more adjacent layers of the plurality of layers is wound.

In some implementations, the coupling component includes at least one magnet and the method further includes magnetically coupling the coupling component of the endoscope and the coupling member of the endoscope.

In some implementations, the method further includes providing irrigation fluid to the surgical cutting assembly via an irrigation fluid delivery channel defined within the endoscope, the irrigation fluid delivery channel including an entry port at a proximal end of the endoscope and a fluid exit port positioned towards the distal end of the endoscope and fluidly coupled to an irrigation entry opening of the surgical cutting assembly, the irrigation entry opening of the surgical cutting assembly fluidly coupled to an irrigation pathway defined between the outer cannula and the inner cannula of the cutter assembly.

In some implementations, a portion of the irrigation fluid delivery channel is positioned adjacent to at least one of the torque generation component, the coupling component or the torque delivery component to provide a cooling effect to the torque generation component, the coupling component or the torque delivery component.

In some implementations, positioning, by rotating the outer cannula of the surgical cutting assembly, the cutting window at the lesion within the mammalian cavity to be resected includes actuating an articulation assembly disposed at the distal end of the endoscope, the articular assembly configured to engage with the outer cannula and configured to cause the outer cannula to rotate relative to the endoscope.

In some implementations, positioning, by rotating the outer cannula of the surgical cutting assembly, the cutting window at the lesion within the mammalian cavity to be resected includes rotating an outer tubing coupled to the outer cannula, the outer tubing configured to cause the outer cannula to rotate relative to the endoscope based on rotating the outer tubing.

Figure 63A:
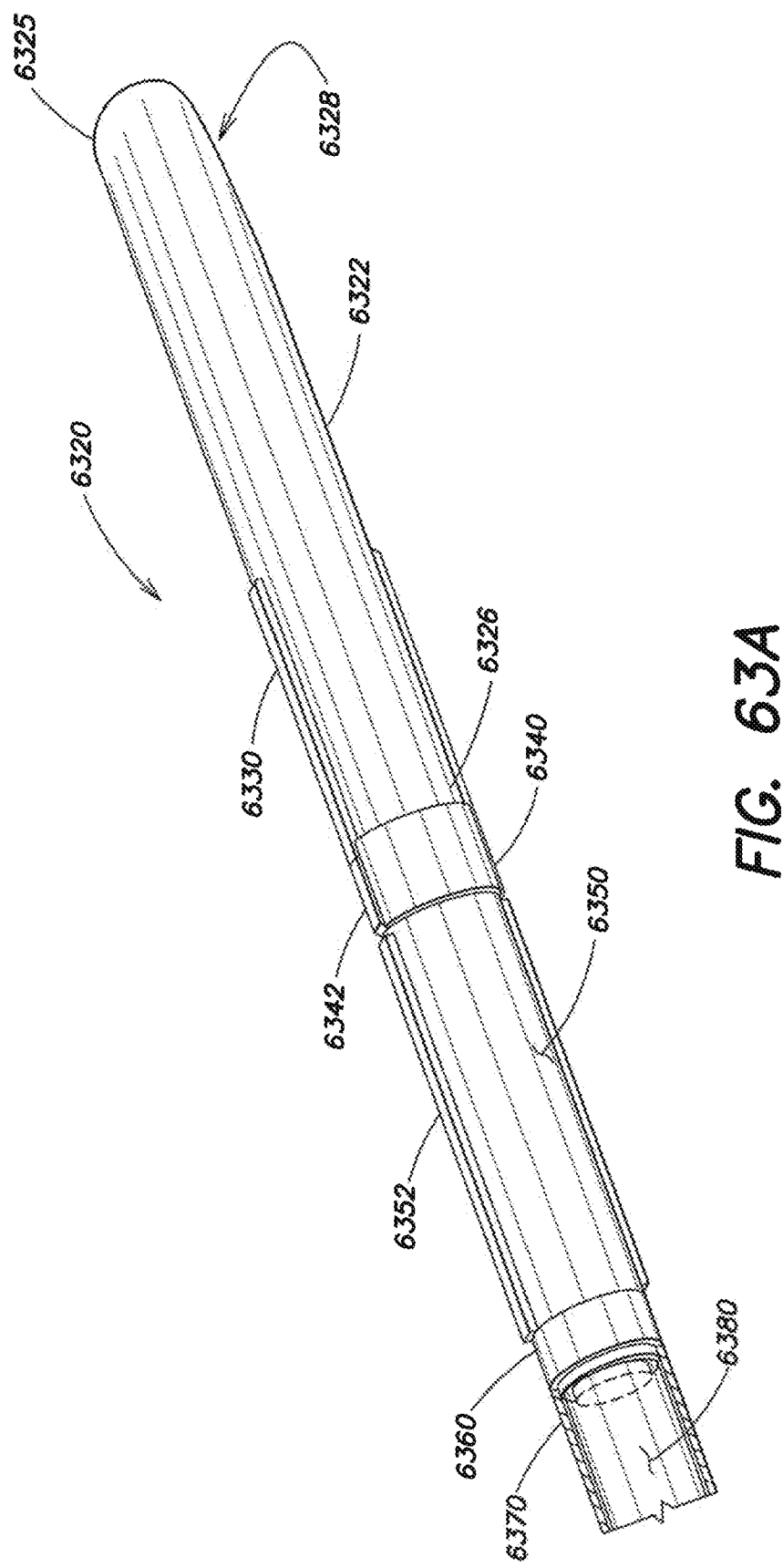
FIG. 63A is a perspective view of a distal portion of a surgical cutting assembly according to embodiments of the present disclosure.
Figure 63B:
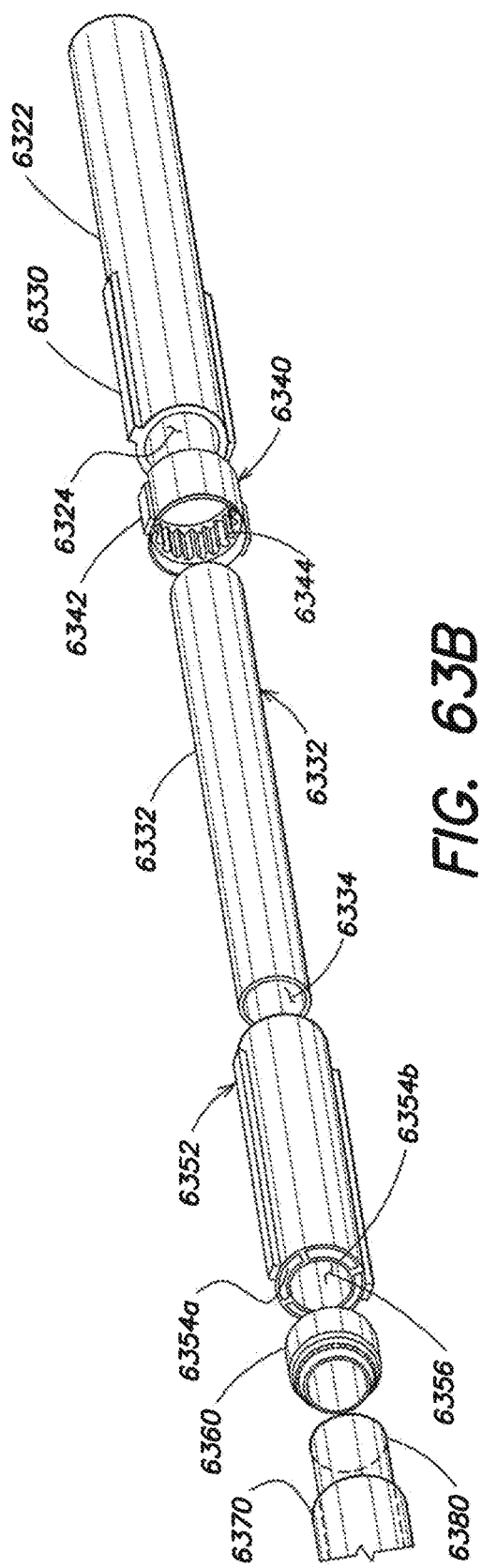
FIG. 63B is an exploded view of the distal portion surgical cutting assembly shown in FIG. 63A.
Figure 63C:
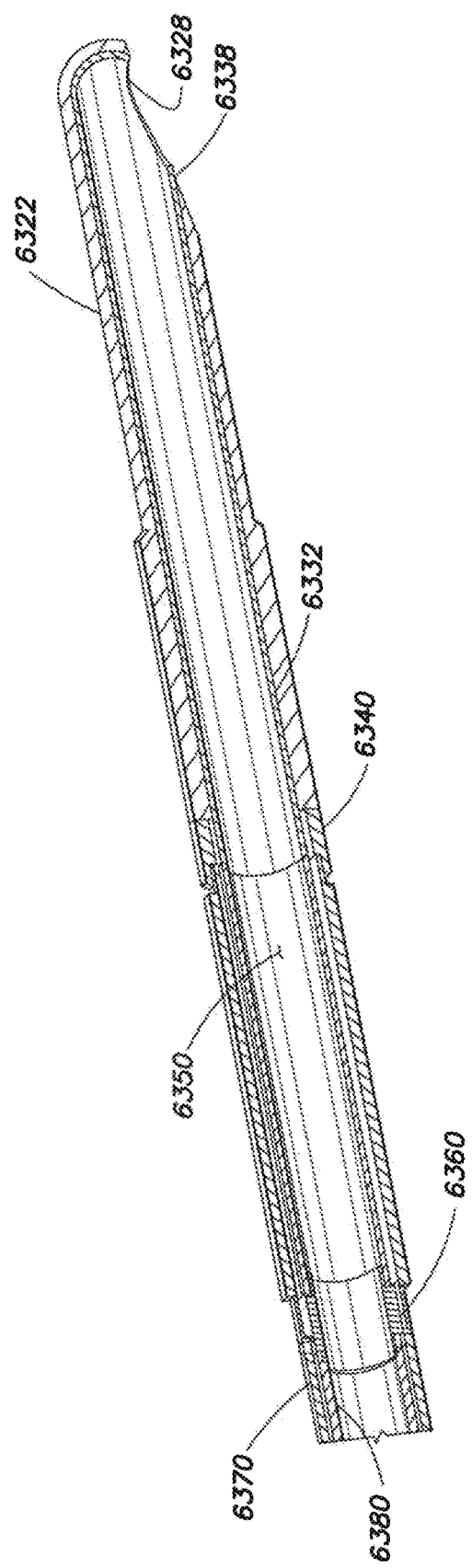
FIG. 63C is a perspective cross-sectional view of the distal portion of the surgical cutting assembly shown in FIG. 63A.
Figure 63E:
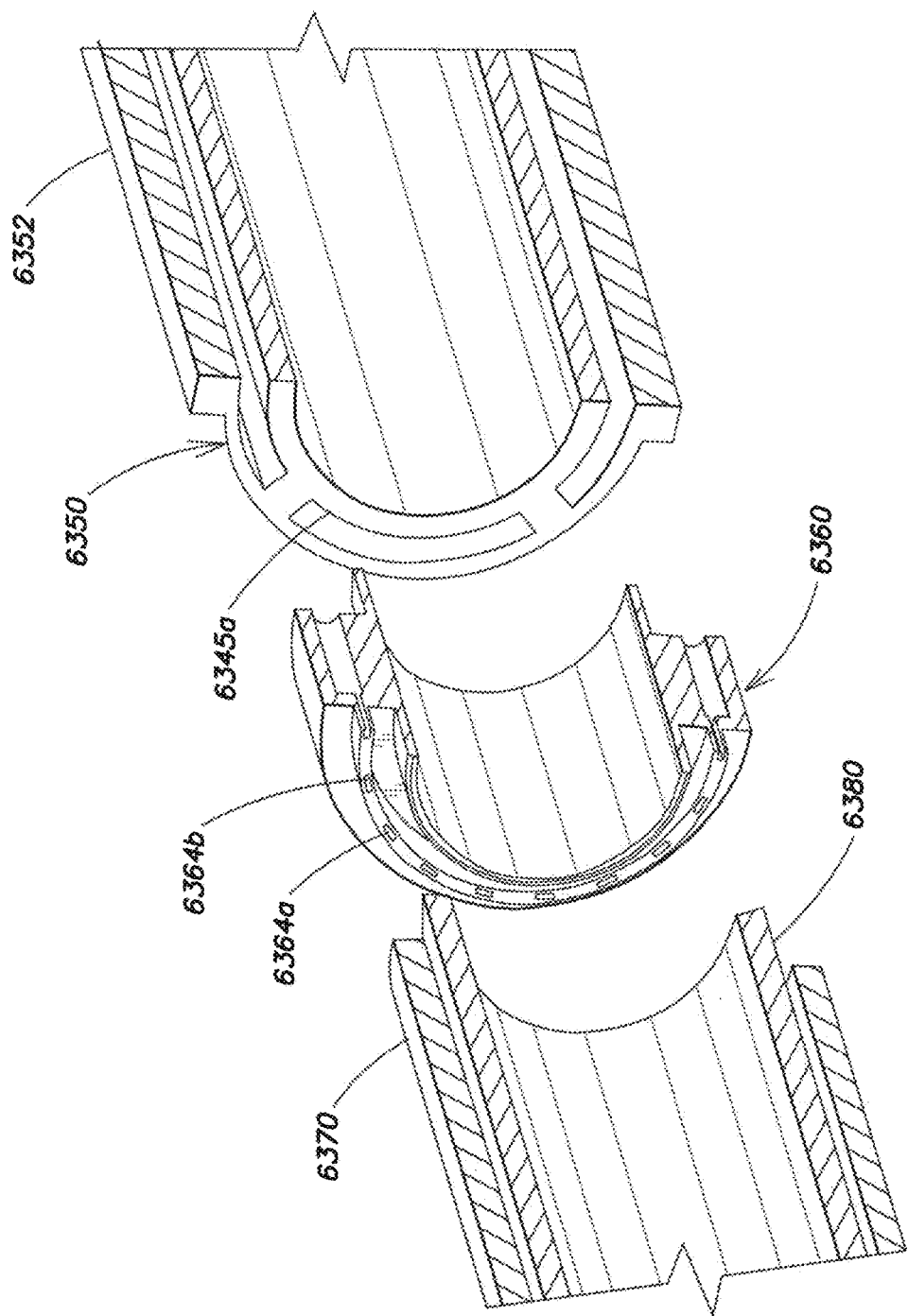
FIG. 63E is an enlarged view of a portion of FIG. 63B including the second coupler of the surgical cutting assembly shown in FIG. 63A.
Figure 63F:
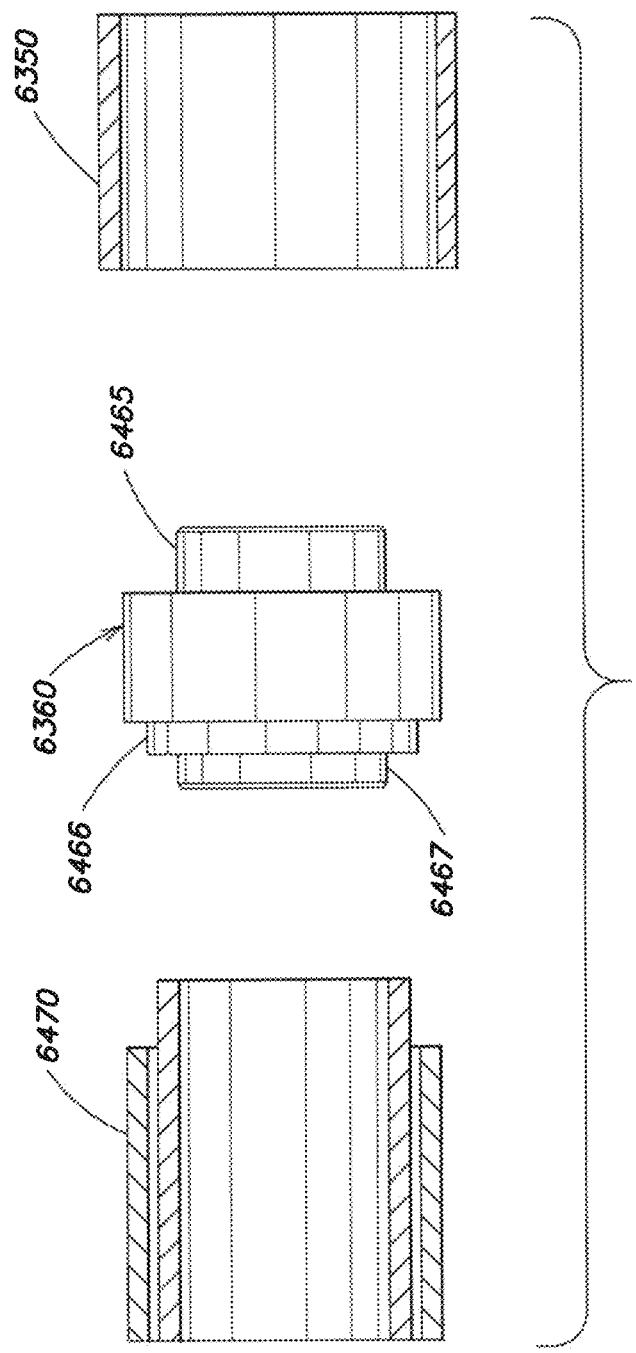
FIG. 63F is a side view of the second coupler of the surgical cutting assembly shown in FIG. 63A.

FIG. 63A is a perspective view of a distal portion of a surgical cutting assembly according to embodiments of the present disclosure. FIG. 63B is an exploded view of the distal portion surgical cutting assembly shown in FIG. 63A. FIG. 63C is a perspective cross-sectional view of the distal portion of the surgical cutting assembly shown in FIG. 63A. FIG. 63D is an enlarged view of a portion of FIG. 63B including a first coupler of the surgical cutting assembly shown in FIG. 63A. FIG. 63E is an enlarged view of a portion of FIG. 63B including a second coupler of the surgical cutting assembly shown in FIG. 63A. FIG. 63F is a side view of the second coupler of the surgical cutting assembly shown in FIG. 63A.

Similar to other surgical cutting assemblies described above with respect to FIGS. 53A-61, the surgical cutting assembly 6320 is configured to be insertable within an endoscope and configured to be driven or actuated via the endoscope. In some implementations, the surgical cutting assembly 6320 can be actuated via a rotary actuator or torque generation component of the endoscope or via a torque delivery component configured to deliver torque to the surgical cutting assembly via the endoscope.

Referring now to FIGS. 63A-63F, the surgical cutting assembly can include an outer cannula 6322 that has a distal end 6325 and a proximal end 6326. A cutting window or opening 6328 is defined along a radial wall towards the distal end 6325. The outer surface of the outer cannula can include one or more key structures 6330 configured to engage with opposing structures defined within a portion of the endoscope through which the surgical cutting assembly 6320 is inserted. The outer cannula further includes an inner wall 6324 that defines a portion of an irrigation channel or pathway 6338.

The surgical cutting assembly 6320 also includes an inner cannula 6322 configured to be disposed within the outer cannula 6322. The inner cannula includes a cutting tip at a distal end of the inner cannula. The inner cannula 6332 is disposed within the outer cannula 6322 such that the cutting tip of the inner cannula 6332 is adjacent to the cutting window 6328 of the outer cannula such that when the inner cannula rotates relative to the outer cannula, material entering the cutting window 6328 is resected or cut by the cutting tip of the inner cannula 6332.

The surgical cutting assembly 6320 also includes a coupling member 6350. The coupling member 6350 includes an outer wall on which at least one key structure 6352 is formed. The key structure 6352 can be aligned with the key structure 6330 formed on the outer cannula 6322. The coupling member 6350 also includes an inner wall 6356. The coupling member can further include one or more fluid pathways 6354a and 6354b that are defined in between the outer wall and the inner wall of the coupling member 6350. The coupling member 6350 is configured to engage with a corresponding component of the endoscope within which the surgical cutting assembly 6320 is inserted. The coupling member 6350 can be configured to rotate when the corresponding component of the endoscope rotates. The coupling member 6350 can be coupled to the inner cannula 6332 such that when the coupling member 6350 rotates, the inner cannula 6332 also rotates relative to the outer cannula 6322. In some implementations, the coupling member 6350 can be coupled to the inner cannula via a press fit, weld, coupler or any other means to couple the coupling member 6350 to the inner cannula 6332. To prevent the outer cannula from rotating when the coupling member 6350 and the inner cannula 6332 rotate, the outer cannula 6322 can be configured to engage with an articulation assembly of the endoscope that is configured to rotate the outer cannula relative to the inner cannula 6332 and the coupling member 6350. Details of the articulation assembly are provided above with respect to FIGS. 58A and 58B.

The surgical cutting assembly 6320 can also include a first coupler 6140 that is configured to couple the coupling member 6350 with the outer cannula 6330. The first coupler 6140 can include a corresponding key structure 6342 that may be aligned with the key structures 6330 and 6352. The first coupler 6140 can be configured to allow irrigation fluid flowing through the irrigation channels 6354a and 6354b to a region defined by the inner wall 6324 of the outer cannula 6322 and an outer wall of the inner cannula 6332, while preventing the irrigation fluid from leaking outside of the surgical cutting assembly 6320. In some implementations, the first coupler 6140 can also be configured to couple the inner cannula 6332 to the coupling member 6350 and also prevent material flowing in an aspiration channel partially defined by the inner wall 6334 of the inner cannula 6332 and the inner wall 6356 of the coupling member 6350 from leaking or escaping. In some implementations, the inner wall of the first coupler 6140 can include a plurality of ridges configured to frictionally engage with the inner cannula. The grooves between the ridges in the first coupler 6140 can serve as fluid pathways for allowing irrigation fluid to flow from the coupling member 6350 to the region between the outer cannula 6322 and the inner cannula 6332.

The surgical cutting assembly 6320 can also include an outer tubing 6370 that is configured to couple to the coupling member 6350. The outer tubing 6370 can be similar to the outer tubings described above with respect to FIGS. 53A-61. Irrigation fluid that passes through the irrigation pathways 6354a and 6354b can be provided via the outer tubing. In some implementations, the inner wall of the outer tubing and an outer wall of an aspiration tubing 6380 can define a portion of the irrigation channel 6338 that extends from the proximal end of the surgical cutting assembly that remains outside the endoscope to the cutting window 6326 of the surgical cutting assembly 6320.

The aspiration tubing 6380 can be coupled to the inner wall of the coupling member 6350. In some implementations, the aspiration tubing is fluidly coupled to the inner wall of the coupling member 6350 such that material entering the surgical cutting assembly via the cutting window 6326 can flow into a portion of an aspiration channel defined by the aspiration tubing 6380.

The surgical cutting assembly 6320 can include a second coupler 6360 configured to couple the outer tubing 6370 and the aspiration tubing 6380 to the coupling member 6350. The second coupler 6360 is configured to allow the coupling member 6350 to rotate relative to the outer tubing 6370 and the aspiration tubing 6380. The second coupler 6360 can include one or more openings 6364a and 6364b that extend along a length of the second coupler 6360. The openings 6364a and 6364b can be sized and configured to allow irrigation fluid flowing between the outer tubing 6370 and the aspiration tubing 6380 to flow to the region between the outer cannula 6322 and the inner cannula 6332 via the fluid pathways 6354a and 6354b of the coupling member 6350.

The second coupler 6360 can include a first portion 6465 configured to engage with the coupling member 6350, a second portion 6466 configured to engage with the outer tubing 6470 and a third portion 6467 configured to engage with the aspiration tubing 6480. The inner wall of the third portion 6467 may define a portion of the aspiration channel.

Figure 63H:
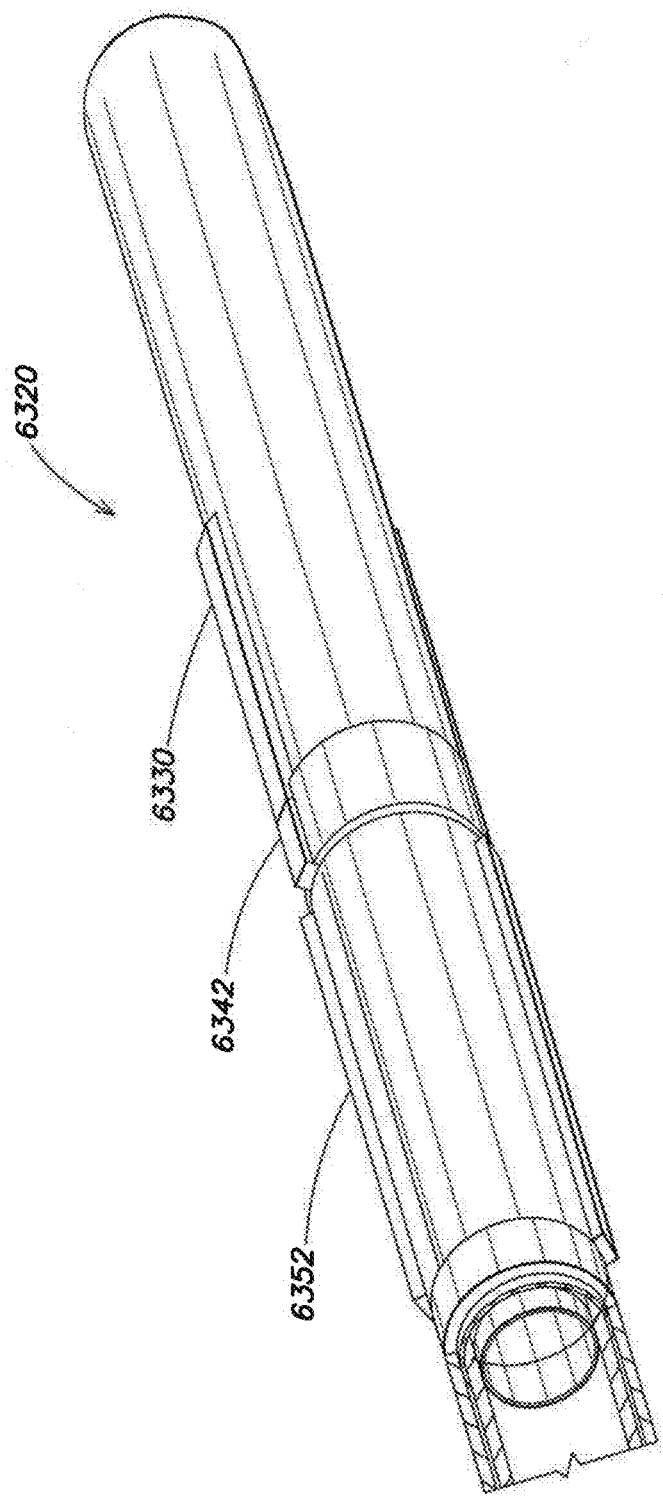
FIG. 63H shows a perspective view of the surgical cutting assembly of FIG. 63A including the coupling member at a second position.

FIG. 63G shows a perspective view of the surgical cutting assembly 6320 including the coupling member in a first position. FIG. 63H shows a perspective view of the surgical cutting assembly 6320 including the coupling member at a second position. When the surgical cutting assembly is inserted within the instrument channel of the endoscope, the surgical cutting assembly may be arranged such that the key structures 6330, 6342 and 6352 are all aligned with one another. In this way, the key structures can engage with a corresponding groove or locking structure that is configured to engage with the key structures. In some implementations, the instrument channel can include a groove or locking structure that extends from a proximal end of the instrument channel towards the distal end of the instrument channel and is configured to engage with the key structures 6330, 6342 and 6352.

When the endoscope is actuated to cause the surgical cutting assembly to begin cutting, a coupling component of the endoscope causes the coupling member 6350 of the surgical cutting assembly 6320 to rotate, which in turn, causes the inner cannula 6332 to rotate relative to the outer cannula 6322. The first coupler 6140 and the second coupler 6360 allow the coupling member 6350 to rotate relative to both the outer cannula 6322 and the outer tubing 6370. In some implementations, the outer cannula 6322 may remain stationary because the key structure 6330 of the outer cannula 6322 may engage with an articulation assembly of the endoscope that is positioned such that it is adjacent to the outer cannula when the coupling component of the endoscope is engaged with the coupling member 6350 of the surgical cutting assembly 6320.

Figure 64A:
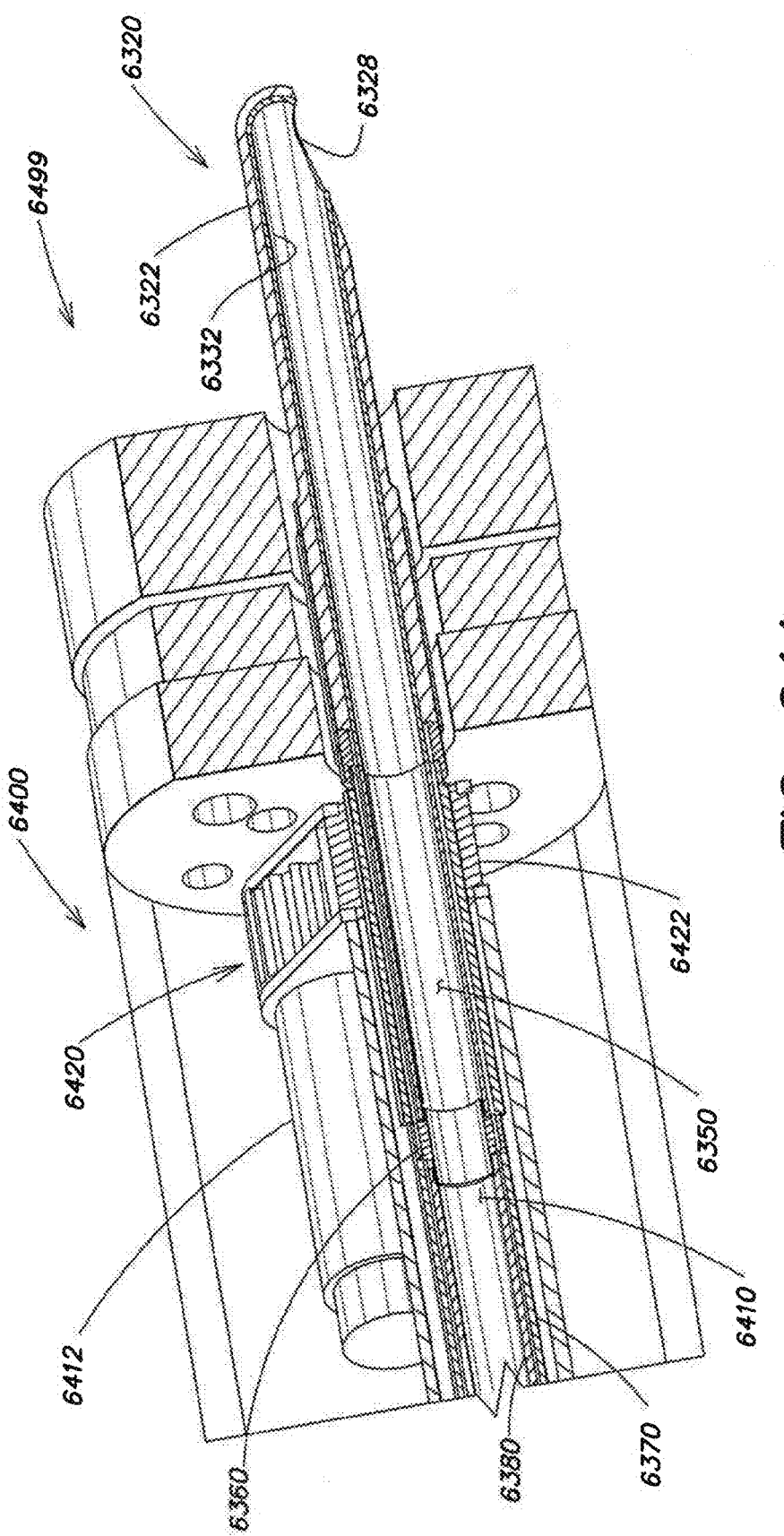
FIG. 64A is a perspective cross-sectional view of an endoscopic assembly including an endoscope and the surgical cutting assembly shown in FIG. 63A according to embodiments of the present disclosure.
Figure 64B:
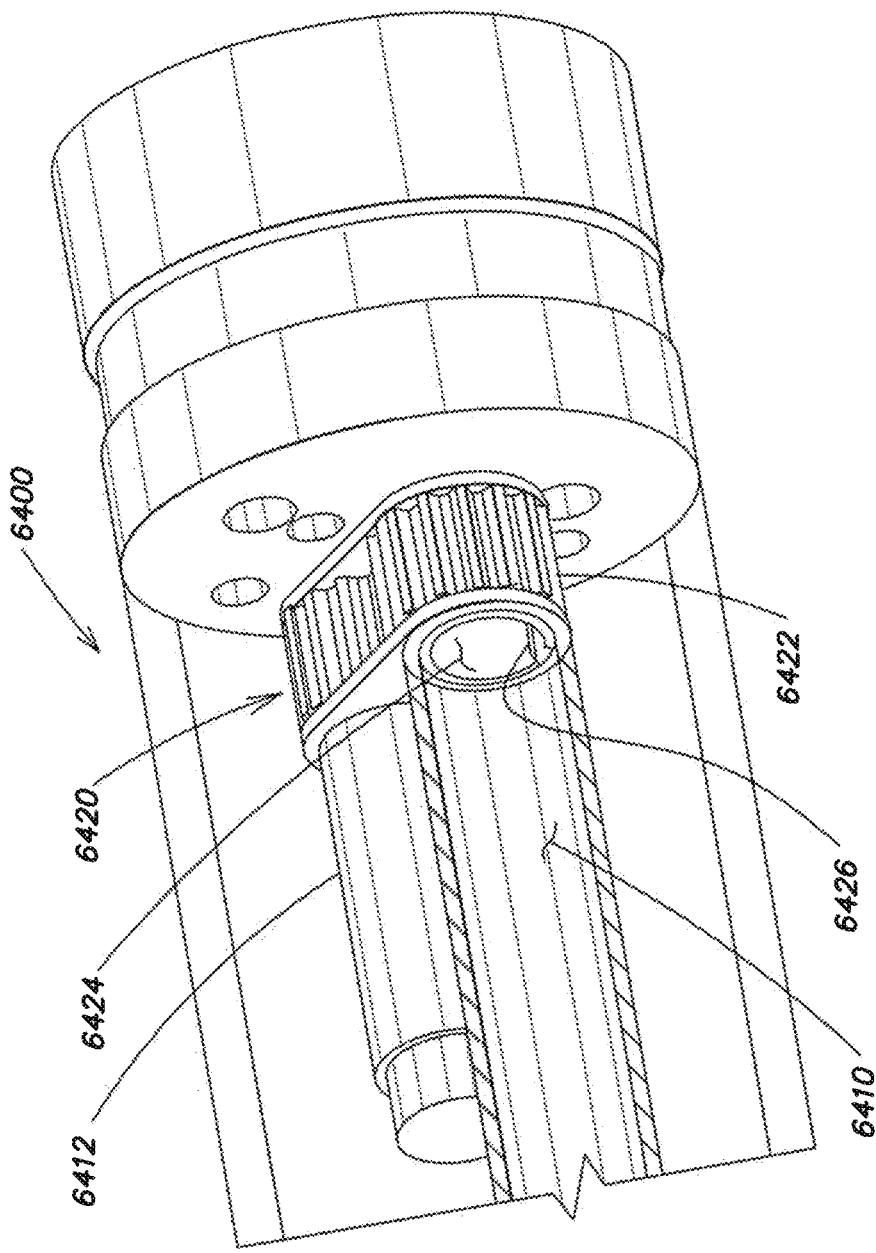
FIG. 64B is a perspective view of a distal portion of the endoscope shown in FIG. 64A.
Figure 64C:
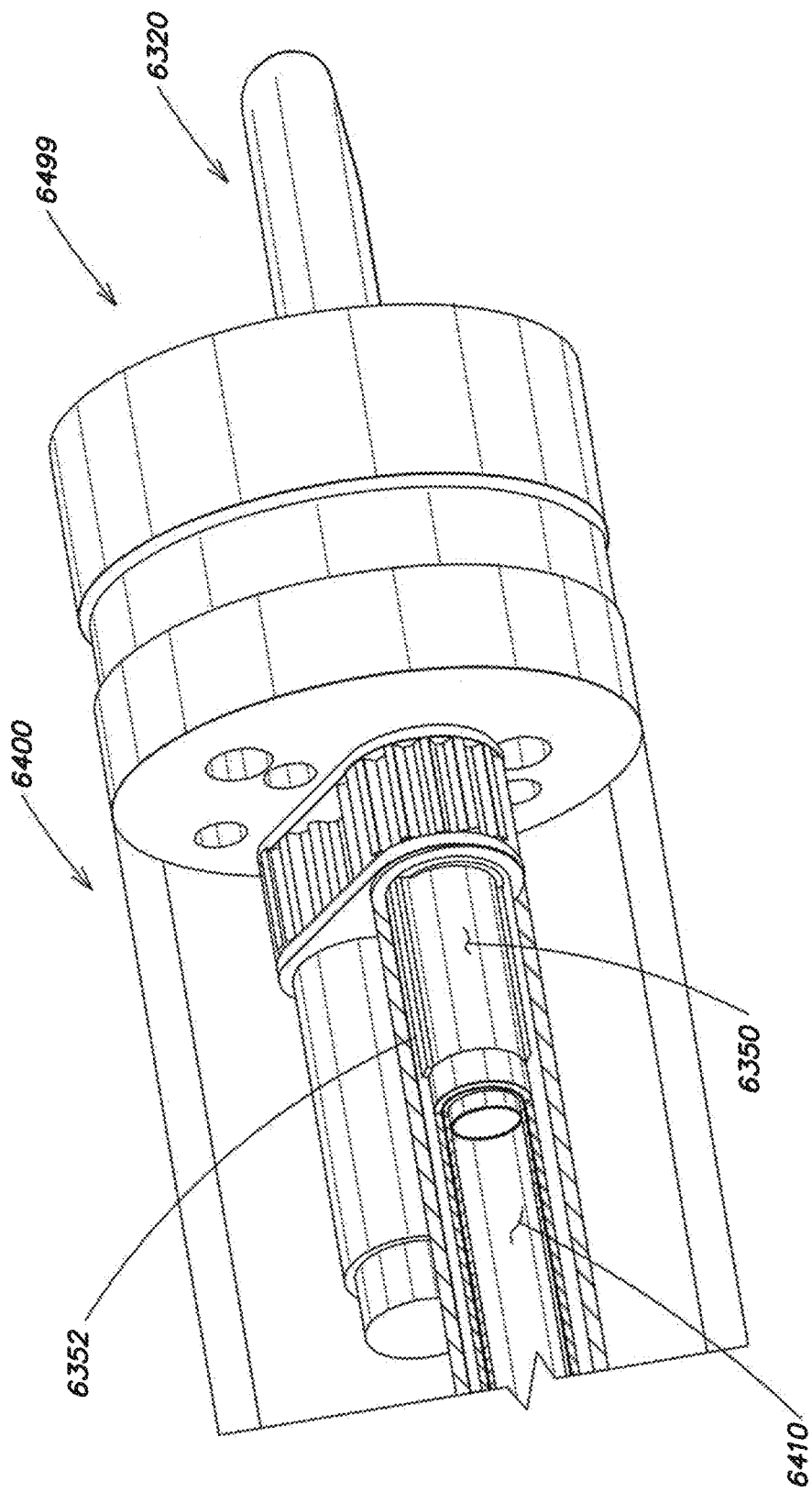
FIG. 64C is a perspective view of the endoscopic assembly shown in FIG. 64A.
Figure 64D:
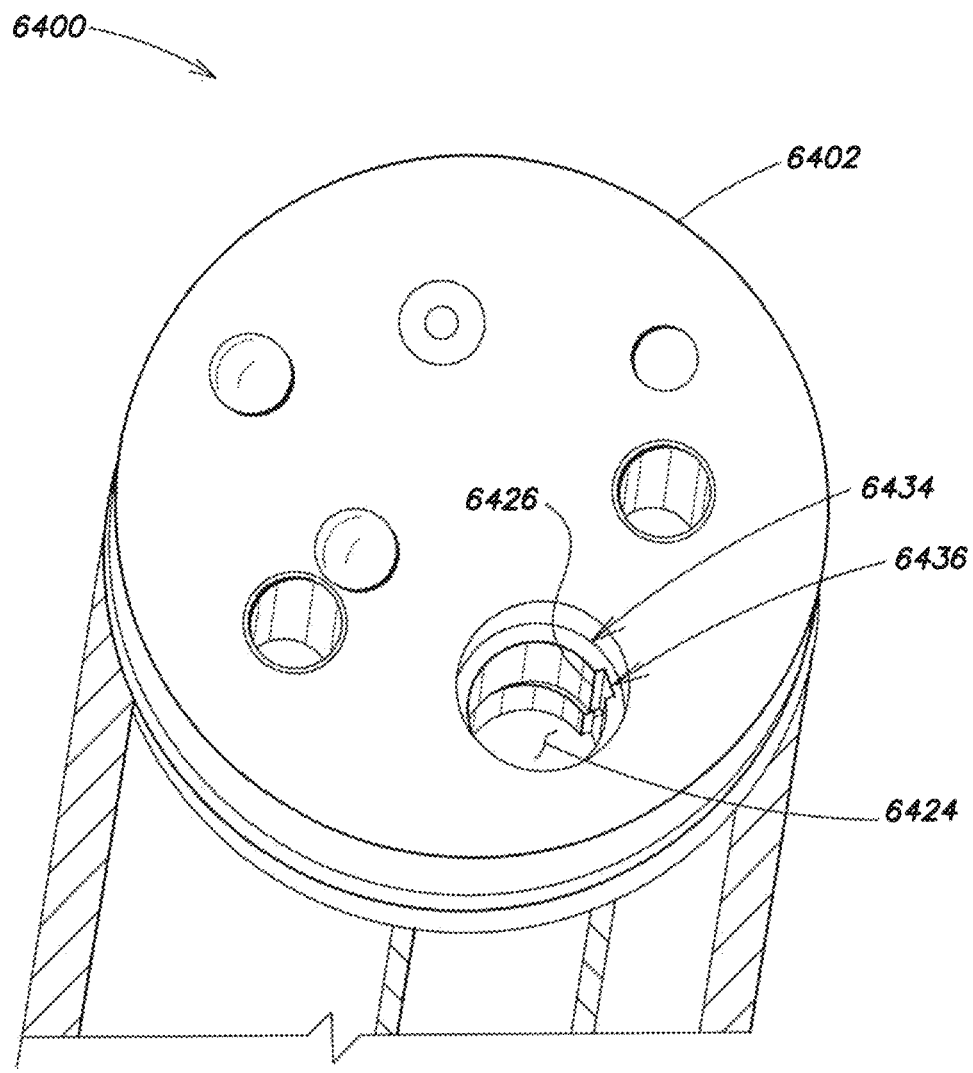
FIG. 64D is a perspective view of a distal tip of the endoscope shown in FIG. 64A.

FIG. 64A is a perspective cross-sectional view of an endoscopic assembly including an endoscope and the surgical cutting assembly shown in FIG. 63A according to embodiments of the present disclosure. FIG. 64B is a perspective view of a distal portion of the endoscope shown in FIG. 64A. FIG. 64C is a perspective view of the endoscopic assembly shown in FIG. 64A. Referring now to FIGS. 64A-64C, the endoscopic assembly 6400 includes the endoscope 6400 similar to other endoscopes described above with respect to FIGS. 51A-61. The endoscope 6400 can include a coupling component 6422 configured to couple to the coupling member 6350 of the surgical cutting assembly 6320 disposed within the instrument channel 6410 of the endoscope 6400.

The endoscope 6400 includes a torque generation component 6412 that is coupled to the coupling component 6422 via a torque transfer component 6420. The torque transfer component 6420 can transfer the torque generated by the torque generation component 6412 to the coupling component 6422. The coupling component 6422 can be positioned such that a portion of the instrument channel is disposed within an inner wall of the coupling component 6422. The portion of the instrument channel disposed within the inner wall of the coupling component 6422 can correspond to a portion where the coupling member 6350 of the surgical cutting assembly 6320 will be positioned when the outer cannula 6322 of the surgical cutting assembly 6320 is engaged with a corresponding structure formed within the endoscope 6400. The coupling component 6422 and the coupling member 6350 may be brought into contact with another via one or more actuation mechanisms. In some implementations, the inner diameter of the coupling component 6422 of the endoscope 6400 can be designed and configured to be reduced in size upon actuation such that the inner wall of the coupling component can engage with the coupling member 6350 of the surgical cutting assembly. In some implementations, the coupling member may include an actuation mechanism through which the coupling member can engage with coupling component 6422. In some implementations, the key structure 6352 of the coupling member can be configured to engage with corresponding engagement components of the coupling component such that when the coupling component rotates, the engagement components come into contact with the key structures 6352 of the coupling member 6350 causing the coupling member to rotate. In some implementations, the engagement components may be ribs, fins, grooves, or other structures formed on an inner wall of the coupling component. The engagement structures may be configured to not engage with the outer cannula when the surgical cutting assembly 6320 is being inserted within the instrument channel 6410 of the endoscope but may engage with the coupling component once the surgical cutting assembly 6320 is inserted and the torque generation component 6412 is actuated.

As shown in 64B, the inner wall 6424 of the coupling component 6422 includes a groove structure 6426 configured to engage with the key structure 6352 of the coupling member 6350 of the surgical cutting assembly 6320.

FIG. 64C is a perspective view of a distal tip of the endoscope shown in FIG. 64A. The distal tip 6402 of the endoscope 6400 includes an opening of the instrument channel 6410. As shown, the endoscope 6400 can include an articulation component 6434 including at least one groove structure 6436 configured to engage with the key structure 6330 of the outer cannula 6322 to articulate the orientation of the cutting window of the outer cannula and also keep the outer cannula stationary as the coupling member 6350 rotates upon actuation of the torque generation component 6412.

Figure 65:
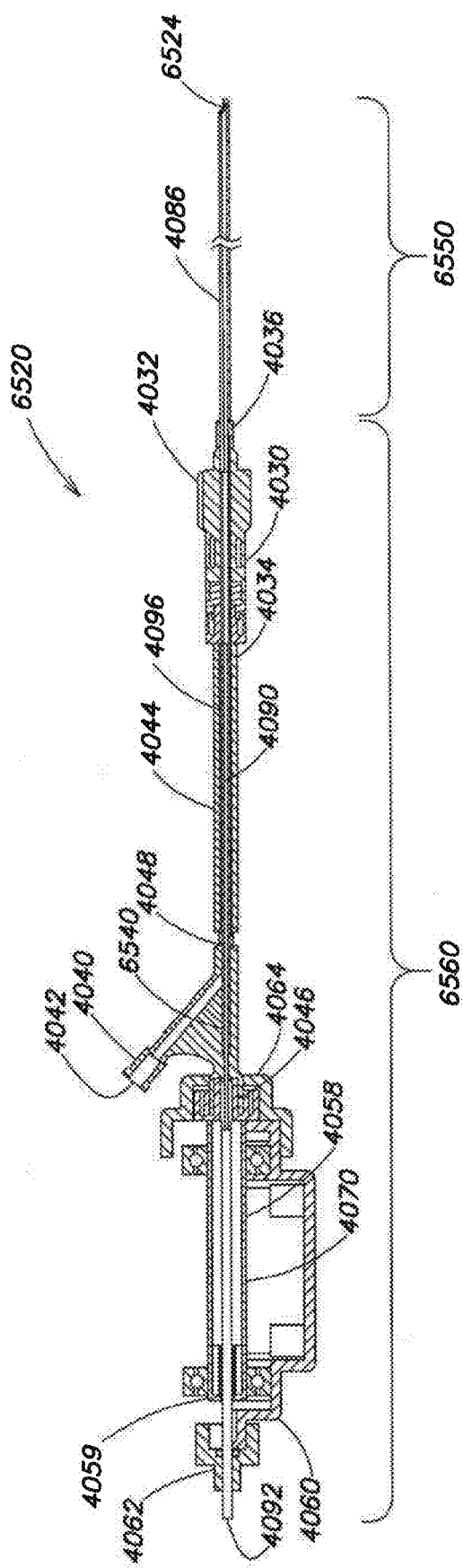
FIG. 65 is a cross-sectional view of a surgical cutting assembly according to embodiments of the present disclosure.

FIG. 65 is a cross-sectional view of a surgical cutting assembly according to embodiments of the present disclosure. The surgical cutting assembly 6520 includes a distal end 6550 that is insertable within the endoscope and a proximal end 6560 that remains outside of the endoscope after the surgical cutting assembly 6520 is inserted within the endoscope. The surgical cutting assembly 6520 includes a cutting window 6524 defined at a distal tip of the surgical cutting assembly 6520 and an aspiration tube 6540 that extends from the proximal end of the surgical cutting assembly 6520 towards the distal end 6550. The remaining portion of the surgical cutting assembly 6520 is substantially similar to the endoscopic instrument 4000 shown in FIG. 42 and the reference numerals shown in FIG. 65 correspond to the description provided above with respect to FIG. 42. The proximal end of the surgical cutting assembly 6500 can be similar to the surgical cutting assemblies described above with respect to FIGS. 51A-61. In contrast to the endoscopic instrument 4000 shown in FIG. 42 which includes the flexible torque coil 4080, the surgical cutting assembly 6500 includes an aspiration tube. The aspiration tube may be any type of tubing capable of allowing fluid to aspirate from the distal end of the surgical cutting assembly to an aspiration port 4092.

What is claimed is:

1. A method of removing material from within a mammalian cavity of a patient, comprising:

inserting a flexible endoscope within an opening to a mammalian cavity of a patient, the flexible endoscope inserted within the opening via a distal end of the endoscope;

disposing a surgical cutting assembly within an instrument channel of the flexible endoscope, the surgical cutting assembly inserted into the instrument channel via an instrument channel opening to the instrument channel at a proximal end of the endoscope that remains outside the opening to the mammalian cavity, the surgical cutting assembly including a cutter assembly having an outer cannula, an inner cannula disposed within an outer cannula, and a cutting window defined along a portion of a radial wall of the outer cannula, a proximal end of the inner cannula fluidly coupled to an aspiration channel that extends along a length of the flexible endoscope, the inner cannula configured to rotate relative to the outer cannula to cut material entering the cutting window of the outer cannula, the surgical cutting assembly further comprising a rotational coupler and a tubular member, a proximal end of the outer cannula coupled to a distal end of a flexible outer tubing, a proximal end of the flexible outer tubing coupled to a distal end of the rotational coupler, a proximal end of the rotational coupler coupled to a distal end of the tubular member, the flexible torque component extending through the tubular member, the rotational coupler, and the flexible outer tubing, the rotational coupler configured to cause the outer cannula and the flexible outer tubing to rotate relative to the the tubular member;

positioning, by rotating the outer cannula of the surgical cutting assembly via the rotational coupler, the cutting window at the material within the mammalian cavity to be removed;

providing torque to rotate the inner cannula relative to the outer cannula, the torque provided to the inner cannula via a flexible torque component extending from a proximal end of the endoscope to the distal end of the endoscope, the torque sufficient to rotate the inner cannula relative to the outer cannula to remove at least a portion of the material entering the cutting window of the outer cannula; and actuating a vacuum source coupled to the surgical cutting assembly to remove the material via the aspiration channel.

2. A method of removing lesions from within a mammalian cavity of a patient, comprising:

inserting a flexible endoscope within an opening to a mammalian cavity of a patient;

disposing an endoscopic instrument within an instrument channel of the flexible endoscope to remove at least one lesion from within the mammalian cavity, the endoscopic instrument including a cutting assembly having an outer cannula, an inner cannula disposed within an outer cannula, and an opening defined along a portion of a radial wall of the outer cannula, the inner cannula rotatably coupled to a flexible torque component having a length that extends along a length of the flexible endoscope, the flexible torque component, upon actuation, providing torque to the inner cannula, the endoscopic instrument including a rotational coupler and a tubular member, a proximal end of the outer cannula coupled to a distal end of a flexible outer tubing, a proximal end of the flexible outer tubing coupled to a distal end of the rotational coupler, a proximal end of the rotational coupler coupled to a distal end of the tubular member, the flexible torque component extending through the tubular member, the rotational coupler, and the flexible outer tubing;

providing irrigation fluid from a lavage port of the endoscopic instrument that remains outside the flexible endoscope while the endoscopic instrument is disposed within the instrument channel, the lavage port fluidly coupled to the outer cannula through the rotational coupler coupling the lavage port to the flexible outer tubing, the rotational coupler causing the flexible outer tubing and the outer cannula to rotate relative to the lavage port upon rotating a portion of the rotational coupler;

rotating, via rotation of the portion of the rotational coupler of the endoscopic instrument, the outer cannula to a position in which the opening of the outer cannula is viewable via a camera of the flexible endoscope;

positioning the opening at the lesion of the mammalian cavity;

actuating the flexible torque component to rotate the inner cannula relative to the outer cannula, the inner cannula cutting a portion of the lesion as the inner cannula rotates adjacent to the opening; and actuating a vacuum source coupled to the endoscopic instrument to remove the cut portion of the lesion from within the mammalian cavity via an aspiration channel defined by an inner wall of the inner cannula and the flexible torque component.

3. The method of claim 2, wherein disposing the endoscopic instrument within the instrument channel of the flexible endoscope includes inserting a distal end of the endoscopic instrument in the instrument channel of the flexible endoscope.

4. The method of claim 2, further comprising engaging a proximal connector that is coupled to the flexible torque component and positioned at a proximal end of the endoscopic instrument with a drive assembly configured to provide torque to the flexible torque component.

5. The method of claim 2, further comprising fluidly coupling the vacuum source to a distal end of the endoscopic instrument to remove, from the endoscopic instrument, the portion of the lesion entering the endoscopic instrument via the opening of the outer cannula.

6. The method of claim 2, wherein the flexible torque component includes a flexible torque coil having a plurality of layers of one or more threads, each of the plurality of layers is wound in a direction opposite to a direction in which one or more adjacent layers of the plurality of layers is wound and the aspiration channel is partially defined by an inner wall of the flexible torque coil.

7. The method of claim 2, wherein actuating the flexible torque component and actuating a vacuum source coupled to the endoscopic instrument includes actuating the flexible torque component and actuating the vacuum source coupled to the endoscopic instrument simultaneously.

8. The method of claim 2, wherein actuating the flexible torque component includes providing torque to the inner cannula that is sufficient to cut the portion of the lesion.

9. The method of claim 2, wherein actuating the flexible torque component includes actuating the flexible torque component to cause an inner cannula of the cutting assembly to rotate relative to the outer cannula via a foot pedal.

10. The method of claim 2, wherein the lesion is a first lesion and further comprising:

upon cutting the portion of the first lesion and without removing the endoscopic instrument from the flexible endoscope, positioning the opening of the outer cannula at a second lesion within the mammalian cavity;

actuating the flexible torque component to rotate the inner cannula relative to the outer cannula, the inner cannula cutting at least a portion of the second lesion; and actuating the vacuum source coupled to the endoscopic instrument to remove the cut portion of the second lesion from within the mammalian cavity.

11. A method of removing material from within a patient, comprising:

inserting a flexible endoscope within an opening of a patient;

disposing an endoscopic instrument within an instrument channel of the flexible endoscope to remove material from the surgical site, the endoscopic instrument including a cutting assembly having an outer cannula, an inner cannula disposed within an outer cannula, and an opening defined along a portion of a radial wall of the outer cannula, the inner cannula rotatably coupled to a flexible torque component having a length that extends along a length of the flexible endoscope, the flexible torque component, upon actuation, providing torque to the inner cannula, the outer cannula coupled to a flexible outer tubing configured to cause the outer cannula to rotate relative to the inner cannula, the endoscopic instrument including a rotational coupler and a tubular member, a proximal end of the outer cannula coupled to a distal end of a flexible outer tubing, a proximal end of the flexible outer tubing coupled to a distal end of the rotational coupler, a proximal end of the rotational coupler coupled to a distal end of the tubular member, the flexible torque component extending through the tubular member, the rotational coupler, and the flexible outer tubing;

positioning the opening of the outer cannula at the material;

actuating the flexible torque component to rotate the inner cannula relative to the outer cannula, the inner cannula cutting a portion of the material as the inner cannula rotates adjacent to the opening; and actuating a vacuum source coupled to the endoscopic instrument to remove the cut portion of the material from within the patient via an aspiration channel defined by an inner wall of the inner cannula and the flexible torque component.

12. The method of claim 11, further comprising providing irrigation fluid from a lavage port of the endoscopic instrument that remains outside the flexible endoscope while the endoscopic instrument is disposed within the instrument channel, the lavage port fluidly coupled to the outer cannula through the rotational coupler coupling the lavage port to the flexible outer tubing connected to the outer cannula, the rotational coupler allowing the outer tubing and the outer cannula to rotate relative to the lavage port upon rotating a portion of the rotational coupler.

13. The method of claim 12, further comprising rotating, via rotation of the portion of the rotational coupler, the outer cannula to a position in which the opening of the outer cannula is viewable via a camera of the flexible endoscope.

14. The method of claim 11, wherein disposing the endoscopic instrument within the instrument channel of the flexible endoscope includes inserting a distal end of the endoscopic instrument in the instrument channel of the flexible endoscope.

15. The method of claim 11, further comprising engaging a proximal connector that is coupled to the flexible torque component and positioned at a proximal end of the endoscopic instrument with a drive assembly configured to provide torque to the flexible torque component.

16. The method of claim 11, further comprising fluidly coupling the vacuum source to a distal end of the endoscopic instrument to remove, from the endoscopic instrument, the cut portion of the material entering the endoscopic instrument via the opening of the outer cannula.

17. The method of claim 11, wherein the flexible torque component includes a flexible torque coil having a plurality of layers of one or more threads, each of the plurality of layers is wound in a direction opposite to a direction in which one or more adjacent layers of the plurality of layers is wound and the aspiration channel is partially defined by an inner wall of the flexible torque coil.

18. The method of claim 11, wherein actuating the flexible torque component and actuating a vacuum source coupled to the endoscopic instrument includes actuating the flexible torque component and actuating the vacuum source coupled to the endoscopic instrument simultaneously.

19. The method of claim 11, wherein actuating the flexible torque component includes providing torque to the inner cannula that is sufficient to cut the portion of the material.

20. The method of claim 11, wherein the material is a first material and further comprising:
 upon cutting at least a portion of the first material and without removing the endoscopic instrument from the flexible endoscope, positioning the opening of the outer cannula at a second material at site;
 actuating the flexible torque component to rotate the inner cannula relative to the outer cannula, the inner cannula cutting at least a portion of the second material; and
 actuating the vacuum source coupled to the endoscopic instrument to remove the cut portion of the second material from within the patient.

* * * * *